United States Patent
Cho et al.

(10) Patent No.: US 9,260,472 B2
(45) Date of Patent: *Feb. 16, 2016

(54) MODIFIED HUMAN FOUR HELICAL BUNDLE POLYPEPTIDES AND THEIR USES

(75) Inventors: Ho Sung Cho, San Diego, CA (US); Thomas O. Daniel, La Jolla, CA (US); Richard D. Dimarchi, Carmel, IN (US); Anna-Maria A. Hays, San Diego, CA (US); Troy E. Wilson, San Marino, CA (US); Bee-Cheng Sim, San Diego, CA (US); David C. Litzinger, Poway, CA (US)

(73) Assignee: AMBRX, Inc., La Jolla, CA (US)

( * ) Notice: Subject to any disclaimer, the term of this patent is extended or adjusted under 35 U.S.C. 154(b) by 366 days.

This patent is subject to a terminal disclaimer.

(21) Appl. No.: 11/874,761

(22) Filed: Oct. 18, 2007

(65) Prior Publication Data

US 2008/0161539 A1 Jul. 3, 2008

Related U.S. Application Data

(63) Continuation of application No. 10/587,371, filed as application No. PCT/US2005/003537 on Jan. 28, 2005.

(60) Provisional application No. 60/541,528, filed on Feb. 2, 2004, provisional application No. 60/581,314, filed on Jun. 18, 2004, provisional application No. 60/581,175, filed on Jun. 18, 2004, provisional application No. 60/580,885, filed on Jun. 18, 2004, provisional application No. 60/638,616, filed on Dec. 22, 2004.

(51) Int. Cl.
| | |
|---|---|
| C07K 1/00 | (2006.01) |
| A61K 38/24 | (2006.01) |
| C07H 21/04 | (2006.01) |
| A61K 38/21 | (2006.01) |
| A61K 38/27 | (2006.01) |
| A61K 47/48 | (2006.01) |
| C07K 14/475 | (2006.01) |
| C07K 14/52 | (2006.01) |
| C07K 14/61 | (2006.01) |
| C08G 65/333 | (2006.01) |
| G01N 33/68 | (2006.01) |
| C07K 14/575 | (2006.01) |

(52) U.S. Cl.
CPC ............. *C07H 21/04* (2013.01); *A61K 38/21* (2013.01); *A61K 38/27* (2013.01); *A61K 47/48215* (2013.01); *C07K 14/475* (2013.01); *C07K 14/52* (2013.01); *C07K 14/575* (2013.01); *C07K 14/61* (2013.01); *C08G 65/33396* (2013.01); *G01N 33/6875* (2013.01); *G01N 2500/00* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,289,872 A | 9/1981 | Denkewalter et al. |
| 4,412,989 A | 11/1983 | Iwashita et al. |
| 4,414,148 A | 11/1983 | Jansen et al. |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | DeBoer |
| 4,569,789 A | 2/1986 | Blattler et al. |
| 4,619,794 A | 10/1986 | Hauser |
| 4,659,839 A | 4/1987 | Nicolotti et al. |
| 4,670,417 A | 6/1987 | Iwasaki et al. |
| 4,671,958 A | 6/1987 | Rodwell et al. |
| 4,680,338 A | 7/1987 | Sundoro |
| 4,689,406 A | 8/1987 | Banks et al. |
| 4,699,784 A | 10/1987 | Shih et al. |
| 4,738,921 A | 4/1988 | Belagaje et al. |
| 4,755,465 A | 7/1988 | Gray et al. |
| 4,837,148 A | 6/1989 | Cregg |
| 4,859,600 A | 8/1989 | Gray et al. |
| 4,876,197 A | 10/1989 | Burke et al. |
| 4,880,734 A | 11/1989 | Burke et al. |
| 4,902,502 A | 2/1990 | Nitecki et al. |
| 4,904,584 A | 2/1990 | Shaw |
| 4,929,555 A | 5/1990 | Cregg et al. |
| 5,021,234 A | 6/1991 | Ehrenfeld |
| 5,089,398 A | 2/1992 | Rosenberg et al. |
| 5,122,614 A | 6/1992 | Zalipsky |
| 5,162,601 A | 11/1992 | Slightom |
| 5,219,564 A | 6/1993 | Zalipsky et al. |
| 5,229,490 A | 7/1993 | Tam |
| 5,231,178 A | 7/1993 | Holtz et al. |
| 5,252,714 A | 10/1993 | Harris et al. |
| 5,281,698 A | 1/1994 | Nitecki |

(Continued)

FOREIGN PATENT DOCUMENTS

| | | |
|---|---|---|
| DE | 3218121 A1 | 11/1983 |
| EP | 036 676 A1 | 9/1981 |

(Continued)

OTHER PUBLICATIONS

UniProtKBSwissProt. P01588.*

(Continued)

*Primary Examiner* — Shulamith H Shafer
(74) *Attorney, Agent, or Firm* — Kristin S. Eaton

(57) ABSTRACT

Modified human four helical bundle (4HB) polypeptides and uses thereof are provided.

18 Claims, 22 Drawing Sheetse

(56) References Cited

U.S. PATENT DOCUMENTS

| | | | |
|---|---|---|---|
| 5,290,686 A | 3/1994 | Kendal et al. |
| 5,324,639 A | 6/1994 | Brierley et al. |
| 5,324,844 A | 6/1994 | Zalipsky |
| 5,382,657 A | 1/1995 | Karasiewicz et al. |
| 5,446,090 A | 8/1995 | Harris |
| 5,468,478 A | 11/1995 | Saifer et al. |
| 5,473,034 A | 12/1995 | Yasui et al. |
| 5,476,653 A | 12/1995 | Pitt et al. |
| 5,516,657 A | 5/1996 | Murphy et al. |
| 5,516,673 A | 5/1996 | Margel et al. |
| 5,532,142 A | 7/1996 | Johnston et al. |
| 5,559,213 A | 9/1996 | Hakimi et al. |
| 5,571,709 A | 11/1996 | Devauchelle et al. |
| 5,580,723 A | 12/1996 | Wells et al. |
| 5,583,023 A | 12/1996 | Cerutti et al. |
| 5,602,034 A | 2/1997 | Tekamp-Olson |
| 5,605,827 A | 2/1997 | Jackwood et al. |
| 5,612,460 A | 3/1997 | Zalipsky |
| 5,629,203 A | 5/1997 | Shuster |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,674,706 A | 10/1997 | Shuster |
| RE35,749 E | 3/1998 | Rosenberg et al. |
| 5,736,625 A | 4/1998 | Callstrom et al. |
| 5,739,208 A | 4/1998 | Harris |
| 5,747,446 A * | 5/1998 | Sytkowski ............... 514/8 |
| 5,747,646 A | 5/1998 | Hakimi et al. |
| 5,750,373 A | 5/1998 | Garrard et al. |
| 5,753,220 A | 5/1998 | Suzuki et al. |
| 5,762,939 A | 6/1998 | Smith et al. |
| 5,766,885 A | 6/1998 | Carrington et al. |
| 5,808,096 A | 9/1998 | Zalipsky |
| 5,824,778 A | 10/1998 | Ishikawa et al. |
| 5,824,784 A | 10/1998 | Kinstler et al. |
| 5,834,250 A | 11/1998 | Wells et al. |
| 5,834,594 A | 11/1998 | Hakimi et al. |
| 5,843,733 A | 12/1998 | Estes |
| 5,849,860 A | 12/1998 | Hakimi et al. |
| 5,858,368 A | 1/1999 | Smith et al. |
| 5,861,279 A | 1/1999 | Zhang et al. |
| 5,871,986 A | 2/1999 | Boyce |
| 5,891,676 A | 4/1999 | Estes |
| 5,900,461 A | 5/1999 | Harris |
| 5,932,462 A | 8/1999 | Harris et al. |
| 5,939,285 A | 8/1999 | Devauchelle et al. |
| 5,965,393 A | 10/1999 | Hasnain et al. |
| 5,980,948 A | 11/1999 | Goedemoed et al. |
| 5,989,868 A | 11/1999 | Harrison et al. |
| 5,990,237 A | 11/1999 | Bentley et al. |
| 6,004,573 A | 12/1999 | Rathi et al. |
| 6,013,433 A | 1/2000 | Pellett et al. |
| 6,013,478 A | 1/2000 | Wells et al. |
| 6,017,731 A | 1/2000 | Tekamp-Olson et al. |
| 6,083,723 A | 7/2000 | Tekamp-Olson |
| 6,096,304 A | 8/2000 | McCutchen |
| 6,126,944 A | 10/2000 | Pellett et al. |
| 6,129,912 A | 10/2000 | Hortin et al. |
| 6,168,932 B1 | 1/2001 | Uckun et al. |
| 6,183,985 B1 | 2/2001 | Shuster |
| 6,183,987 B1 | 2/2001 | Van De Wiel et al. |
| 6,201,072 B1 | 3/2001 | Rathi et al. |
| 6,214,966 B1 | 4/2001 | Harris |
| 6,225,060 B1 | 5/2001 | Clark et al. |
| 6,245,528 B1 | 6/2001 | Chao |
| 6,261,805 B1 | 7/2001 | Wood |
| RE37,343 E | 8/2001 | Tekamp-Olson |
| 6,281,211 B1 | 8/2001 | Cai et al. |
| 6,306,821 B1 | 10/2001 | Mikos et al. |
| 6,312,923 B1 | 11/2001 | Tekamp-Olson |
| 6,337,191 B1 | 1/2002 | Swartz et al. |
| 6,338,846 B1 | 1/2002 | Kang et al. |
| 6,342,216 B1 | 1/2002 | Fidler et al. |
| 6,361,969 B1 | 3/2002 | Galeotti |
| 6,368,825 B1 | 4/2002 | Chao |
| 6,420,339 B1 | 7/2002 | Gegg et al. |
| 6,423,685 B1 | 7/2002 | Drummond et al. |
| 6,428,954 B1 | 8/2002 | Wells et al. |
| 6,436,386 B1 | 8/2002 | Roberts et al. |
| 6,451,346 B1 | 9/2002 | Shah et al. |
| 6,451,561 B1 | 9/2002 | Wells et al. |
| 6,461,603 B2 | 10/2002 | Bentley et al. |
| 6,515,100 B2 | 2/2003 | Harris |
| 6,521,427 B1 | 2/2003 | Evans |
| 6,552,167 B1 | 4/2003 | Rose |
| 6,586,207 B2 | 7/2003 | Tirrell et al. |
| 6,602,498 B2 | 8/2003 | Shen |
| 6,608,183 B1 | 8/2003 | Cox |
| 6,610,281 B2 | 8/2003 | Harris |
| 6,638,500 B1 | 10/2003 | El-Tayar et al. |
| 6,646,110 B2 | 11/2003 | Nissen et al. |
| 6,927,042 B2 | 8/2005 | Schultz et al. |
| 7,045,337 B2 | 5/2006 | Schultz et al. |
| 7,083,970 B2 | 8/2006 | Schultz et al. |
| 2001/0021763 A1 | 9/2001 | Harris |
| 2001/0044526 A1 | 11/2001 | Shen |
| 2001/0056171 A1 | 12/2001 | Kozlowski |
| 2002/0002250 A1 | 1/2002 | Bentley et al. |
| 2002/0037949 A1 | 3/2002 | Harris et al. |
| 2002/0040076 A1 | 4/2002 | Harris et al. |
| 2002/0042097 A1 | 4/2002 | Tirrell et al. |
| 2002/0052009 A1 | 5/2002 | Hornauer et al. |
| 2002/0052430 A1 | 5/2002 | Harris et al. |
| 2002/0055169 A1 | 5/2002 | Tekamp-Olson |
| 2002/0072573 A1 | 6/2002 | Bentley et al. |
| 2002/0081660 A1 | 6/2002 | Swartz et al. |
| 2002/0082345 A1 | 6/2002 | Kozlowski et al. |
| 2002/0086939 A1 | 7/2002 | Kozlowski |
| 2002/0099133 A1 | 7/2002 | Kozlowski |
| 2002/0156047 A1 | 10/2002 | Zhao |
| 2003/0023023 A1 | 1/2003 | Harris et al. |
| 2003/0082575 A1 | 5/2003 | Schultz et al. |
| 2003/0105224 A1 | 6/2003 | Roberts et al. |
| 2003/0105275 A1 | 6/2003 | Bentley et al. |
| 2003/0108885 A1 | 6/2003 | Schultz et al. |
| 2003/0114647 A1 | 6/2003 | Harris et al. |
| 2003/0143596 A1 | 7/2003 | Bentley et al. |
| 2003/0158333 A1 | 8/2003 | Roberts |
| 2003/0162949 A1 | 8/2003 | Cox |
| 2003/0220447 A1 | 11/2003 | Harris |
| 2003/0228274 A1 | 12/2003 | Rose |
| 2004/0001838 A1 | 1/2004 | Zhao et al. |
| 2004/0013637 A1 | 1/2004 | Bentley |
| 2004/0115774 A1 * | 6/2004 | Kochendoerfer et al. ... 435/69.5 |
| 2004/0198637 A1 | 10/2004 | Schultz et al. |
| 2005/0009049 A1 | 1/2005 | Chin et al. |
| 2005/0085619 A1 | 4/2005 | Wilson et al. |
| 2005/0170404 A1 | 8/2005 | Cho et al. |
| 2005/0220762 A1 | 10/2005 | Cho et al. |

FOREIGN PATENT DOCUMENTS

| | | |
|---|---|---|
| EP | 036 776 A2 | 9/1981 |
| EP | 052 322 A2 | 5/1982 |
| EP | 058 481 A1 | 8/1982 |
| EP | 073 657 A1 | 3/1983 |
| EP | 102 324 A2 | 3/1984 |
| EP | 121 775 A1 | 10/1984 |
| EP | 127 839 A2 | 12/1984 |
| EP | 133 988 A2 | 3/1985 |
| EP | 143 949 A1 | 6/1985 |
| EP | 154 316 A2 | 9/1985 |
| EP | 155 476 A1 | 9/1985 |
| EP | 164 556 A2 | 12/1985 |
| EP | 183 503 A2 | 6/1986 |
| EP | 188 256 A2 | 7/1986 |
| EP | 229 108 B1 | 7/1987 |
| EP | 244 234 A2 | 11/1987 |
| EP | 267 851 A2 | 5/1988 |
| EP | 284 044 A1 | 9/1988 |
| EP | 324 274 A1 | 7/1989 |
| EP | 329 203 A1 | 8/1989 |
| EP | 340 986 A2 | 11/1989 |

(56) References Cited

FOREIGN PATENT DOCUMENTS

| | | |
|---|---|---|
| EP | 400 472 A2 | 12/1990 |
| EP | 402 378 B1 | 12/1990 |
| EP | 439 508 B1 | 8/1991 |
| EP | 480 480 A1 | 4/1992 |
| EP | 510 356 A1 | 10/1992 |
| EP | 605 963 A1 | 7/1994 |
| EP | 732 403 A1 | 9/1996 |
| EP | 809 996 A2 | 12/1997 |
| EP | 921 131 A1 | 6/1999 |
| EP | 946 736 B1 | 10/1999 |
| EP | 1219636 A2 | 7/2002 |
| GB | 2426521 A2 | 11/2006 |
| GB | 2426762 A2 | 12/2006 |
| GB | 2429207 A2 | 2/2007 |
| JP | 83-118008 A | 1/1985 |
| WO | 88/07082 A1 | 9/1988 |
| WO | 89/01037 A1 | 2/1989 |
| WO | 89/01038 A1 | 2/1989 |
| WO | 90/01556 A1 | 2/1990 |
| WO | 90/02186 A1 | 3/1990 |
| WO | 90/02566 A1 | 3/1990 |
| WO | 90/05785 A1 | 5/1990 |
| WO | 90/10078 A1 | 9/1990 |
| WO | 90/10277 A1 | 9/1990 |
| WO | 90/13540 A1 | 11/1990 |
| WO | 90/14428 A1 | 11/1990 |
| WO | 91/00357 A1 | 1/1991 |
| WO | 92/01801 A1 | 2/1992 |
| WO | 92/02628 A1 | 2/1992 |
| WO | 92/16555 A1 | 10/1992 |
| WO | 92/16619 A1 | 10/1992 |
| WO | 93/15189 A1 | 10/1992 |
| WO | 93/21259 A1 | 10/1993 |
| WO | 94/04193 A1 | 3/1994 |
| WO | 94/09027 A1 | 4/1994 |
| WO | 94/14758 A1 | 7/1994 |
| WO | 94/15625 A1 | 7/1994 |
| WO | 94/17039 A1 | 8/1994 |
| WO | 94/18247 A1 | 8/1994 |
| WO | 94/28024 A1 | 12/1994 |
| WO | 95/00162 A1 | 1/1995 |
| WO | 95/06058 A1 | 3/1995 |
| WO | 95/11924 A1 | 5/1995 |
| WO | 95/13090 A1 | 5/1995 |
| WO | 95/13312 A1 | 5/1995 |
| WO | 95/20672 A1 | 8/1995 |
| WO | 95/33490 A1 | 12/1995 |
| WO | 96/00080 A1 | 1/1996 |
| WO | 96/06161 A1 | 2/1996 |
| WO | 96/07670 A1 | 3/1996 |
| WO | 96/21469 A1 | 7/1996 |
| WO | 96/25496 A1 | 8/1996 |
| WO | 96/29400 A1 | 9/1996 |
| WO | 96/40791 A1 | 12/1996 |
| WO | 96/41813 A2 | 12/1996 |
| WO | 97/03106 A1 | 1/1997 |
| WO | 97/18832 A1 | 5/1997 |
| WO | 97/26332 A1 | 7/1997 |
| WO | 97/32607 A2 | 9/1997 |
| WO | 98/05363 A2 | 2/1998 |
| WO | 98/26080 A1 | 6/1998 |
| WO | 98/32466 A1 | 7/1998 |
| WO | 98/37208 A1 | 8/1998 |
| WO | 98/41562 A1 | 9/1998 |
| WO | 98/48837 A1 | 11/1998 |
| WO | 99/03887 A1 | 1/1999 |
| WO | 99/05297 A1 | 2/1999 |
| WO | 99/07862 A1 | 2/1999 |
| WO | 99/09193 A1 | 2/1999 |
| WO | 99/10515 A1 | 3/1999 |
| WO | 99/31257 A2 | 6/1999 |
| WO | 99/32134 A1 | 7/1999 |
| WO | 99/32139 A1 | 7/1999 |
| WO | 99/32140 A1 | 7/1999 |
| WO | 99/45130 A1 | 9/1999 |
| WO | 99/51721 A1 | 10/1999 |
| WO | 99/67291 A2 | 12/1999 |
| WO | WO 00/17361 A2 | 3/2000 |
| WO | 00/20032 A1 | 4/2000 |
| WO | 00/26354 A1 | 5/2000 |
| WO | 00/55345 A2 | 9/2000 |
| WO | 00/55353 A1 | 9/2000 |
| WO | WO 00/68387 A2 | 11/2000 |
| WO | 01/05956 A2 | 1/2001 |
| WO | 01/27301 A2 | 4/2001 |
| WO | 01/90390 A1 | 11/2001 |
| WO | 02/06305 A1 | 1/2002 |
| WO | 02/085923 A2 | 10/2002 |
| WO | 02/086075 A2 | 10/2002 |
| WO | WO 02/085923 A2 | 10/2002 |
| WO | 03/101972 A1 | 12/2003 |
| WO | 2004/035605 A2 | 4/2004 |
| WO | 2004/035743 A2 | 4/2004 |
| WO | 2004/058946 A2 | 7/2004 |
| WO | 2004/094593 A2 | 11/2004 |
| WO | WO 2004/094593 A2 | 11/2004 |
| WO | 2005/007624 A2 | 1/2005 |
| WO | 2005/007870 A2 | 1/2005 |
| WO | WO 2005/003294 A2 | 1/2005 |
| WO | 2005/019415 A2 | 3/2005 |
| WO | 2005/035727 A2 | 4/2005 |
| WO | 2005/074524 A2 | 8/2005 |
| WO | 2005/074546 A2 | 8/2005 |
| WO | 2005/074650 A2 | 8/2005 |
| WO | WO 2005/074524 A2 | 8/2005 |
| WO | WO 2005/074546 A2 | 8/2005 |
| WO | WO 2005/074650 A2 | 8/2005 |

OTHER PUBLICATIONS

Dieters et al., "Adding Amino Acids with Novel Reactivity to the Genetic Code of *Saccharomyces cerevisiae*", J. Am. Chem. Soc., Oct. 1, 2003, 125(39):11782-11783.

Dieters et al., "Site-Specific PEGylation of Proteins Containing Unnatural Amino Acids", Bioorg. & Med. Chem. Letters, Dec. 6, 2004, 14(23):5743-5745.

Abuchowski, A. et al. "Cancer therapy with chemically modified enzymes. I. Antitumor properties of polyethylene glycol-asparaginase conjugates," Cancer Biochem Biophys. Jun. 1984;7(2):175-86.

Altschul, SF et al. "Gapped BLAST and PSI-BLAST: a new generation of protein database search programs," Nucleic Acids Res. Sep. 1, 1997;25(17):3389-402.

Altschul, SF et al. "Basic local alignment search tool," J Mol Biol. Oct. 5, 1990;215(3):403-10.

Amann, E et al., "Vectors bearing a hybrid trp-lac promoter useful for regulated expression of cloned genes in *Escherichia coli*",' Gene. Nov. 1983;25(2-3):167-78.

Anderson, JC et al., "Exploring the limits of codon and anticodon size," Chem Biol. Feb. 2002;9(2):237-44.

Andresz, H et al. Abstract of "Chemische Synthese verzweigter Polysaccharide, 5; Kopplung von Oligosacchariden and Amylose an verschiedene Träger durch Hydrazonbindung," Makromol. Chem. 1978;179:301 Abstract.

Arnold, FH. "Protein engineering for unusual environments," Curr Opin Biotechnol. Aug. 1993;4(4):450-5.

Azoulay, M., et al. "Glutamine analogues as Potential Antimalarials," Eur. J. Med. Chem. (1991); 26(2):201-5.

Bain, JD, et al. "Biosynthetic site-specific incorporation of a non-natural amino acid into a polypeptide," J. Am Chem Soc 1989;111(20):8013-8014.

Ballance, DJ et al., "Transformation of Aspergillus nidulans by the orotidine-5'-phosphate decarboxylase gene of Neurospora crassa," Biochem Biophys Res Commun. Apr. 15, 1983;112(1):284-9.

Barany, F. et al., "Genetic disease detection and DNA amplification using cloned thermostable ligase," Proc Natl Acad Sci U S A. Jan. 1, 1991;88(1):189-93.

Barton, DHR et al., "Synthesis of Novel alpha-Amino-Acids and Derivatives Using Radical Chemistry: Synthesis of L- and D-alpha-

(56) References Cited

OTHER PUBLICATIONS

Amino-Adipic Acids, L-alpha-aminopimelic Acid and Appropriate Unsaturated Derivatives," Tetrahedron (1987) 43:4297-4308.
Bass, S et al., "Mutant Trp repressors with new DNA-binding specificities," Science (1988) 242:240-245.
Batzer, MA et al., "Enhanced evolutionary PCR using oligonucleotides with inosine at the 3'-terminus," Nucleic Acids Res. Sep. 25, 1991;19(18):5081.
Beach, D et al., "Functionally homologous cell cycle control genes in budding and fission yeast," Nature Dec. 1982; 300:706-709.
Beauchamp, CO et al., "A new procedure for the synthesis of polyethylene glycol-protein adducts; effects on function, receptor recognition, and clearance of superoxide dismutase, lactoferrin, and alpha 2-macroglobulin," Anal Biochem. May 1983;131(1):25-33.
Bernstein, FC, et al. "The protein data bank: a computer-based archival file for macromolecular structures," J. Mol. Biol. 1977; 112:535-542.
Boissel, JP et al., "Erythropoietin structure-function relationships. Mutant proteins that test a model of tertiary structure," J Biol Chem. Jul. 25, 1993;268(21):15983-93.
Boles, JO et al. "Bio-incorporation of telluromethionine into buried residues of dihydrofolate reductase," Nat Struct Biol. May 1994;1(5):283-4.
Botstein, D et D Shortle, "Strategies and applications of in vitro mutagenesis," Science. Sep. 20, 1985;229(4719):1193-201.
Brunner, J. "New photolabeling and crosslinking methods," Annu Rev Biochem. 1993;62:483-514.
Buchner, J. et al., "A method for increasing the yield of properly folded recombinant fusion proteins: Single-chain immunotoxins from renaturation of bacterial inclusion bodies," Anal. Biochem. 1992; 205(2): 263-270.
Bückmann et al. "Functionalization of Poly(ethylene glycol) and Monomethoxy-Poly(ethylene glycol)," Makromol. Chem. 1981;182:1379-84.
Budisa, N et al. "High-level biosynthetic substitution of methionine in proteins by its analogs 2-aminohexanoic acid, selenomethionine, telluromethionine and ethionine in *Escherichia coli*," Eur J Biochem. Jun. 1, 1995;230(2):788-96.
Budisa, N et al., "Bioincorporation of telluromethionine into proteins: a promising new approach for X-ray structure analysis of proteins," J Mol Biol. Jul. 25, 1997;270(4):616-23.
Budisa, N. et al., "Toward the experimental codon reassignment in vivo: protein building with an expanded amino acid repertoire," FASEB J. Jan. 1999;13(1):41-51.
Cai, X-Y et al., "Expression, Purification, and Characterization of an Activated Cytokine-Suppressive Anti-inflammatory Drug-Binding Protein 2 (CSBP2) Kinase from Baculovirus-Infected Insect Cells," Protein Expression and Purification 1997; 10(2):263-74.
Carbonell, LF et al., "Baculovirus-mediated expression of bacterial genes in dipteran and mammalian cells," J Virol. Oct. 1985;56(1):153-60.
Carrasco, M. and R. Brown, "A Versatile Set of Aminooxy Amino Acids for the Synthesis of Neoglycopeptides," J. Org. Chem. (2003); 68(23): 8853-8858.
Carter, P. "Site-directed mutagenesis," Biochem J. Jul. 1, 1986; 237(1):1-7.
Carter, P et al. "Improved oligonucleotide site-directed mutagenesis using M13 vectors" Nucleic Acids Res. Jun. 25, 1985;13(12):4431-43.
Carter, P. "Improved oligonucleotide-directed mutagenesis using M13 vectors" Methods Enzymol. 1987;154:382-403.
Chaiken, IM. "Semisynthetic peptides and proteins," CRC Crit Rev Biochem. 1981;11(3):255-301.
Chin, JW et al., "Addition of p-azido-L-phenylalanine to the genetic code of *E. coli*," J Am Chem Soc. Aug. 7, 2002;124 (31):9026-7.
Chin, JW et al., "Addition of a photocrosslinking amino acid to the genetic code of *Escherichia coli*," Proc Nati Acad Sci U S A. Aug. 20, 2002;99(17):11020-4. Epub Aug. 1, 2002.
Chin, JW et al., "An expanded eukaryotic genetic code," Science. Aug. 15, 2003;301(5635):964-7.
Chin, JW & P. G. Schultz, "In vivo photocrosslinking with unnatural amino acid mutagenesis," Chembiochem. Nov. 4, 2002; 3(11): 1135-7.
Christie, B.D. & Rapoport, H. "Synthesis of Optically Pure Pipecolates from L-Asparagine. Application to the Total Synthesis of (+)—Apovincamine through Amino Acid Decarbonylation and Iminium Ion Cyclization," J. Org. Chem. 1985;50(8):1239-1246.
Clark, R et al., "Long-acting growth hormones produced by conjugation with polyethylene glycol," J Biol Chem. Sep. 6, 1996;271(36):21969-77.
Corey, D.R., Schultz, P.G. "Generation of a hybrid sequence-specific single-stranded deoxyribonuclease," Science 1987; 238(4832):1401-1403.
Cornish, VW, et al., "Site-Specific Protein Modification Using a Ketone Handle," J. Am. Chem. Soc. 1996; 118 (34):8150-8151.
Cornish, VW et al., "Probing Protein Structure and Function with an Expanded Genetic Code,"Angew Chem Int Ed Engl,1995;34(6):621-33.
Craig, J.C. et al. "Absolute Configuration of the Enantiomers of 7-Chloro-4 [[4-(diethylamino)-1-methylbutyl]amino] quinoline (Chloroquine)," J. Org. Chem. 1988; 53(6):1167-1170.
Cregg, JM et al., "Pichia pastoris as a host system for transformations," Mol Cell Biol. Dec. 1985;5(12):3376-85.
Crick, FHC, et al. "General nature of the genetic code for proteins," Nature. Dec. 30, 1961;192:1227-32.
Dale et al., Oligonucleotide-directed random mutagenesis using the phosphorothioate method, Methods Mol. Biol.1996;57:369-374.
Das, S et al., "Transformation of Kluyveromyces fragilis," J Bacteriol. Jun. 1984;158(3):1165-7.
Dawson, P. E. and S. B. H. Kent, "Synthesis of native proteins by chemical ligation," Annu. Rev. Biochem. 2000; 69:923-60.
De Boer, HA et al., "The tac promoter: a functional hybrid derived from the trp and lac promoters," Proc Natl Acad Sci U S A. Jan. 1983;80(1):21-5.
De Louvencourt, L et al., "Transformation of Kluyveromyces lactis by killer plasmid DNA," J Bacteriol. May 1983;154(2):737-42.
Van Hest, J. C. et al., "Efficient Incorporation of Unsaturated Methionine Analogues into Proteins in Vivo," J. Am. Chem. Soc2000 ;122 (7); 1282-1288.
Van Solingen, P. et JB van der Plaat. "Fusion of yeast spheroplasts," J Bacteriol. May 1977;130(2):946-7.
Veronese, FM et al., "Surface modification of proteins. Activation of monomethoxy-polyethylene glycols by phenylchloroformates and modification of ribonuclease and superoxide dismutase," Appl Biochem Biotechnol. Apr. 1985; 11(2):141-52.
Vlak, JM et al., "Functional studies on the p10 gene of Autographa californica nuclear polyhedrosis virus using a recombinant expressing a p10-beta-galactosidase fusion gene," J Gen Virol. Apr. 1988;69 ( Pt 4):765-76.
Wang, Q., et al., "Bioconjugation by Copper(I)-Catalyzed Azide-Alkyne [3+2] Cycloaddition," J. Am. Chem. Soc. 2003; 125(11):3192-3193.
Wang, L. et al., "Addition of the keto functional group to the genetic code of *Escherichia coli*," Proc. Natl. Acad. Sci. (2003); 100(1):56-61.
Wang, L et al., "Expanding the genetic code of *Escherichia coli*," Science. Apr. 20, 2001;292(5516):498-500.
Debinski, W et al. "A wide range of human cancers express interleukin 4 (IL4) receptors that can be targeted with chimeric toxin composed of IL4 and Pseudomonas exotoxin," J Biol Chem. Jul. 5, 1993;268(19):14065-70.
Deiters, A., et al., "Adding Amino Acids with Novel Reactivity to the Genetic Code of *Saccharomyces cerevisiae*," J. Am. Chem. Soc. 2003; 125(39): 11782-11783.
Delgado, C et al., "The uses and properties of PEG-linked proteins," Crit Rev Ther Drug Carrier Syst. 1992;9(3-4):249-304.
Dennis, MS et al., "Albumin binding as a general strategy for improving the pharmacokinetics of proteins," J Biol Chem. Sep. 20, 2002;277(38):35035-43. Epub Jul. 15, 2002.
Dolphin, CT et al., "Missense mutation in flavin-containing monooxygenase 3 gene, FMO3, underlies fish-odour syndrome," Nat Genet. Dec. 1997;17(4):491-4.

(56) References Cited

OTHER PUBLICATIONS

Doring, V et al., "Enlarging the amino acid set of *Escherichia coli* by infiltration of the valine coding pathway," Science. Apr. 20, 2001;292(5516):501-4.
Dougherty, DA. "Unnatural amino acids as probes of protein structure and function," Curr Opin Chem Biol. Dec. 2000;4(6):645-52.
Duewel, H et al., "Incorporation of trifluoromethionine into a phage lysozyme: implications and a new marker for use in protein 19F NMR," Biochemistry. Mar. 18, 1997;36(11):3404-16.
Eghtedarzadeh MK & S Henikoff "Use of oligonucleotides to generate large deletions" Nucleic Acids Res. Jun. 25, 1986;14(12):5115.
Elling L et MR Kula., "Immunoaffinity partitioning: synthesis and use of polyethylene glycol-oxirane for coupling to bovine serum albumin and monoclonal antibodies," Biotechnol Appl Biochem. Jun. 1991;13(3):354-62.
Elliott, S et al., "Yeast-derived recombinant human insulin-like growth factor I: production, purification, and structural characterization," J Protein Chem. Feb. 1990;9(1):95-104.
Ellman, J.A., Mendel, D., Anthony-Cahill, S., Noren, C.J., Schultz, P.G. "Biosynthetic method for introducing unnatural amino acids site-specifically into proteins," Methods in Enz., 1992; 202:301-336.
Ellman, JA, et al. "Site-specific incorporation of novel backbone structures into proteins," Science. Jan. 10, 1992;255(5041):197-200.
England, P. M., et al., "Backbone mutations in transmembrane domains of a ligand-gated ion channel: implications for the mechanism of gating," Cell. Jan. 8, 1999;96(1):89-98.
Eppstein et al., "Biological Activity of Liposome-Encapsulated Murine Interferon is Mediated by a Cell Membrane Receptor," Proc. Natl. Acad. Sci. U.S.A.(1985); 82: 3688-3692.
Fieschko, JC et al., "Controlled expression and purification of human immune interferon from high-cell-density fermentations of *Saccharomyces cerevisiae*," Biotech. Bioeng. (1987) 29(9):1113-21.
Forster, AC et al., "Programming peptidomimetic syntheses by translating genetic codes designed de novo," Proc Natl Acad Sci U S A. May 27, 2003;100(11):6353-7. Epub May 16, 2003.
Frankel, A et al., "Encodamers: unnatural peptide oligomers encoded in RNA," Chem Biol. Nov. 2003; 10(11):1043-50.
Fraser, MJ et al., "Expression of eucaryotic genes in insect cell cultures," In Vitro Cell. Dev. Biol. 1989; 25:225-235.
Friedman, O.M. & R. Chatterrji. "Synthesis of Derivatives of Glutamine as Model Substrates for Anti-Tumor Agents," J. Am. Chem. Soc. 1959; 81(14):3750-3752.
Fritz HJ et al., "Oligonucleotide-directed construction of mutations: a gapped duplex DNA procedure without enzymatic reactions in vitro," Nucleic Acids Res. Jul. 25, 1988;16(14B):6987-99.
Fromm, M. et al., "Expression of Genes Transferred into Monocot and Dicot Plant Cells by Electroporation," Proc. Natl. Acad. Sci. USA (1985) 82:5824-8.
Furter, R. "Expansion of the genetic code: site-directed p-fluorophenylalanine incorporation in *Escherichia coli*," Protein Sci. Feb. 1998;7(2):419-26.
Gaertner, HF et al., "Construction of protein analogues by site-specific condensation of unprotected fragments," Bioconjug Chem. May-Jun. 1992;3(3):262-8.
Gaertner, HF et al., "Chemo-enzymic backbone engineering of proteins. Site-specific incorporation of synthetic peptides that mimic the 64-74 disulfide loop of granulocyte colony-stimulating factor," J Biol Chem. Mar. 11, 1994;269(10):7224-30.
Gallivan, JP et al., "Site-specific incorporation of biotinylated amino acids to identify surface-exposed residues in integral membrane proteins," Chem Biol. Oct. 1997;4(10):739-49.
Gellissen, G et al., "Heterologous protein production in yeast," Antonie Van Leeuwenhoek. Aug. 1992;62(1-2):79-93.
Geoghegan, KF and JG Stroh, "Site-directed conjugation of nonpeptide groups to peptides and proteins via periodate oxidation of a 2-amino alcohol. Application to modification at N-terminal serine," Bioconjug Chem. Mar.-Apr. 1992;3(2):138-46.
Gillam, S. & M Smith, "Site-specific mutagenesis using synthetic oligodeoxyribonucleotide primers: I. Optimum conditions and minimum oligodeoxyribonucleotide length," Gene 1979; 8(1):81-97.

Gleeson, MA et al., "Transformation of the methylotrophic yeast hansenula polymorphica," J. Gen. Microbiol. (1986) 132:3459-3465.
Goeddel, DV, "Systems for heterologous gene expression," Methods Enzymol. 1990;185:3-7.
Goeddel, DV et al., "Synthesis of human fibroblast interferon by *E. coli*," Nucleic Acids Res. Sep. 25, 1980;8(18):4057-74.
Goodson RJ et NV Katre. "Site-directed pegylation of recombinant interleukin-2 at its glycosylation site," Biotechnology (N Y). Apr. 1990;8(4):343-6.
Graves, SW et al., "Expression, purification, and initial kinetic characterization of the large subunit of the human mitochondrial DNA polymerase," Biochemistry. Apr. 28, 1998;37(17):6050-8.
Griffin, BA et al., "Specific Covalent Labeling of Recombinant Protein Molecules Inside Live Cells," Science (1998) 281:269-272.
Grundström T et al., "Oligonucleotide-directed mutagenesis by microscale 'shot-gun' gene synthesis," Nucleic Acids Res. May 10, 1985;13(9):3305-16.
Guckian, KM and ET Kool, "Highly Precise Shape Mimicry by a Difluorotoluene Deoxynucleoside, a Replication-Competent Substitute for Thymidine," Angew. Chem. Int. Ed. Engl (1998) 36(24):2825-8.
Hamano-Takaku, F et al., "A mutant *Escherichia coli* tyrosyl-tRNA synthetase utilizes the unnatural amino acid azatyrosine more efficiently than tyrosine," J Biol Chem. Dec. 22, 2000;275(51):40324-8.
Hang, HC and CR Bertozzi, "Chemoselective approaches to glycoprotein assembly," Acc Chem Res. Sep. 2001;34(9):727-36.
Harris, JM et al. "Synthesis and Characterization of Poly(ethylene Glycol) Derivatives," J. Polym. Sci. Chem. Ed. 1984; 22:341-352.
Harris, JM. "Laboratory Synthesis of Polyethylene Glycol Derivatives," JMS—Rev. Macromol. Chem. Phys. 1985;C25(3): 325-373.
Hendrickson, WA et al., "Selenomethionyl proteins produced for analysis by multiwavelength anomalous diffraction (MAD): a vehicle for direct determination of three-dimensional structure," EMBO J. May 1990; 9(5):1665-72.
Henikoff, S and JG Henikoff "Amino Acid Substitution Matrices from Protein Blocks," Proc. Natl. Acad. Sci. USA 1992; 89:10915-9.
Hess, B. et al., "Cooperation of glycolytic enzymes," J. Adv. Enzyme Reg. (1969) 7:149-67.
Hinnen, A et al., "Transformation of yeast," Proc Natl Acad Sci U S A. Apr. 1978;75(4):1929-33.
Hirao, I et al., "An unnatural base pair for incorporating amino acid analogues into proteins," Nat Biotechnol. Feb. 2002;20(2):177-82.
Hitzeman, RA et al., "Isolation and characterization of the yeast 3-phosphoglycerokinase gene (PGK) by an immunological screening technique," J. Biol Chem. Dec. 25, 1980;255(24):12073-80.
Hofmann, K., et H. Bohn. "Studies on polypeptides. XXXVI. The effect of pyrazole-imidazole replacements on the S-protein activating potency of an S-peptide fragment," J. Am Chem, (1966); 88(24):5914-5919.
Hohsaka, T et al., "Efficient Incorporation of Nonnatural Amino Acids with Large Aromatic Groups into Streptavidin in In Vitro Protein Synthesizing Systems," J. Am. Chem. Soc. 1999; 121(1); 34-40.
Hohsaka, T et al., "Incorporation of Two Different Nonnatural Amino Acids Independently into a Single Protein through Extension of the Genetic Code," J. Am. Chem. Soc. 1999; 121(51):12194-12195.
Liu, H. et al. "A Method for the Generation of Glycoprotein Mimetics," J. Am. Chem. Soc. 2003 125(7): 1702-1703.
Liu, D.R. & Schultz, P.G. "Progress toward the evolution of an organism with an expanded genetic code," Proc Natl Acad Sci U S A. Apr. 27, 1999;96(9):4780-5.
Lorimer, I. A. et I. Pastan, "Random recombination of antibody single chain Fv sequences after fragmentation with DNaseI in the presence of Mn2+," Nucleic Acids Res. Aug. 11, 1995;23(15):3067-8.
Lu, T. et al. "Probing ion permeation and gating in a K +channel with backbone mutations in the selectivity filter," Nature Neurosci. Mar. 2001;4(3):239-246.
Luckow, VA and MD Summers, "High level expression of nonfused foreign genes with Autographa californica nuclear polyhedrosis virus expression vectors," Virology. May 1989;170(1):31-9.
Ma, C et al., "In vitro protein engineering using synthetic tRNA(Ala) with different anticodons," Biochemistry. Aug. 10, 1993;32(31):7939-45.

(56) References Cited

OTHER PUBLICATIONS

Magliery, TJ et al. "Expanding the Genetic Code: Selection of Efficient Suppressors of Four-base Codons and Identification of "Shifty" Four-base Codons with a Library Approach in *Escherichia coli*," J Mol Biol. Mar. 30, 2001;307(3):755-69.

Mahal, L. K., et al., "Engineering chemical reactivity on cell surfaces through oligosaccharide biosynthesis," Science. May 16, 1997;276(5315):1125-8.

Makrides, SC et al., "Extended in vivo half-life of human soluble complement receptor type 1 fused to a serum albumin-binding receptor," J Pharmacol Exp Ther. Apr. 1996;277(1):534-42.

Mamot, C, et al., "Epidermal growth factor receptor (EGFR)-targeted immunoliposomes mediate specific and efficient drug delivery to EGFR- and EGFRvIII-overexpressing tumor cells," Cancer Res. Jun. 15, 2003;63(12):3154-61.

Mandecki, W. Oligonucleotide-directed double-strand break repair in plasmids of *Escherichia coli*: a method for site-specific mutagenesis, Proc Natl Acad Sci U S A. Oct. 1986;83(19):7177-81.

Mann, SG and LA King, "Efficient transfection of insect cells with baculovirus DNA using electroporation," J Gen Virol. Dec. 1989;70 (Pt 12):3501-5.

Matsoukas, JM et al., "Differences in backbone structure between angiotensin II agonists and type I antagonists," J Med Chem. Nov. 10, 1995;38(23):4660-9.

McMinn, DL et al., "Efforts toward Expansion of the Genetic Alphabet: DNA Polymerase Recognition of a Highly Stable, Self-Pairing Hydrophobic Base," J. Am. Chem. Soc. 1999; 121(49):11585-6.

Meggers, E et al., "A Novel Copper-Mediated DNA Base Pair," J. Am. Chem. Soc. 2000; 122(43):10714-10715.

Mehvar, R.,"Modulation of the pharmacokinetics and pharmacodynamics of proteins by polyethylene glycol conjugation" J Pharm Pharm Sci. Jan.-Apr. 2000;3(1):125-36.

Mendel, D, et al. "Site-directed mutagenesis with an expanded genetic code," Annu Rev Biophys Biomol Struct. 1995;24:435-62.

Miller, LK, "Baculoviruses as gene expression vectors," Ann. Rev. Microbiol. 1988; 42:177-99.

Miller, LK. "Insect baculoviruses: powerful gene expression vectors," Bioessays. Oct. 1989;11(4):91-5.

Miller, JC et al. "Flash decaging of tyrosine sidechains in an ion channel," Neuron. Apr. 1998;20(4):619-24.

Minks, C. et al., Noninvasive tracing of recombinant proteins with "fluorophenylalanine-fingers," Anal Biochem. Aug. 15, 2000;284(1):29-34.

Miyanohara, A et al., "Expression of hepatitis B surface antigen gene in yeast," Proc Natl Acad Sci U S A. Jan. 1983;80(1):1-5.

Moore, B. et al., "Quadruplet codons: implications for code expansion and the specification of translation step size," J. Mol. Biol. 2000; 298(2):195-209.

Mosbach, K. et al., "Formation of proinsulin by immobilized Bacillus subtilis," Nature Apr. 1983; 302:543-545.

Nakamaye, KL & Eckstein F, "Inhibition of restriction endonuclease Nci I cleavage by phosphorothioate groups and its application to oligonucleotide-directed mutagenesis" Nucleic Acids Res. Dec. 22, 1986;14(24):9679-98.

Nakatsuka, T., et al. "Peptide segment coupling catalyzed by the semisynthetic enzyme thiosubtilisin," J Am Chem Soc, 1987; 109(12): 3808-3810.

Nambiar, KP et al., "Total synthesis and cloning of a gene coding for the ribonuclease S protein," Science (1984) 223: 1299-1301.

Needleman, SB and Wunsch CD, "A general method applicable to the search for similarities in the amino acid sequence of two proteins," J Mol Biol. Mar. 1970;48(3):443-53.

Nielsen, UB, et al., "Therapeutic efficacy of anti-ErbB2 immunoliposomes targeted by a phage antibody selected for cellular endocytosis," Biochim Biophys Acta. Aug. 19, 2002;1591(1-3):109-118.

Nomura, T. et al., "Purification, cDNA Cloning, and Expression of UDP-Gal: Glucosylceramide-1, 4-Galactosyltransferase from Rat Brain," J. Biol. Chem. 1998; 273(22):13570-7.

Noren, CJ et al. "A general method for site-specific incorporation of unnatural amino acids into proteins," Science. Apr. 14, 1989;244(4901):182-8.

Nowak, MW et al., "Nicotinic receptor binding site probed with unnatural amino acid incorporation in intact cells," Science. Apr. 21, 1995;268(5209):439-42.

Ogawa, AK et al., "Efforts toward the Expansion of the Genetic Alphabet: Information Storage and Replication with Unnatural Hydrophobic Base Pairs," J. Am. Chem. Soc. 2000; 122(14):3274-3287.

Ogawa, AK et al., "Rational Design of an Unnatural Base Pair with Increased Kinetic Selectivity," J. Am. Chem. Soc. 2000; 122(36); 8803-8804.

Ohtsuka, E et al., "An alternative approach to deoxyoligonucleotides as hybridization probes by insertion of deoxyinosine at ambiguous codon positions," J Biol Chem. Mar. 10, 1985;260(5):2605-8.

Olson et al. "Preparation and Characterization of Poly(ethylene glycol)yated Human Growth Hormone Antagonist," in Poly(ethylene glycol) Chemistry & Biological Applications, 1997; Eds. JM Harris & S. Zalipsky; ACS, Washington, D.C., 170-181.

Padwa, A. "Intermolecular 1,3-Dipolar Cycloadditions," in Comprehensive Organic Synthesis, vol. 4, (1991) Ed. Trost, B. M.; Pergamon, Oxford, 1069-1109.

Palva, I et al., "Secretion of interferon by Bacillus subtilis," Gene. May-Jun. 1983;22(2-3):229-35.

Park, JW, et al., "Development of anti-p185HER2 immunoliposomes for cancer therapy," Proc Natl Acad Sci U S A. Feb. 28, 1995;92(5):1327-31.

Park, JW, et al., "Anti-HER2 immunoliposomes: enhanced efficacy attributable to targeted delivery," Clin Cancer Res. Apr. 2002;8(4):1172-81.

Patnaik, R. and JR Swartz, "*E. coli*-based in vitro transcription/translation: in vivo-specific synthesis rates and high yields in a batch system," Biotechniques. May 1998;24(5):862-8.

Pearson, WR and DJ Lipman, "Improved tools for biological sequence comparison," Proc Natl Acad Sci U S A. Apr. 1988;85(8):2444-8.

Pepinsky, RB., et al., "Improved pharmacokinetic properties of a polyethylene glycol-modified form of interferon-beta-1a with preserved in vitro bioactivity," J Pharmacol Exp Ther. Jun. 2001;297(3):1059-66.

Piccirilli, JA et al., "Enzymatic incorporation of a new base pair into DNA and RNA extends the genetic alphabet," Nature 1990; 343:33-37.

Pintar, A et al. "CX, an algorithm that identifies protruding atoms in proteins," Bioinformatics. Jul. 2002;18(7):980-4.

Pitha, J et al. "Detergents linked to polysaccharides: preparation and effects on membranes and cells," Eur J Biochem. Feb. 15, 1979;94(1):11-8.

Polgar, L. and ML Bender. "A new enzyme containing a synthetically formed active site. Thiol-subtilisin." J. Am Chem Soc., 1966; 88(13): 3153-3154.

Pollack, SJ et al. "Introduction of nucleophiles and spectroscopic probes into antibody combining sites," Science. Nov. 18, 1988;242(4881):1038-40.

Preneta, AZ. "Separation on the basis of size: gel permeation chromatography," in Protein Purification Methods, a practical approach, 1989; Eds. Harris & Angal; IRL Press, Oxford; 293-306.

Tondelli, L. et al. "Poly(ethylene Glycol) Imidazolyl Formates as Oligomeric Drug-Binding Matrices," J. Controlled Release 1985;1(4):251-7.

Tornoe, CW et al., "Peptidotriazoles on solid phase: [1,2,3]-triazoles by regiospecific copper(i)-catalyzed 1,3-dipolar cycloadditions of terminal alkynes to azides," J Org Chem. May 3, 2002;67(9):3057-64.

Trotter, KM and HA Wood, "Transfection techniques for producing recombinant baculoviruses," in Methods in Molecular Biology—Baculovirus Expression Protocols, vol. 39 (1995); Ed. C.D. Richardson, 97-107.

Tschumper, G. et al., "Sequence of a yeast DNA fragment containing a chromosomal replicator and the TRP1 gene," Gene 1980; 10(2):157-66.

(56) References Cited

OTHER PUBLICATIONS

Turcatti, G et al. "Probing the structure and function of the tachykinin neurokinin-2 receptor through biosynthetic incorporation of fluorescent amino acids at specific sites," J Biol Chem. Aug. 16, 1996;271(33):19991-8.
Van Den Berg, JA et al., "Kluyveromyces as a host for heterologous gene expression: expression and secretion of prochymosin," Biotechnology (N Y). Feb. 1990;8(2):135-9.
Van Hest, JC and DA Tirrell, "Efficient introduction of alkene functionality into proteins in vivo," FEBS Lett. May 22, 1998;428(1-2):68-70.
Yelton, MM et al., "Transformation of Aspergillus nidulans by using a trpC plasmid," Proc Natl Acad Sci U S A. Mar. 1984;81(5):1470-4.
Yelverton, E et al., "Bacterial synthesis of a novel human leukocyte interferon," Nucleic Acids Res. Feb. 11, 1981;9(3):731-41.
Zalipsky, S et al. "Attachment of drugs to polyethylene glycols," Eur. Polymer Journal. 1983 19(12):1177-83.
Zalipsky, S. "Functionalized poly(ethylene glycol) for preparation of biologically relevant conjugates," Bioconjug Chem. Mar.-Apr. 1995;6(2):150-65.
Zhang, Z., et al. "A new strategy for the site-specific modification of proteins in vivo," Biochemistry. Jun. 10. 2003;42(22):6735-46.
Zoller, MJ & M Smith, "Oligonucleotide-directed mutagenesis using M13-derived vectors: an efficient and general procedure for the production of point mutations in any fragment of DNA" Nucleic Acids Res. Oct. 25, 1982;10(20):6487-500.
Zoller, MJ & M. Smith, "Oligonucleotide-directed mutagenesis of DNA fragments cloned into M13 vectors" Methods Enzymol. 1983;100:468-500.
Zoller, MJ & Smith M, "Oligonucleotide-directed mutagenesis: a simple method using two oligonucleotide primers and a single-stranded DNA template," Methods Enzymol. 1987;154:329-50.
Mehl, RA et al. "Generation of a bacterium with a 21 amino acid genetic code," J Am Chem Soc. Jan. 29, 2003;125(4):935-9.
Santoro, SW et al. "An efficient system for the evolution of aminoacyl-tRNA synthetase specificity," Nat Biotechnol. Oct. 2002;20(10):1044-8. Epub Sep. 16, 2002.
Caliceti, P et FM Veronese. "Pharmacokinetic and biodistribution properties of poly(ethylene glycol)-protein conjugates," Adv Drug Deliv Rev. Sep. 26, 2003;55(10):1261-77.
Clark, EDB, "Refolding of recombinant proteins," Curr Opin Biotechnol Apr. 1, 1998;9(2):157-63.
Clark, EDB, "Protein refolding for industrial processes," Curr Opin Biotechnol Apr. 2001;12(2):202-7.
Davis, GD et al., "New fusion protein systems designed to give soluble expression in *Escherichia coli*," Biotechnol Bioeng Nov. 20, 1999;65(4):382-8.
Raibaud, O et M Schwartz. "Positive control of transcription initiation in bacteria," Annu Rev Genet. 1984;18:173-206.
Reverey, H. et al., "Differential Fatty Acid Selection during Biosynthetic S-Acylation of a Transmembrane Protein (HEF) and Other Proteins in Insect Cells (Sf9) and in Mammalian Cells (CV1)," J. Biol. Chem. 1996; 271(39):23607-10.
Rivier, J et R McClintock, "Reversed-phase high-performance liquid chromatography of insulins from different species," J Chromatogr. Sep. 23, 1983;268(1):112-9.
Roberts, et al., "Generation of an antibody with enhanced affinity and specificity for its antigen by protein engineering," Nature 1987;328:731-734.
Roberts, RW and JW Szostak, "RNA-peptide fusions for the in vitro selection of peptides and proteins," Proc Natl Acad Sci U S A. Nov. 11, 1997;94(23):12297-302.
Roggenkamp, R. et al., "Transformation of the methylotrophic yeast Hansenula polymorpha by autonomous replication and integration vectors," Mol. Genetics and Genomics 1986;202(2):302-8.
Romani et al. "Synthesis of unsymmetrical cystine peptides: directed disulfide pairing with the sulfenohydrazide method," in Chemistry of Peptides and Proteins 1984; eds. Voelter, W. et al.; Walter de Gruyter et al., Berlin; vol. 2:29-33.

Romanos, MA et al., "Foreign gene expression in yeast: a review," Yeast. Jun. 1992;8(6):423-88.
Rosenthal, GA. "L-canaline: a potent antimetabolite and anti-cancer agent from leguminous plants," Life Sci.1997;60(19):1635-41.
Rossolini, GM et al., "Use of deoxyinosine-containing primers vs degenerate primers for polymerase chain reaction based on ambiguous sequence information," Mol. Cell. Probes 1994; 8:91-98.
Rostovtsev, VV et al., "A stepwise huisgen cycloaddition process: copper(I)-catalyzed regioselective "ligation" of azides and terminal alkynes," Angew Chem Int Ed Engl Jul. 15, 2002;41(14):2596-9.
Rowles, J et al., "Cloning and characterization of PDK4 on 7q21.3 encoding a fourth pyruvate dehydrogenase kinase isoenzyme in human," J Biol Chem. Sep. 13, 1996;271(37):22376-82.
Sakmar, TP and Khorana HG, "Total synthesis and expression of a gene for the alpha-subunit of bovine rod outer segment guanine nucleotide-binding protein (transducin)" Nucleic Acids Res. Jul. 25, 1988;16(14A):6361-72.
Sandler and Karo, "Polyoxyalkylation of hydroxyl compounds," in Polymer Synthesis, vol. 3, 1980; Academic Press, New York, 138-161.
Sartore, L et al., "Enzyme modification by MPEG with an amino acid or peptide as spacer arms," Appl Biochem Biotechnol. Jan. 1991;27(1):45-54.
Sawhney, AS et al., "Bioerodible Hydrogels Based on Photopolymerized Poly(ethylene glycol)-co-poly(alpha-hydroxy acid) Diacrylate Macromers," Macromolecules 1993; 26(4):581-7.
Saxon, E and C. Bertozzi, "Cell Surface Engineering by a Modified Staudinger Reaction," Science (2000); 287(5460):2007-2010.
Sayers, JR et al., "Strand specific cleavage of phosphorothioate-containing DNA by reaction with restriction endonucleases in the presence of ethidium bromide" Nucleic Acids Res. Feb. 11, 1988;16(3):803-14.
Sayers, JR, et al. "5'-3' exonucleases in phosphorothioate-based oligonucleotide-directed mutagenesis," Nucleic Acids Res. Feb. 11, 1988;16(3):791-802.
Schanbacher, FL et al. "Galactosyltransferase Acceptor Specificity of the Lactose Synthetase A Protein," J. Biol. Chem. 1970; 245(19):5057-5061.
Schmidt, M et al., "Baculovirus-mediated large-scale expression and purification of a polyhistidine-tagged rubella virus capsid protein," Protein Expr Purif. Apr. 1998;12(3):323-30.
Schneider, E., et al., "Functional Purification of a Bacterial ATP-Binding Cassette Transporter Protein (MaIK) from the Cytoplasmic Fraction of an Overproducing Strain," Protein Expr. Purif. 1995; 6(1):10-14.
Schnolzer, M. and SBH Kent. "Constructing proteins by dovetailing unprotected synthetic peptides: backbone-engineered HIV protease," Science. Apr. 10, 1992;256(5054):221-5.
Scouten, WH. "A survey of enzyme coupling techniques," Methods Enzymol. 1987;135:30-65.
Shao, J and JP Tam, "Unprotected Peptides as Building Blocks for the Synthesis of Peptide Dendrimers with Oxime, Hydrazone, and Thiazolidine Linkages," J. Am. Chem. Soc. 1995; 117(14):3893-3899.
Sharma, N et al., "Efficient introduction of aryl bromide functionality into proteins in vivo," FEBS Lett. Feb. 4, 2000;467(1):37-40.
Shimatake, H et M Rosenberg, "Purified gamma regulatory protein cII positively activates promoters for lysogenic development," Nature Jul. 1981; 292:128-132.
Shine, J and L Dalgarno, "Determinant of cistron specificity in bacterial ribosomes," Nature. Mar. 6, 1975;254(5495):34-8.
Sidman, KR et al., "Controlled release of macromolecules and pharmaceuticals from synthetic polypeptides based on glutamic acid," Biopolymers. Jan. 1983;22(1):547-56.
Sieber, V. et al., "Libraries of hybrid proteins from distantly related sequences," Nature Biotechnology, May 2001;19:456-460.
Siffert, W et al., "Association of a human G-protein beta3 subunit variant with hypertension," Nat Genet. Jan. 1998;18(1):45-8.
Sikorski, RS et al., "A System of Shuttle Vectors and Yeast Host Strains Designed for Efficient Manipulation of DNA in *Saccharomyces cerevisiae*," Genetics (1989) 122:19-27.

(56) References Cited

OTHER PUBLICATIONS

Sisk, WP et al., "High-level expression and purification of secreted forms of herpes simplex virus type 1 glycoprotein gD synthesized by baculovirus-infected insect cells," J Virol. Feb. 1994;68(2):766-75.
Sjolander, A et al., "The serum albumin-binding region of streptococcal protein G: a bacterial fusion partner with carrier-related properties," J Immunol Methods. Feb. 14, 1997;201(1):115-23.
Smith, M. "In vitro mutagenesis" Ann. Rev. Genet. 1985; 19:423-462.
Smith, GE et al., "Production of human beta interferon in insect cells infected with a baculovirus expression vector," Mol Cell Biol. Dec. 1983;3(12):2156-65.
Stanley, SL et al., "The serine-rich Entamoeba histolytica protein is a phosphorylated membrane protein containing O-linked terminal N-acetylglucosamine residues," J Biol Chem. Feb. 24, 1995;270(8):4121-6.
Steitz, JA et al. "Genetic signals and nucleotide sequences in messenger RNA," in Biological Regulation and Development: Gene Expression 1979; ed. R. F. Goldberger; Plenum Press, New York; 349-399.
Stemmer, WPC, "Rapid evolution of a protein in vitro by DNA shuffling," Nature 1994;370(4):389-391.
Stemmer, WP "DNA shuffling by random fragmentation and reassembly: In vitro recombination for molecular evolution," Proc Natl Acad Sci U S A. Oct. 25, 1994;91(22):10747-51.
Studier, FW et BA Moffatt, "Use of bacteriophage T7 RNA polymerase to direct selective high-level expression of cloned genes," J. Mol Biol. May 5, 1986;189(1):113-30.
Subasinghe, N. et al., "Quisqualic acid analogues: synthesis of beta-heterocyclic 2-aminopropanoic acid derivatives and their activity at a novel quisqualate-sensitized site," J Med Chem. Nov. 27, 1992;35(24):4602-7.
Switzer, C et al., "Enzymatic incorporation of a new base pair into DNA and RNA," J. Am. Chem. Soc. 1989; 111(21):8322-8323.
Tabor, S et CC Richardson, "A bacteriophage T7 RNA polymerase/promoter system for controlled exclusive expression of specific genes," Proc Natl Acad Sci U S A. Feb. 1985;82(4):1074-8.
Tae, EL et al., "Efforts toward Expansion of the Genetic Alphabet: Replication of DNA with Three Base Pairs," J. Am. Chem. Soc. 2001; 123(30):7439-7440.
Tang, Y et al., "Fluorinated Coiled-Coil Proteins Prepared In Vivo Display Enhanced Thermal and Chemical Stability," Angew Chem Int Ed Engl. Apr. 17, 2001;40(8):1494-1496.
Taylor, JW et al., "The use of phosphorothioate-modified DNA in restriction enzyme reactions to prepare nicked DNA," Nucleic Acids Res. Dec. 20, 1985;13(24):8749-64.
Taylor, JW et al., "The rapid generation of oligonucleotide-directed mutations at high frequency using phosphorothioate-modified DNA," Nucleic Acids Res. Dec. 20, 1985;13(24):8765-85.
Tijssen, P. "Overview of principles of hybridization and the strategy of nucleic acid assays," in Laboratory Techniques in Biochemistry and Molecular Biology—Hybridization with Nucleic Probes, Part I, 1993; Elsevier Science Publishers, Amsterdam, 19-78.
Tilburn, J. et al., "Transformation by integration in Aspergillus nidulans," Gene. Dec. 1983;26(2-3):205-21.
Wang, L & PG Schultz, "Expanding the genetic code," Chem Commun (Camb). Jan. 7, 2002;1:1-11.
Weissmann, C. "The cloning of interferon and other mistakes." in Interferon 3 1981; ed. I. Gresser; Academic Press, London, 101-134.
Wells, JA et al., "Importance of hydrogen-bond formation in stabilizing the transition state of subtilisin," Phil. Trans. R. Soc. Lond. A 1986; 317: 415-423.
Wells, JA et al., "Cassette mutagenesis: an efficient method for generation of multiple mutations at defined sites," Gene. 1985;34(2-3):315-23.
Woghiren, C et al. "Protected thiol-polyethylene glycol: a new activated polymer for reversible protein modification," Bioconjug Chem. Sep.-Oct. 1993;4(5):314-8.

Wong, SS et LJ Wong, "Chemical crosslinking and the stabilization of proteins and enzymes," Enzyme Microb Technol. Nov. 1992;14(11):866-74.
Wright, K. "Biotechnology: Insect virus as super-vector?," Nature (1986) 321(6072):718.
Duncan, R. "The dawning era of polymer therapeutics," Nat Rev Drug Discov May 2003;2(5):347-60.
Gaertner, HF et RE Offord. "Site-specific attachment of functionalized poly(ethylene glycol) to the amino terminus of proteins," Bioconjug Chem Jan.-Feb. 1996;7(1):38-44.
Gu, Z et al. "Chromatographic methods for the isolation of, and refolding of proteins from, *Escherichia coli* inclusion bodies," Protein Expr Purif. Jun. 2002;25(1):174-9.
Hohsaka, T et M Sisido. "Incorporation of non-natural amino acids into proteins," Curr Opin Chem Biol. Dec. 2002;6(6):809-15.
Lilie, H et al. "Advances in refolding of proteins produced in *E. coli*," Curr Opin Biotechnol. Oct. 1998;9(5):497-501.
Tsumoto, K et al. "Practical considerations in refolding proteins from inclusion bodies," Protein Expr Purif. Mar. 2003;28(1):1-8.
Wang, W. "Instability, stabilization, and formulation of liquid protein pharmaceuticals," Int J Pharm. Aug. 20, 1999;185(2):129-88.
Holland, MJ et JP Holland., "Isolation and identification of yeast messenger ribonucleic acids coding for enolase, glyceraldehyde-3-phosphate dehydrogenase, and phosphoglycerate kinase," Biochemistry. Nov. 14, 1978;17(23):4900-7.
Holland, MJ et al., "The primary structures of two yeast enolase genes. Homology between the 5' noncoding flanking regions of yeast enolase and glyceraldehyde-3-phosphate dehydrogenase genes," J Biol Chem. Feb. 10, 1981;256(3):1385-95.
Hsiao, CL et J Carbon, "High-frequency transformation of yeast by plasmids containing the cloned yeast ARG4 gene," Proc Natl Acad Sci U S A. Aug. 1979;76(8):3829-33.
Huisgen, R. in 1,3-Dipolar Cycloaddition Chemistry, vol. 1, 1984; Ed. Padwa A.; John Wiley and Sons, New York, p. 1-176.
Hwang, KJ et al., "Hepatic uptake and degradation of unilamellar sphingomyelin/cholesterol liposomes: a kinetic study," Proc Natl Acad Sci U S A. Jul. 1980;77(7):4030-4.
Ibba, M et al., "Substrate specificity is determined by amino acid binding pocket size in *Escherichia coli* phenylalanyl-tRNA synthetase," Biochemistry. Jun. 14, 1994;33(23):7107-12.
Ibba, M and H Hennecke, "Relaxing the substrate specificity of an aminoacyl-tRNA synthetase allows in vitro and in vivo synthesis of proteins containing unnatural amino acids," FEBS Lett. May 15, 1995;364(3):272-5.
Ito, H. et al., "Transformation of intact yeast cells treated with alkali cations," J. Bacteriol. 1983; 153(1):163-8.
Jackson, DY et al. "A designed peptide ligase for total synthesis of ribonuclease A with unnatural catalytic residues," Science. Oct. 14, 1994;266(5183):243-7.
Jakobsson, PJ et al., "Identification and characterization of a novel human microsomal glutathione S-transferase with leukotriene C4 synthase activity and significant sequence identity to 5-lipoxygenase-activating protein and leukotriene C4 synthase," J Biol Chem. Sep. 6, 1996;271(36):22203-10.
Jencks, W.P., "Studies on the Mechanism of Oxime and Semicarbazone Formation," J. Am. Chem. Soc.; 1959; 81(2):475-481.
Joppich, M. et al. "Peptides Flanked by Two Polymer Chains, 1; Synthesis of Glycyl-L-tryptophylglycine Substituted by Poly(ethylene oxide) at both the Carboxy and the Amino End Groups," Makromol. Chem. 1979;180:1381-4.
Kaiser, ET. "Synthetic approaches to biologically active peptides and proteins including enzymes," Acc Chem Res, (1989); 22(2):47-54.
Kaiser, ET et al. "The chemical modification of enzymatic specificity," Annu Rev Biochem. 1985;54:565-95.
Kaiser, ET and DS Lawrence. "Chemical mutation of enzyme active sites," Science. Nov. 2, 1984;226(4674):505-11.
Karlin, S and SF Altschul "Applications and statistics for multiple high-scoring segments in molecular sequences," Proc Natl Acad Sci U S A. Jun. 15, 1993;90(12):5873-7.
Kayser, B., et al., "Alkyne bridged alpha-amino acids by palladium mediated coupling of alkynes with N-t-Boc-4-iodo-phenylalanine methyl ester," Tetrahedron (1997); 53(7): 2475-2484.

(56) References Cited

OTHER PUBLICATIONS

Kelly, JM and MJ Hynes, "Transformation of Aspergillus niger by the amdS gene of Aspergillus nidulans," EMBO J. 1985; 4(2):475-479.
Kiick, K. L. and D. A. Tirrell, "Protein Engineering by In Vivo Incorporation of Non-Natural Amino Acids: Control of Incorporation of Methionine Analogues by Methionyl-tRNA Synthetase," Tetrahedron (2000), 56:9487-9493.
Kiick, KL et al., "Incorporation of azides into recombinant proteins for chemoselective modification by the Staudinger ligation," Proc Natl Acad Sci U S A. Jan. 8, 2002;99(1):19-24. Epub Dec. 18, 2001.
Kim, DM and JR Swartz, "Regeneration of adenosine triphosphate from glycolytic intermediates for cell-free protein synthesis," Biotechnol Bioeng. Aug. 20, 2001;74(4):309-16.
Kim, DM and JR Swartz, "Oxalate improves protein synthesis by enhancing ATP supply in a cell-free system derived from *Escherichia coli*," Biotechnology Letters, 2000; 22:1537-1542.
Kim, DM, and JR Swartz, "Prolonging cell-free protein synthesis by selective reagent additions," Biotechnol Prog. May-Jun. 2000;16(3):385-90.
Kim, DM, and JR Swartz, "Prolonging cell-free protein synthesis with a novel ATP regeneration system," Biotechnol Bioeng. 1999;66(3):180-8.
King, F.E. & Kidd, D.A.A. "A New Synthesis of Glutamine and of gamma-Dipeptides of Glutamic Acid from Phthylated Intermediates," J. Chem. Soc. 1949; 3315-3319.
Kingsman, AJ et al., "Replication in *Saccharomyces cerevisiae* of plasmid pBR313 carrying DNA from the yeast trpl region," Gene. Oct. 1979;7(2):141-52.
Kitts, PA et al. "Linearization of baculovirus DNA enhances the recovery of recombinant virus expression vectors," Nucleic Acids Res. Oct. 11, 1990;18(19):5667-72.
Klein, TM et al., "High-velocity microprojectiles for delivering nucleic acids into living cells," Nature 1987; 327(6117):70-73.
Kobayashi, T. et al., "Structural basis for orthogonal tRNA specificities of tyrosyl-tRNA synthetases for genetic code expansion," Nature Structural Biology (2003); 10(6):425-432.
Kogan, TP. "The synthesis of substituted methoxy-poly(ethyleneglycol) derivatives suitable for selective protein modification," Synthetic Comm. 1992; 22(16):2417-24.
Kool, ET. "Synthetically modified DNAs as substrates for polymerases," Curr Opin Chem Biol. Dec. 2000;4(6):602-8.
Koskinen, A.M.P. & Rapoport, H. "Synthesis of 4-Substituted Prolines as Conformationally Constrained Amino Acid Analogues," J. Org. Chem. (1989) 54(8):1859-1866.
Kost, TA et al., "Production of a urokinase plasminogen activator-IgG fusion protein (uPA-IgG) in the baculovirus expression system," Gene. Apr. 29, 1997;190(1):139-44.
Kramer, W et al., "The gapped duplex DNA approach to oligonucleotide-directed mutation construction," Nucleic Acids Res. Dec. 21, 1984;12(24):9441-56.
Kramer, W & Fritz HJ. "Oligonucleotide-directed construction of mutations via gapped duplex DNA" Methods Enzymol. 1987;154:350-67.
Kramer, W. et al., "Improved enzymatic in vitro reactions in the gapped duplex DNA approach to oligonucleotide-directed construction of mutations," Nucleic Acids Res. Jul. 25, 1988;16(14B):7207.
Kramer, B. et al., "Different base/base mismatches are corrected with different efficiencies by the methyl-directed DNA mismatch-repair system of *E. coli*," Cell. Oct. 1984;38(3):879-87.
Kreitman, RJ and I. Pastan "Purification and characterization of IL6-PE4E, a recombinant fusion of interleukin 6 with Pseudomonas exotoxin," Bioconjug Chem. Nov.-Dec. 1993;4(6):581-5.
Krieg, UC, et al. "Photocrosslinking of the signal sequence of nascent preprolactin to the 54-kilodalton polypeptide of the signal recognition particle," Proc Natl Acad Sci U S A. Nov. 1986;83(22):8604-8.
Kunitani, M. et al., "Reversed-phase chromatography of interleukin-2 muteins," J Chromatogr. May 30, 1986 ;359:391-402.
Kunkel, "The efficiency of oligonucleotide directed mutagenesis," in Nucleic Acids & Molecular Biology 1987; Eckstein, F. and Lilley, D.M.J. eds.; Springer Verlag, Berlin; 124-135.
Kunkel, TA "Rapid and efficient site-specific mutagenesis without phenotypic selection," Proc Natl Acad Sci U S A. Jan. 1985;82(2):488-92.
Kunkel, TA et al., "Rapid and efficient site-specific mutagenesis without phenotypic selection," Methods Enzymol. 1987;154:367-82.
Kurtz et al., "Integrative transformation of Candida albicans, using a cloned Candida ADE2 gene," Mol Cell Biol. Jan. 1986;6(1):142-9.
Kurtzhals, P et al., "Albumin binding of insulins acylated with fatty acids: characterization of the ligand-protein interaction and correlation between binding affinity and timing of the insulin effect in vivo," Biochem J. Dec. 15, 1995;312 ( Pt 3):725-31.
Langer, R et al., "Biocompatibility of polymeric delivery systems for macromolecules," J Biomed Mater Res. Mar. 1981;15(2):267-77.
Langer, R. "Controlled release of macromolecules, " Chem. Tech. 1982; 12: 98-105.
Liebman, JM et al., "When less is more: enhanced baculovirus production of recombinant proteins at very low multiplicities of infection," Biotechniques. Jan. 1999;26(1):36-8, 40, 42.
Ling, MM et BH Robinson, "Approaches to DNA mutagenesis: an overview" Anal Biochem. Dec. 15, 1997 15;254(2):157-78.
Mott et al., "Four-helix Bundle Growth Factors and Their Receptors: Protein-Protein Interactions" Current Opinion in Structural Biology, 1995 5:114-121.
Deiters et al., "Site-specific PEGylation of Proteins Containing Unnatural Amino Acids", Bioorganic & Medicinal Chemistry Letters, Dec. 6, 2004, 14(23):5743-5745.
E.A. Cornish, "Probing Protein Structure and Function with Expanded Genetic Code", Angew. Chem. Int. Ed. Eng, 1995 34:621-633.
Kunze, G et al., "Transformation of the industrially important yeasts Candida maltosa and Pichia guilliermondii," J. Basic Microbiol. 1985; 25:141-4.
Neet et al. "Properties of thiol-subtilisin. The consequences of converting the active serine residue to cysteine in a serine protease," J Biol Chem., Dec. 25, 1968; 243(24):6392-401.

\* cited by examiner

A Four Helical Bundle Protein hGH

EPO

IFNα-2

G-CSF

Figure 7, Panel A:
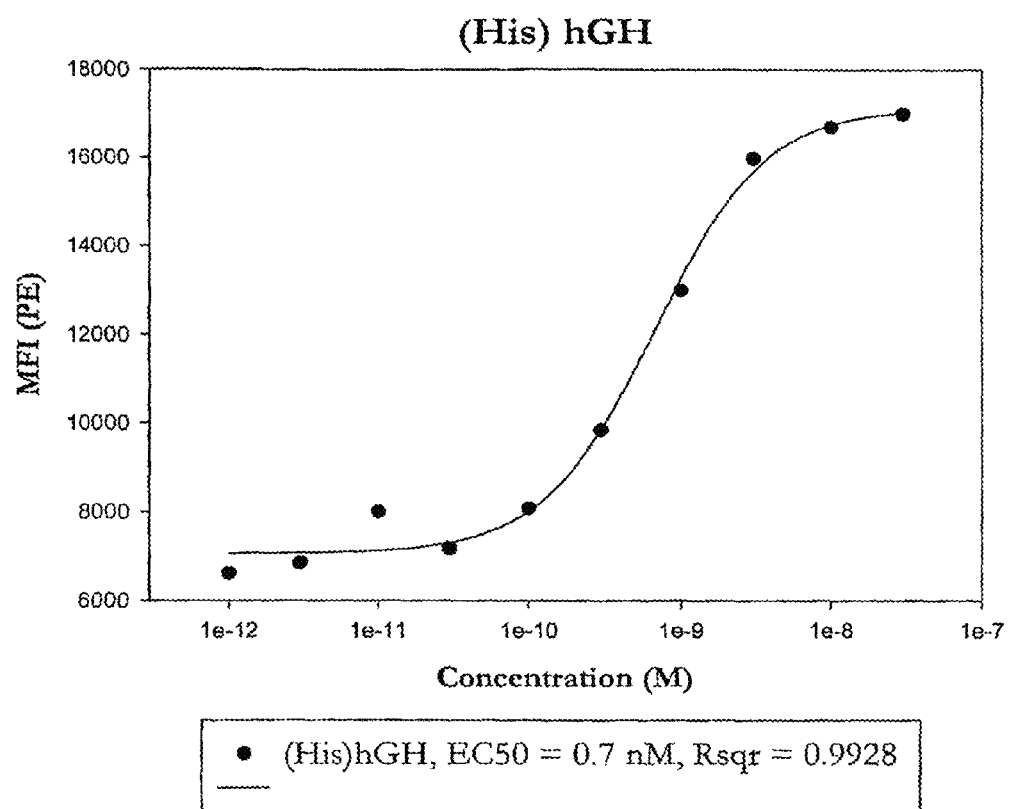

Figure 7, Panel B:
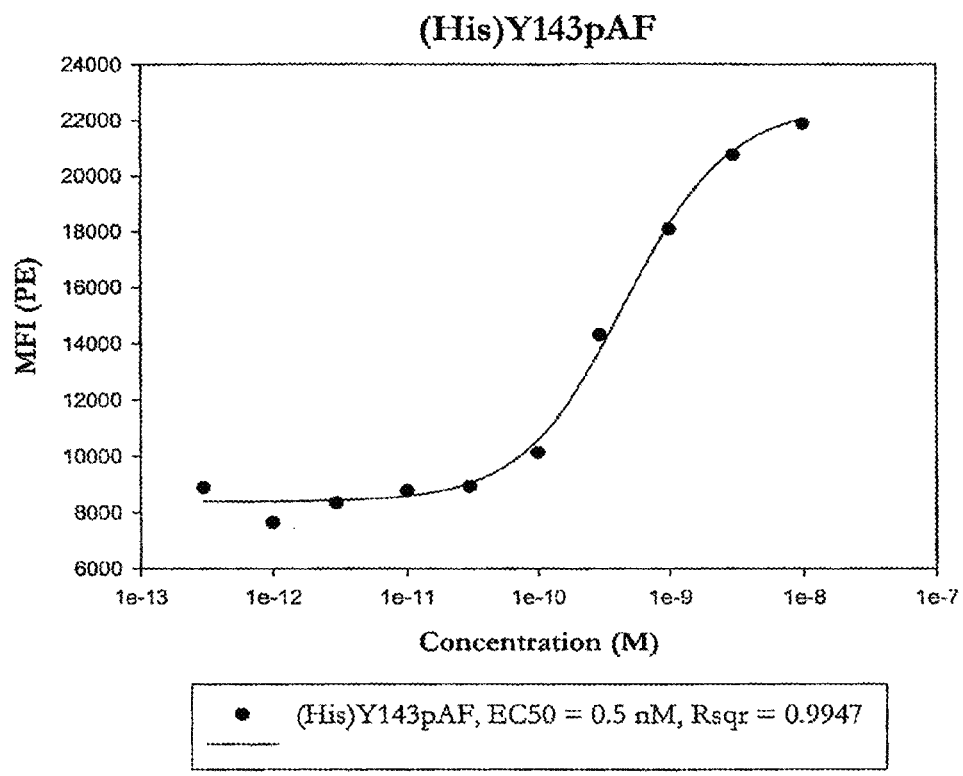

- ● (His)F92pAF, EC50 = 0.9 nM
- ■ (His)F92pAF-5K, EC50 = 1.5 nM
- ▲ (His)F92pAF-20K, EC50 = 4.6 nM
- ▼ (His)F92-pAF-30K, EC50 = 4.1 nM
- ◆ (His)hGH, EC50 = 0.5 nM

Figure 10, Panel A:
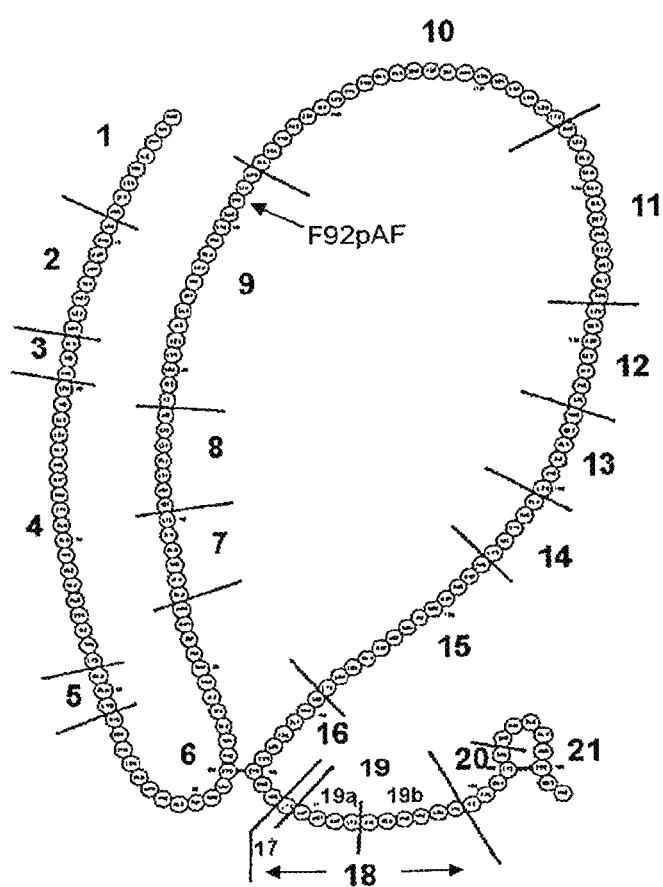

Figure 10, cont.
Panel B:
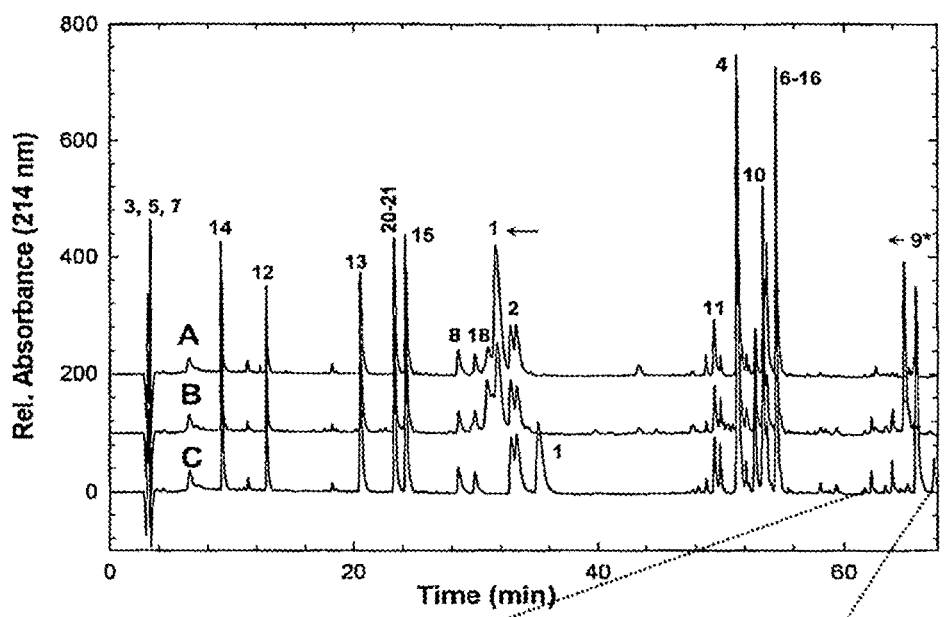
Panel C:
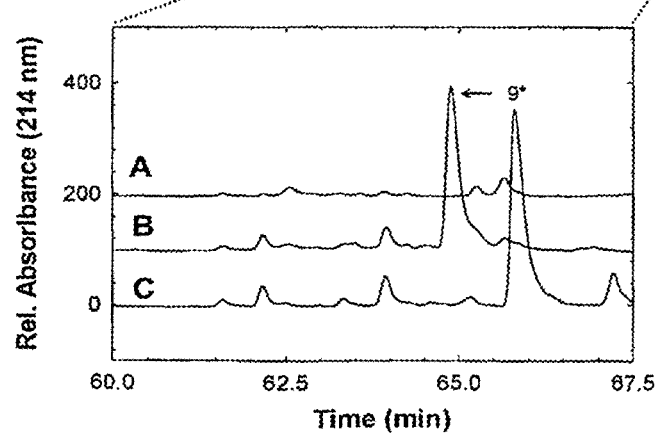

Figure 11
Panel A:
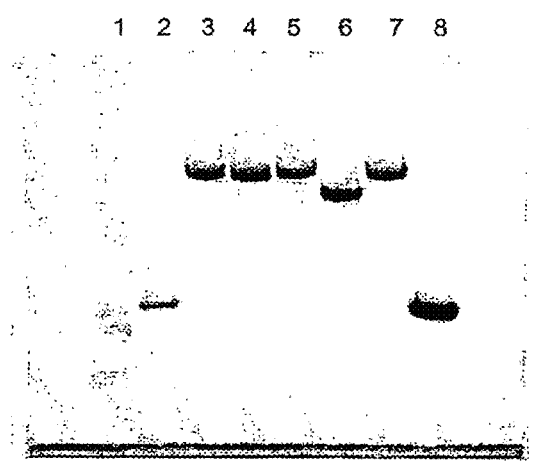
Panel B:
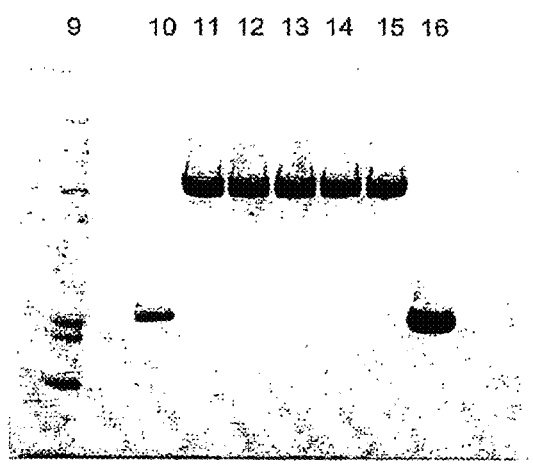

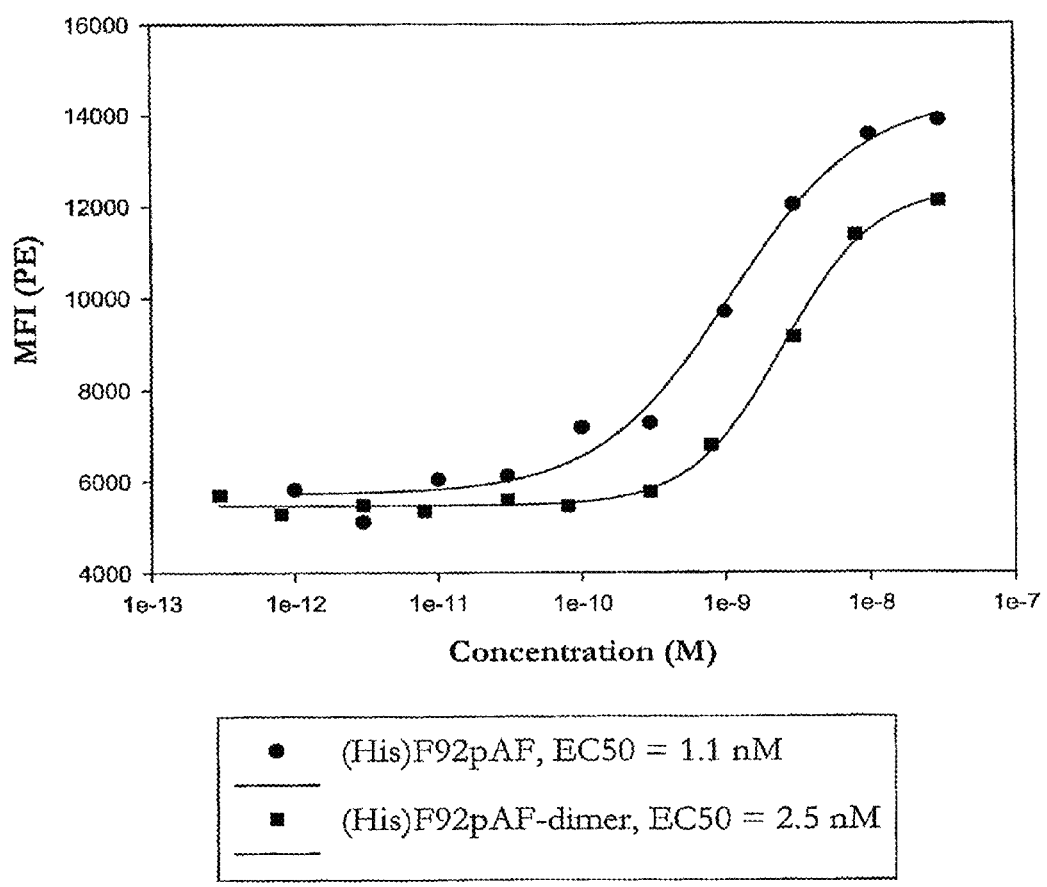

Figure 13, Panel A:
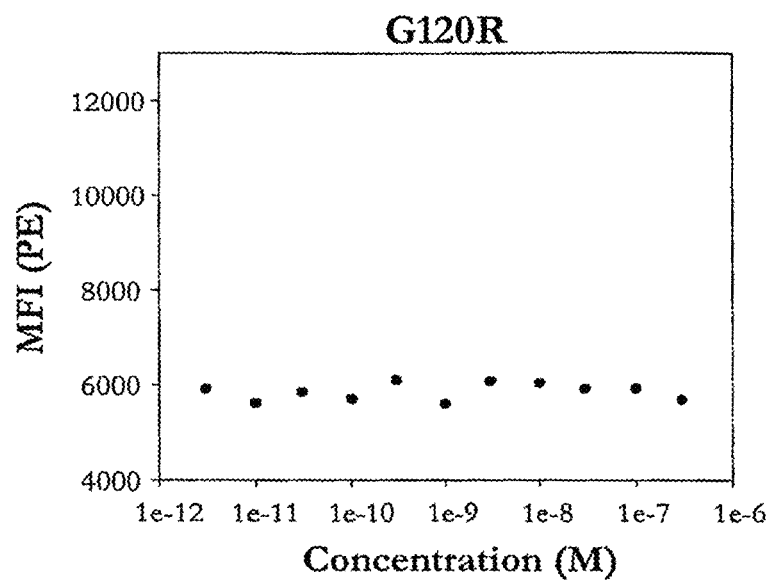
Figure 13, Panel B:
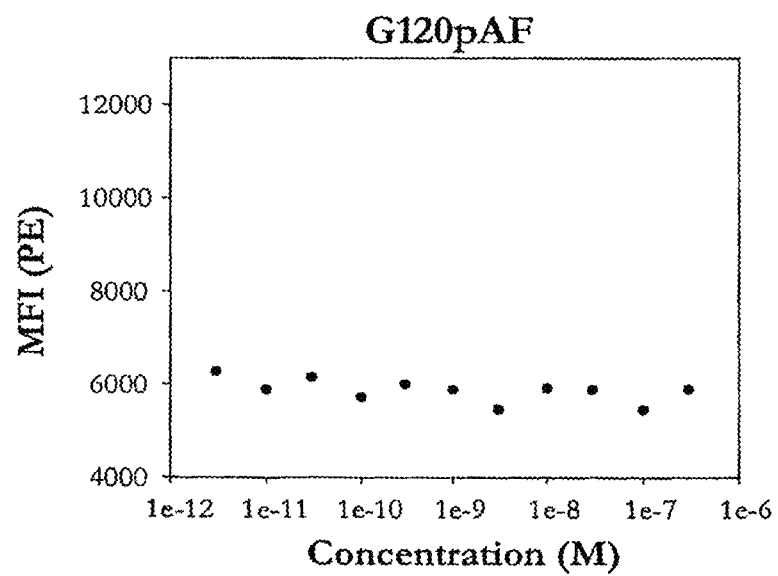

Figure 18, Panel A
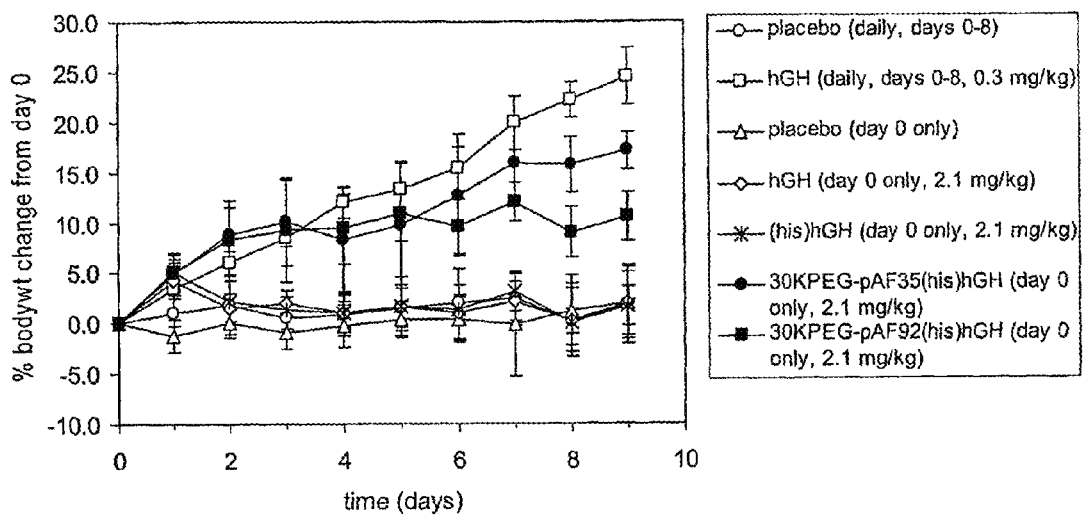
Figure 18, Panel B
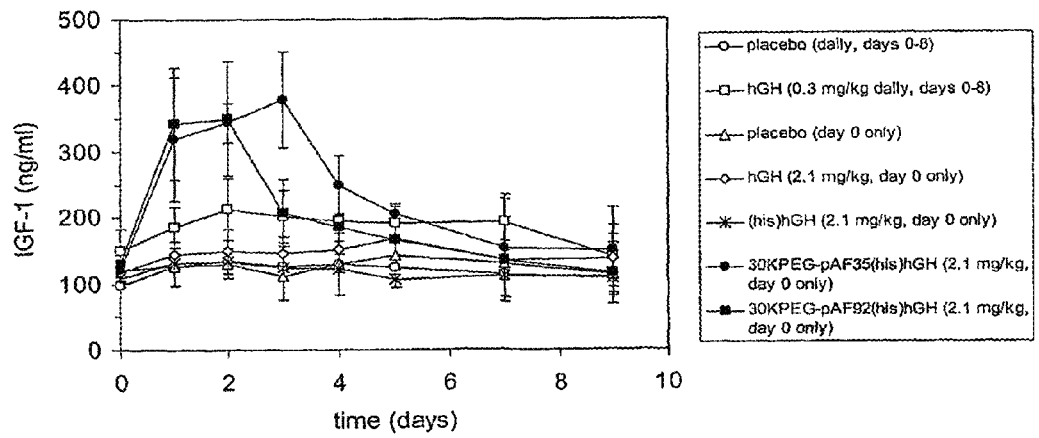

Figure 18, Panel C
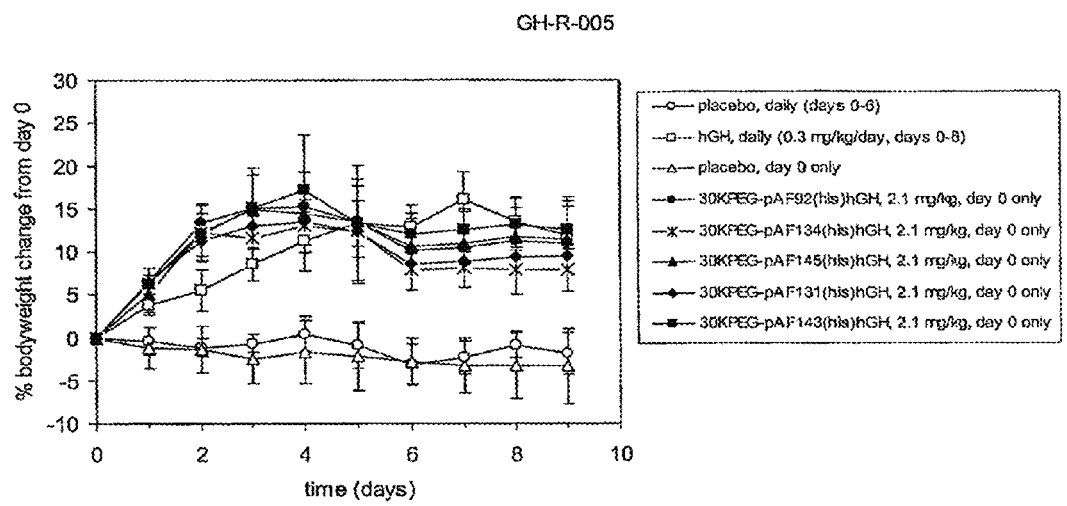
Figure 18, Panel D
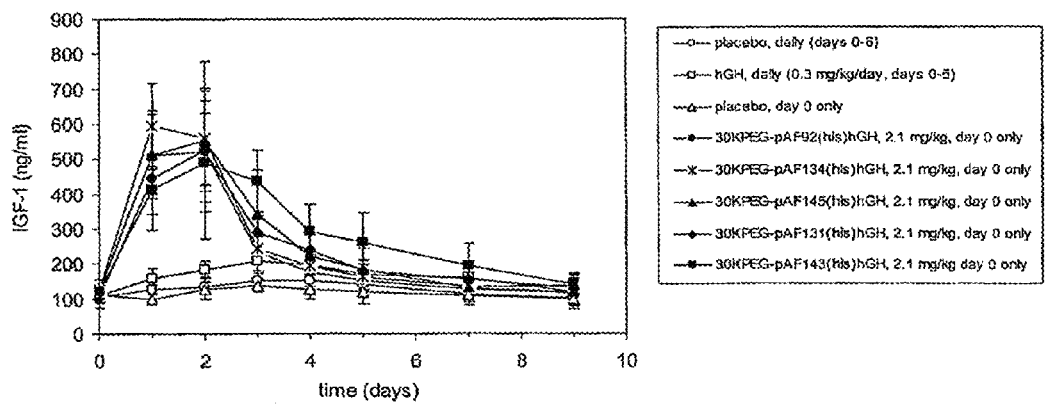

Figure 18, Panel E
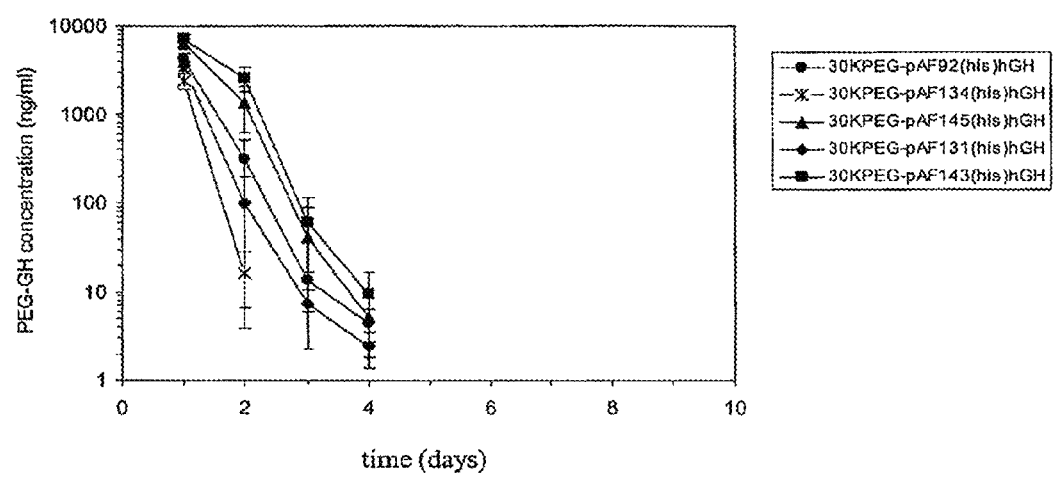

MODIFIED HUMAN FOUR HELICAL BUNDLE POLYPEPTIDES AND THEIR USES

CROSS-REFERENCE TO RELATED APPLICATIONS

This application is a continuation of U.S. patent application Ser. No. 10/587,371 filed on Jul. 26, 2006. which is incorporated by reference herein in its entirety and claims the benefit of priority to International Application Number PCT/US2005/003537, which has an international filing date of Jan. 28, 2005, and which designated the United States of America, U.S. provisional patent application Ser. No. 60/541,528, filed Feb. 2, 2004, U.S. provisional patent application Ser. No. 60/581,314, filed Jun. 18, 2004, U.S. provisional patent application Ser. No. 60/581,175, filed Jun. 18, 2004. U.S. provisional patent application Ser. No. 60/580,885, filed Jun. 18, 2004, and U.S. provisional patent application entitled 60/638,616 filed Dec. 22, 2004, the specifications and disclosures of which are incorporated herein in their entirety for all purposes.

FIELD OF THE INVENTION

This invention relates to four helical bundle polypeptides modified with at least one non-naturally-encoded amino acid.

BACKGROUND OF THE INVENTION

The growth hormone (GH) supergene family (Bazan, F. *Immunology Today* 11: 350-354 (1991); Mott, H. R. and Campbell, I. D. *Current Opinion in Structural Biology* 5: 114-121 (1995); Silvennoinen, O. and Ihle, J. N. (1996) SIGNALING BY THE HEMATOPOIETIC CYTOKINE RECEPTORS) represents a set of proteins with similar structural characteristics. Each member of this family of proteins comprises a four helical bundle, the general structure of which is shown in FIG. 1. Family members are referred to herein as "four helical bundle polypeptides" or "4HB" polypeptides. While there are still more members of the family yet to be identified, some members of the family include the following: growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-1, IL-12 (p35 subunit), IL-13, IL-15, oncostatin M, ciliary neurotrophic factor, leukemia inhibitory factor, alpha interferon, beta interferon, gamma interferon, omega interferon, tau interferon, epsilon interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). Members of the GH supergene family have similar secondary and tertiary structures, despite the fact that they generally have limited amino acid or DNA sequence identity. The shared structural features allow new members of the gene family to be readily identified. The general structures of family members hGH, EPO, IFNα-2, and G-CSF are shown in FIGS. 2, 3, 4, and 5, respectively.

One member of the GH supergene family is human growth hormone (hGH). Human growth hormone participates in much of the regulation of normal human growth and development. This naturally-occurring single-chain pituitary hormone consists of 191 amino acid residues and has a molecular weight of approximately 22 kDa. hGH exhibits a multitude of biological effects, including linear growth (somatogenesis), lactation, activation of macrophages, and insulin-like and diabetogenic effects, among others (Chawla, R., et al., *Ann. Rev. Med.* 34:519-547 (1983); Isaksson, O., et al., *Ann. Rev. Physiol.*, 47:483-499 (1985); Hughes, J. and Friesen, H., *Ann. Rev. Physiol.*, 47:469-482 (1985)).

The structure of hGH is well known (Goeddel, D., et al., *Nature* 281:544-548 (1979)), and the three-dimensional structure of hGH has been solved by x-ray crystallography (de Vos, A., et al., *Science* 255:306-312 (1992)). The protein has a compact globular structure, comprising four amphipathic alpha helical bundles, termed A-D beginning from the N-terminus, which are joined by loops. hGH also contains four cysteine residues, which participate in two intramolecular disulfide bonds: C53 is paired with C165 and C182 is paired with C189. The hormone is not glycosylated and has been expressed in a secreted form in *E. coli* (Chang, C., et al., *Gene* 55:189-196 (1987)).

A number of naturally occurring mutants of hGH have been identified. These include hGH-V (Seeberg, *DNA* 1: 239 (1982); U.S. Pat. Nos. 4,446,235, 4,670,393, and 4,665,180, which are incorporated by reference herein) and a 20-kDa hGH containing a deletion of residues 32-46 of hGH (Kostyo et al., *Biochem. Biophys. Acta* 925: 314 (1987); Lewis, U., et al., *J. Biol. Chem.*, 253:2679-2687 (1978)). In addition, numerous hGH variants, arising from post-transcriptional, post-translational, secretory, metabolic processing, and other physiological processes, have been reported (Baumann, G., *Endocrine Reviews* 12: 424 (1991)).

The biological effects of hGH derive from its interaction with specific cellular receptors. The hormone is a member of a family of homologous proteins that include placental lactogens and prolactins. hGH is unusual among the family members, however, in that it exhibits broad species specificity and binds to either the cloned somatogenic (Leung, D., et al., *Nature* 330:537-543 (1987)) or prolactin (Boutin, J., et al., *Cell* 53:69-77 (1988)) receptor. Based on structural and biochemical studies, functional maps for the lactogenic and somatogenic binding domains have been proposed (Cunningham, B. and Wells, J., Proc. Natl. Acad. Sci. 88: 3407 (1991)). The hGH receptor is a member of the hematopoietic/cytokine/growth factor receptor family, which includes several other growth factor receptors, such as the interleukin (IL)-3, -4 and -6 receptors, the granulocyte macrophage colony-stimulating factor (GM-CSF) receptor, the erythropoietin (EPO) receptor, as well as the G-CSF receptor. See, Bazan, *Proc. Natl. Acad. Sci. USA* 87: 6934-6938 (1990). Members of the cytokine receptor family contain four conserved cysteine residues and a tryptophan-serine-X-tryptophan-serine motif positioned just outside the transmembrane region. The conserved sequences are thought to be involved in protein-protein interactions. See, e.g., Chiba et al., *Biochim. Biophys. Res. Comm.* 184: 485-490 (1992). The interaction between hGH and extracellular domain of its receptor (hGHbp) is among the most well understood hormone-receptor interactions. High-resolution X-ray crystallographic data (Cunningham, B., et al., *Science,* 254:821-825 (1991)) has shown that hGH has two receptor binding sites and binds two receptor molecules sequentially using distinct sites on the molecule. The two receptor binding sites are referred to as Site I and Site II. Site I includes the carboxy terminal end of helix D and parts of helix A and the A-B loop, whereas Site II encompasses the amino terminal region of helix A and a portion of helix C. Binding of GH to its receptor occurs sequentially, with Site I binding first. Site II then engages a second GH receptor, resulting in receptor dimerization and activation of the intracellular signaling pathways that lead to cellular responses to the hormone. An hGH mutein in which a G120R substitution has been introduced into site II is able to bind a single hGH receptor, but is unable to dimerize two receptors. The mutein acts as an hGH antagonist in vitro, presumably by occupying receptor sites without activating intracellular signaling pathways (Fuh, G., et al., *Science* 256:1677-1680 (1992)).

Recombinant hGH is used as a therapeutic and has been approved for the treatment of a number of indications. hGH deficiency leads to dwarfism, for example, which has been successfully treated for more than a decade by exogenous administration of the hormone. In addition to hGH deficiency, hGH has also been approved for the treatment of renal failure (in children), Turner's Syndrome, and cachexia in AIDS patients. Recently, the Food and Drug Administration (FDA) has approved hGH for the treatment of non-GH-dependent short stature. hGH is also currently under investigation for the treatment of aging, frailty in the elderly, short bowel syndrome, and congestive heart failure.

Recombinant hGH is currently sold as a daily injectable product, with five major products currently on the market: Humatrope™ (Eli Lilly & Co.), Nutropin™ (Genentech), Norditropin™ (Novo-Nordisk), Genotropin™ (Pfizer) and Saizen/Serostim™ (Serono). A significant challenge to using growth hormone as a therapeutic, however, is that the protein has a short in vivo half-life and, therefore, it must be administered by daily subcutaneous injection for maximum effectiveness (MacGillivray, et al., *J. Clin. Endocrinol. Metab.* 81: 1806-1809 (1996)). Considerable effort is focused on means to improve the administration of hGH agonists and antagonists, by lowering the cost of production, making administration easier for the patient, improving efficacy and safety profile, and creating other properties that would provide a competitive advantage. For example, Genentech and Alkermes formerly marketed Nutropin Depot™, a depot formulation of hGH, for pediatric growth hormone deficiency. While the depot permits less frequent administration (once every 2-3 weeks rather than once daily), it is also associated with undesirable side effects, such as decreased bioavailability and pain at the injection site and was withdrawn from the market in 2004. Another product, Pegvisomant™ (Pfizer), has also recently been approved by the FDA. Pegvisomant™ is a genetically-engineered analogue of hGH that functions as a highly selective growth hormone receptor antagonist indicated for the treatment of acromegaly (van der Lely, et al., *The Lancet* 358: 1754-1759 (2001). Although several of the amino acid side chain residues in Pegvisomant™ are derivatized with polyethylene glycol (PEG) polymers, the product is still administered once-daily, indicating that the pharmaceutical properties are not optimal. In addition to PEGylation and depot formulations, other administration routes, including inhaled and oral dosage forms of hGH, are under early-stage pre-clinical and clinical development and none has yet received approval from the FDA. Accordingly, there is a need for a polypeptide that exhibits growth hormone activity but that also provides a longer serum half-life and, therefore, more optimal therapeutic levels of hGH and an increased therapeutic half-life.

Interferons are relatively small, single-chain glycoproteins released by cells invaded by viruses or exposed to certain other substances. Interferons are presently grouped into three major classes, designated: 1) leukocyte interferon (interferon-alpha, α-interferon, IFN-α), 2) fibroblast interferon (interferon-beta, β-interferon, IFN-β), and 3) immune interferon (interferon-gamma, γ-interferon, IFN-γ). In response to viral infection, lymphocytes synthesize primarily α-interferon (with omega interferon, IFN-ω), while infection of fibroblasts usually induces production of β-interferon. IFNα and IFNβ share about 20-30 percent amino acid sequence homology. The gene for human IFN-β lacks introns, and encodes a protein possessing 29% amino acid sequence identity with human IFN-α, suggesting that IFN-α and IFN-β genes have evolved from a common ancestor (Taniguchi et al., *Nature* 285 547-549 (1980)). By contrast, IFN-γ is synthesized by lymphocytes in response to mitogens. IFNα; IFN β and IFNω are known to induce MHC Class I antigen expression and are referred to as type I interferons, while IFNγ induces MHC Class II antigen expression, and is referred to as type II interferon.

A large number of distinct genes encoding different species of IFNα have been identified. Alpha interferons fall into two major classes, I and II, each containing a plurality of discrete proteins (Baron et al., *Critical Reviews in Biotechnology* 10, 179-190 (1990); Nagata et al., *Nature* 287, 401-408 (1980); Nagata et al., *Nature* 284, 316-320 (1980); Streuli et al., *Science* 209, 1343-1347 (1980); Goeddel et al., *Nature* 290, 20-26 (1981); Lawn et al., *Science* 212, 1159-1162 (1981); Ullrich et al., *J. Mol. Biol.* 156, 467-486 (1982); Weissmann et al., *Phil. Trans. R. Soc. Lond.* B299, 7-28 (1982); Lund et al., *Proc. Natl. Acad. Sci.* 81, 2435-2439 (1984); Capon et al., *Mol. Cell. Biol.* 5, 768 (1985)). The various IFN-α species include IFN-αA (IFN-α2), IFN-αB, IFN-αC, IFN-αC1, IFN-αD (IFN-α1), IFN-αE, IFN-αF, IFN-αG, IFN-αH, IFN-αI, IFN-αJ1, IFN-αJ2, IFN-αK, IFN-αL, IFN-α4B, IFN-α5, IFN-α6, IFN-α74, IFN-α76 IFN-α4a), IFN-α88, and alleles thereof.

Interferons were originally derived from naturally occurring sources, such as buffy coat leukocytes and fibroblast cells, optionally using inducing agents to increase interferon production. Interferons have also been produced by recombinant DNA technology.

The cloning and expression of recombinant IFNαA (IFNαA, also known as IFNα2) was described by Goeddel et al., *Nature* 287, 411 (1980). The amino acid sequences of IFNαA, B, C, D, F, G, H, K and L, along with the encoding nucleotide sequences, are described by Pestka in *Archiv. Biochem. Biophys.* 221, 1 (1983). The cloning and expression of mature IFNβ is described by Goeddel et al., *Nucleic Acids Res.* 8, 4057 (1980). The cloning and expression of mature IFNγ are described by Gray et al., *Nature* 295, 503 (1982). IFNω has been described by Capon et al., *Mol. Cell. Biol.* 5, 768 (1985). IFNτ has been identified and disclosed by Whaley et al., *J. Biol. Chem.* 269, 10864-8 (1994).

Interferons have a variety of biological activities, including anti-viral, immunoregulatory and anti-proliferative properties, and have been utilized as therapeutic agents for treatment of diseases such as cancer, and various viral diseases. As a class, the interferon-α's have been shown to inhibit various types of cellular proliferation, and are especially useful for the treatment of a variety of cellular proliferation disorders frequently associated with cancer, particularly hematologic malignancies such as leukemias. These proteins have shown anti-proliferative activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, E. M. et al. (1984) *J. Biol. Response Modifiers* 3:580; Oldham, R. K. (1985) *Hospital Practice* 20:71).

Specific examples of commercially available IFN products include IFNγ-1b (Actimmune®), IFNβ-1a (Avonex®, and Rebif®, IFNβ-1b (Betaseron®), IFN alfacon-1 (Infergen A®), IFNα-2 (Intron®), IFNα-2a (Roferon-A®), Peginterferon alfa-2a (Pegasys®), and Peginterferon alfa-2b (PEG-Intron®). Some of the problems associated with the production of PEGylated versions of IFN proteins are described in Wang et al. (2002) *Adv. Drug Deliv. Rev.* 54:547-570; and Pedder, S. C. *Semin Liver Dis.* 2003; 23 Suppl 1:19-22. Wang et al. characterized positional isomers of PEG-Intron®, and Pedder at al. compared Pegasys® with PEG-Intron® describing the lability of the PEGylation chemistries used and effects upon formulation. Despite the number of IFN products currently available on the market, there is still an unmet need for interferon therapeutics.

Another member of the GH supergene family is human Granulocyte Colony Stimulating Factor (G-CSF). Naturally-occurring G-CSF is a glycoprotein hormone of about 177 amino acids, having a molecular weight of about 20 kiloDaltons (kDa). The crystal structure of G-CSF is known (Hill et al., (1993) Proc. Natl. Acad. Sci. USA 90:5167-71), and a crystal structure of G-CSF bound to its receptor is also known (Aritomi et al., (1999) Nature, 401:713-717). The three dimensional structure of G-CSF is known at the atomic level. From the three-dimensional structure of G-CSF, predictions of how changes in the amino acid composition of a G-CSF molecule may result in structural changes can be made. These structural characteristics or changes may be correlated with biological activity to design and produce G-CSF analogs.

G-CSF is a pharmaceutically active protein which regulates proliferation, differentiation, and functional activation of neutrophilic granulocytes (Metcalf, Blood 67:257 (1986); Yan, et al. Blood 84(3): 795-799 (1994); Bensinger, et al. Blood 81(11): 3158-3163 (1993); Roberts, et al., Expt'l Hematology 22: 1156-1163 (1994); Neben, et al. Blood 81(7): 1960-1967 (1993); Welte et al. PNAS-USA 82: 1526-1530 (1985); Souza et al. Science 232: 61-65 (1986) and Gabrilove, J. Seminars in Hematology 26:2 1-14 (1989)). G-CSF was purified to homogeneity from cell culture supernatants of the human bladder carcinoma cell line 5637 (Welte et al., Proc. Natl. Acad. Sci. (1985) 82:1526-30). The sequence of the cDNA coding for native G-CSF is known from Souza et al., Science (1986) 232:61-65. As a consequence of alternative splicing in the second intron two naturally occurring forms of G-CSF exist with 204 or 207 amino acids of which the first 30 represent a signal peptide (Lymphokines, IRL Press, Oxford, Washington D.C., Editors D. Male and C. Rickwood). The mature protein was shown to have a molecular weight of about 19 kDa and has 5 cysteine residues which can form intermolecular or intramolecular disulfide bridges. Binding studies have shown that G-CSF binds to neutrophilic granulocytes. Little to no binding is observed with erythroid, lymphoid eosinophilic cell lines as well as with macrophages.

In humans, endogenous G-CSF is detectable in blood plasma (Jones et al. Bailliere's Clinical Hematology 2:1 83-111 (1989)). G-CSF is produced by fibroblasts, macrophages, T cells, trophoblasts, endothelial cells and epithelial cells and is the expression product of a single copy gene comprised of four exons and five introns located on chromosome seventeen. Transcription of this locus produces a mRNA species which is differentially processed, resulting in two forms of G-CSF mRNA, one version coding for a protein of 177 amino acids, the other coding for a protein of 174 amino acids (Nagata et al. EMBO J 5: 575-581 (1986)), and the form comprised of 174 amino acids has been found to have the greatest specific in vivo biological activity. G-CSF is species cross-reactive, such that when human G-CSF is administered to another mammal such as a mouse, canine or monkey, sustained neutrophil leukocytosis is elicited (Moore et al. PNAS-USA 84: 7134-7138 (1987)).

Human G-CSF can be obtained and purified from a number of sources. Natural human G-CSF (nhG-CSF) can be isolated from the supernatants of cultured human tumor cell lines. The development of recombinant DNA technology, see, for instance, U.S. Pat. No. 4,810,643 (Souza) incorporated herein by reference, has enabled the production of commercial scale quantities of G-CSF in glycosylated form as a product of eukaryotic host cell expression, and of G-CSF in non-glycosylated form as a product of prokaryotic host cell expression.

G-CSF has been found to be useful in the treatment of indications where an increase in neutrophils will provide benefits. G-CSF can mobilize stem and precursor cells from bone marrow and is used to treat patients whose granulocytes have been depleted by chemotherapy, or as a prelude to bone marrow transplants. For example, for cancer patients, G-CSF is beneficial as a means of selectively stimulating neutrophil production to compensate for hematopoietic deficits resulting from chemotherapy or radiation therapy. Other indications include treatment of various infectious diseases and related conditions, such as sepsis, which is typically caused by a metabolite of bacteria. G-CSF is also useful alone, or in combination with other compounds, such as other cytokines, for growth or expansion of cells in culture, for example, for bone marrow transplants.

The G-CSF receptor (G-CSFR) is a member of the hematopoietic/cytokine/growth factor receptor family, which includes several other growth factor receptors, such as the interleukin (IL)-3, -4 and -6 receptors, the granulocyte macrophage colony-stimulating factor (GM-CSF) receptor, the erythropoietin (EPO) receptor, as well as the prolactin and growth hormone receptors. See, Bazan, *Proc. Natl. Acad. Sci. USA* 87: 6934-6938 (1990). Members of the cytokine receptor family contain four conserved cysteine residues and a tryptophan-serine-X-tryptophan-serine motif positioned just outside the transmembrane region. The conserved sequences are thought to be involved in protein-protein interactions. See, e.g., Chiba et al., *Biochim. Biophys. Res. Comm.* 184: 485-490 (1992). The G-CSF receptor consists of a single peptide chain with a molecular weight of about 150 kD (Nicola, Immunol. Today 8 (1987), 134).

Glycosylated hG-CSF has been compared with de-glycosylated hG-CSF, prepared by in vitro enzymatic digestion with neuraminidase and endo-α-N-acetylgalactosaminidase, with respect to its stability as a function of pH and temperature (Oh-eda et al., 1990, J. Biol. Chem. 265 (20): 11432-35). The de-glycosylated hG-CSF, dissolved at a concentration of 1 μg/mL in 20 mM phosphate buffer containing 0.2 M NaCl and 0.01% Tween 20 was rapidly inactivated within the pH range of from about pH 7 to about pH 8 after a two-day incubation at 37° C. In contrast, glycosylated hG-CSF retained over 80% of its activity under the same conditions. Furthermore, evaluation of the thermal stability of both forms of hG-CSF, measured by biological assay and calorimetric analysis, indicated that de-glycosylated hG-CSF was less thermally stable than the native form of hG-CSF.

A number of approaches have been taken in order to provide stable, pharmaceutically acceptable G-CSF compositions. One approach to improving the composition stability of G-CSF involves the synthesis of derivatives of the protein. U.S. Pat. No. 5,665,863 discloses the formation of recombinant chimeric proteins comprising G-CSF coupled with albumin, which have new pharmacokinetic properties. U.S. Pat. No. 5,824,784 and U.S. Pat. No. 5,320,840, disclose the chemical attachment of water-soluble polymers to proteins to improve stability and provide protection against proteolytic degradation, and more specifically, N-terminally modified G-CSF molecules carrying chemically attached polymers, including polyethylene glycol.

An alternative approach to increasing stability of G-CSF in composition involves alteration of the amino acid sequence of the protein. U.S. Pat. No. 5,416,195 discloses genetically engineered analogues of G-CSF having improved composition stability, wherein the cysteine residue normally found at position 17 of the mature polypeptide chain, the aspartic acid residue found at position 27, and at least one of the tandem proline residues found at positions 65 and 66, are all replaced with a serine residue. U.S. Pat. No. 5,773,581 discloses the genetically engineered G-CSF analogues of G-CSF that have been covalently conjugated to a water soluble polymer.

Another member of the GH supergene family is human erythropoietin (hEPO). Naturally-occurring erythropoietin (EPO) is a glycoprotein hormone of molecular weight 34 kilo Daltons (kDa) that is produced in the mammalian kidney and liver. EPO is a key component in erythropoiesis, inducing the proliferation and differentiation of red cell progenitors. EPO activity also is associated with the activation of a number of erythroid-specific genes, including globin and carbonic anhydrase. See, e.g., Bondurant et al., *Mol. Cell. Biol.* 5:675-683 (1985); Koury et al, *J. Cell. Physiol.* 126: 259-265 (1986).

The erythropoietin receptor (EpoR) is a member of the hematopoietic/cytokine/growth factor receptor family, which includes several other growth factor receptors, such as the interleukin (IL)-3, -4 and -6 receptors, the G-CSF receptor (G-CSFR), the granulocyte macrophage colony-stimulating factor (GM-CSF) receptor as well as the prolactin and growth hormone receptors. See, Bazan, *Proc. Natl. Acad. Sci. USA* 87: 6934-6938 (1990). Members of the cytokine receptor family contain four conserved cysteine residues and a tryptophan-serine-X-tryptophan-serine motif positioned just outside the transmembrane region. The conserved sequences are thought to be involved in protein-protein interactions. See, e.g., Chiba et al., *Biochim. Biophys. Res. Comm.* 184: 485-490 (1992).

U.S. Pat. Nos. 5,441,868; 5,547,933; 5,618,698; and 5,621,080 describe DNA sequences encoding human EPO and the purified and isolated polypeptide having part or all of the primary structural conformation and the biological properties of naturally occurring EPO.

The biological effects of hEPO derive from its interaction with specific cellular receptors. The interaction between hEPO and extracellular domain of its receptor (hEPObp) is well understood. High-resolution X-ray crystallographic data has shown that hEPO has two receptor binding sites and binds two receptor molecules sequentially using distinct sites on the molecule. The two receptor binding sites are referred to as Site I and Site II. Site I includes the carboxy terminal end of helix D and parts of helix A and the A-B loop, whereas Site II encompasses the amino terminal region of helix A and a portion of helix C. Binding of EPO to its receptor occurs sequentially, with site I binding first. Site II then engages a second EPO receptor, resulting in receptor dimerization and activation of the intracellular signaling pathways that lead to cellular responses to the hormone.

Recombinant hEPO is used as a therapeutic and has been approved for the treatment of human subjects. hEPO deficiency leads to anemia, for example, which has been successfully treated by exogenous administration of the hormone.

Covalent attachment of the hydrophilic polymer poly(ethylene glycol), abbreviated PEG, is a method of increasing water solubility, bioavailability, increasing serum half-life, increasing therapeutic half-life, modulating immunogenicity, modulating biological activity, or extending the circulation time of many biologically active molecules, including proteins, peptides, and particularly hydrophobic molecules. PEG has been used extensively in pharmaceuticals, on artificial implants, and in other applications where biocompatibility, lack of toxicity, and lack of immunogenicity are of importance. In order to maximize the desired properties of PEG, the total molecular weight and hydration state of the PEG polymer or polymers attached to the biologically active molecule must be sufficiently high to impart the advantageous characteristics typically associated with PEG polymer attachment, such as increased water solubility and circulating half life, while not adversely impacting the bioactivity of the parent molecule.

PEG derivatives are frequently linked to biologically active molecules through reactive chemical functionalities, such as lysine, cysteine and histidine residues, the N-terminus and carbohydrate moieties. Proteins and other molecules often have a limited number of reactive sites available for polymer attachment. Often, the sites most suitable for modification via polymer attachment play a significant role in receptor binding, and are necessary for retention of the biological activity of the molecule. As a result, indiscriminate attachment of polymer chains to such reactive sites on a biologically active molecule often leads to a significant reduction or even total loss of biological activity of the polymer-modified molecule. R. Clark et al., (1996), *J. Biol. Chem.,* 271:21969-21977. To form conjugates having sufficient polymer molecular weight for imparting the desired advantages to a target molecule, prior art approaches have typically involved random attachment of numerous polymer arms to the molecule, thereby increasing the risk of a reduction or even total loss in bioactivity of the parent molecule.

Reactive sites that form the loci for attachment of PEG derivatives to proteins are dictated by the protein's structure. Proteins, including enzymes, are composed of various sequences of alpha-amino acids, which have the general structure $H_2N$—CHR—COOH. The alpha amino moiety ($H_2N$—) of one amino acid joins to the carboxyl moiety (—COOH) of an adjacent amino acid to form amide linkages, which can be represented as —(NH—CR—CO)$_n$—, where the subscript "n" can equal hundreds or thousands. The fragment represented by R can contain reactive sites for protein biological activity and for attachment of PEG derivatives.

For example, in the case of the amino acid lysine, there exists an —$NH_2$ moiety in the epsilon position as well as in the alpha position. The epsilon —$NH_2$ is free for reaction under conditions of basic pH. Much of the art in the field of protein derivatization with PEG has been directed to developing PEG derivatives for attachment to the epsilon —$NH_2$ moiety of lysine residues present in proteins. "Polyethylene Glycol and Derivatives for Advanced PEGylation", Nektar Molecular Engineering Catalog, 2003, pp. 1-17. These PEG derivatives all have the common limitation, however, that they cannot be installed selectively among the often numerous lysine residues present on the surfaces of proteins. This can be a significant limitation in instances where a lysine residue is important to protein activity, existing in an enzyme active site for example, or in cases where a lysine residue plays a role in mediating the interaction of the protein with other biological molecules, as in the case of receptor binding sites.

A second and equally important complication of existing methods for protein PEGylation is that the PEG derivatives can undergo undesired side reactions with residues other than those desired. Histidine contains a reactive imino moiety, represented structurally as —N(H)—, but many chemically reactive species that react with epsilon —$NH_2$ can also react with —N(H)—. Similarly, the side chain of the amino acid cysteine bears a free sulfhydryl group, represented structurally as —SH. In some instances, the PEG derivatives directed at the epsilon —$NH_2$ group of lysine also react with cysteine, histidine or other residues. This can create complex, heterogeneous mixtures of PEG-derivatized bioactive molecules and risks destroying the activity of the bioactive molecule being targeted. It would be desirable to develop PEG derivatives that permit a chemical functional group to be introduced at a single site within the protein that would then enable the selective coupling of one or more PEG polymers to the bioactive molecule at specific sites on the protein surface that are both well-defined and predictable.

In addition to lysine residues, considerable effort in the art has been directed toward the development of activated PEG reagents that target other amino acid side chains, including cysteine, histidine and the N-terminus. See, e.g., U.S. Pat. No. 6,610,281 which is incorporated by reference herein, and "Polyethylene Glycol and Derivatives for Advanced PEGylation", Nektar Molecular Engineering Catalog, 2003, pp. 1-17. A cysteine residue can be introduced site-selectively into the structure of proteins using site-directed mutagenesis and other techniques known in the art, and the resulting free sulfhydryl moiety can be reacted with PEG derivatives that bear thiol-reactive functional groups. This approach is complicated, however, in that the introduction of a free sulfhydryl group can complicate the expression, folding and stability of the resulting protein. Thus, it would be desirable to have a means to introduce a chemical functional group into bioactive molecules that enables the selective coupling of one or more PEG polymers to the protein while simultaneously being compatible with (i.e., not engaging in undesired side reactions with) sulfhydryls and other chemical functional groups typically found in proteins.

As can be seen from a sampling of the art, many of these derivatives that have been developed for attachment to the side chains of proteins, in particular, the —NH$_2$ moiety on the lysine amino acid side chain and the —SH moiety on the cysteine side chain, have proven problematic in their synthesis and use. Some form unstable linkages with the protein that are subject to hydrolysis and therefore decompose, degrade, or are otherwise unstable in aqueous environments, such as in the bloodstream. See Pedder, S. C. Semin Liver Dis. 2003; 23 Suppl 1:19-22 for a discussion of the stability of linkages in PEG-Intron®. Some form more stable linkages, but are subject to hydrolysis before the linkage is formed, which means that the reactive group on the PEG derivative may be inactivated before the protein can be attached. Some are somewhat toxic and are therefore less suitable for use in vivo. Some are too slow to react to be practically useful. Some result in a loss of protein activity by attaching to sites responsible for the protein's activity. Some are not specific in the sites to which they will attach, which can also result in a loss of desirable activity and in a lack of reproducibility of results. In order to overcome the challenges associated with modifying proteins with poly(ethylene glycol) moieties, PEG derivatives have been developed that are more stable (e.g., U.S. Pat. No. 6,602, 498, which is incorporated by reference herein) or that react selectively with thiol moieties on molecules and surfaces (e.g., U.S. Pat. No. 6,610,281, which is incorporated by reference herein). There is clearly a need in the art for PEG derivatives that are chemically inert in physiological environments until called upon to react selectively to form stable chemical bonds.

Recently, an entirely new technology in the protein sciences has been reported, which promises to overcome many of the limitations associated with site-specific modifications of proteins. Specifically, new components have been added to the protein biosynthetic machinery of the prokaryote *Escherichia coli* (*E. coli*) (e.g., L. Wang, et al., (2001), *Science* 292:498-500) and the eukaryote *Saccharomyces cerevisiae* (*S. cerevisiae*) (e.g., J. Chin et al., *Science* 301:964-7 (2003)), which has enabled the incorporation of non-genetically encoded amino acids to proteins in vivo. A number of new amino acids with novel chemical, physical or biological properties, including photoaffinity labels and photoisomerizable amino acids, keto amino acids, and glycosylated amino acids have been incorporated efficiently and with high fidelity into proteins in *E. coli* and in yeast in response to the amber codon, TAG, using this methodology. See, e.g., J. W. Chin et al., (2002), *Journal of the American Chemical Society* 124:9026-9027; J. W. Chin, & P. G. Schultz, (2002), *ChemBioChem* 11:1135-1137; J. W. Chin, et al., (2002), *PNAS United States of America* 99:11020-11024; and, L. Wang, & P. G. Schultz, (2002), *Chem. Comm.*, 1-10. These studies have demonstrated that it is possible to selectively and routinely introduce chemical functional groups, such as ketone groups, alkyne groups and azide moieties, that are not found in proteins, that are chemically inert to all of the functional groups found in the 20 common, genetically-encoded amino acids and that may be used to react efficiently and selectively to form stable covalent linkages.

The ability to incorporate non-genetically encoded amino acids into proteins permits the introduction of chemical functional groups that could provide valuable alternatives to the naturally-occurring functional groups, such as the epsilon —NH$_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2] cycloaddition reaction in aqueous conditions in the presence of a catalytic amount of copper. See, e.g., Tornoe, et al., (2002) *Org. Chem.* 67:3057-3064; and, Rostovtsev, et al., (2002) *Angew. Chem. Int. Ed.* 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of four helical bundle (4HB) polypeptides, and also addresses the production of a 4HB polypeptide with improved biological or pharmacological properties, such as improved therapeutic half-life.

BRIEF SUMMARY OF THE INVENTION

This invention provides GH supergene family members, including hGH polypeptides, hIFN polypeptides, hG-CSF polypeptides, and hEPO polypeptides comprising one or more non-naturally encoded amino acids.

In some embodiments, the 4HB polypeptide comprises one or more post-translational modifications. In some embodiments, the 4HB polypeptide is linked to a linker, polymer, or biologically active molecule. In some embodiments, the 4HB polypeptide is linked to a bifunctional polymer, bifunctional linker, or at least one additional 4HB polypeptide.

In some embodiments, the non-naturally encoded amino acid is linked to a water soluble polymer. In some embodiments, the water soluble polymer comprises a poly(ethylene glycol) moiety. In some embodiments, the poly(ethylene glycol) molecule is a bifunctional polymer. In some embodiments, the bifunctional polymer is linked to a second polypeptide. In some embodiments, the second polypeptide is a 4HB polypeptide.

In some embodiments, the 4HB polypeptide comprises at least two amino acids linked to a water soluble polymer comprising a poly(ethylene glycol) moiety. In some embodiments, at least one amino acid is a non-naturally encoded amino acid.

Regions of hGH can be illustrated as follows, wherein the amino acid positions in hGH are indicated in the middle row:

| | | Helix A | | Helix B | | Helix C | | Helix D | |
|---|---|---|---|---|---|---|---|---|---|
| [1-5]- | | [6-33]- | [34-74]- | [75-96]- | [97-105]- | [106-129]- | [130-153]- | [154-183]- | [184-191] |
| N-term | | | A-B loop | | B-C loop | | C-D loop | | C-term |

In some embodiments, one or more non-naturally encoded amino acids are incorporated at any position in one or more of the following regions corresponding to secondary structures in hGH as follows: 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus) from SEQ ID NO: 2 or the corresponding amino acids of SEQ ID NO: 1 or 3. In other embodiments, the non-naturally encoded amino acid is substituted at a position selected from the group consisting of residues 1-5, 32-46, 97-105, 132-149, and 184-191 from hGH SEQ ID NO: 2 or the corresponding amino acids of SEQ ID NO: 1 or 3. In some embodiments, one or more non-naturally encoded amino acids are incorporated in one or more of the following positions in hGH: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3).

In some embodiments, one or more non-naturally encoded amino acids are substituted at one or more of the following positions: 29, 30, 33, 34, 35, 37, 39, 40, 49, 57, 59, 66, 69, 70, 71, 74, 88, 91, 92, 94, 95, 98, 99, 101, 103, 107, 108, 111, 122, 126, 129, 130, 131, 133, 134, 135, 136, 137, 139, 140, 141, 142, 143, 145, 147, 154, 155, 156, 159, 183, 186, and 187 (SEQ ID NO: 2 or the corresponding amino acids of SEQ ID NO: 1 or 3).

In some embodiments, one or more non-naturally encoded amino acids are substituted at one or more of the following positions: 29, 33, 35, 37, 39, 49, 57, 69, 70, 71, 74, 88, 91, 92, 94, 95, 98, 99, 101, 103, 107, 108, 111, 129, 130, 131, 133, 134, 135, 136, 137, 139, 140, 141, 142, 143, 145, 147, 154, 155, 156, 186, and 187 (SEQ TD NO: 2 or the corresponding amino acids of SEQ ID NO: 1 or 3).

In some embodiments, one or more non-naturally encoded amino acids are substituted at one or more of the following positions: 35, 88, 91, 92, 94, 95, 99, 101, 103, 111, 131, 133, 134, 135, 136, 139, 140, 143, 145, and 155 (SEQ ID NO: 2 or the corresponding amino acids of SEQ ID NO: 1 or 3).

In some embodiments, one or more non-naturally encoded amino acids are substituted at one or more of the following positions: 30, 74, 103 (SEQ ID NO: 2 or the corresponding amino acids of SEQ ID NO: 1 or 3). In some embodiments, one or more non-naturally encoded amino acids are substituted at one or more of the following positions: 35, 92, 143, 145 (SEQ ID NO: 2 or the corresponding amino acids of SEQ ID NO: 1 or 3).

In some embodiments, the non-naturally occurring amino acid at one or more of these positions is linked to a water soluble polymer, including but not limited to, positions: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3). In some embodiments, the non-naturally occurring amino acid at one or more of these positions is linked to a water soluble polymer: 30, 35, 74, 92, 103, 143, 145 (SEQ ID NO: 2 or the corresponding amino acids of SEQ ID NO: 1 or 3). In some embodiments, the non-naturally occurring amino acid at one or more of these positions is linked to a water soluble polymer: 35, 92, 143, 145 (SEQ ID NO: 2 or the corresponding amino acids of SEQ ID NO: 1 or 3).

Human GH antagonists include, but are not limited to, those with substitutions at: 1, 2, 3, 4, 5, 8, 9, 11, 12, 15, 16, 19, 22, 103, 109, 112, 113, 115, 116, 119, 120, 123, and 127 or an addition at position 1 (i.e., at the N-terminus), or any combination thereof (SEQ ID NO:2, or the corresponding amino acid in SEQ ID NO: 1, 3, or any other GH sequence).

In some embodiments, one or more non-naturally encoded amino acids are incorporated at any position in one or more of the following regions corresponding to secondary structures in IFN as follows: 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus) (SEQ ID NO: 24, or the corresponding amino acids in SEQ ID NO: 23 or 25). In some embodiments, one or more non-naturally encoded amino acids are incorporated in one or more of the following positions in IFN: before position 1 (i.e. at the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus of the protein) (SEQ ID NO: 24, or the corresponding amino acids in SEQ ID NO: 23 or 25). In some embodiments, the IFN polypeptides of the invention comprise one or more non-naturally occurring amino acids at one or more of the following positions: 100, 106, 107, 108, 111, 113, 114 (SEQ ID NO: 24, or the corresponding amino acids in SEQ ID NO: 23 or 25). In some embodiments, the IFN polypeptides of the invention comprise one or more non-naturally occurring amino acids at one or more of the following positions: 41, 45, 46, 48, 49 (SEQ ID NO: 24, or the corresponding amino acids in SEQ ID NO: 23 or 25). In some embodiments, the IFN polypeptides of the invention comprise one or more non-naturally occurring amino acids at one or more of the following positions: 61, 64, 65, 101, 103, 110, 117, 120, 121, 149 (SEQ ID NO: 24, or the corresponding amino acids in SEQ ID NO: 23 or 25). In some embodiments, the IFN polypeptides of the invention comprise one or more non-naturally occurring amino acids at one or more of the following positions: 6, 9, 12, 13, 16, 96, 156, 159, 160, 161, 162 (SEQ ID NO: 24, or the corresponding amino acids in SEQ ID NO: 23 or 25). In some embodiments, the IFN polypeptides of the invention comprise one or more non-naturally occurring amino acids at one or more of the following positions: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 24, or the corresponding amino acids in SEQ ID NO: 23 or 25). In some embodiments, the non-naturally occurring amino acid at one or more of these positions is linked to a water soluble polymer, including but not limited to positions: before position 1 (i.e. at the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus) (SEQ ID NO: 24, or the corresponding amino acids in SEQ ID NO: 23 or 25). In some embodiments, the non-naturally occurring amino acid is linked to a water soluble polymer at one or more of the following positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 24, or the corresponding amino acids in SEQ ID NO: 23 or 25). In some embodiments, the IFN polypeptides of the invention comprise one or more non-naturally occurring amino acids at one or more of the following positions providing an antagonist: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165, or any combination thereof (SEQ ID NO: 24, or the corresponding amino acids in SEQ ID NO: 23 or 25); a hIFN polypeptide comprising one of these substitutions may potentially act as a weak antagonist or weak agonist depending on the site selected and desired activity. Human IFN antagonists include, but are not limited to, those with substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combination thereof (hIFN; SEQ ID NO: 24 or the corresponding amino acids in SEQ ID NO: 23 or 25).

In some embodiments, one or more non-naturally encoded amino acids are incorporated at any position in one or more of the following regions corresponding to secondary structures in G-CSF as follows: 1-10 (N-terminus), 11-39 (A helix), 40-70 (region between A helix and B helix), 71-91 (B helix), 92-99 (region between B helix and C helix), 100-123 (C helix), 124-142 (region between C helix and D helix), 143-172 (D helix), 173-175 (C-terminus), including the short helical segment, the mini-E Helix, at 44-53 between the A Helix and B Helix composed of a $3_{10}$ helix (44-47) and an $\alpha$ helix (48-53) (SEQ ID NO: 29, or the corresponding amino acids in SEQ ID NO: 28, 30, 35, or 36). In some embodiments, one or more non-naturally encoded amino acids are incorporated in one or more of the following positions in G-CSF: before position 1 (i.e. at the N terminus), 1, 2, 3, 4, 5, 6, 7, 8, 9, 10, 11, 12, 13, 16, 17, 19, 20, 21, 23, 24, 28, 30, 31, 33, 34, 35, 38, 39, 40, 41, 44, 45, 46, 47, 48, 49, 50, 51, 53, 54, 55, 56, 58, 59, 61, 63, 64, 66, 67, 68, 69, 70, 71, 72, 73, 77, 78, 81, 84, 87, 88, 91, 92, 94, 95, 97, 98, 99, 101, 102, 103, 105, 106, 108, 109, 110, 112, 113, 116, 117, 120, 121, 123, 124, 125, 126, 127, 130, 131, 132, 133, 134, 135, 136, 137, 138, 139, 140, 142, 143, 144, 145, 146, 147, 148, 156, 157, 159, 160, 163, 164, 166, 167, 170, 171, 173, 174, 175, 176 (i.e. at the carboxyl terminus) (SEQ ID NO: 29, or the corresponding amino acids in SEQ ID NO: 28, 30, 35, or 36). In some embodiments, the G-CSF polypeptides of the invention comprise one or more non-naturally occurring amino acids at one or more of the following positions: 30, 31, 33, 58, 59, 61, 63, 64, 66, 67, 68, 77, 78, 81, 87, 88, 91, 95, 101, 102, 103, 130, 131, 132, 134, 135, 136, 137, 156, 157, 159, 160, 163, 164, 167, 170, 171 (SEQ ID NO: 29, or the corresponding amino acids in SEQ ID NO: 28, 30, 35, or 36). Exemplary positions for incorporation of a non-naturally encoded amino acid include 59, 63, 67, 130, 131, 132, 134, 137, 160, 163, 167, and 171, or combination thereof (as in SEQ ID NO: 29, or the corresponding amino acids in SEQ ID NO: 28, 30, 35, or 36). In some embodiments, the non-naturally occurring amino acid at one or more of these positions is linked to a water soluble polymer, including but not limited to positions: before position 1 (i.e. at the N terminus), 1, 2, 3, 4, 5, 6, 7, 8, 9, 10, 11, 12, 13, 16, 17, 19, 20, 21, 23, 24, 28, 30, 31, 33, 34, 35, 38, 39, 40, 41, 44, 45, 46, 47, 48, 49, 50, 51, 53, 54, 55, 56, 58, 59, 61, 63, 64, 66, 67, 68, 69, 70, 71, 72, 73, 77, 78, 81, 84, 87, 88, 91, 92, 94, 95, 97, 98, 99, 101, 102, 103, 105, 106, 108, 109, 110, 112, 113, 116, 117, 120, 121, 123, 124, 125, 126, 127, 130, 131, 132, 133, 134, 135, 136, 137, 138, 139, 140, 142, 143, 144, 145, 146, 147, 148, 156, 157, 159, 160, 163, 164, 166, 167, 170, 171, 173, 174, 175, 176 (i.e. at the carboxyl terminus) (SEQ ID NO: 29, or the corresponding amino acids in SEQ ID NO: 28, 30, 35, or 36). In some embodiments, one or more non-naturally occurring amino acid at these or other positions is linked to a water soluble polymer, including but not limited to, positions: 59, 63, 67, 130, 131, 132, 134, 137, 160, 163, 167, 171, or any combination thereof (SEQ ID NO: 29, or the corresponding amino acids in SEQ ID NO: 28, 30, 35, or 36). Human G-CSF antagonists include, but are not limited to, those with substitutions at: 6, 7, 8, 9, 10, 11, 12, 13, 16, 17, 19, 20, 21, 23, 24, 28, 30, 41, 47, 49, 50, 70, 71, 105, 106, 109, 110, 112, 113, 116, 117, 120, 121, 123, 124, 125, 127, 145, or any combination thereof (SEQ ID NO: 29, or the corresponding amino acid in SEQ ID NO: 28, 30, 35, or 36).

In some embodiments, one or more non-naturally encoded amino acids are incorporated at any position in one or more of the following regions corresponding to secondary structures in EPO as follows: 1-7 (N-terminus), 8-26 (A helix), 27-54 (AB loop, containing beta sheet 1 (39-41) and mini B' helix (47-52)), 55-83 (13 helix), 84-89 (BC loop), 90-112 (C helix), 113-137 (CD loop, containing mini C' helix (114-121) and beta sheet 2 (133-135)), 138-161 (D helix), 162-166 (C-terminus) (SEQ ID NO: 38 or the corresponding amino acids in SEQ ID NO: 37 or 39). In some embodiments, one or more non-naturally encoded amino acids are incorporated in one or more of the following positions in EPO: before position 1 (i.e. at the N terminus), 1, 2, 3, 4, 5, 6, 8, 9, 10, 11, 14, 15, 16, 17, 18, 20, 21, 23, 24, 25, 26, 27, 28, 30, 31, 32, 34, 35, 36, 37, 38, 39, 40, 43, 44, 45, 46, 47, 48, 49, 50, 51, 52, 53, 54, 55, 56, 57, 58, 65, 68, 72, 75, 76, 77, 78, 79, 80, 82, 83, 84, 85, 86, 87, 88, 89, 90, 91, 92, 93, 96, 97, 99, 100, 103, 104, 107, 108, 110, 111, 113, 114, 115, 116, 117, 118, 119, 120, 121, 122, 123, 124, 125, 126, 127, 128, 129, 130, 131, 132, 133, 134, 136, 140, 143, 144, 146, 147, 150, 154, 155, 157, 158, 159, 160, 162, 163, 164, 165, 166, 167 (i.e. at the carboxyl terminus)

(SEQ ID NO: 38 or the corresponding amino acids in SEQ ID NO: 37 or 39). A subset of exemplary sites for incorporation of one or more non-naturally encoded amino acid include, but are not limited to, 1, 2, 4, 9, 17, 20, 21, 24, 25, 27, 28, 30, 31, 32, 34, 36, 37, 38, 40, 50, 53, 55, 58, 65, 68, 72, 76, 79, 80, 82, 83, 85, 86, 87, 89, 113, 115, 116, 119, 120, 121, 122, 123, 124, 125, 126, 127, 128, 129, 130, 131, 132, 134, 136, 159, 162, 163, 164, 165, and 166 in EPO (SEQ ID NO: 38 or the corresponding amino acids in SEQ ID NO: 37 or 39). Exemplary positions for incorporation of one or more non-naturally encoded amino acid include: 21, 24, 28, 30, 31, 36, 37, 38, 55, 72, 83, 85, 86, 87, 89, 113, 116, 119, 120, 121, 123, 124, 125, 126, 127, 128, 129, 130, 162, 163, 164, 165, and 166 in EPO (SEQ ID NO: 38 or the corresponding amino acids in SEQ ID NO: 37 or 39).

In some embodiments, the non-naturally occurring amino acid at one or more of these positions is linked to a water soluble polymer, including but not limited to, positions: before position 1 (i.e. at the N terminus), 1, 2, 3, 4, 5, 6, 8, 9, 10, 11, 14, 15, 16, 17, 18, 20, 21, 23, 24, 25, 26, 27, 28, 30, 31, 32, 34, 35, 36, 37, 38, 39, 40, 43, 44, 45, 46, 47, 48, 49, 50, 51, 52, 53, 54, 55, 56, 57, 58, 65, 68, 72, 75, 76, 77, 78, 79, 80, 82, 83, 84, 85, 86, 87, 88, 89, 90, 91, 92, 93, 96, 97, 99, 100, 103, 104, 107, 108, 110, 111, 113, 114, 115, 116, 117, 118, 119, 120, 121, 122, 123, 124, 125, 126, 127, 128, 129, 130, 131, 132, 133, 134, 136, 140, 143, 144, 146, 147, 150, 154, 155, 157, 158, 159, 160, 162, 163, 164, 165, 166, 167 (i.e. at the carboxyl terminus) (SEQ ID NO: 38 or the corresponding amino acids in SEQ ID NO: 37 or 39). In some embodiments, one or more non-naturally occurring amino acids at these or other positions linked to a water soluble polymer, including but not limited to, positions 21, 24, 38, 83, 85, 86, 89, 116, 119, 121, 124, 125, 126, 127, and 128, or combination thereof (SEQ ID NO: 38 or the corresponding amino acids in SEQ ID NO: 37 or 39).

Human EPO antagonists include, but are not limited to, those with substitutions at: 2, 3, 5, 8, 9, 10, 11, 14, 15, 16, 17, 18, 20, 23, 43, 44, 45, 46, 47, 48, 49, 50, 52, 75, 78, 93, 96, 97, 99, 100, 103, 104, 107, 108, 110, 131, 132, 133, 140, 143, 144, 146, 147, 150, 154, 155, 159, or any combination thereof (hEPO; SEQ ID NO: 38, or corresponding amino acids in SEQ ID NO: 37 or 39).

In some embodiments, the 4HB polypeptide comprises a substitution, addition or deletion that modulates affinity of the 4HB polypeptide for a 4HB polypeptide receptor. In some embodiments, the 4HB polypeptide comprises a substitution, addition, or deletion that increases the stability of the 4HB polypeptide. In some embodiments, the hGH polypeptide comprises an amino acid substitution selected from the group consisting of F10A, F10H, F10I; M14W, M14Q, M14G; H18D; $H_{21}N$; G120A; R167N; D171S; E174S; F176Y, I179T or any combination thereof in hGH SEQ ID NO: 2. In some embodiments, the 4HB polypeptide comprises a substitution, addition, or deletion that modulates the immunogenicity of the 4HB polypeptide. In some embodiments, the 4HB polypeptide comprises a substitution, addition, or deletion that modulates serum half-life or circulation time of the 4HB polypeptide.

In some embodiments, the 4HB polypeptide comprises a substitution, addition, or deletion that increases the aqueous solubility of the 4HB polypeptide. In some embodiments, the 4HB polypeptide comprises a substitution, addition, or deletion that increases the solubility of the 4HB polypeptide produced in a host cell. In some embodiments, the 4HB polypeptide comprises a substitution, addition, or deletion that increases the expression of the 4HB polypeptide in a host cell or synthesized in vitro. In some embodiments, the hGH polypeptide comprises an amino acid substitution G120A. The hGH polypeptide comprising this substitution retains agonist activity and retains or improves expression levels in a host cell. In some embodiments, the hG-CSF polypeptide comprises a substitution of an amino acid selected from the group consisting of, but not limited to, T38A, H52A, L71A, T102A, L108A, W118A, S159A (Biochemistry 35:9034 (1996), or the corresponding amino acid position of SEQ ID NO: 29) and combinations thereof. In some embodiments, the hEPO polypeptide comprises a substitution of an amino acid selected from the group consisting of, but not limited to, N24, N36, N38, Q58, Q65, N83, Q86, G113, Q115, and S126 or combination thereof in SEQ ID NO: 38. In some embodiments, the 4HB polypeptide comprises a substitution, addition, or deletion that increases protease resistance of the 4HB polypeptide.

In some embodiments the amino acid substitutions in the 4HB polypeptide may be with naturally occurring or non-naturally occurring amino acids, provided that at least one substitution is with a non-naturally encoded amino acid.

In some embodiments, the non-naturally encoded amino acid comprises a carbonyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

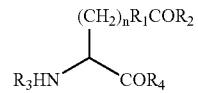

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

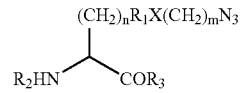

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

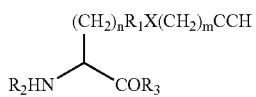

wherein n is 0-10; $R_1$ is an alkyl, aryl, substituted alkyl, or substituted aryl; X is O, N, S or not present; in is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is a 4HB polypeptide agonist, partial agonist, antagonist, partial antagonist, or inverse agonist. In some embodiments, the 4HB polypeptide agonist, partial agonist, antagonist, partial antagonist, or inverse agonist comprises a non-naturally encoded amino acid linked to a water soluble polymer. In some embodiments, the water soluble polymer comprises a poly(ethylene glycol) moiety. In some embodiments, the 4HB agonist, partial agonist, antagonist, partial antagonist, or inverse agonist comprises a non-naturally encoded amino acid and one or more post-translational modification, linker, polymer, or biologically active molecule. In some embodiments, the non-naturally encoded amino acid linked to a water soluble polymer is present within the Site II region (the region of the protein encompassing the AC helical-bundle face, amino terminal region of helix A and a portion of helix C) of the 4HB polypeptide. In some embodiments, the 4HB polypeptide comprising a non-naturally encoded amino acid linked to a water soluble polymer prevents dimerization of the 4HB polypeptide receptor by preventing the 4HB polypeptide antagonist from binding to a second 4HB polypeptide receptor molecule. In some embodiments, an amino acid other than glycine is substituted for G120 in SEQ ID NO: 2 (hGH). In some embodiments, arginine is substituted for G120 in SEQ ID NO: 2. In some embodiments, a non-naturally encoded amino acid is substituted for G120 in SEQ ID NO: 2. In some embodiments, an amino acid other than leucine is substituted for L70 in SEQ ID NO: 29 (hG-CSF). In some embodiments, arginine or lysine is substituted for L70 in SEQ ID NO: 29. In some embodiments, a non-naturally encoded amino acid is substituted for L70 in SEQ ID NO: 29. Ea some embodiments, all amino acid other than leucine is substituted for L108 in SEQ ID NO: 38 (hEPO). In some embodiments, arginine or lysine is substituted for L108 in SEQ ID NO: 38. In some embodiments, a non-naturally encoded amino acid is substituted for L108 in SEQ ID NO: 38.

The present invention also provides isolated nucleic acids comprising a polynucleotide that hybridizes under stringent conditions to SEQ ID NO: 21, 22, 26, 27, 31, 32, 33, 34, 40, 41, 42, or 43 wherein the polynucleotide comprises at least one selector codon. In some embodiments, the selector codon is selected from the group consisting of an amber codon, ochre codon, opal codon, a unique codon, a rare codon, and a four-base codon.

The present invention also provides methods of making a 4HB polypeptide linked to a water soluble polymer. In some embodiments, the method comprises contacting an isolated 4HB polypeptide comprising a non-naturally encoded amino acid with a water soluble polymer comprising a moiety that reacts with the non-naturally encoded amino acid. In some embodiments, the non-naturally encoded amino acid incorporated into the 4HB polypeptide is reactive toward a water soluble polymer that is otherwise unreactive toward any of the 20 common amino acids. In some embodiments, the non-naturally encoded amino acid incorporated into the 4HB polypeptide is reactive toward a linker, polymer, or biologically active molecule that is otherwise unreactive toward any of the 20 common amino acids.

In some embodiments, the 4HB polypeptide linked to the water soluble polymer is made by reacting a 4HB polypeptide comprising a carbonyl-containing amino acid with a poly(ethylene glycol) molecule comprising an aminooxy, hydrazine, hydrazide or semicarbazide group. In some embodiments, the aminooxy, hydrazine, hydrazide or semicarbazide group is linked to the poly(ethylene glycol) molecule through an amide linkage.

In some embodiments, the 4HB polypeptide linked to the water soluble polymer is made by reacting a poly(ethylene glycol) molecule comprising a carbonyl group with a polypeptide comprising a non-naturally encoded amino acid that comprises an aminooxy, hydrazine, hydrazide or semicarbazide group.

In some embodiments, the 4HB polypeptide linked to the water soluble polymer is made by reacting a 4HB polypeptide comprising an alkyne-containing amino acid with a poly(ethylene glycol) molecule comprising an azide moiety. In some embodiments, the azide or alkyne group is linked to the poly(ethylene glycol) molecule through an amide linkage.

In some embodiments, the 4HB polypeptide linked to the water soluble polymer is made by reacting a 4HB polypeptide comprising an azide-containing amino acid with a poly(ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some embodiments, the water soluble polymer linked to the 4HB polypeptide comprises a polyalkylene glycol moiety. In some embodiments, the non-naturally encoded amino acid residue incorporated into the 4HB polypeptide comprises a carbonyl group, an aminooxy group, a hydrazide group, a hydrazine, a semicarbazide group, an azide group, or an alkyne group. In some embodiments, the non-naturally encoded amino acid residue incorporated into the 4HB polypeptide comprises a carbonyl moiety and the water soluble polymer comprises an aminooxy, hydrazide, hydrazine, or semicarbazide moiety. In some embodiments, the non-naturally encoded amino acid residue incorporated into the 4HB polypeptide comprises an alkyne moiety and the water soluble polymer comprises an azide moiety. In some embodiments, the non-naturally encoded amino acid residue incorporated into the 4HB polypeptide comprises an azide moiety and the water soluble polymer comprises an alkyne moiety.

The present invention also provides compositions comprising a 4HB polypeptide comprising a non-naturally-encoded amino acid and a pharmaceutically acceptable carrier. In some embodiments, the non-naturally encoded amino acid is linked to a water soluble polymer.

The present invention also provides cells comprising a polynucleotide encoding the 4HB polypeptide comprising a selector codon. In some embodiments, the cells comprise an orthogonal RNA synthetase and/or an orthogonal tRNA for substituting a non-naturally encoded amino acid into the 4HB polypeptide.

The present invention also provides methods of making a 4HB polypeptide comprising a non-naturally encoded amino acid. In some embodiments, the methods comprise culturing cells comprising a polynucleotide or polynucleotides encoding a 4HB polypeptide, an orthogonal RNA synthetase and/or an orthogonal tRNA under conditions to permit expression of the 4HB polypeptide; and purifying the 4HB polypeptide from the cells and/or culture medium.

The present invention also provides methods of increasing therapeutic half-life, serum half-life or circulation time of 4HB polypeptides. The present invention also provides methods of modulating immunogenicity of 4HB polypeptides. In some embodiments, the methods comprise substituting a non-naturally encoded amino acid for any one or more amino acids in naturally occurring 4HB polypeptides and/or linking the 4HB polypeptide to a linker, a polymer, a water soluble polymer, or a biologically active molecule.

The present invention also provides methods of treating a patient in need of such treatment with an effective amount of a 4HB molecule of the present invention. In some embodiments, the methods comprise administering to the patient a therapeutically-effective amount of a pharmaceutical composition comprising a 4HB polypeptide comprising a non-naturally-encoded amino acid and a pharmaceutically acceptable carrier. In some embodiments, the non-naturally encoded amino acid is linked to a water soluble polymer.

The present invention also provides 4HB polypeptides comprising a sequence shown in SEQ ID NO: 1, 2, 3, or any other GH polypeptide sequence, SEQ ID NO: 23, 24, 25 or any other hIFN polypeptide sequence, SEQ ID NO: 28, 29, 30, 35, 36, or any other hG-CSF polypeptide sequence, SEQ ID NO: 37, 38, 39, or any other hEPO polypeptide sequence, except that at least one amino acid is substituted by a non-naturally encoded amino acid. In some embodiments, the non-naturally encoded amino acid is linked to a water soluble polymer. In some embodiments, the water soluble polymer comprises a poly(ethylene glycol) moiety. In some embodiments, the non-naturally encoded amino acid comprises a carbonyl group, an aminooxy group, a hydrazide group, a hydrazine group, a semicarbazide group, an azide group, or an alkyne group. In some embodiments, the non-naturally encoded amino acid is substituted at a position selected from the group consisting of residues 1-5, 82-90, 117-134, and 169-176 from SEQ ID NO: 3 (hGH). In some embodiments, the non-naturally encoded amino acid is substituted at a position selected from the group consisting of residues including but not limited to, 1-16, 30-109, 125-175 as in SEQ ID NO: 29 (G-CSF), or the corresponding amino acid position of SEQ ID NO: 28, 30, 35, or 36. In some embodiments, the non-naturally encoded amino acid is substituted at a position selected from the group consisting of residues including but not limited to 1-6, 21-40, 68-89, 116-136, 162-166 from SEQ ID NO: 38 (EPO), or SEQ ID NO: 39, or the corresponding amino acid position of SEQ ID NO: 37.

The present invention also provides pharmaceutical compositions comprising a pharmaceutically acceptable carrier and a 4HB polypeptide comprising the sequence shown in SEQ ID NO: 1, 2, 3, or any other GH polypeptide sequence, SEQ ID NO: 23, 24, 25 or any other IFN polypeptide sequence, SEQ ID NO: 28, 29, 30, 35, 36, or any other G-CSF polypeptide sequence, SEQ ID NO: 37, 38, 39 or any other EPO polypeptide sequence, wherein at least one amino acid is substituted by a non-naturally encoded amino acid. In some embodiments, the non-naturally encoded amino acid comprises a saccharide moiety. In some embodiments, the water soluble polymer is linked to the polypeptide via a saccharide moiety. In some embodiments, a linker, polymer, or biologically active molecule is linked to the 4HB polypeptide via a saccharide moiety.

The present invention also provides a 4HB polypeptide comprising a water soluble polymer linked by a covalent bond to the polypeptide at a single amino acid. In some embodiments, the water soluble polymer comprises a poly (ethylene glycol) moiety. In some embodiments, the amino acid covalently linked to the water soluble polymer is a non-naturally encoded amino acid present in the polypeptide.

The present invention provides a polypeptide comprising at least one linker, polymer, or biologically active molecule, wherein said linker, polymer, or biologically active molecule is attached to the polypeptide through a functional group of a non-naturally encoded amino acid ribosomally incorporated into the polypeptide. In some embodiments, the polypeptide is monoPEGylated. The present invention also provides a polypeptide comprising a linker, polymer, or biologically active molecule that is attached to one or more non-naturally encoded amino acid wherein said non-naturally encoded amino acid is ribosomally incorporated into the polypeptide at pre-selected sites.

BRIEF DESCRIPTION OF THE DRAWINGS

FIG. 7, Panels A and B—A diagram of the biological activity of the hGH comprising a non-naturally encoded amino acid (Panel B) and wild-type hGH (Panel A) on IM9 cells is shown.

FIG. 10, Panel A—This figure depicts the primary structure of hGH with the trypsin cleavage sites indicated and the non-natural amino acid substitution, F92pAF, specified with an arrow (Figure modified from Becker et al. Biotechnol Appl Biochem. (1988) 10(4):326-337). FIG. 10, Panel B—Superimposed tryptic maps are shown of peptides generated from a hGH polypeptide comprising a non-naturally encoded amino acid that is PEGylated (labeled A), peptides generated from a hGH polypeptide comprising a non-naturally encoded amino acid (labeled B), and peptides generated from WHO rhGH (labeled C). FIG. 10, Panel C—A magnification of peak 9 from Panel B is shown.

FIG. 11, Panel A and Panel B show Coomassie blue stained SDS-PAGE analysis of purified PEG-hGH polypeptides.

FIG. 12—A diagram of the biological activity of a hGH dimer molecule on IM9 cells is shown.

FIG. 13, Panel A—A diagram is shown of the IM-9 assay data measuring phosphorylation of pSTAT5 by hGH antagonist with the G120R substitution. FIG. 13, Panel B—A diagram is shown of the IM-9 assay data measuring phosphorylation of pSTAT5 by a hGH polypeptide with a non-natural amino acid incorporated at the same position (G120).

FIG. 18, Panel A—A diagram is shown of the effect on rat body weight gain after administration of a single dose of hGH polypeptides comprising a non-naturally encoded amino acid that is PEGylated (position 35, 92). FIG. 18, Panel B—A diagram is shown of the effect on circulating plasma IGF-1 levels after administration of a single dose of hGH polypeptides comprising a non-naturally encoded amino acid that is PEGylated (position 35, 92). FIG. 18, Panel C—A diagram is shown of the effect on rat body weight gain after administration of a single dose of hGH polypeptides comprising a non-naturally encoded amino acid that is PEGylated (position 92, 134, 145, 131, 143). FIG. 18, Panel D—A diagram is shown of the effect on circulating plasma IGF-1 levels after administration of a single dose of hGH polypeptides comprising a non-naturally encoded amino acid that is PEGylated (position 92, 134, 145, 131, 143). FIG. 18, Panel E—A diagram is shown comparing the serum half-life in rats of hGH polypeptides comprising a non-naturally encoded amino acid that is PEGylated (position 92, 134, 145, 131, 143).

DEFINITIONS

Figure 1:
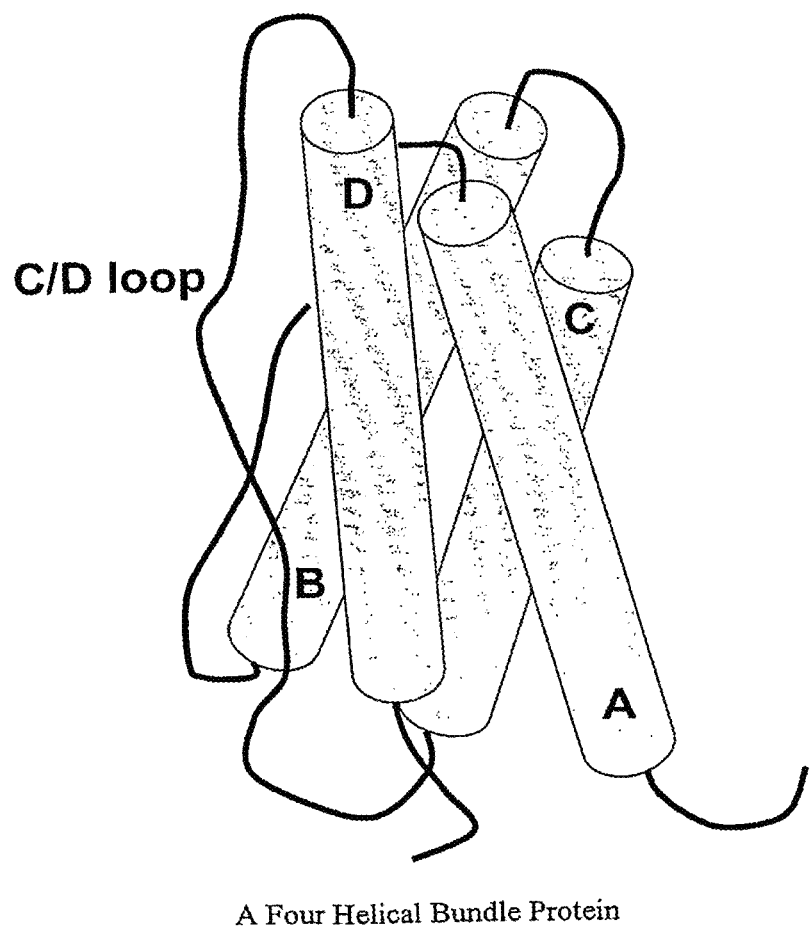
FIG. 1—A diagram of the general structure for four helical bundle (4HB) proteins is shown.
Figure 2:
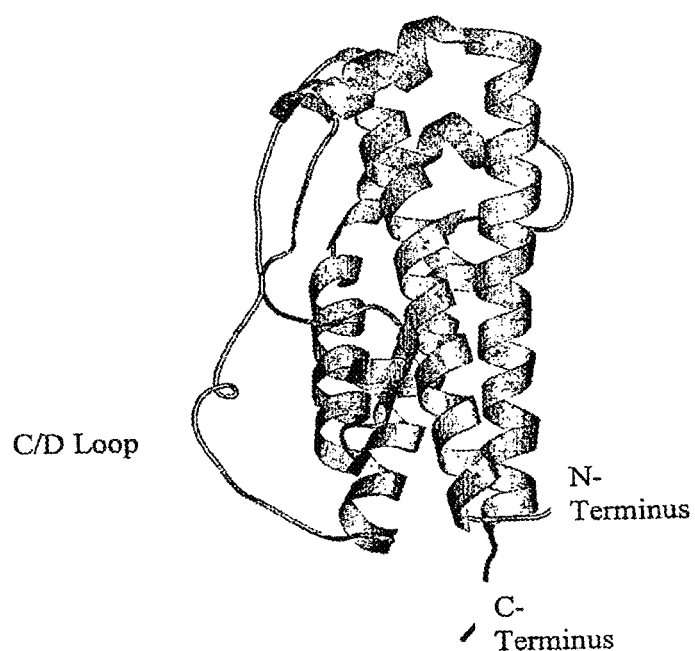
FIG. 2—A diagram of the general structure for the four helical bundle protein Growth Hormone (GH) is shown.
Figure 3:
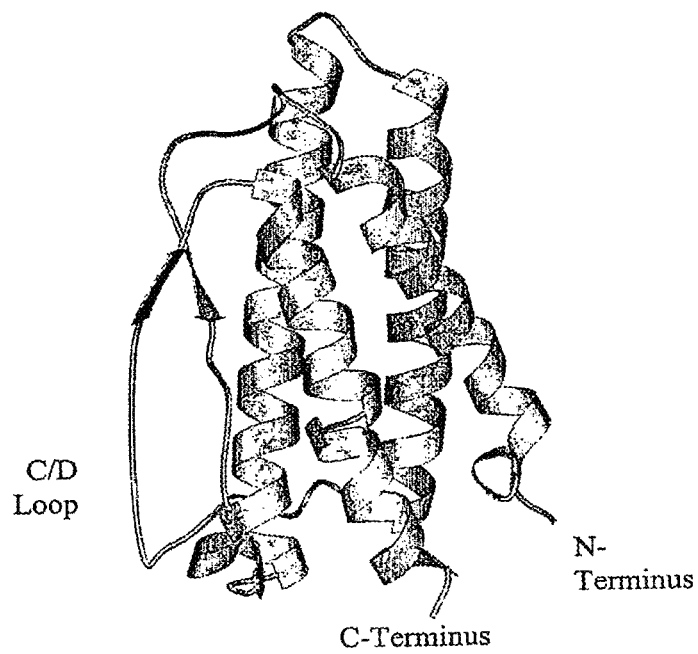
FIG. 3—A diagram of the general structure for the four helical bundle protein Erythropoietin (EPO) is shown.
Figure 4:
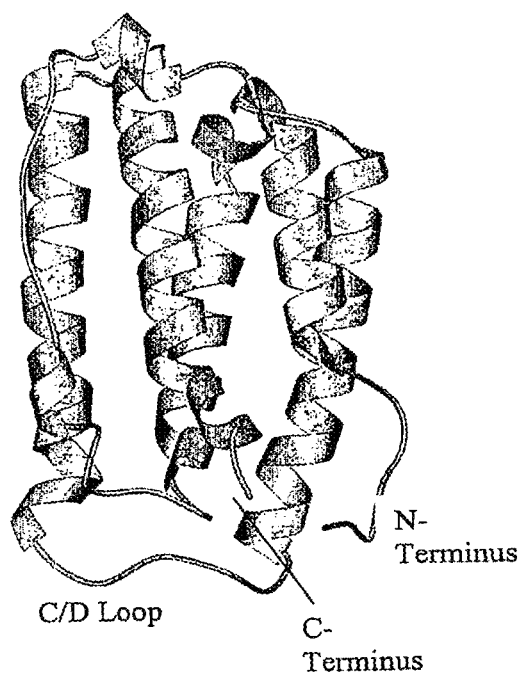
FIG. 4—A diagram of the general structure for the four helical bundle protein Interferon alpha-2 (IFNα-2) is shown.
Figure 5:
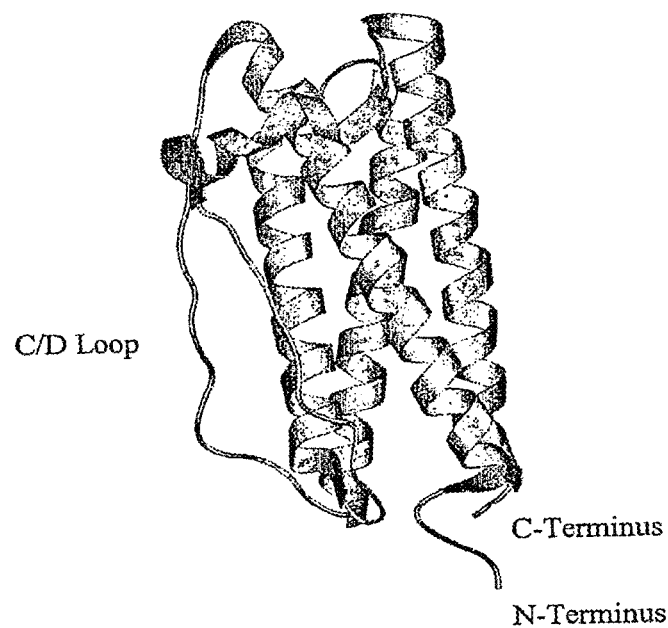
FIG. 5—A diagram of the general structure for the four helical bundle protein Granulocyte Colony Stimulating Factor (G-CSF) is shown.

It is to be understood that this invention is not limited to the particular methodology, protocols, cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "hGH", a "hIFN", a "G-CSF", or a "hEPO" is a reference to one or more such proteins and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to a 4HB polypeptide that may be substantially or essentially free of components that normally accompany or interact with the protein as found in its naturally occurring environment, i.e. a native cell, or host cell in the case of recombinantly produced 4HB polypeptides. 4HB polypeptide that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the 4HB polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the 4HB polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/b, or about 1 mg/L or less of the dry weight of the cells. Thus, "substantially purified" 4HB polypeptide as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells or *E. coli*, and cell contents. Thus, the term may encompass medium in which the host cell has been grown, e.g., medium into which the 4HB polypeptide has been secreted, including medium either before or after a proliferation step. The term also may encompass buffers or reagents that contain host cell lysates, such as in the case where the 4HB polypeptide is produced intracellularly and the host cells are lysed or disrupted to release the 4HB polypeptide.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used hereinwith respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N→2, 3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

The terms "four helical bundle polypeptide", "4HB polypeptide", and "4HB" as used herein refers to any of the known, and those that become known, polypeptides or proteins of the GH supergene family. These terms include, but are not limited to, hGH polypeptides, hIFN polypeptides, hG-CSF polypeptides, hEPO polypeptides, and further encompasses any other GH supergene family members including those comprising one or more amino acid substitutions, additions, or deletions as well as variants, fusions, mutants, fragments, agonists, antagonists, dimers, multimers, polypeptides covalently bound to polymers, polypeptides that share 90% or greater amino acid sequence identity to a GH supergene family member, and polypeptides that possess the four helical bundle structure. The terms include plural reference unless the context clearly indicates otherwise.

As used herein, "growth hormone" or "GH" shall include those polypeptides and proteins that have at least one biological activity of a human growth hormone, as well as GH analogs, GH isoforms, GH mimetics, GH fragments, hybrid GH proteins, fusion proteins oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods.

The term "hGH polypeptide" encompasses hGH polypeptides comprising one or more amino acid substitutions, additions or deletions. Exemplary substitutions include, e.g., substitution of the lysine at position 41 or the phenylalanine at position 176 of native hGH. In some cases, the substitution may be an isoleucine or arginine residue if the substitution is at position 41 or is a tyrosine residue if the position is 176. Position F10 can be substituted with, e.g., A, H or I. Position M14 may be substituted with, e.g., W, Q or G. Other exemplary substitutions include any substitutions or combinations thereof, including but not limited to:

R167N, D171S, E174S, F176Y, I179T;
R167E, D171S, E174S, F176Y;
F10A, M14W, H18D, H21N;
F10A, M14W, H18D, H21N, R167N, D171S, E174S, F176Y, I179T;
F10A, M14W, H18D, $H_{21}$N, R167N, D171A, E174S, F176Y, I179T;
F10H, M14G, $H_{18}$N, $H_{21}$N;
F10A, M14W, H18D, $H_{21}$N, R167N, D171A, T175T, I179T; or
F10I, M14Q, H18E, R167N, D171S, I179T. See, e.g., U.S. Pat. No. 6,143,523, which is incorporated by reference herein.

Exemplary substitutions in a wide variety of amino acid positions in naturally-occurring hGH have been described, including substitutions that increase agonist activity, increase protease resistance, convert the polypeptide into an antagonist, etc. and are encompassed by the term "hGH polypeptide."

Agonist hGH sequences include, e.g., the naturally-occurring hGH sequence comprising the following modifications H18D, $H_{21}$N, R167N, D171S, E174S, I179T. See, e.g., U.S. Pat. No. 5,849,535, which is incorporated by reference herein. Additional agonist hGH sequences include H18D, Q22A, F25A, D26A, Q29A, E65A, K168A, E174S;
H18A, Q22A, F25A, D26A, Q29A, E65A, K168A, E174S; or
H18D, Q22A, F25A, D26A, Q29A, E65A, K168A, E174A. See, e.g. U.S. Pat. No. 6,022,711, which is incorporated by reference herein. hGH polypeptides comprising substitutions at H18A, Q22A, F25A, D26A, Q29A, E65A, K168A, E174A enhance affinity for the hGH receptor at site I. See, e.g. U.S. Pat. No. 5,854,026, which is incorporated by reference herein. hGH sequences with increased resistance to proteases include, but are not limited to, hGH polypeptides comprising one or more amino acid substitutions within the C-D loop. In some embodiments, substitutions include, but are not limited to, R134D, T135P, K140A, and any combination thereof. See, e.g., Alam et al. (1998) *J. Biotechnol.* 65:183-190.

Human Growth Hormone antagonists include, e.g., those with a substitution at G120 (e.g., G120R, G120K, G120W, G120Y, G120F, or G120E) and sometimes further including the following substitutions: H18A, Q22A, F25A, D26A, Q29A, E65A, K168A, E174A. See, e.g. U.S. Pat. No. 6,004, 931, which is incorporated by reference herein. In some embodiments, hGH antagonists comprise at least one substitution in the regions 106-108 or 127-129 that cause GH to act as an antagonist. See, e.g., U.S. Pat. No. 6,608,183, which is incorporated by reference herein. In some embodiments, the hGH antagonist comprises a non-naturally encoded amino acid linked to a water soluble polymer that is present in the Site II binding region of the hGH molecule. In some embodiments, the hGH polypeptide further comprises the following substitutions: H18D, H$_{21}$N, R167N, K168A, D171S, K172R, E174S, I179T with a substitution at G120. (See, e.g, U.S. Pat. No. 5,849,535)

For the complete full-length naturally-occurring GH amino acid sequence as well as the mature naturally-occurring GH amino acid sequence and naturally occurring mutant, see SEQ ID NO: 1, SEQ ID NO: 2 and SEQ ID NO: 3, respectively, herein. In some embodiments, hGH polypeptides of the invention are substantially identical to SEQ ID NO: 1, or SEQ ID NO: 2, or SEQ ID NO: 3 or any other sequence of a growth hormone polypeptide. A number of naturally occurring mutants of hGH have been identified. These include hGH-V (Seeberg, *DNA* 1: 239 (1982); U.S. Pat. Nos. 4,446,235, 4,670,393, and 4,665,180, which are incorporated by reference herein) and a 20-kDa hGH containing a deletion of residues 32-46 of hGH (SEQ ID NO: 3) (Kostyo et al., *Biochem. Biophys. Acta* 925: 314 (1987); Lewis, U., et al., *J. Biol. Chem.*, 253:2679-2687 (1978)). Placental growth hormone is described in Igout, A., et al., *Nucleic Acids Res.* 17(10):3998 (1989)). In addition, numerous hGH variants, arising from post-transcriptional, post-translational, secretory, metabolic processing, and other physiological processes, have been reported including proteolytically cleaved or 2 chain variants (Baumann, G., *Endocrine Reviews* 12: 424 (1991)). hGH dimers linked directly via Cys-Cys disulfide linkages are described in Lewis, U. J., et al., *J. Biol. Chem.* 252:3697-3702 (1977); Brostedt, P. and Roos, P., *Prep. Biochem.* 19:217-229 (1989)). Nucleic acid molecules encoding hGH mutants and mutant hGH polypeptides are well known and include, but are not limited to, those disclosed in U.S. Pat. Nos. 5,534,617; 5,580,723; 5,688,666; 5,750,373; 5,834,250; 5,834,598; 5,849,535; 5,854,026; 5,962,411; 5,955,346; 6,013,478; 6,022,711; 6,136,563; 6,143,523; 6,428,954; 6,451,561; 6,780,613 and U.S. Patent Application Publication 2003/0153003; which are incorporated by reference herein.

Commercial preparations of hGH are sold under the names: Humatrope™ (Eli Lilly & Co.), Nutropin™ (Genentech), Norditropin™ (Novo-Nordisk), Genotropin™ (Pfizer) and Saizen/Serostim™ (Serono).

The term "hGH polypeptide" also includes the pharmaceutically acceptable salts and prodrugs, and prodrugs of the salts, polymorphs, hydrates, solvates, biologically-active fragments, biologically active variants and stereoisomers of the naturally-occurring hGH as well as agonist, mimetic, and antagonist variants of the naturally-occurring hGH and polypeptide fusions thereof. Fusions comprising additional amino acids at the amino terminus, carboxyl terminus, or both, are encompassed by the term "hGH polypeptide." Exemplary fusions include, but are not limited to, e.g., methionyl growth hormone in which a methionine is linked to the N-terminus of hGH resulting from the recombinant expression, fusions for the purpose of purification (including, but not limited to, to poly-histidine or affinity epitopes), fusions with serum albumin binding peptides and fusions with serum proteins such as serum albumin.

As used herein, "interferon" or "IFN" shall include those polypeptides and proteins that have at least one biological activity of a human interferon, including but not limited to IFNα, IFNβ, IFN-γ, IFNω, IFNε, or IFNτ (such as those described in U.S. Pat. Nos. 4,414,150; 4,456,748; 4,727,138; 4,762,791; 4,929,554; 5,096,705; 4,695,623; 4,614,651; 4,678,751; 4,925,793; 5,460,811; 5,120,832; 4,780,530; 4,908,432; 4,970,161; 4,973,479; 4,975,276; 5,098,703; 5,278,286; 5,661,009; 6,372,206; 6,433,144; 6,472,512; 6,572,853; 6,703,225; 6,200,780; 6,299,869; 6,300,475; 6,323,006; 6,350,589; 5,705,363; 5,738,845; 5,789,551; 6,117,423; 6,174,996; 5,540,923; 5,541,293; 5,541,312; 5,554,513; 5,593,667 which are incorporated by reference herein), as well as IFN analogs, IFN isoforms, IFN mimetics, IFN fragments, hybrid IFN proteins, fusion proteins oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods. Specific examples of IFN include, but are not limited to, IFNγ-1b (Actimmune®), IFNβ-1a (Avonex®, and Rebif®), IFNβ-1b (Betaseron®), consensus IFN, IFN alfacon-1 (Infergen®), IFNα-2 (Intron A®), IFNα-2a (Roferon-A®), Peginterferon alfa-2a (Pegasys®), Peginterferon alfa-2b (PEG-Intron®), IFN analog, IFN mutants, altered glycosylated human IFN, and PEG conjugated IFN analogs. Specific examples of cells modified for expression of endogenous human IFN are described in Devlin et al., J. Leukoc. Biol. 41:306 (1987); U.S. Pat. Nos. 6,716, 606; 6,610,830; 6,482,613; 6,489,144; 6,159,712; 5,814,485; 5,710,027; 5,595,888; 4,966,843; 6,379,661; 6,004,548; 5,830,705; 5,582,823; 4,810,643; and 6,242,218; which are incorporated by reference herein.

The term "human IFN (hIFN)" or "hIFN polypeptide" refers to interferon or IFN as described above, as well as a polypeptide that retains at least one biological activity of a naturally-occurring hIFN. hIFN polypeptides include the pharmaceutically acceptable salts and prodrugs, and prodrugs of the salts, polymorphs, hydrates, solvates, biologically-active fragments, biologically-active variants and stereoisomers of the naturally-occurring human IFN as well as agonist, mimetic, and antagonist variants of the naturally-occurring human IFN and polypeptide fusions thereof. Examples of hIFN polypeptides include, but are not limited to, those described in U.S. Pat. Nos. 4,604,284; 5,582,824; 6,531,122; 6,204,022; 6,120,762; 6,046,034; 6,036,956; 5,939,286; 5,908,626; 5,780,027; 5,770,191; 5,723,125; 5,594,107; 5,378,823; 4,898,931; 4,892,743, which are incorporated by reference herein. Fusions comprising additional amino acids at the amino terminus, carboxyl terminus, or both, are encompassed by the term "hIFN polypeptide." Exemplary fusions include, but are not limited to, e.g., methionyl IFN in which a methionine is linked to the N-terminus of hIFN resulting from the recombinant expression of the mature form of hIFN lacking the secretion signal peptide or portion thereof, fusions for the purpose of purification (including but not limited to, to poly-histidine or affinity epitopes), fusions with serum albumin binding peptides and fusions with serum proteins such as serum albumin. The naturally-occurring hIFN nucleic acid and amino acid sequences for full-length and mature forms are known, as are variants such as single amino acid variants or splice variants.

Consensus interferon is a recombinant type 1 interferon containing 166 amino acids. Consensus IFN was derived by scanning the sequences of several natural alpha interferons and assigning the most frequently observed amino acid in each corresponding position. Consensus IFN, when compared on an equal mass basis with IFNα-2a and α-2b in in vitro assays, typically displays 5-10 times higher biological activity (Blatt et al. J. Interferon Cytokine Res. 1996; 16:489-99).

For the complete full-length naturally-occurring IFNα-2a amino acid sequence as well as the mature naturally-occurring IFNα-2a amino acid sequence, see SEQ ID NO: 23, and SEQ ID NO: 24, respectively, herein. In some embodiments, hIFN polypeptides of the invention are substantially identical to SEQ ID NO: 23, SEQ ID NO: 24, SEQ ID NO: 25, or any other sequence of an interferon polypeptide. Nucleic acid molecules encoding hIFN mutants and mutant hIFN polypeptides are well known and include, but are not limited to, those disclosed in U.S. Pat. Nos. 6,331,525; 6,069,133; 5,955,307; 5,869,293; 5,831,062; 5,081,022; 5,004,689; 4,738,931; 4,686,191; which are incorporated by reference herein. Examples of hIFN mutants include those disclosed in U.S. Pat. Nos. 6,514,729 and 5,582,824, which are incorporated by reference herein.

Interferons have a variety of biological activities, including anti-viral, immunoregulatory and anti-proliferative properties, and have been utilized as therapeutic agents for treatment of diseases such as cancer, and various viral diseases. Interferon-α's have been shown to inhibit various types of cellular proliferation, and are especially useful for the treatment of a variety of cellular proliferation disorders frequently associated with cancer, particularly hematologic malignancies such as leukemias. These proteins have shown anti-proliferative activity against multiple myeloma, chronic lymphocytic leukemia, low-grade lymphoma, Kaposi's sarcoma, chronic myelogenous leukemia, renal-cell carcinoma, urinary bladder tumors and ovarian cancers (Bonnem, E. M. et al. (1984) J. Biol. Response Modifiers 3:580; Oldham, R. K. (1985) Hospital Practice 20:71).

IFNα's are useful against various types of viral infections (Finter, N. B. et al. (1991) Drugs 42(5):749). Interferon-α's have shown activity against human papillomavirus infection, Hepatitis B, and Hepatitis C infections (Finter, N. B. et al., 1991, supra; Kashima, H. et al. (1988) Laryngoscope 98:334; Dusheiko, G. M. et al. (1986) J. Hematology 3 (Supple. 2):S199; Davis, G L et al. (1989) N. England J. Med. 321: 1501). The role of interferons and interferon receptors in the pathogenesis of certain autoimmune and inflammatory diseases has also been investigated (Benoit, P. et al. (1993) J. Immunol. 150(3):707). In addition, interferon-α has been approved for use for the treatment of diseases such as hairy cell leukemia, renal cell carcinoma, basal cell carcinoma, malignant melanoma, AIDS-related Kaposi's sarcoma, multiple myeloma, chronic myelogenous leukemia, non-Hodgkin's lymphoma, laryngeal papillomatosis, mycosis fungoides, condyloma acuminata, chronic hepatitis B, hepatitis C, chronic hepatitis D, and chronic non-A, non-B/C hepatitis.

Interferons have been implicated in the pathogenesis of various autoimmune diseases, such as systemic lupus erythematoses, Beheet's disease, and insulin-dependent diabetes mellitus (IDDM, also referred to as type I diabetes). It has been demonstrated in a transgenic mouse model that β cell expression of IFN-α can cause insulitis and IDDM, and IFN-α antagonists (including antibodies) have been proposed for the treatment of IDDM (WO 93/04699, published Mar. 18, 1993). Impaired IFN-γ and IFN-α production has been observed in multiple sclerosis (MS) patients. IFN-α has been detected in the serum of many AIDS patients, and it has been reported that the production of IFN-γ is greatly suppressed in suspensions of mitogen-stimulated mononuclear cells derived from AIDS patients. For a review see, for example, Chapter 16, "The Presence and Possible Pathogenic Role of Interferons in Disease", In: Interferons and other Regulatory Cytokines, Edward de Maeyer (1988, John Wiley and Sons publishers). Alpha and beta interferons have been used in the treatment of the acute viral disease herpes zoster (T. C. Merigan et al, N. Engl. J. Med. 298, 981-987 (1978); E. Heidemann et al., Onkologie 7, 210-212 (1984)), chronic viral infections, e.g. hepatitis C and hepatitis B infections (R. L. Knobler et al., Neurology 34, 1273078 (1984); M. A. Faerkkilae et al., Act. Neurol. Sci. 69, 184-185 (1985)). rIFNα-2a (Roferon®, Roche) is an injection formulation indicated in use for the treatment of hairy cell leukemia and AIDS-related Kaposi's sarcoma. Recombinant IFNα-2b (Litron A™, Schering) has been approved for the treatment of hairy cell leukemia, selected cases of condylomata acuminata, AIDS-related Kaposi's sarcoma, chronic hepatitis C, and chronic hepatitis B infections in certain patients. Compositions of multiple subtypes of IFNα are also used to treat a variety of diseases (Multiferon®, Viragen, Inc.). IFNγ1b (Actimmune®, Intermune Pharmaceuticals, Inc.) is commercially available for the treatment of chronic granulomatous disease and malignant osteopetrosis.

The biologic activities of type I IFNs have been disclosed and are known in the art, and can be found, for example, in Pfeffer, Semin. Oncol. 24 (suppl 9), S9-63-S9-69 (1997) and U.S. Pat. Nos. 6,436,391; 6,372,218; 6,270,756; 6,207,145; 6,086,869; 6,036,949; 6,013,253; 6,007,805; 5,980,884; 5,958,402; 5,863,530; 5,849,282; 5,846,526; 5,830,456; 5,824,300; 5,817,307; 5,780,021; 5,624,895; 5,480,640; 5,268,169; 5,208,019; 5,196,191; 5,190,751; 5,104,653; 5,019,382; 5,959,210; which are incorporated by reference herein.

IFNα's are members of the diverse helical-bundle superfamily of cytokine genes (Sprang, S. R. et al. (1993) Curr. Opin. Struct. Biol. 3:815-827). The human interferon α's are encoded by a family of over 20 tandemly duplicated nonallelic genes that share 85-98% sequence identity at the amino acid level (Henco, K. et al. (1985) J. Mol. Biol. 185:227-260). Human IFNβ is a regulatory polypeptide with a molecular weight of about 22 kDa consisting of 166 amino acid residues. It can be produced by most cells in the body, in particular fibroblasts, in response to viral infection or exposure to other agents. It binds to a multimeric cell surface receptor, and productive receptor binding results in a cascade of intracellular events leading to the expression of IFNβ inducible genes which in turn produces effects which can be classified as anti-viral, anti-proliferative and immunomodulatory.

The amino acid sequence of human IFNβ is known and was reported for example by Taniguchi, Gene 10:11-15, 1980, and in EP 83069, EP 41313 and U.S. Pat. No. 4,686,191 which are incorporated by reference herein. Crystal structures have been reported for human and murine IFNβ, respectively (Proc. Natl. Acad. Sci. USA 94:11813-11818, 1997; J. Mol. Biol. 253:187-207, 1995; U.S. Pat. Nos. 5,602,232; 5,460,956; 5,441,734; 4,672,108; which are incorporated by reference herein). They have been reviewed in Cell Mol. Life Sci. 54:1203-1206, 1998. Variants of IFN)β have been reported (WO 95/25170, WO 98/48018, U.S. Pat. No. 5,545,723, U.S. Pat. No. 4,914,033, EP 260350, U.S. Pat. No. 4,588,585, U.S. Pat. No. 4,769,233, Stewart et al, DNA Vol. 6 no. 2 1987 pp. 119-128, Runkel et al, 1998, J. Biol. Chem. 273, No. 14, pp. 8003-8008, which are incorporated by reference herein). Expression of IFNβ in CHO cells has been reported (U.S. Pat. No. 4,966,843, U.S. Pat. No. 5,376,567 and U.S. Pat. No. 5,795,779, which are incorporated by reference herein). IFNβ molecules with a particular glycosylation pattern and methods for their preparation have been reported (EP 287075 and EP 529300).

Commercial preparations of IFNβ are sold under the names Betaseron® (also termed interferon β1b, which is non-glycosylated, produced using recombinant bacterial cells, has a deletion of the N-terminal methionine residue and the C17S mutation), and Avonex™ and Rebif® (also termed interferon β1a, which is glycosylated, produced using recombinant mammalian cells) for treatment of patients with multiple sclerosis, have shown to be effective in reducing the exacerbation rate, and more patients remain exacerbation-free for prolonged periods of time as compared with placebo-treated patients. Furthermore, the accumulation rate of disability is reduced (Neurol. 51:682-689, 1998).

Comparison of IFNβ1a and β1b with respect to structure and function has been presented in Pharmaceut. Res. 15:641-649, 1998. IFNβ has been shown to delay the progression of multiple sclerosis, a relapsing then progressive inflammatory degenerative disease of the central nervous system. IFNβ may have inhibitory effects on the proliferation of leukocytes and antigen presentation. IFNβ may modulate the profile of cytokine production towards an anti-inflammatory phenotype. IFNβ can reduce T-cell migration by inhibiting the activity of T-cell matrix metalloproteases. These activities are likely to act in concert to account for the mechanism of IFNβ in MS (Neurol. 51:682-689, 1998).

IFNβ may be used for the treatment of osteosarcoma, basal cell carcinoma, cervical dysplasia, glioma, acute myeloid leukemia, multiple myeloma, Hodgkin's disease, breast carcinoma, melanoma, and viral infections such as papilloma virus, viral hepatitis, herpes genitalis, herpes zoster, herpetic keratitis, herpes simplex, viral encephalitis, cytomegalovirus pneumonia, and rhinovirus, Various side effects are associated with the use of current preparations of IFNβ, including injection site reactions, fever, chills, myalgias, arthralgias, and other flu-like symptoms (Clin. Therapeutics, 19:883-893, 1997).

Given the multitude of side effects with current IFNβ products, their association with frequent injection, the risk of developing neutralizing antibodies impeding the desired therapeutic effect of IFNβ, and the potential for obtaining more optimal therapeutic IFNβ levels with concomitant enhanced therapeutic effect, there is clearly a need for improved IFNβ-like molecules.

As used herein, "granulocyte colony stimulating factor" or "G-CSF" shall include those polypeptides and proteins that have at least one biological activity of human hG-CSF (such as those described in U.S. Pat. Nos. 6,716,606; 6,689,351; 6,565,841; 6,162,426; 5,811,301; 5,776,895; 5,718,893; 5,580,755; 5,536,495; 5,202,117; 5,043,156; 4,999,291; 4,810,643; and 4,968,618 which are incorporated by reference herein), as well as G-CSF analogs, G-CSF isoforms, G-CSF mimetics, G-CSF fragments, hybrid G-CSF proteins, fusion proteins oligomers and multimers, homologues, glycosylation pattern variants, and muteins, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods. Specific examples of G-CSF include, but are not limited to, peg-filgrastim (NEULASTA®), filgrastim (NREUPOGEN®), G-CSF analog, G-CSF mutants, altered glycosylated human G-CSF, and PEG conjugated G-CSF analogs. Specific examples of cell lines modified for expression of endogenous human G-CSF are described in Devlin et al., J. Leukoc. Biol. 41:306 (1987); U.S. Pat. Nos. 6,716,606; 6,379,661; 6,004,548; 5,830,705; 5,582,823; 4,810,643; and 6,242,218, which are incorporated by reference herein.

The term "human G-CSF (hG-CSF)" or "hG-CSF polypeptide" refers to granulocyte colony stimulating factor or G-CSF as described above, as well as a polypeptide that retains at least one biological activity of naturally-occurring hG-CSF. hG-CSF polypeptides include the pharmaceutically acceptable salts and prodrugs, and prodrugs of the salts, polymorphs, hydrates, solvates, biologically-active fragments, biologically-active variants and stereoisomers of the naturally-occurring human G-CSF as well as agonist, mimetic, and antagonist variants of the naturally-occurring human G-CSF and polypeptide fusions thereof. Examples of hG-CSF polypeptides and mimetics include those described in U.S. Pat. Nos. 6,716,606; 6,689,351; 6,565,841; 6,162,426; 5,824,784; 5,811,301; 5,776,895; 5,718,893; 5,202,117; 5,043,156; 4,968,618; 6,630,470; 6,346,531, which are incorporated by reference herein. Fusions comprising additional amino acids at the amino terminus, carboxyl terminus, or both, are encompassed by the term "hG-CSF polypeptide." Exemplary fusions include, but are not limited to, e.g., methionyl G-CSF in which a methionine is linked to the N-terminus of hG-CSF (such as the polypeptide in SEQ ID NO: 29) resulting from the recombinant expression of the mature form of hG-CSF lacking the secretion signal peptide, fusions for the purpose of purification (including but not limited to, to poly-histidine or affinity epitopes), fusions with serum albumin binding peptides and fusions with serum proteins such as serum albumin. The methionine at position 1 of SEQ ID NO: 29 replaced an alanine found in the naturally occurring mature form of hG-CSF. The naturally-occurring hG-CSF nucleic acid and amino acid sequences for full-length and mature forms are known, as are variants such as single amino acid variants and splice variants. For the complete full-length naturally-occurring hG-CSF amino acid sequence as well as a mature methionyl hG-CSF amino acid sequence, as well as a splice variant, see SEQ ID NO: 28, SEQ ID NO: 29, and SEQ ID NO: 30, respectively, herein. For the naturally-occurring hG-CSF single amino acid sequence variants see SEQ ID NO: 35, and SEQ ID NO: 36 herein. In some embodiments, hG-CSF polypeptides of the invention are substantially identical to SEQ ID NO: 28, SEQ ID NO: 29, SEQ ID NO: 30, SEQ ID NO: 35, or SEQ ID NO: 36. Nucleic acid molecules encoding hG-CSF mutants and mutant hG-CSF polypeptides are known as well. Examples of hG-CSF mutants include those disclosed in U.S. Pat. Nos. 6,489,293; 6,153,407; 6,048,971; 5,614,184; 5,416,195; 5,399,345; and 5,457,089, which are incorporated by reference herein.

Granulocyte colony stimulating factor or hG-CSF has a variety of biological activities including but not limited to binding to its receptor, causing dimerization of its receptor, stimulation of neutrophil production, and stimulating cell proliferation and differentiation. Examples of some of the biological activities of granulocyte colony stimulating factor and hG-CSF are described above and in U.S. Pat. Nos. 6,676,947; 6,579,525; 6,531,121, 6,521,245; 6,489,293; 6,368,854; 6,316,254; 6,268,336; 6,239,109; 6,165,283; 5,986,047; 5,830,851; 5,043,156; and 5,773,569, which are incorporated by reference herein.

Biologically-active fragments/variants of hG-CSF include but are not limited to the gene product containing 207, or 204 (splice variant missing V66, S67, and E68) amino acids, of which the first 30 are cleaved during secretion (Nagata et al. Nature 319:415 (1986); Souza et al., Science 232:61 (1986)).

As used herein, "erythropoietin" or "EPO" shall include those polypeptides and proteins that have at least one biological activity of EPO, as well as human EPO (hEPO), erythropoietin analogs, erythropoietin isoforms (such as those described in U.S. Pat. No. 5,856,298 which is incorporated by reference herein), erythropoietin mimetics (such as those described in U.S. Pat. No. 6,310,078 which is incorporated by reference herein), erythropoietin fragments, hybrid erythropoietin proteins, fusion proteins oligomers and multimers, homologues, glycosylation pattern variants, and muteins, regardless of the biological activity of same, and further regardless of the method of synthesis or manufacture thereof including, but not limited to, recombinant (whether produced from cDNA or genomic DNA), synthetic (U.S. Pat. Nos. 6,552,167, 6,001,364, 6,174,530, 6,217,873, 6,663,869, 6,673,347; WO 00/12587, incorporated by reference herein), transgenic, and gene activated methods. Specific examples of non-human EPO include, but are not limited to, bovine, canine (U.S. Pat. No. 6,696,411), feline, primate (U.S. Pat. Nos. 6,555,343 and 6,831,060), porcine, and equine EPO. See also, Wen et al. "Erythropoietin structure-function relationships: high degree of sequence homology among mammals," Blood, (1993) 82: 1507-1516 for an analysis of EPO sequences from a variety of mammals including horse, pig, cat, and sheep and Lin et al. "Monkey erythropoietin gene: cloning, expression and comparison with the human erythropoietin gene," Gene, (1986) 44(2-3):201-9. All citations are incorporated by reference herein. Specific examples of erythropoietin include, but are not limited to, epoetin alfa (such as those described in U.S. Pat. Nos. 4,667,016; 4,703,008; 5,441,868; 5,547,933; 5,618,698; 5,621,080; 5,756,349; and 5,955,422 which are incorporated by reference herein), darbepoetin alfa (such as described in European patent application EP640619), DYNEPO™ (epoetin delta), human erythropoietin analog (such as the human serum albumin fusion proteins described in International patent application WO99/66054 and U.S. Pat. No. 6,548,653; and U.S. Pat. No. 5,888,772, which are incorporated by reference herein), erythropoietin mutants (such as those described in International patent application WO99/38890, and U.S. Pat. Nos. 6,489,293; 5,888,772; 5,614,184; and 5,457,089 which are incorporated by reference herein), erythropoietin omega (which may be produced from an Apa I restriction fragment of the human erythropoietin gene described in U.S. Pat. Nos. 5,688,679; 6,099,830; 6,316,254; and 6,682,910, which are incorporated by reference herein), altered glycosylated human erythropoietin (such as those described in International patent application WO99/11781 and EP1064951), and PEG conjugated erythropoietin analogs (such as those described in WO98/05363 and U.S. Pat. Nos. 5,643,575; 6,583,272; 6,340,742; and 6,586,398, which are incorporated by reference herein). Specific examples of cell lines modified for expression of endogenous human erythropoietin are described in International patent applications WO99/05268 and WO94/12650 and U.S. Pat. No. 6,376,218 which are incorporated by reference herein.

The term "human Erythropoietin (hEPO)" or "hEPO polypeptide" refers to erythropoietin or EPO as described above, as well as a polypeptide that retains at least one biological activity of naturally-occurring hEPO. hEPO polypeptides include the pharmaceutically acceptable salts and prodrugs, and prodrugs of the salts, polymorphs, hydrates, solvates, biologically-active fragments, biologically-active variants and stereoisomers of the naturally-occurring human Erythropoietin as well as agonist, mimetic, and antagonist variants of the naturally-occurring human Erythropoietin and polypeptide fusions thereof. Examples of hEPO polypeptides and mimetics include those described in U.S. Pat. Nos. 6,310,078; 5,106,954; 6,703,480; 6,642,353; 5,986,047; and 5,712,370, which are incorporated by reference herein. Fusions comprising additional amino acids at the amino terminus, carboxyl terminus, or both, are encompassed by the term "hEPO polypeptide." Exemplary fusions include, but are not limited to, e.g., methionyl erythropoietin in which a methionine is linked to the N-terminus of hEPO, fusions for the purpose of purification (including but not limited to, to polyhistidine or affinity epitopes), fusions with serum albumin binding peptides and fusions with serum proteins such as serum albumin. The naturally-occurring hEPO nucleic acid and amino acid sequences are known. For the complete naturally-occurring hEPO amino acid sequence as well as the mature naturally-occurring hEPO amino acid sequence and a variant of mature EPO, see SEQ ID NO: 37, SEQ ID NO: 38, and SEQ ID NO: 39, respectively, herein. In some embodiments, hEPO polypeptides of the invention are substantially identical to SEQ ID NO: 37, SEQ ID NO: 38 or SEQ ID NO: 39. Nucleic acid molecules encoding hEPO mutants and mutant hEPO polypeptides are known as well. Examples of hEPO mutants include those disclosed in U.S. Pat. Nos. 6,489,293; 6,153,407; 6,048,971; 5,614,184; and 5,457,089, which are incorporated by reference herein.

Erythropoietin or hEPO has a variety of biological activities including but not limited to binding to its receptor, causing dimerization of its receptor, stimulation of red blood cell production, and stimulating cell proliferation. Examples of some of the biological activities of erythropoietin and hEPO are described in U.S. Pat. Nos. 6,676,947; 6,579,525; 6,531,121; 6,521,245; 6,489,293; 6,368,854; 6,316,254; 6,268,336; 6,239,109; 6,165,283; 5,986,047; 5,830,851; and 5,773,569, which are incorporated by reference herein.

Various references disclose modification of polypeptides by polymer conjugation or glycosylation. The term "4HB polypeptide" includes polypeptides conjugated to a polymer such as PEG and may be comprised of one or more additional derivatizations of cysteine, lysine, or other residues. In addition, the 4HB polypeptide may comprise a linker or polymer, wherein the amino acid to which the linker or polymer is conjugated may be a non-natural amino acid according to the present invention, or may be conjugated to a naturally encoded amino acid utilizing techniques known in the art such as coupling to lysine or cysteine.

Polymer conjugation of hGH polypeptides has been reported. See, e.g. U.S. Pat. Nos. 5,849,535, 6,136,563 and 6,608,183, which are incorporated by reference herein. Polymer modification of native IFNβ or a C17S variant thereof has been reported (EP 229108, U.S. Pat. No. 5,382,657; EP 593868; U.S. Pat. No. 4,917,888 and WO 99/55377, which are incorporated by reference herein). U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been substituted with a non-essential amino acid residue located in a specified region of the polypeptide. Examples of PEGylated IFN molecules include those disclosed in U.S. Pat. Nos. 6,524,570; 6,250,469; 6,180,096; 6,177,074; 6,042,822; 5,981,709; 5,951,974; 5,908,621; 5,738,846; 5,711,944; 5,382,657, which are incorporated by reference herein. IFNβ is mentioned as one example of a polypeptide belonging to the growth hormone superfamily. WO 00/23114 discloses glycosylated and pegylated IFNβ. WO 00/23472 discloses IFNβ fusion proteins. WO 00/26354 discloses a method of producing a glycosylated polypeptide variant with reduced allergenicity, which as compared to a corresponding parent polypeptide comprises at least one additional glycosylation site. U.S. Pat. No. 5,218,092 discloses modification of granulocyte colony stimulating factor (G-CSF) and other polypeptides so as to introduce at least one additional carbohydrate chain as compared to the native polypeptide. IFNβ is disclosed as one example among many polypeptides that can be modified according to the technology described in U.S. Pat. No. 5,218,092.

The term "4HB polypeptide" also includes N-linked or O-linked glycosylated forms of the polypeptide. These forms included, but are not limited to, a polypeptide with an O-linked glycosylation site at position 129 of SEQ ID) NO: 23, or the equivalent position of SEQ ID NO: 24 or 25, or any other IFN polypeptide (Adolf et al., Biochem. J. 276:511 (1991)). The term "hG-CSF polypeptide" also includes glycosylated forms of the polypeptide, including but not limited to a polypeptide with an O-linked glycosylation site at position 134 of SEQ ID NO: 29 (J. Chromatogr. A 637:55-62 (1993). The term "hEPO polypeptide" also includes the glycosylated forms, with N-linked glycosylation sites at 24, 38, and 83, and O-linked glycosylation site at 126 (Takeuchi et al. (1988) JBC 263: 3657-3663; Saski et al. (1988) Biochemistry 27: 8618-8626).

Variants containing single nucleotide changes are also considered as biologically active variants of 4HB polypeptide. In addition, splice variants are also included. The term "4HB polypeptide" also includes 43B polypeptide heterodimers, homodimers, heteromultimers, or homomultimers of any one or more 4H B polypeptides or any other polypeptide, protein, carbohydrate, polymer, small molecule, ligand, or other active molecule of any type, linked by chemical means or expressed as a fusion protein, as well as polypeptide analogues containing, for example, specific deletions or other modifications yet maintain biological activity. Variants containing single nucleotide changes (i.e. L127M and A144T) are also considered as biologically active variants of hG-CSF (see SEQ ID NO: 35 and 36). In addition, splice variants are also included, such as, but not limited to the variant shown in SEQ ID NO: 30 which is missing V66, S67 and E68 of SEQ ID NO: 28. The term "hG-CSF polypeptide" also includes hG-CSF heterodimers, homodimers, heteromultimers, or homomultimers of any one or more hG-CSF or any other polypeptide, protein, carbohydrate, polymer, small molecule, ligand, or other active molecule of any type, linked by chemical means or expressed as a fusion protein (U.S. Pat. Nos. 6,261,550; 6,166,183; 6,204,247; 6,261,550; 6,017,876, which are incorporated by reference herein), as well as polypeptide analogues containing, for example, specific deletions or other modifications yet maintain biological activity (U.S. Pat. Nos. 6,261,550; 6,004,548; 6,632,426, which are incorporated by reference herein). Biologically-active fragments/variants of hEPO include the gene product containing 193 amino acids, of which the first 27 are cleaved during secretion (Jacobs et al., (1985) Nature 313:806-810; Lin et al., (1985) PNAS, USA 82: 7580-7584) (SEQ ID NO: 38) as well as the removal of one or more of the last four amino acids during the formation of the mature form of erythropoietin. Variants containing single nucleotide changes (i.e. S104N and L105F, P122Q, E13Q, Q58→QQ, G113R) are also considered as biologically active variants of hEPO (Jacobs et al., (1985) Nature 313: 806-810; Funakoshi et al., (1993) Biochem. Biophys. Res. Comm. 195: 717-722). The term "hEPO polypeptide" also includes hEPO heterodimers, homodimers, heteromultimers, or homomultimers of any one or more hEPO or any other polypeptide, protein, carbohydrate, polymer, small molecule, ligand, or other active molecule of any type, linked by chemical means or expressed as a fusion protein (Sytkowski et al., (1998) Proc. Natl. Acad. Sci. USA 95(3):1184-8; and Sytkowski et al. (1999) J. Biol. Chem. 274(35):24773-8, and U.S. Pat. Nos. 6,187,564; 6,703,480; 5,767,078 which are incorporated by reference herein), as well as polypeptide analogues containing specific deletions, yet maintain biological activity (Boissel et al., (1993) JBC 268: 15983-15993; Wen et al., (1994) JBC 269: 22839-22846; Bittorf et al., (1993) FEBS 336: 133-136; and U.S. Pat. No. 6,153,407 which is incorporated by reference herein).

All references to amino acid positions in hGH described herein are based on the position in SEQ ID NO: 2, unless otherwise specified (i.e., when it is stated that the comparison is based on SEQ ID NO: 1, 3, or other hGH sequence). All references to amino acid positions in hIFN described herein are based on the position in SEQ ID NO: 24, unless otherwise specified (i.e., when it is stated that the comparison is based on SEQ ID NO: 23, 25, or other hIFN sequence). All references to amino acid positions in hG-CSF described herein are based on the position in SEQ ID NO: 29, unless otherwise specified (i.e., when it is stated that the comparison is based on SEQ ID NO: 28, 30, 35, 36, or other hG-CSF sequence). All references to amino acid positions in hEPO described herein are based on the position in SEQ ID NO: 38, unless otherwise specified (i.e., when it is stated that the comparison is based on SEQ ID NO: 37, 39, or other hEPO sequence). Those of skill in the art will appreciate that amino acid positions corresponding to positions in SEQ ID NO: 1, 2, 3, or any other GH sequence can be readily identified in any other hGH molecule such as hGH fusions, variants, fragments, etc. For example, sequence alignment programs such as BLAST can be used to align and identify a particular position in a protein that corresponds with a position in SEQ ID NO: 1, 2, 3, or other GH sequence. Substitutions, deletions or additions of amino acids described herein in reference to SEQ ID NO: 1, 2, 3, or other GH sequence are intended to also refer to substitutions, deletions or additions in corresponding positions in hGH fusions, variants, fragments, etc. described herein or known in the art and are expressly encompassed by the present invention. Similar identifications and analyses apply to SEQ ID NO: 23, 24, 25, or any other IFN sequence, SEQ ID NO: 28, 29, 30, 35, 36, or any other hG-CSF sequence, and SEQ ID NO: 37, 38, 39, or any other EPO sequence.

The term "4HB polypeptide" encompasses four helical bundle polypeptides comprising one or more amino acid substitutions, additions or deletions. 4HB polypeptides of the present invention may be comprised of modifications with one or more natural amino acids in conjunction with one or more non-natural amino acid modification. Exemplary substitutions in a wide variety of amino acid positions in naturally-occurring 4HB polypeptides have been described, including but not limited to substitutions that modulate one or more of the biological activities of the 4HB polypeptide, such as but not limited to, increase agonist activity, increase solubility of the polypeptide, convert the polypeptide into an antagonist, etc. and are encompassed by the term "4HB polypeptide."

Human GH antagonists include, but are not limited to, those with substitutions at: 1, 2, 3, 4, 5, 8, 9, 11, 12, 15, 16, 19, 22, 103, 109, 112, 113, 115, 116, 119, 120, 123, and 127 or an addition at position 1 (i.e., at the N-terminus), or any combination thereof (SEQ ID NO:2, or the corresponding amino acid in SEQ ID NO: 1, 3, or any other GH sequence). In some embodiments, hGH antagonists comprise at least one substitution in the regions 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus) that cause GH to act as an antagonist. In other embodiments, the exemplary sites of incorporation of a non-naturally encoded amino acid include residues within the amino terminal region of helix A and a portion of helix C. In another embodiment, substitution of G120 with a non-naturally encoded amino acid such as p-azido-L-phenylalanine or O-propargyl-L-tyrosine. In other embodiments, the above-listed substitutions are combined with additional substitutions that cause the hGH polypeptide to be an hGH antagonist. For instance, a non-naturally encoded amino acid is substituted at one of the positions identified herein and a simultaneous substitution is introduced at G120 (e.g., G120R, G120K, G120W, G120Y, G120F, or G120E). In some embodiments, the hGH antagonist comprises a non-naturally encoded amino acid linked to a water soluble polymer that is present in a receptor binding region of the hGH molecule.

Human IFN antagonists include, but are not limited to, those with substitutions at: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165, or any combination thereof (SEQ ID NO: 24, or the corresponding amino acid in SEQ ID NO: 23, 25, or any other IFN sequence); a hIFN polypeptide comprising one of these substitutions may potentially act as a weak antagonist or weak agonist depending on the site selected and the desired activity. Human IFN antagonists include, but are not limited to, those with substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combination thereof (hIFN; SEQ ID NO: 24 or the corresponding amino acids in SEQ ID NO: 23 or 25). In some embodiments, hIFN antagonists comprise at least one substitution in the regions 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus) that cause IFN to act as an antagonist. In other embodiments, the exemplary sites of incorporation of a non-naturally encoded amino acid include residues within the amino terminal region of helix A and a portion of helix C. In other embodiments, the above-listed substitutions are combined with additional substitutions that cause the hIFN polypeptide to be a hIFN antagonist. In some embodiments, the hIFN antagonist comprises a non-naturally encoded amino acid linked to a water soluble polymer that is present in a receptor binding region of the hIFN molecule.

Human G-CSF antagonists include, but are not limited to, those with substitutions at: 6, 7, 8, 9, 10, 11, 12, 13, 16, 17, 19, 20, 21, 23, 24, 28, 30, 41, 47, 49, 50, 70, 71, 105, 106, 109, 110, 112, 113, 116, 117, 120, 121, 123, 124, 125, 127, 145, or any combination thereof (SEQ ID NO: 29, or the corresponding amino acid in SEQ ID NO: 28, 30, 35, or 36). In some embodiments, hG-CSF antagonists comprise at least one substitution in the regions 6-30, 40-70, or 105-130 that cause G-CSF to act as an antagonist. In other embodiments, the exemplary sites of incorporation of a non-naturally encoded amino acid include residues within the amino terminal region of helix A and a portion of helix C. In another embodiment, substitution of L70 with a non-naturally encoded amino acid such as p-azido-L-phenylalanine or O-propargyl-L-tyrosine. In other embodiments, the above-listed substitutions are combined with additional substitutions that cause the hG-CSF polypeptide to be a hG-CSF antagonist. For instance, a non-naturally encoded amino acid is substituted at one of the positions identified herein and a simultaneous substitution is introduced at L70. In some embodiments, the hG-CSF antagonist comprises a non-naturally encoded amino acid linked to a water soluble polymer that is present in a receptor binding region of the hG-CSF molecule.

Human EPO antagonists include, but are not limited to, those with substitutions at: 2, 3, 5, 8, 9, 10, 11, 14, 15, 16, 17, 18, 20, 23, 43, 44, 45, 46, 47, 48, 49, 50, 52, 75, 78, 93, 96, 97, 99, 100, 103, 104, 107, 108, 110, 131, 132, 133, 140, 143, 144, 146, 147, 150, 154, 155, 159, or any combination thereof (hEPO; SEQ ID NO: 38, or corresponding amino acids in SEQ ID NO: 37 or 39). In some embodiments, hEPO antagonists comprise at least one substitution in the regions 10-15 or 100-108 that cause EPO to act as an antagonist. See Elliott et al. (1997) Blood 89: 493-502 and Cheetham et al. (1998) Nature Structural Biology 5: 861-866. In some embodiments, the hEPO polypeptide is modified by containing one or more the following substitutions: V11S, R14Q, Y15I, S100E, R103A, S104I, and L108K found in the low affinity receptor binding site (site 2). In other embodiments, the exemplary sites of incorporation of a non-naturally encoded amino acid include residues within the amino terminal region of helix A and a portion of helix C. In another embodiment, substitution of L108 with a non-naturally encoded amino acid such as p-azido-L-phenylalanine or O-propargyl-L-tyrosine. In other embodiments, the above-listed substitutions are combined with additional substitutions that cause the hEPO polypeptide to be a hEPO antagonist. For instance, a non-naturally encoded amino acid is substituted at one of the positions identified herein and a simultaneous substitution is introduced at L108 (including but not limited to, L108K, L108R, L108H, L108D, or L108E). In some embodiments, the hEPO antagonist comprises a non-naturally encoded amino acid linked to a water soluble polymer that is present in the Site 2 binding region of the hEPO molecule.

In some embodiments, the 4HB polypeptides further comprise an addition, substitution or deletion that modulates biological activity of the 4HB polypeptide. For example, the additions, substitutions or deletions may modulate affinity for the 4HB polypeptide receptor, modulate (including but not limited to, increases or decreases) receptor dimerization, stabilize receptor dimers, modulate circulating half-life, modulate therapeutic half-life, modulate stability of the polypeptide, modulate dose, modulate release or bio-availability, facilitate purification, or improve or alter a particular route of administration. Similarly, 4HB polypeptides may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "4HB polypeptide" also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, water soluble polymers such as poly(ethylene glycol) or polydextran or a polypeptide.

A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological organism, including but not limited to, viruses, bacteria, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671, 958, 4,659,839, 4,414,148, 4,699,784; 4,680,338; 4,569,789; and 4,589,071 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages.

Where substituent groups are specified by their conventional chemical formulas, written from left to right, they equally encompass the chemically identical substituents that would result from writing the structure from right to left, for example, the structure —$CH_2O$— is equivalent to the structure —$OCH_2$—.

The term "substituents" includes but is not limited to "non-interfering substituents". "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{12}$ aralkyl, $C_1$-$C_{12}$ alkaryl, $C_3$-$C_{12}$ cycloalkyl, $C_3$-$C_{12}$ cycloalkenyl, phenyl, substituted phenyl, toluoyl, xylenyl, biphenyl, $C_2$-$C_{12}$ alkoxyalkyl, $C_2$-$C_{12}$ alkoxyaryl, $C_7$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{10}$ alkyl), $C_2$-$C_{10}$ alkyl thioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-$CF_3$, —C(O)—CF3, —C(O)NR2, —($C_1$-$C_{10}$ aryl)-S—($C_6$-$C_{10}$ aryl), —C(O)—($C_1$-$C_{10}$ aryl), —$(CH_2)_m$—O—(—$(CH_2)_m$—O—($C_1$-$C_{10}$ alkyl) wherein each m is from 1 to 8, —C(O) $NR_2$, —C(S)$NR_2$, —$SO_2NR_2$, —NRC(O)$NR_2$, —NRC(S)

$NR_2$, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —$CH_2CH_2$— and —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated and unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

As used herein, the term "water soluble polymer" refers to any polymer that is soluble in aqueous solvents. Linkage of water soluble polymers to 4HB polypeptides can result in changes including, but not limited to, increased or modulated serum half-life, or increased or modulated therapeutic half-life relative to the un-modified form, modulated immunogenicity, modulated physical association characteristics such as aggregation and multimer formation, altered receptor binding and altered receptor dimerization or multimerization. The water soluble polymer may or may not have its own biological activity. Suitable polymers include, but are not limited to, polyethylene glycol, polyethylene glycol propionaldehyde, mono $C_1$-$C_{10}$ alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water soluble polymers include, but are not limited to, polyethylene glycol and serum albumin.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom, (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such a radical. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, but are not limited to: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified biologically active molecule relative to its non-modified form. Serum half-life is measured by taking blood samples at various time points after administration of the biologically active molecule, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of a modified biologically active molecule, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, or an increase or decrease in another parameter or mechanism of action of the non-modified molecule.

The term "isolated," when applied to a nucleic acid or protein, denotes that the nucleic acid or protein is substantially free of other cellular components with which it is associated in the natural state. It can be in a homogeneous state. Isolated substances can be in either a dry or semi-dry state, or in solution, including but not limited to, an aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it means that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins: Structures and Molecular Properties* (W H Freeman & Co.; 2nd edition (December 1993))

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, optionally about 65%, about 70%, about 75%, about 80%, about 85%, about 90%, or about 95% identity over a specified region), when compared and aligned for maximum correspondence over a comparison window, or designated region as measured using one of the following sequence comparison algorithms or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence or a polynucleotide or polypeptide.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, including but not limited to, by the local homology algorithm of Smith and Waterman (1970) *Adv. Appl Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01 to 1.0 M sodium ion concentration (or other salts) at pH 7.0 to 8.3 and the temperature is at least about 30° C. for short probes (including but not limited to, 10 to 50 nucleotides) and at least about 60° C. for long probes (including but not limited to, greater than 50 nucleotides). Stringent conditions may also be achieved with the addition of destabilizing agents such as formamide. For selective or specific hybridization, a positive signal may be at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, preferably a mammal, most preferably a human, who is the object of treatment, observation or experiment.

The term "effective amount" as used herein refers to that amount of the (modified) non-natural amino acid polypeptide being administered which will relieve to some extent one or more of the symptoms of the disease, condition or disorder being treated. Compositions containing the (modified) non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to the presence of a post-translational modification on a polypeptide. The form "(modified)" term means that the polypeptides being discussed are optionally modified, that is, the polypeptides under discussion can be modified or unmodified.

The term "post-translationally modified" and "modified" refers to any modification of a natural or non-natural amino acid that occurs to such an amino acid after it has been incorporated into a polypeptide chain. The term encompasses, by way of example only, co-translational in vivo modifications, post-translational in vivo modifications, and post-translational in vitro modifications.

In prophylactic applications, compositions containing the (modified) non-natural amino acid polypeptide are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

The term "protected" refers to the presence of a "protecting group" or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in or with the methods and compositions described herein.

By way of example only, blocking/protecting groups may be selected from:

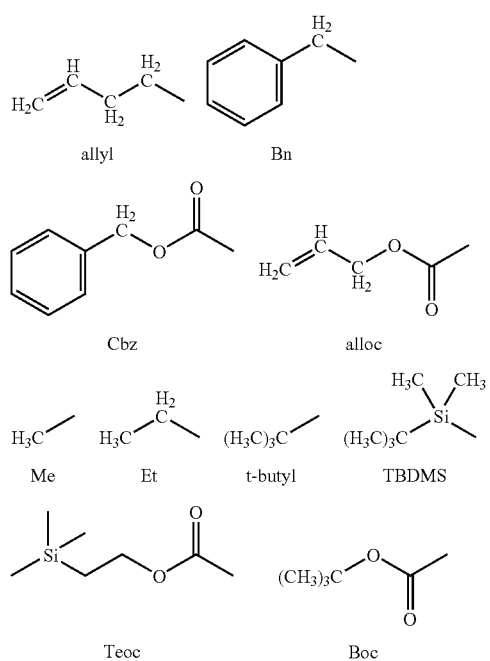

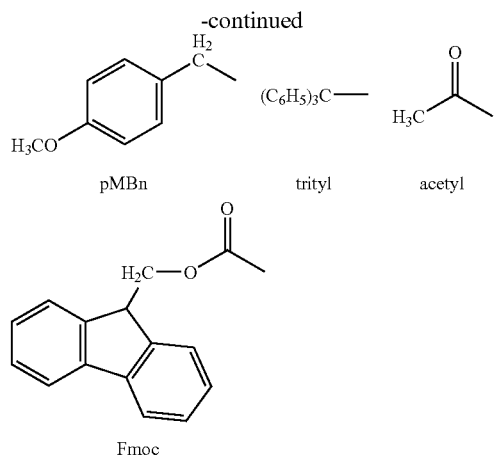

Other protecting groups are described in Greene and Wuts, Protective Groups in Organic Synthesis, 3rd Ed., John Wiley & Sons, New York, N.Y., 1999, which is incorporated herein by reference in its entirety.

In therapeutic applications, compositions containing the (modified) non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction

Four helical bundle molecules comprising at least one unnatural amino acid are provided in the invention. In certain embodiments of the invention, the 4HB polypeptide with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry methodologies are utilized. In another example, the first reactive group is the azido moiety (including but not limited to, in the unnatural amino acid p-azido-L-phenylalanine) and the second reactive group is the alkynyl moiety. In certain embodiments of the modified 4HB polypeptide of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, acetylation, acylation, lipid-modification, palmitoylation, palmitate addition, phosphorylation, glycolipid-linkage modification, and the like. In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on members of the GH supergene family, in particular hGH, hIFN, hG-CSF, and hEPO, comprising at least one non-naturally encoded amino acid. Introduction of at least one non-naturally encoded amino acid into a GH supergene family member can allow for the application of conjugation chemistries that involve specific chemical reactions, including, but not limited to, with one or more non-naturally encoded amino acids while not reacting with the commonly occurring 20 amino acids. In some embodiments, the GH supergene family member comprising the non-naturally encoded amino acid is linked to a water soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the naturally encoded amino acid. Known chemistry methodologies of a wide variety are suitable for use in the present invention to incorporate a water soluble polymer into the protein. Such methodologies include but are not limited to a Huisgen [3+2] cycloaddition reaction (see, e.g., Padwa, A. in *Comprehensive Organic Synthesis, Vol.* 4, (1991) Ed. Trost, B. M., Pergamon, Oxford, p. 1069-1109; and, Huisgen, R. in 1,3-*Dipolar Cycloaddition Chemistry*, (1984) Ed. Padwa, A., Wiley, New York, p. 1-176) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tornoe, et al., (2002) *Org. Chem.* 67:3057-3064; and, Rostovtsev, et al., (2002) *Angew. Chem. Int. Ed.* 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more important, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; or any combination of the above, or any other desirable compound or substance). The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2] cycloaddition product.

It is well established in the art that PEG can be used to modify the surfaces of biomaterials (see, e.g., U.S. Pat. No. 6,610,281; Mehvar, R., J. Pharmaceut. Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2] cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives containing sulfonyl acid halides, halogen atoms and other leaving groups are well known to the skilled artisan. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are well known to the skilled artisan.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives is well established to practitioners in the art.

The invention also provides a method for the selective modification of proteins to add other substances to the modified protein, including but not limited to water soluble polymers such as PEG and PEG derivatives containing an azide or acetylene moiety. The azide- and acetylene-containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II. Growth Hormone Supergene Family

The following proteins include those encoded by genes of the growth hormone (GH) supergene family (Bazan, F., *Immunology Today* 11: 350-354 (1991); Bazan, J. F. *Science* 257: 410-411 (1992); Mott, H. R. and Campbell, I. D., *Current Opinion in Structural Biology* 5: 114-121 (1995); Silvennoinen, O. and Ihle, J. N., SIGNALLING BY THE HEMATOPOIETIC CYTOKINE RECEPTORS (1996)): growth hormone, prolactin, placental lactogen, erythropoietin (EPO), thrombopoietin (TPO), interleukin-2 (IL-2), IL-3, IL-4, IL-5, IL-6, IL-7, IL-9, IL-10, IL-11, IL-12 (p35 subunit), IL-13, IL-15, oncostatin M, ciliary neurotrophic factor (CNTF), leukemia inhibitory factor (LIF), alpha interferon, beta interferon, epsilon interferon, gamma interferon, omega interferon, tau interferon, granulocyte-colony stimulating factor (G-CSF), granulocyte-macrophage colony stimulating factor (GM-CSF), macrophage colony stimulating factor (M-CSF) and cardiotrophin-1 (CT-1) ("the GH supergene family"). It is anticipated that additional members of this gene family will be identified in the future through gene cloning and sequencing. Members of the GH supergene family have similar secondary and tertiary structures, despite the fact that they generally have limited amino acid or DNA sequence identity. The shared structural features allow new members of the gene family to be readily identified and the non-natural amino acid methods and compositions described herein similarly applied. Given the extent of structural homology among the members of the GH supergene family, non-naturally encoded amino acids may be incorporated into any members of the GH supergene family using the present invention. Each member of this family of proteins comprises a four helical bundle, the general structure of which is shown in FIG. 1. The general structures of family members hGH, EPO, IFNα-2, and G-CSF are shown in FIGS. 2, 3, 4, and 5, respectively.

Structures of a number of cytokines, including G-CSF (Zink et al., FEBS Lett. 314:435 (1992); Zink et al., Biochemistry 33:8453 (1994); Hill et al., Proc. Natl. Acad. Sci. USA 90:5167 (1993)), GM-CSF (Diederichs, K., et al. *Science* 154: 1779-1782 (1991); Walter et al., *J. Mol. Biol.* 224:1075-1085 (1992)), IL-2 (Bazan, J. F. *Science* 257: 410-411 (1992); McKay, D. B. *Science* 257: 412 (1992)), IL-4 (Redfield et al., *Biochemistry* 30: 11029-11035 (1991); Powers et al., *Science* 256:1673-1677 (1992)), and IL-5 (Milburn et al., *Nature* 363: 172-176 (1993)) have been determined by X-ray diffraction and NMR studies and show striking conservation with the GH structure, despite a lack of significant primary sequence homology. IFN is considered to be a member of this family based upon modeling and other studies (Lee et al., J. Growth hormone Cytokine Res. 15:341 (1995); Murgolo et al., Proteins 17:62 (1993); Radhakrishnan et al., Structure 4:1453 (1996); Klaus et al., J. Mol. Biol. 274:661 (1997)). EPO is considered to be a member of this family based upon modeling and mutagenesis studies (Boissel et al., *J. Biol. Chem.* 268: 15983-15993 (1993); Wen et al., J. Biol. Chem. 269: 22839-22846 (1994)). All of the above cytokines and growth factors are now considered to comprise one large gene family.

In addition to sharing similar secondary and tertiary structures, members of this family share the property that they must oligomerize cell surface receptors to activate intracellular signaling pathways. Some GH family members, including but not limited to; GH and EPO, bind a single type of receptor and cause it to form homodimers. Other family members, including but not limited to, IL-2, IL-4, and IL-6, bind more than one type of receptor and cause the receptors to form heterodimers or higher order aggregates (Davis et al., (1993), *Science* 260: 1805-1808; Paonessa et al., (1995), EMBO J. 14: 1942-1951; Mott and Campbell, *Current Opinion in Structural Biology* 5: 114-121 (1995)). Mutagenesis studies have shown that, like GH, these other cytokines and growth factors contain multiple receptor binding sites, typically two, and bind their cognate receptors sequentially (Mott and Campbell, *Current Opinion in Structural Biology* 5: 114-121 (1995); Matthews et al., (1996) *Proc. Natl. Acad. Sci. USA* 93: 9471-9476). Like GH, the primary receptor binding sites for these other family members occur primarily in the four alpha helices and the A-B loop. The specific amino acids in the helical bundles that participate in receptor binding differ amongst the family members. Most of the cell surface receptors that interact with members of the GH supergene family are structurally related and comprise a second large multi-gene family. See, e.g. U.S. Pat. No. 6,608,183, which is incorporated by reference herein.

A general conclusion reached from mutational studies of various members of the GH supergene family is that the loops joining the alpha helices generally tend to not be involved in receptor binding. In particular the short B-C loop appears to be non-essential for receptor binding in most, if not all, family members. For this reason, the B-C loop may be substituted with non-naturally encoded amino acids as described herein in members of the GH supergene family. The A-B loop, the C-D loop (and D-E loop of interferon/IL-10-like members of the GH superfamily) may also be substituted with a non-naturally-occurring amino acid. Amino acids proximal to helix A and distal to the final helix also tend not to be involved in receptor binding and also may be sites for introducing non-naturally-occurring amino acids. In some embodiments, a non-naturally encoded amino acid is substituted at any position within a loop structure, including but not limited to, the first 1, 2, 3, 4, 5, 6, 7, or more amino acids of the A-B, B-C, C-D or D-E loop. In some embodiments, one or more non-naturally encoded amino acids are substituted within the last 1, 2, 3, 4, 5, 6, 7, or more amino acids of the A-B, B-C, C-D or D-E loop.

Certain members of the GH family, including but not limited to, EPO, IL-2, IL-3, IL-4, IL-6, G-CSF, GM-CSF, TPO, IL-10, IL-12 p35, IL-13, IL-15 and beta interferon contain N-linked and/or O-linked sugars. The glycosylation sites in the proteins occur almost exclusively in the loop regions and not in the alpha helical bundles. Because the loop regions generally are not involved in receptor binding and because they are sites for the covalent attachment of sugar groups, they may be useful sites for introducing non-naturally-occurring amino acid substitutions into the proteins. Amino acids that comprise the N- and O-linked glycosylation sites in the proteins may be sites for non-naturally-occurring amino acid substitutions because these amino acids are surface-exposed. Therefore, the natural protein can tolerate bulky sugar groups attached to the proteins at these sites and the glycosylation sites tend to be located away from the receptor binding sites.

Additional members of the GH supergene family are likely to be discovered in the future. New members of the GH supergene family can be identified through computer-aided secondary and tertiary structure analyses of the predicted protein sequences. Members of the GH supergene family typically possess four or five amphipathic helices joined by non-helical amino acids (the loop regions). The proteins may contain a hydrophobic signal sequence at their N-terminus to promote secretion from the cell. Such later discovered members of the GH supergene family also are included within this invention.

Thus, the description of the growth hormone supergene family is provided for illustrative purposes and by way of example only and not as a limit on the scope of the methods, compositions, strategies and techniques described herein. Further, reference to GH, IFN, G-CSF, and EPO polypeptides in this application is intended to use the generic term as an example of any member of the GH supergene family. Thus, it is understood that the modifications and chemistries described herein with reference to hGH, hIFN, hG-CSF, or hEPO polypeptides or protein can be equally applied to any member of the GH supergene family, including those specifically listed herein.

III. General Recombinant Nucleic Acid Methods for Use with the Invention

In numerous embodiments of the present invention, nucleic acids encoding a 4HB polypeptide of interest will be isolated, cloned and often altered using recombinant methods. Such embodiments are used, including but not limited to, for protein expression or during the generation of variants, derivatives, expression cassettes, or other sequences derived from a 4HB polypeptide. In some embodiments, the sequences encoding the polypeptides of the invention are operably linked to a heterologous promoter. Isolation of hGH and production of GH in host cells are described in, e.g., U.S. Pat. Nos. 4,601,980, 4,604,359, 4,634,677, 4,658,021, 4,898,830, 5,424,199, 5,795,745, 5,854,026, 5,849,535; 6,004,931; 6,022,711; 6,143,523 and 6,608,183, which are incorporated by reference herein. Isolation of hIFN and production of IFN in host cells are described in, e.g., U.S. Pat. Nos. 6,489,144; 6,410,697; 6,159,712; 5,955,307; 5,814,485; 5,710,027; 5,595,888; 5,391,713; 5,244,655; 5,196,323; 5,066,786; 4,966,843; 4,894,330; 4,364,863, which are incorporated by reference herein. Isolation of hG-CSF and production of G-CSF in host cells are described in, e.g., U.S. Pat. Nos. 4,810,643; 4,999,291; 5,580,755; and 6,716,606, which are incorporated by reference herein. Isolation of hEPO is described in, e.g., U.S. Pat. Nos. 5,441,868; 5,547,933; 5,618,698; 5,621,080; and 6,544,748, and production of EPO in human cells is described in WO 93/09222.

A nucleotide sequence encoding a 4HB polypeptide comprising a non-naturally encoded amino acid may be synthesized on the basis of the amino acid sequence of the parent polypeptide, including but not limited to, having the amino acid sequence shown in SEQ ID NO: 2 (hGH), 24 (hIFN), 29 (hG-CSF), or 38 (EPO) and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning, A Laboratory Manual* (3rd ed. 2001); Kregler, *Gene Transfer and Expression: A Laboratory Manual* (1990); and *Current Protocols in Molecular Biology* (Ausubel et al., eds., 1994)).

General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel")). These texts describe mutagenesis, the use of vectors, promoters and many other relevant topics related to, including but not limited to, the generation of genes that include selector codons for production of proteins that include unnatural amino acids, orthogonal tRNAs, orthogonal synthetases, and pairs thereof.

Various types of mutagenesis are used in the invention for a variety of purposes, including but not limited to, to produce libraries of tRNAs, to produce libraries of synthetases, to produce selector codons, to insert selector codons that encode unnatural amino acids in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also included in the present invention. In one embodiment, mutagenesis can be guided by known information of the naturally occurring molecule or altered or mutated naturally occurring molecule, including but not limited to, sequence, sequence comparisons, physical properties, crystal structure or the like.

The texts and examples found herein describe these procedures. Additional information is found in the following publications and references cited within: Ling et al., *Approaches to DNA mutagenesis: an overview, Anal Biochem.* 254(2): 157-178 (1997); Dale et al., *Oligonucleotide-directed random mutagenesis using the phosphorothioate method, Methods Mol. Biol.* 57:369-374 (1996); Smith, *In vitro mutagenesis, Ann. Rev. Genet.* 19:423-462 (1985); Botstein & Shortle, *Strategies and applications of in vitro mutagenesis, Science* 229:1193-1201 (1985); Carter, *Site-directed mutagenesis, Biochem. J.* 237:1-7 (1986); Kunkel, *The efficiency of oligonucleotide directed mutagenesis*, in *Nucleic Acids & Molecular Biology* (Eckstein, F. and Lilley, D. M. J. eds., Springer Verlag, Berlin) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Bass et al., *Mutant Trp repressors with new DNA-binding specificities, Science* 242:240-245 (1988); Methods in Enzymol. 100: 468-500 (1983); Methods in Enzymol. 154: 329-350 (1987); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); Zoller & Smith, *Oligonucleotide-directed mutagenesis: a simple method using two oligonucleotide primers and a single-stranded DNA template, Methods in Enzymol.* 154: 329-350 (1987); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Nakamaye & Eckstein, *Inhibition of restriction endonuclease Nci I cleav-*

*age by phosphorothioate groups and its application to oligonucleotide-directed mutagenesis, Nucl. Acids Res.* 14: 9679-9698 (1986); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Improved enzymatic in vitro reactions in the gapped duplex DNA approach to oligonucleotide-directed construction of mutations, Nucl. Acids Res.* 16: 7207 (1988); Fritz et al., *Oligonucleotide-directed construction of mutations: a gapped duplex DNA procedure without enzymatic reactions in vitro, Nucl. Acids Res.* 16: 6987-6999 (1988); Kramer et al., *Point Mismatch Repair, Cell* 38:879-887 (1984); Carter et al., *Improved oligonucleotide site-directed mutagenesis using M13 vectors, Nucl. Acids Res.* 13: 4431-4443 (1985); Carter, *Improved oligonucleotide-directed mutagenesis using M13 vectors*, Methods in Enzymol. 154: 382-403 (1987); Eghtedarzadeh & Henikoff, *Use of oligonucleotides to generate large deletions, Nucl. Acids Res.* 14: 5115 (1986); Wells et al., *Importance of hydrogen-bond formation in stabilizing the transition state of subtilisin, Phil. Trans. R. Soc. Lond. A* 317: 415-423 (1986); Nambiar et al., *Total synthesis and cloning of a gene coding for the ribonuclease S protein, Science* 223: 1299-1301 (1984); Sakamar and Khorana, *Total synthesis and expression of a gene for the α-subunit of bovine rod outer segment guanine nucleotide-binding protein (transducin), Nucl. Acids Res.* 14: 6361-6372 (1988); Wells et al., *Cassette mutagenesis: an efficient method for generation of multiple mutations at defined sites, Gene* 34:315-323 (1985); Grundström et al., *Oligonucleotide-directed mutagenesis by microscale 'shot-gun' gene synthesis, Nucl. Acids Res.* 13: 3305-3316 (1985); Mandecki, *Oligonucleotide-directed double-strand break repair in plasmids of Escherichia coli: a method for site-specific mutagenesis, Proc. Natl. Acad. Sci. USA*, 83:7177-7181 (1986); Arnold, *Protein engineering for unusual environments, Current Opinion in Biotechnology* 4:450-455 (1993); Sieber, et al., Nature Biotechnology, 19:456-460 (2001); W. P. C. Stemmer, *Nature* 370, 389-91 (1994); and, I. A. Lorimer, I. Pastan, *Nucleic Acids Res.* 23, 3067-8 (1995). Additional details on many of the above methods can be found in *Methods in Enzymology* Volume 154, which also describes useful controls for trouble-shooting problems with various mutagenesis methods.

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)).

The engineered host cells can be cultured in conventional nutrient media modified as appropriate for such activities as, for example, screening steps, activating promoters or selecting transformants. These cells can optionally be cultured into transgenic organisms. Other useful references, including but not limited to for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds.) (1995) *Plant Cell, Tissue and Organ Culture*; Fundamental Methods Springer Lab Manual, Springer-Verlag (Berlin Heidelberg New York) and Atlas and Parks (eds.) *The Handbook of Microbiological Media* (1993) CRC Press, Boca Raton, Fla.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria, (see, e.g., EasyPrep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). A catalogue of bacteria and bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. available on the World Wide Web at mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), or an opal codon (UGA), an unnatural codon, a four or more base codon, a rare codon, or the like. It is readily apparent to those of ordinary skill in the art that there is a wide range in the number of selector codons that can be introduced into a desired gene, including but not limited to, one or more, two or more, more than three, 4, 5, 6, 7, 8, 9, 10 or more in a single polynucleotide encoding at least a portion of the 4HB polypeptide.

In one embodiment, the methods involve the use of a selector codon that is a stop codon for the incorporation of unnatural amino acids in vivo in a eukaryotic cell. For example, an O-tRNA is produced that recognizes the stop codon, including but not limited to, UAG, and is aminoacylated by an O—RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5',3' *Exonuclease in phosphorothioate-based oligonucleotide-directed mutagenesis. Nucleic Acids Res.* 791-802. When the O—RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Selector codons also comprise extended codons, including but not limited to, four or more base codons, such as, four, five, six or more base codons. Examples of four base codons include, including but not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., (2002) *Exploring the Limits of Codon and Anticodon Size, Chemistry and Biology*, 9:237-244; Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.* 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) *J. Mol. Biol.,* 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.,* 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.* 121:11586; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) *J. Am. Chem. Soc.,* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See, Meggers et al., (2000) *J. Am. Chem. Soc.*, 122:10714. Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as a 4BB polypeptide may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of the 4HB polypeptide are well known in the art, such as those described in U.S. Pat. No. 6,608,183, which is incorporated by reference herein, and standard mutagenesis techniques.

IV. Non-Naturally Encoded Amino Acids

A very wide variety of non-naturally encoded amino acids are suitable for use in the present invention. Any number of non-naturally encoded amino acids can be introduced into a 4HB polypeptide. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a 4HB polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

The generic structure of an alpha-amino acid is illustrated as follows (Formula I):

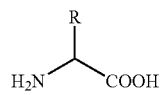

I

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N— or O— linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

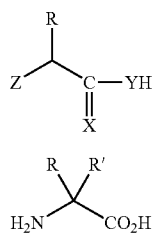

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) *Incorporation of azides into recombinant proteins for chemoselective modification by the Staudinzger ligation, PNAS* 99:19-24, for additional methionine analogs.

In one embodiment, compositions of a 4HB polypeptide that include an unnatural amino acid (such as p-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2]cycloaddition reaction.

A non-natural amino acid incorporated into a polypeptide at the amino terminus can be composed of an R group that is any substituent other than one used in the twenty natural amino acids and a $2^{nd}$ reactive group different from the $NH_2$ group normally present in α-amino acids (see Formula I). A similar non-natural amino acid can be incorporated at the carboxyl terminus with a $2^{nd}$ reactive group different from the COOH group normally present in α-amino acids (see Formula I).

Chemical Synthesis of Unnatural Amino Acids

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.* 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4 [[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 1989:1859-1866; Barton et al., (1987) *Synthesis of Novel α-Amino-Acids and Derivatives Using Radical Chemistry: Synthesis of L-and D-α-Amino-Adipic Acids, L-α-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also, patent applications entitled "Protein Arrays," filed Dec. 22, 2003, Ser. No. 10/744,899 and Ser. No. 60/435,821 filed on Dec. 22, 2002.

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

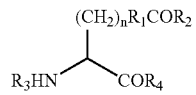

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one skilled in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et al., *Bioconjug. Chem.* 3: 262-268 (1992); Geoghegan, K. & Stroh, J., *Bioconjug. Chem.* 3:138-146 (1992); Gaertner et al., *J. Biol. Chem.* 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., *J. Am. Chem. Soc.* 81, 475-481 (1959); Shao, J. and Tam, J. P., *J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Am. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

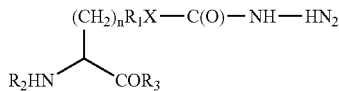

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the alphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., *J. Am. Chem. Soc.* 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., *J. Am. Chem. Soc.* 117:3893-3899 (1995); H. Hang and C. Bertozzi, *Acc. Chem. Res.* 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

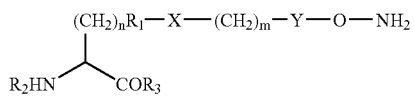

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J. Org. Chem.* 68: 8853-8858 (2003). Certain aminooxy-containing amino acids, such as L-2-amino-4-(aminooxy)butyric acid), have been isolated from natural sources (Rosenthal, G. et al., *Life Sci.* 60: 1635-1641 (1997). Other aminooxy-containing amino acids can be prepared by one skilled in the art.

D. Azide and Alkyne Reactive Groups

The unique reactivity of azide and alkyne functional groups makes them extremely useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., *Science* 301:964-7 (2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in COMPRHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing 4HB polypeptide can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al, *J. Am. Chem. Soc.* 125, 3192-3193 (2003); Tornoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the 4HB polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azidophenylalanine).

Exemplary water soluble polymers containing an aryl ester and a phosphine moiety can be represented as follows:

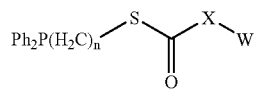

wherein X can be O, N, S or not present, Ph is phenyl, W is a water soluble polymer and R can be H, alkyl, aryl, substituted alkyl and substituted aryl groups. Exemplary R groups include but are not limited to —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R'", R'" and R'"' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R'"' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

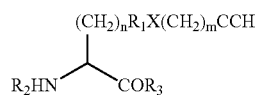

wherein n is 1-10; X can be O, N, S or not present, Ph is phenyl, and W is a water soluble polymer.

Exemplary alkyne-containing amino acids can be represented as follows:

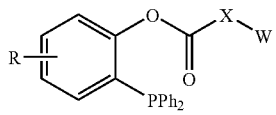

wherein n is 0-10; R$_1$ is an alkyl, aryl, substituted alkyl, or substituted aryl or not present; X is O, N, S or not present; m is 0-10, R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the acetylene moiety is positioned in the para position relative to the alkyl side chain. In some embodiments, n is 1, R$_1$ is phenyl, X is O, m is 1 and the propargyloxy group is positioned in the para position relative to the alkyl side chain (i.e., O-propargyl-tyrosine). In some embodiments, n is 1, R$_1$ and X are not present and m is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53(7): 2475-2484 (1997). Other alkyne-containing amino acids can be prepared by one skilled in the art.

Exemplary azide-containing amino acids can be represented as follows:

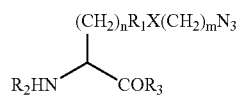

wherein n is 0-10; R$_1$ is an alkyl, aryl, substituted alkyl, substituted aryl or not present; X is O, N, S or not present; m is 0-10; R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the azide moiety is positioned para to the alkyl side chain. In some embodiments, n is 0-4 and R$_1$ and X are not present, and m=0. In some embodiments, n is 1, R$_1$ is phenyl, X is O, m is 2 and the β-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., *Advanced Organic Chemistry* by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J. Am. Chem. Soc.* 1995, 117 (14) 3893-3899. In some embodiments, beta-substituted aminothiol amino acids can be incorporated into 4HB polypeptides and then reacted with water soluble polymers comprising an aldehyde functionality. In some embodiments, a water soluble polymer, drug conjugate or other payload can be coupled to a 4HB polypeptide comprising a beta-substituted aminothiol amino acid via formation of the thiazolidine.

Cellular Uptake of Unnatural Amino Acids

Unnatural amino acid uptake by a eukaryotic cell is one issue that is typically considered when designing and selecting unnatural amino acids, including but not limited to, for incorporation into a protein. For example, the high charge density of α-amino acids suggests that these compounds are unlikely to be cell permeable. Natural amino acids are taken up into the eukaryotic cell via a collection of protein-based transport systems. A rapid screen can be done which assesses which unnatural amino acids, if any, are taken up by cells. See, e.g., the toxicity assays in, e.g., the applications entitled "Protein Arrays," filed Dec. 22, 2003, Ser. No. 10/744,899 and Ser. No. 60/435,821 filed on Dec. 22, 2002; and Liu, D. R. & Schultz, P. G. (1999) Progress toward the evolution of an organism with an expanded genetic code. *PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, including but not limited to, in a eukaryotic cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923 entitled "In vivo incorporation of unnatural amino acids") relies on the addition of a combination of known enzymes from other organisms. The genes for these enzymes can be introduced into a eukaryotic cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, for example, in Genbank. Artificially evolved enzymes are also optionally added into a cell in the same manner. In this manner, the cellular machinery and resources of a cell are manipulated to produce unnatural amino acids.

A variety of methods are available for producing novel enzymes for use in biosynthetic pathways or for evolution of existing pathways. For example, recursive recombination, including but not limited to, as developed by Maxygen, Inc. (available on the World Wide Web at maxygen.com), is optionally used to develop novel enzymes and pathways. See, e.g., Stemmer (1994), *Rapid evolution of a protein in vitro by DNA shuffling,* Nature 370(4):389-391; and, Stemmer, (1994), *DNA shuffling by random fragmentation and reassembly: In vitro recombination for molecular evolution, Proc. Natl. Acad. Sci. USA.,* 91:10747-10751. Similarly Design-Path™, developed by Genencor (available on the World Wide Web at genencor.com) is optionally used for metabolic pathway engineering, including but not limited to, to engineer a pathway to create O-methyl-L-tyrosine in a cell. This technology reconstructs existing pathways in host organisms using a combination of new genes, including but not limited to, identified through functional genomics, and molecular evolution and design. Diversa Corporation (available on the World Wide Web at diversa.com) also provides technology for rapidly screening libraries of genes and gene pathways, including but not limited to, to create new pathways.

Typically, the unnatural amino acid produced with an engineered biosynthetic pathway of the invention is produced in a concentration sufficient for efficient protein biosynthesis, including but not limited to, a natural cellular amount, but not to such a degree as to affect the concentration of the other amino acids or exhaust cellular resources. Typical concentrations produced in vivo in this manner are about 10 mM to about 0.05 mM. Once a cell is transformed with a plasmid comprising the genes used to produce enzymes desired for a specific pathway and an unnatural amino acid is generated, in vivo selections are optionally used to further optimize the production of the unnatural amino acid for both ribosomal protein synthesis and cell growth.

Polypeptides with Unnatural Amino Acids

The incorporation of an unnatural amino acid can be done for a variety of purposes, including but not limited to, tailoring changes in protein structure and/or function, changing size, acidity, nucleophilicity, hydrogen bonding, hydrophobicity, accessibility of protease target sites, targeting to a moiety (including but not limited to, for a protein array), etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, (2000) *Unnatural Amino Acids as Probes of Protein Structure and Function, Current Opinion in Chemical Biology,* 4:645-652.

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like. In one aspect, the post-translational modification includes attachment of an oligosaccharide (including but not limited to, (GlcNAc-Man)$_2$-Man-GlcNAc-GlcNAc)) to an asparagine by a GlcNAc-asparagine linkage. See Table 1 which lists some examples of N-linked oligosaccharides of eukaryotic proteins (additional residues can also be present, which are not shown). In another aspect, the post-translational modification includes attachment of an oligosaccharide (including but not limited to, Gal-GalNAc, Gal-GlcNAc, etc.) to a serine or threonine by a GalNAc-serine or GalNAc-threonine linkage, or a GlcNAc-serine or a GlcNAc-threonine linkage.

cortin and the like), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like. U.S. Pat. Nos. 4,963,495 and 6,436,674, which are incorporated herein by reference, detail constructs designed to improve secretion of hGH polypeptides.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., (1996) *Am. Chem. Soc.,* 118:8150-8151; Mahal, et al., (1997) *Science,* 276:1125-1128; Wang, et al., (2001) *Science* 292:498-500; Chin, et al., (2002) *Am. Chem. Soc.* 124:9026-9027; Chin, et al., (2002) *Proc. Natl. Acad. Sci.,* 99:11020-11024; Wang, et al., (2003) *Proc. Natl. Acad. Sci.,* 100:56-61; Zhang, et al., (2003) *Biochemistry,* 42:6735-6746; and, Chin, et al., (2003) *Science,* in press. This allows the selective labeling of virtually any protein with a host of reagents

TABLE 1

EXAMPLES OF OLIGOSACCHARIDES THROUGH GlcNAc-LINKAGE

| Type | Base Structure |
|---|---|
| High-mannose | Manα1-6\\Manα1-3/Manα1-6\\Manα1-3/ Manβ1-4GlcNAcβ1-4GlcNAcβ1-Asn |
| Hybrid | Manα1-6\\GlcNAcβ1-2—Manα1-3/ Manβ1-4GlcNAcβ1-4GlcNAcβ1-Asn |
| Complex | GlcNAcβ1-2—Manα1-6\\GlcNAcβ1-2—Manα1-3/ Manβ1-4GlcNAcβ1-4GlcNAcβ1-Asn |
| Xylose | Manα1-6\\Xylβ1-2/ Manβ1-4GlcNAcβ1-4GlcNAcβ1-Asn |

In yet another aspect, the post-translation modification includes proteolytic processing of precursors (including but not limited to, calcitonin precursor, calcitonin gene-related peptide precursor, preproparathyroid hormone, preproinsulin, proinsulin, prepro-opiomelanocortin, pro-opiomelanoincluding fluorophores, crosslinking agents, saccharide derivatives and cytotoxic molecules. See also, U.S. patent application Ser. No. 10/686,944 entitled "Glycoprotein synthesis" filed Jan. 16, 2003, which is incorporated by reference herein. Post-translational modifications, including but not limited to, through an azido amino acid, can also made through the Staudinger ligation (including but not limited to, with triarylphosphine reagents). See, e.g., Kiick et al., (2002) *Incorporation of azides into recombinant proteins for chemoselective modification by the Staudinger ligation, PNAS* 99:19-24.

This invention provides another highly efficient method for the selective modification of proteins, which involves the genetic incorporation of unnatural amino acids, including but not limited to, containing an azide or alkynyl moiety into proteins in response to a selector codon. These amino acid side chains can then be modified by, including but not limited to, a Huisgen [3+2] cycloaddition reaction (see, e.g., Padwa, A. in *Comprehensive Organic Synthesis, Vol.* 4, (1991) Ed. Trost, B. M., Pergamon, Oxford, p. 1069-1109; and, Huisgen, R. in 1,3-*Dipolar Cycloaddition Chemistry* (1984) Ed. Padwa, A., Wiley, New York, p. 1-176) with, including but not limited to, alkynyl or azide derivatives, respectively. Because this method involves a cycloaddition rather than a nucleophilic substitution, proteins can be modified with extremely high selectivity. This reaction can be carried out at room temperature in aqueous conditions with excellent regioselectivity (1,4>1,5) by the addition of catalytic amounts of Cu(I) salts to the reaction mixture. See, e.g., Tomoe, et al., (2002) *Org. Chem.* 67:3057-3064; and, Rostovtsev, et al., (2002) *Angew. Chem. Int. Ed.* 41:2596-2599. Another method that can be used is the ligand exchange on a bisarsenic compound with a tetracysteine motif, see, e.g., Griffin, et al., (1998) *Science* 281:269-272.

A molecule that can be added to a protein of the invention through a [3+2] cycloaddition includes virtually any molecule with an azide or alkynyl derivative. Molecules include, but are not limited to, dyes, fluorophores, crosslinking agents, saccharide derivatives, polymers (including but not limited to, derivatives of polyethylene glycol), photocrosslinkers, cytotoxic compounds, affinity labels, derivatives of biotin, resins, beads, a second protein or polypeptide (or more), polynucleotide(s) (including but not limited to, DNA, RNA, etc.), metal chelators, cofactors, fatty acids, carbohydrates, and the like. These molecules can be added to an unnatural amino acid with an alkynyl group, including but not limited to, p-propargyloxyphenylalanine, or azido group, including but not limited to, p-azido-phenylalanine, respectively.

V. In Vivo Generation of Four Helical Bundle Polypeptides Comprising Non-Genetically-Encoded Amino Acids The 4HB polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Patent Application Publications 2003/0082575 (Ser. No. 10/126,927) and 2003/0108885 (Ser. No. 10/126,931) which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O—RS). Typically, the O—RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides, and are generally suitable for use in the present invention. For example, keto-specific O-tRNA/aminoacyl-tRNA synthetases are described in Wang, L., et al., *Proc. Natl. Acad. Sci. USA* 100:56-61 (2003) and Zhang, Z. et al., *Biochem.* 42(22): 6735-6746 (2003). Exemplary O—RS, or portions thereof, are encoded by polynucleotide sequences and include amino acid sequences disclosed in U.S. Patent Application Publications 2003/0082575 and 2003/0108885, each incorporated herein by reference. Corresponding O-tRNA molecules for use with the O—RSs are also described in U.S. Patent Application Publications 2003/0082575 (Ser. No. 10/126,927) and 2003/0108885 (Ser. No. 10/126,931) which are incorporated by reference herein.

An example of an azide-specific O-tRNA/aminoacyl-tRNA synthetase system is described in Chin, J. W., et al., *J. Am. Chem. Soc.* 124:9026-9027 (2002). Exemplary O—RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Patent Application Publication 2003/0108885 (Ser. No. 10/126,931) which is incorporated by reference herein. Exemplary O-tRNA sequences suitable for use in the present invention include, but are not limited to, nucleotide sequences SEQ ID NOs: 1-3 as disclosed in U.S. Patent Application Publication 2003/0108885 (Ser. No. 10/126,931) which is incorporated by reference herein. Other examples of O-tRNA/aminoacyl-tRNA synthetase pairs specific to particular non-naturally encoded amino acids are described in U.S. Patent Application Publication 2003/0082575 (Ser. No. 10/126,927) which is incorporated by reference herein. O—RS and O-tRNA that incorporate both keto- and azide-containing amino acids in *S. cerevisiae* are described in Chin, J. W., et al., *Science* 301:964-967 (2003).

Use of O-tRNA/aminoacyl-tRNA synthetases involves selection of a specific codon which encodes the non-naturally encoded amino acid. While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the 4HB polynucleotide coding sequence using mutagenesis methods known in the art (including but not limited to, site-specific mutagenesis, cassette mutagenesis, restriction selection mutagenesis, etc.).

Methods for generating components of the protein biosynthetic machinery, such as O—RSs, O-tRNAs, and orthogonal O-tRNA/O—RS pairs that can be used to incorporate a non-naturally encoded amino acid are described in Wang, L., et al., *Science* 292: 498-500 (2001); Chin, J. W., et al., *J. Am. Chem. Soc.* 124:9026-9027 (2002); Zhang, Z. et al., *Biochemistry* 42: 6735-6746 (2003). Methods and compositions for the in vivo incorporation of non-naturally encoded amino acids are described in U.S. Patent Application Publication 2003/0082575 (Ser. No. 10/126,927) which is incorporated by reference herein. Methods for selecting an orthogonal tRNA-tRNA synthetase pair for use in in vivo translation system of an organism are also described in U.S. Patent Application Publications 2003/0082575 (Ser. No. 10/126,927) and 2003/0108885 (Ser. No. 10/126,931) which are incorporated by reference herein.

Methods for producing at least one recombinant orthogonal aminoacyl-tRNA synthetase (O—RS) comprise: (a) generating a library of (optionally mutant) RSs derived from at least one aminoacyl-tRNA synthetase (RS) from a first organism, including but not limited to, a prokaryotic organism, such as *Methanococcus jannaschii*, *Methanobacterium thermoautotrophicum*, *Halobacterium*, *Escherichia coli*, *A. fulgidus*, *P. furiosus*, *P. horikoshii*, *A. pernix*, *T. thermophilus*, or the like, or a eukaryotic organism; (b) selecting (and/or screening) the library of RSs (optionally mutant RSs) for members that aminoacylate an orthogonal tRNA (O-tRNA) in the presence of a non-naturally encoded amino acid and a natural amino acid, thereby providing a pool of active (optionally mutant) RSs; and/or, (c) selecting (optionally through negative selection) the pool for active RSs (including but not limited to, mutant RSs) that preferentially aminoacylate the O-tRNA in the absence of the non-naturally encoded amino acid, thereby providing the at least one recombinant O—RS; wherein the at least one recombinant O—RS preferentially aminoacylates the O-tRNA with the non-naturally encoded amino acid.

In one embodiment, the RS is an inactive RS. The inactive RS can be generated by mutating an active RS. For example, the inactive RS can be generated by mutating at least about 1, at least about 2, at least about 3, at least about 4, at least about 5, at least about 6, or at least about 10 or more amino acids to different amino acids, including but not limited to, alanine.

Libraries of mutant RSs can be generated using various techniques known in the art, including but not limited to rational design based on protein three dimensional RS structure, or mutagenesis of RS nucleotides in a random or rational design technique. For example, the mutant RSs can be generated by site-specific mutations, random mutations, diversity generating recombination mutations, chimeric constructs, rational design and by other methods described herein or known in the art.

In one embodiment, selecting (and/or screening) the library of RSs (optionally mutant RSs) for members that are active, including but not limited to, that aminoacylate an orthogonal tRNA (O-tRNA) in the presence of a non-naturally encoded amino acid and a natural amino acid, includes: introducing a positive selection or screening marker, including but not limited to, an antibiotic resistance gene, or the like, and the library of (optionally mutant) RSs into a plurality of cells, wherein the positive selection and/or screening marker comprises at least one selector codon, including but not limited to, an amber, ochre, or opal codon; growing the plurality of cells in the presence of a selection agent; identifying cells that survive (or show a specific response) in the presence of the selection and/or screening agent by suppressing the at least one selector codon in the positive selection or screening marker, thereby providing a subset of positively selected cells that contains the pool of active (optionally mutant) RSs. Optionally, the selection and/or screening agent concentration can be varied.

In one aspect, the positive selection marker is a chloramphenicol acetyltransferase (CAT) gene and the selector codon is an amber stop codon in the CAT gene. Optionally, the positive selection marker is a β-lactamase gene and the selector codon is an amber stop codon in the β-lactamase gene. In another aspect the positive screening marker comprises a fluorescent or luminescent screening marker or an affinity based screening marker (including but not limited to, a cell surface marker).

In one embodiment, negatively selecting or screening the pool for active RSs (optionally mutants) that preferentially aminoacylate the O-tRNA in the absence of the non-naturally encoded amino acid includes: introducing a negative selection or screening marker with the pool of active (optionally mutant) RSs from the positive selection or screening into a plurality of cells of a second organism, wherein the negative selection or screening marker comprises at least one selector codon (including but not limited to, an antibiotic resistance gene, including but not limited to, a chloramphenicol acetyltransferase (CAT) gene); and, identifying cells that survive or show a specific screening response in a first medium supplemented with the non-naturally encoded amino acid and a screening or selection agent, but fail to survive or to show the specific response in a second medium not supplemented with the non-naturally encoded amino acid and the selection or screening agent, thereby providing surviving cells or screened cells with the at least one recombinant O—RS. For example, a CAT identification protocol optionally acts as a positive selection and/or a negative screening in determination of appropriate O—RS recombinants. For instance, a pool of clones is optionally replicated on growth plates containing CAT (which comprises at least one selector codon) either with or without one or more non-naturally encoded amino acid. Colonies growing exclusively on the plates containing non-naturally encoded amino acids are thus regarded as containing recombinant O—RS. In one aspect, the concentration of the selection (and/or screening) agent is varied. In some aspects the first and second organisms are different. Thus, the first and/or second organism optionally comprises: a prokaryote, a eukaryote, a mammal, an *Escherichia coli*, a fungi, a yeast, an archaebacterium, a *eubacterium*, a plant, an insect, a protist, etc. In other embodiments, the screening marker comprises a fluorescent or luminescent screening marker or an affinity based screening marker.

In another embodiment, screening or selecting (including but not limited to, negatively selecting) the pool for active (optionally mutant) RSs includes: isolating the pool of active mutant RSs from the positive selection step (b); introducing a negative selection or screening marker, wherein the negative selection or screening marker comprises at least one selector codon (including but not limited to, a toxic marker gene, including but not limited to, a ribonuclease barnase gene, comprising at least one selector codon), and the pool of active (optionally mutant) RSs into a plurality of cells of a second organism; and identifying cells that survive or show a specific screening response in a first medium not supplemented with the non-naturally encoded amino acid, but fail to survive or show a specific screening response in a second medium supplemented with the non-naturally encoded amino acid, thereby providing surviving or screened cells with the at least one recombinant O—RS, wherein the at least one recombinant O—RS is specific for the non-naturally encoded amino acid. In one aspect, the at least one selector codon comprises about two or more selector codons. Such embodiments optionally can include wherein the at least one selector codon comprises two or more selector codons, and wherein the first and second organism are different (including but not limited to, each organism is optionally, including but not limited to, a prokaryote, a eukaryote, a mammal, an *Escherichia coli*, a fungi, a yeast, an archaebacteria, a eubacteria, a plant, an insect, a protist, etc.). Also, some aspects include wherein the negative selection marker comprises a ribonuclease barnase gene (which comprises at least one selector codon). Other aspects include wherein the screening marker optionally comprises a fluorescent or luminescent screening marker or an affinity based screening marker. In the embodiments herein, the screenings and/or selections optionally include variation of the screening and/or selection stringency.

In one embodiment, the methods for producing at least one recombinant orthogonal aminoacyl-tRNA synthetase (O—RS) can further comprise: (d) isolating the at least one recombinant O—RS; (e) generating a second set of O—RS (optionally mutated) derived from the at least one recombinant O—RS; and, (f) repeating steps (b) and (c) until a mutated O—RS is obtained that comprises an ability to preferentially aminoacylate the O-tRNA. Optionally, steps (d)-(f) are repeated, including but not limited to, at least about two times. In one aspect, the second set of mutated O—RS derived from at least one recombinant O—RS can be generated by mutagenesis, including but not limited to, random mutagenesis, site-specific mutagenesis, recombination or a combination thereof.

The stringency of the selection/screening steps, including but not limited to, the positive selection/screening step (b), the negative selection/screening step (c) or both the positive and negative selection/screening steps (b) and (c), in the above-described methods, optionally includes varying the selection/screening stringency. In another embodiment, the positive selection/screening step (b), the negative selection/screening step (c) or both the positive and negative selection/screening steps (b) and (c) comprise using a reporter, wherein the reporter is detected by fluorescence-activated cell sorting (FACS) or wherein the reporter is detected by luminescence. Optionally, the reporter is displayed on a cell surface, on a phage display or the like and selected based upon affinity or catalytic activity involving the non-naturally encoded amino acid or an analogue. In one embodiment, the mutated synthetase is displayed on a cell surface, on a phage display or the like.

Methods for producing a recombinant orthogonal tRNA (O-tRNA) include: (a) generating a library of mutant tRNAs derived from at least one tRNA, including but not limited to, a suppressor tRNA, from a first organism; (b) selecting (including but not limited to, negatively selecting) or screening the library for (optionally mutant) tRNAs that are aminoacylated by an aminoacyl-tRNA synthetase (RS) from a second organism in the absence of a RS from the first organism, thereby providing a pool of tRNAs (optionally mutant); and, (c) selecting or screening the pool of tRNAs (optionally mutant) for members that are aminoacylated by an introduced orthogonal RS(O—RS), thereby providing at least one recombinant O-tRNA; wherein the at least one recombinant O-tRNA recognizes a selector codon and is not efficiency recognized by the RS from the second organism and is preferentially aminoacylated by the O—RS. In some embodiments the at least one tRNA is a suppressor tRNA and/or comprises a unique three base codon of natural and/or unnatural bases, or is a nonsense codon, a rare codon, an unnatural codon, a codon comprising at least 4 bases, an amber codon, an ochre codon, or an opal stop codon. In one embodiment, the recombinant O-tRNA possesses an improvement of orthogonality. It will be appreciated that in some embodiments, O-tRNA is optionally imported into a first organism from a second organism without the need for modification. In various embodiments, the first and second organisms are either the same or different and are optionally chosen from, including but not limited to, prokaryotes (including but not limited to, *Methanococcus jannaschii, Methanobacterium thermoautotrophicum, Escherichia coli, Halobacterium*, etc.), eukaryotes, mammals, fingi, yeasts, archaebacteria, eubacteria, plants, insects, protists, etc. Additionally, the recombinant tRNA is optionally aminoacylated by a non-naturally encoded amino acid, wherein the non-naturally encoded amino acid is biosynthesized in vivo either naturally or through genetic manipulation. The non-naturally encoded amino acid is optionally added to a growth medium for at least the first or second organism.

In one aspect, selecting (including but not limited to, negatively selecting) or screening the library for (optionally mutant) tRNAs that are aminoacylated by an aminoacyl-tRNA synthetase (step (b)) includes: introducing a toxic marker gene, wherein the toxic marker gene comprises at least one of the selector codons (or a gene that leads to the production of a toxic or static agent or a gene essential to the organism wherein such marker gene comprises at least one selector codon) and the library of (optionally mutant) tRNAs into a plurality of cells from the second organism; and, selecting surviving cells, wherein the surviving cells contain the pool of (optionally mutant) tRNAs comprising at least one orthogonal tRNA or nonfunctional tRNA. For example, surviving cells can be selected by using a comparison ratio cell density assay.

In another aspect, the toxic marker gene can include two or more selector codons. In another embodiment of the methods, the toxic marker gene is a ribonuclease barnase gene, where the ribonuclease barnase gene comprises at least one amber codon. Optionally, the ribonuclease barnase gene can include two or more amber codons.

In one embodiment, selecting or screening the pool of (optionally mutant) tRNAs for members that are aminoacylated by an introduced orthogonal RS(O—RS) can include: introducing a positive selection or screening marker gene, wherein the positive marker gene comprises a drug resistance gene (including but not limited to, β-lactamase gene, comprising at least one of the selector codons, such as at least one amber stop codon) or a gene essential to the organism, or a gene that leads to detoxification of a toxic agent, along with the O—RS, and the pool of (optionally mutant) tRNAs into a plurality of cells from the second organism; and, identifying surviving or screened cells grown in the presence of a selection or screening agent, including but not limited to, an antibiotic, thereby providing a pool of cells possessing the at least one recombinant tRNA, where the at least one recombinant tRNA is aminoacylated by the O—RS and inserts an amino acid into a translation product encoded by the positive marker gene, in response to the at least one selector codons. In another embodiment, the concentration of the selection and/or screening agent is varied.

Methods for generating specific O-tRNA/O—RS pairs are provided. Methods include: (a) generating a library of mutant tRNAs derived from at least one tRNA from a first organism; (b) negatively selecting or screening the library for (optionally mutant) tRNAs that are aminoacylated by an aminoacyl-tRNA synthetase (RS) from a second organism in the absence of a RS from the first organism, thereby providing a pool of (optionally mutant) tRNAs; (c) selecting or screening the pool of (optionally mutant) tRNAs for members that are aminoacylated by an introduced orthogonal RS(O—RS), thereby providing at least one recombinant O-tRNA. The at least one recombinant O-tRNA recognizes a selector codon and is not efficiency recognized by the RS from the second organism and is preferentially aminoacylated by the O—RS. The method also includes (d) generating a library of (optionally mutant) RSs derived from at least one aminoacyl-tRNA synthetase (RS) from a third organism; (e) selecting or screening the library of mutant RSs for members that preferentially aminoacylate the at least one recombinant O-tRNA in the presence of a non-naturally encoded amino acid and a natural amino acid, thereby providing a pool of active (optionally mutant) RSs; and, (f) negatively selecting or screening the pool for active (optionally mutant) RSs that preferentially aminoacylate the at least one recombinant O-tRNA in the absence of the non-naturally encoded amino acid, thereby providing the at least one specific O-tRNA/O—RS pair, wherein the at least one specific O-tRNA/O—RS pair comprises at least one recombinant O—RS that is specific for the non-naturally encoded amino acid and the at least one recombinant O-tRNA. Specific O-tRNA/O—RS pairs produced by the methods are included. For example, the specific O-tRNA/O—RS pair can include, including but not limited to, a mutRNATyr-mutTyrRS pair, such as a mutRNATyr-SS12TyrRS pair, a mutRNALeu-mutLeuRS pair, a mutRNAThr-mutThrRS pair, a mutRNAGlu-mutGluRS pair, or the like. Additionally, such methods include wherein the first and third organism are the same (including but not limited to, *Methanococcus jannaschii*).

Methods for selecting an orthogonal tRNA-tRNA synthetase pair for use in an in vivo translation system of a second organism are also included in the present invention. The methods include: introducing a marker gene, a tRNA and an aminoacyl-tRNA synthetase (RS) isolated or derived from a first organism into a first set of cells from the second organism; introducing the marker gene and the tRNA into a duplicate cell set from a second organism; and, selecting for surviving cells in the first set that fail to survive in the duplicate cell set or screening for cells showing a specific screening response that fail to give such response in the duplicate cell set, wherein the first set and the duplicate cell set are grown in the presence of a selection or screening agent, wherein the surviving or screened cells comprise the orthogonal tRNA-tRNA synthetase pair for use in the in the in vivo translation system of the second organism. In one embodiment, comparing and selecting or screening includes an in vivo complementation assay. The concentration of the selection or screening agent can be varied.

The organisms of the present invention comprise a variety of organism and a variety of combinations. For example, the first and the second organisms of the methods of the present invention can be the same or different. In one embodiment, the organisms are optionally a prokaryotic organism, including but not limited to, *Methanococcus jannaschii*, *Methanobacterium thermoautotrophicum*, *Halobacterium*, *Escherichia coli*, *A. fulgidus*, *P. furiosus*, *P. horikoshii*, *A. pernix*, *T thermophilus*, or the like. Alternatively, the organisms optionally comprise a eukaryotic organism, including but not limited to, plants (including but not limited to, complex plants such as monocots, or dicots), algae, protists, fungi (including but not limited to, yeast, etc), animals (including but not limited to, mammals, insects, arthropods, etc.), or the like. In another embodiment, the second organism is a prokaryotic organism, including but not limited to, *Methaniococcus jannaschii*, *Methanobacterium thermoautotrophicum*, *Halobacterium*, *Escherichia coli*, *A. fulgidus*, *Halobacterium*, *P. furiosus*, *P. horikoshii*, *A. pernix*, *T. thermophilus*, or the like. Alternatively, the second organism can be a eukaryotic organism, including but not limited to, a yeast, a animal cell, a plant cell, a fungus, a mammalian cell, or the like. In various embodiments the first and second organisms are different.

VI. Location of Non-Naturally-Occurring Amino Acids in Four Helical Bundle Polypeptides The present invention contemplates incorporation of one or more non-naturally-occurring amino acids into 4HB polypeptides. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids) and/or inserting the non-naturally-occurring amino acid in a location that is not required for activity.

Regions of hGH can be illustrated as follows, wherein the amino acid positions in hGH are indicated in the middle row (SEQ ID NO: 2):

| | Helix A | | Helix B | | Helix C | | Helix D | |
|---|---|---|---|---|---|---|---|---|
| [1-5]- | [6-33]- | [34-74]- | [75-96]- | [97-105]- | [106-129]- | [130-153]- | [154-183]- | [184-191] |
| N-term | | A-B loop | | B-C loop | | C-D loop | | C-term |

Regions of hIFN can be illustrated as follows, wherein the amino acid positions in HFN are according to SEQ ID NO:24: 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix) 137-155 (E helix) 156-165 (C-terminus).

Regions of hG-CSF can be illustrated as follows, wherein the amino acid positions in hG-CSF are indicated in brackets (SEQ ID NO: 29 or the corresponding amino acid position in SEQ ID NO: 30 but lacking the N-terminal 30 amino acid signal sequence): 1-10 (N-terminus), 11-39 (A helix), 40-70 (region between A helix and B helix), 71-91 (3 helix), 92-99 (region between B helix and C helix), 100-123 (C helix), 124-142 (region between C helix and D helix), 143-172 (D helix), 173-175 (C-terminus), including the short helical segment, the mini-E Helix, at 44-53 between the A Helix and B Helix composed of a $3_{10}$ helix (44-47) and an cc helix (48-53).

Regions of hEPO can be illustrated as follows (SEQ ID NO: 38): 1-7 (N-terminus), 8-26 (A helix), 27-54 (AB loop, containing beta sheet 1 (39-41) and mini B' helix (47-52)), 55-83 (B helix), 84-89 (BC loop), 90-112 (C helix), 113-137 (CD loop, containing mini C' helix (114-121) and beta sheet 2 (133-135)), 138-161 (D helix), 162-166 (C-terminus).

A variety of biochemical and structural approaches can be employed to select the desired sites for substitution with a non-naturally encoded amino acid within the 4HB polypeptide. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing a four helical bundle molecule having any desired property or activity, including but not limited to, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of four helical bundle polypeptides can be identified using alanine scanning or homolog scanning methods known in the art. See, e.g., Cunningham, B. and Wells, J., *Science,* 244:1081-1085 (1989) (identifying 14 residues that are critical for hGH bioactivity) and Cunningham, B., et al. *Science* 243: 1330-1336 (1989) (identifying antibody and receptor epitopes using homolog scanning mutagenesis). See, e.g., Di Marco et al., Biochem Biophys Res Corn 202:1445 (1994); Walter et al., Cancer Biotherapy & Radiopharm. 13:143 (1998); Runkel et al., J.B.C. 273:8003 (1998) for IFN. G-CSF alanine scanning mutagenesis studies are described in Reidhaar-Olson J F et al., Biochemistry (1996) July 16; 35(28):9034-41, Young D C et al. Protein Sci. (1997) June; 6(6):1228-36, and Layton et al. (1997) JBC 272(47):29735-29741. See, e.g., Bittorf, T. et al. *FEBS,* 336:133-136 (1993) (identifying critical residues for hEPO activity), Wen, D. et al. *JBC,* 269: 22839-22846 (1994) (alanine scanning mutagenesis employed to identify functionally important domains of hEPO), and Elliot, S. et al. *Blood,* 89:493-502 (1997) (identifying key electrostatic interactions between hEPO and human EPO receptor). Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of naturally-occurring mutants of 4HB polypeptides that contain deletions can also be examined to determine regions of the protein that are likely to be tolerant of substitution with a non-naturally encoded amino acid. See, e.g., Kostyo et al., *Biochem. Biophys. Acta,* 925: 314 (1987); Lewis, U., et al., *J. Biol. Chem.,* 253:2679-2687 (1978) for hGH. See, e.g., Bittorf et al., *FEBS,* 336:133 (1993); Wen et al, *JBC,* 269:22839 (1994) for hEPO. In a similar manner, protease digestion and monoclonal antibodies can be used to identify regions of 4BB polypeptides that are responsible for binding the 4HB polypeptide receptor. See, e.g., Cunningham, B., et al. *Science* 243: 1330-1336 (1989); Mills, J., et al., *Endocrinology,* 107:391-399 (1980); Li, C., *Mol. Cell. Biochem.,* 46:31-41 (1982) (indicating that amino acids between residues 134-149 can be deleted without a loss of activity for hGH). Layton et al. (2001) JBC 276 (39) 36779-36787 describes antibody studies with hG-CSF and its receptor. Once residues that are likely to be intolerant to substitution with non-naturally encoded amino acids have been eliminated, the impact of proposed substitutions at each of the remaining positions can be examined from the three-dimensional crystal structure of the 4HB and its binding proteins. See de Vos, A., et al., *Science,* 255:306-312 (1992) for hGH; all crystal structures of hGH are available in the Protein Data Bank (including 3HHR, 1AXI, and 1HWG) (PDB, available on the World Wide Web at rcsb.org), a centralized database containing three-dimensional structural data of large molecules of proteins and nucleic acids. X-ray crystallographic and NMR structures of hIFN are also available in the Protein Data Bank (1RH2 and 1ITF), as well as U.S. Pat. Nos. 5,602,232; 5,460,956; 5,441,734; 4,672,108, which are incorporated by reference herein. X-ray crystallographic and NMR structures of hG-CSF are available in the Protein Data Bank with PDB ID's: 1CD9, 1PGR, 1RHG, 1GNC, as well as in U.S. Pat. No. 5,581,476; and U.S. Pat. No. 5,790,421, which are incorporated by reference herein. For hEPO, see Syed et al., *Nature,* 395: 511 (1998) and Cheetham et al., *Nature Structural Biology,* 5:861 (1998); X-ray crystallographic and NMR structures of hEPO are available in the Protein Data Bank with PDB ID's: 1CN4, 1EER, and 1BUY. Thus, those of skill in the art can readily identify amino acid positions that can be substituted with non-naturally encoded amino acids.

In some embodiments, the 4HB polypeptides of the invention comprise one or more non-naturally occurring amino acids positioned in a region of the protein that does not disrupt the helices or beta sheet secondary structure of the polypeptide.

Exemplary residues of incorporation of a non-naturally encoded amino acid may be those that are excluded from potential receptor binding regions (including but not limited to, Site I and Site II), may be fully or partially solvent exposed, have minimal or no hydrogen-bonding interactions with nearby residues, may be minimally exposed to nearby reactive residues, and may be in regions that are highly flexible (including but not limited to, C-D loop) or structurally rigid (including but not limited to, B helix) as predicted by the three-dimensional crystal structure of the four helical bundle polypeptide with its receptor.

In some embodiments, one or more non-naturally encoded amino acids are incorporated at any position in one or more of the following regions corresponding to secondary structures in hGH as follows: 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus) from SEQ ED NO: 2. In other embodiments, hGH polypeptides of the invention comprise at least one non-naturally-occurring amino acid substituted for at least one amino acid located in at least one region of hGH selected from the group consisting of the N-terminus (1-5), the N-terminal end of the A-B loop (32-46); the B-C loop (97-105), the C-D loop (132-149), and the C-terminus (184-191). In some embodiments, one or more non-naturally encoded amino acids are incorporated at one or more of the following positions of hGH: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3).

Exemplary sites of incorporation of one or more non-naturally encoded amino acids include 29, 30, 33, 34, 35, 37, 39, 40, 49, 57, 59, 66, 69, 70, 71, 74, 88, 91, 92, 94, 95, 98, 99, 101, 103, 107, 108, 111, 122, 126, 129, 130, 131, 133, 134, 135, 136, 137, 139, 140, 141, 142, 143, 145, 147, 154, 155, 156, 159, 183, 186, and 187, or any combination thereof from SEQ ID NO: 2 or the corresponding amino acids of SEQ ID NO: 1 or 3.

A subset of exemplary sites for incorporation of one or more non-naturally encoded amino acid include 29, 33, 35, 37, 39, 49, 57, 69, 70, 71, 74, 88, 91, 92, 94, 95, 98, 99, 101, 103, 107, 108, 111, 129, 130, 131, 133, 134, 135, 136, 137, 139, 140, 141, 142, 143, 145, 147, 154, 155, 156, 186, and 187, or any combination thereof from SEQ ID NO: 2 or the corresponding amino acids of SEQ ID NO: 1 or 3. An examination of the crystal structure of hGH and its interactions with the hGH receptor indicates that the side chains of these amino acid residues are fully or partially accessible to solvent and the side chain of a non-naturally encoded amino acid may point away from the protein surface and out into the solvent.

Exemplary positions for incorporation of one or more non-naturally encoded amino acids include 35, 88, 91, 92, 94, 95, 99, 101, 103, 111, 131, 133, 134, 135, 136, 139, 140, 143, 145, and 155, or any combination thereof from SEQ ID NO: 2 or the corresponding amino acids of SEQ ID NO: 1 or 3. An examination of the crystal structure of hGH and its interactions with the hGH receptor indicates that the side chains of these amino acid residues are fully exposed to the solvent and the side chain of the native residue points out into the solvent.

A subset of exemplary sites for incorporation of one or more non-naturally encoded amino acids include 30, 74, 103, or any combination thereof, from SEQ ID NO: 2 or the corresponding amino acids of SEQ ID NO: 1 or 3. Another subset of exemplary sites for incorporation of one or more non-naturally encoded amino acids include 35, 92, 143, 145, or any combination thereof, from SEQ ID NO: 2 or the corresponding amino acids of SEQ ID NO: 1 or 3.

In some embodiments, the non-naturally occurring amino acid at one or more of these positions is linked to a water soluble polymer, including but not limited to, positions: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3). In some embodiments, the non-naturally occurring amino acid at one or more of these positions is linked to a water soluble polymer: 30, 35, 74, 92, 103, 143, 145 (SEQ ID NO: 2 or the corresponding amino acids of SEQ ID NO: 1 or 3). In some embodiments, the non-naturally occurring amino acid at one or more of these positions is linked to a water soluble polymer: 35, 92, 143, 145 (SEQ ID NO: 2 or the corresponding amino acids of SEQ ID NO: 1 or 3).

Human GH antagonists include, but are not limited to, those with substitutions at: 1, 2, 3, 4, 5, 8, 9, 11, 12, 15, 16, 19, 22, 103, 109, 112, 113, 115, 116, 119, 120, 123, and 127 or an addition at position 1 (i.e., at the N-terminus), or any combination thereof (SEQ ID NO:2, or the corresponding amino acid in SEQ ID NO: 1, 3, or any other GH sequence).

In some embodiments, one or more non-naturally encoded amino acid are incorporated or substituted in one or more of the following regions corresponding to secondary structures in IFN wherein the amino acid positions in hIFN are according to SEQ ID NO: 24: 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix) 137-155 (E helix) 156-165 (C-terminus).

In some embodiments, one or more non-naturally encoded amino acids are incorporated in one or more of the following positions in IFN: before position 1 (i.e. at the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus of the protein) (as in SEQ ID NO: 24, or the corresponding amino acids in other IFN's). In some embodiments, the IFN polypeptides of the invention comprise one or more non-naturally occurring amino acids at one or more of the following positions: 100, 106, 107, 108, 111, 113, 114 (SEQ ID NO: 24, or the corresponding amino acids in other IFN's). In some embodiments, the IFN polypeptides of the invention comprise one or more non-naturally occurring amino acids at one or more of the following positions: 41, 45, 46, 48, 49 (SEQ ID NO: 24, or the corresponding amino acids in other IFN's). In some embodiments, the IFN polypeptides of the invention comprise one or more non-naturally occurring amino acids at one or more of the following positions: 61, 64, 65, 101, 103, 110, 117, 120, 121, 149 (SEQ ID NO: 24, or the corresponding amino acids in other IFN's). In some embodiments, the IFN polypeptides of the invention comprise one or more non-naturally occurring amino acids at one or more of the following positions: 6, 9, 12, 13, 16, 96, 156, 159, 160, 161, 162 (SEQ ID NO: 24, or the corresponding amino acids in other IFN's). In some embodiments, the IFN polypeptides of the invention comprise one or more non-naturally occurring amino acids at one or more of the following positions: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (SEQ ID NO: 24, or the corresponding amino acids in other IFN's). In some embodiments, the non-naturally occurring amino acid at these or other positions is linked to a water soluble polymer, including but not limited to positions: before position 1 (i.e. the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. the carboxyl terminus) (SEQ ID NO: 24, or the corresponding amino acids in other IFN's). In some embodiments, the water soluble polymer is coupled at one or more amino acid positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 24, or the corresponding amino acid in SEQ ID NO: 23, 25, or any other IFN polypeptide). In some embodiments, the IFN polypeptides of the invention comprise one or more non-naturally occurring amino acids at one or more of the following positions providing an antagonist: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165, or any combination thereof (SEQ ID NO: 24, or the corresponding amino acids in other IFN's); a hIFN polypeptide comprising one of these substitutions may potentially act as a weak antagonist or weak agonist depending on the site selected and the desired activity. Human IFN antagonists include, but are not limited to, those with substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combination thereof (hIFN; SEQ ID NO: 24 or the corresponding amino acids in SEQ ID NO: 23 or 25).

In some embodiments, one or more non-naturally encoded amino acid are incorporated or substituted in one or more of the following regions corresponding to secondary structures in G-CSF as follows: 1-10 (N-terminus), 11-39 (A helix), 40-70 (region between A helix and B helix), 71-91 (B helix), 92-99 (region between B helix and C helix), 100-123 (C helix), 124-142 (region between C helix and D helix), 143-172 (D helix), 173-175 (C-terminus), including the short helical segment, the mini-E Helix, at 44-53 between the A Helix and B Helix composed of a $3_{10}$ helix (44-47) and an a helix (48-53) (as in SEQ ID NO: 29, or the corresponding amino acids in SEQ ID NO: 28, 30, 35, and 36). In some embodiments, one or more non-naturally encoded amino acids are incorporated in one of the following positions in G-CSF: before position 1 (i.e. at the N terminus), 1, 2, 3, 4, 5, 6, 7, 8, 9, 10, 11, 12, 13, 16, 17, 19, 20, 21, 23, 24, 28, 30, 31, 33, 34, 35, 38, 39, 40, 41, 44, 45, 46, 47, 48, 49, 50, 51, 53, 54, 55, 56, 58, 59, 61, 63, 64, 66, 67, 68, 69, 70, 71, 72, 73, 77, 78, 81, 84, 87, 88, 91, 92, 94, 95, 97, 98, 99, 101, 102, 103, 105, 106, 108, 109, 110, 112, 113, 116, 117, 120, 121, 123, 124, 125, 126, 127, 130, 131, 132, 133, 134, 135, 136, 137, 138, 139, 140, 142, 143, 144, 145, 146, 147, 148, 156, 157, 159, 160, 163, 164, 166, 167, 170, 171, 173, 174, 175, 176 (i.e. at the carboxyl terminus) (as in SEQ ID NO: 29, or the corresponding amino acids in SEQ ID NO: 28, 30, 35, or 36). In some embodiments, the G-CSF polypeptides of the invention comprise one or more non-naturally occurring amino acids at one or more of the following positions: 30, 31, 33, 58, 59, 61, 63, 64, 66, 67, 68, 77, 78, 81, 87, 88, 91, 95, 101, 102, 103, 130, 131, 132, 134, 135, 136, 137, 156, 157, 159, 160, 163, 164, 167, 170, and 171 (as in SEQ ID NO: 29, or the corresponding amino acids in SEQ ID NO: 28, 30, 35, or 36). In some embodiments, the non-naturally occurring amino acid at one or more of these positions is linked to a water soluble polymer, including but not limited to positions: before position 1 (i.e. at the N terminus), 1, 2, 3, 4, 5, 6, 7, 8, 9, 10, 11, 12, 13, 16, 17, 19, 20, 21, 23, 24, 28, 30, 31, 33, 34, 35, 38, 39, 40, 41, 44, 45, 46, 47, 48, 49, 50, 51, 53, 54, 55, 56, 58, 59, 61, 63, 64, 66, 67, 68, 69, 70, 71, 72, 73, 77, 78, 81, 84, 87, 88, 91, 92, 94, 95, 97, 98, 99, 101, 102, 103, 105, 106, 108, 109, 110, 112, 113, 116, 117, 120, 121, 123, 124, 125, 126, 127, 130, 131, 132, 133, 134, 135, 136, 137, 138, 139, 140, 142, 143, 144, 145, 146, 147, 148, 156, 157, 159, 160, 163, 164, 166, 167, 170, 171, 173, 174, 175, 176 (i.e. at the carboxyl terminus) (SEQ ID NO: 29, or the corresponding amino acids in SEQ ID NO: 28, 30, 35, or 36). In some embodiments, the non-naturally occurring amino acid at these or other positions are linked to a water soluble polymer, including but not limited to positions: 59, 63, 67, 130, 131, 132, 134, 137, 160, 163, 167, and 171 (as in SEQ ID NO: 29, or the corresponding amino acids in SEQ ID NO: 28, 30, 35, or 36).

A subset of exemplary sites for incorporation of a non-naturally encoded amino acid include, but are not limited to, 30, 31, 33, 58, 59, 61, 63, 64, 66, 67, 68, 77, 78, 81, 87, 88, 91, 95, 101, 102, 103, 130, 131, 132, 134, 135, 136, 137, 156, 157, 159, 160, 163, 164, 167, 170, and 171 (as in SEQ ID NO: 29, or the corresponding amino acids in SEQ ID NO: 28, 30, 35, or 36). An examination of the crystal structure of hG-CSF and its interactions with the hG-CSF receptor indicates that the side chains of these amino acid residues are fully or partially accessible to solvent and the side chain of a non-naturally encoded amino acid may point away from the protein surface and out into the solvent.

Exemplary positions for incorporation of a non-naturally encoded amino acid include 59, 63, 67, 130, 131, 132, 134, 137, 160, 163, 167, and 171 (as in SEQ ID NO: 29, or the corresponding amino acids in SEQ ID NO: 28, 30, 35, or 36). An examination of the crystal structure of hG-CSF and its interactions with the hG-CSF receptor indicates that the side chains of these amino acid residues are fully exposed to the solvent and the side chain of the native residue points out into the solvent.

Human G-CSF antagonists include, but are not limited to, those with substitutions at: 6, 7, 8, 9, 10, 11, 12, 13, 16, 17, 19, 20, 21, 23, 24, 28, 30, 41, 47, 49, 50, 70, 71, 105, 106, 109, 110, 112, 113, 116, 117, 120, 121, 123, 124, 125, 127, 145, or any combination thereof (SEQ ID NO: 29, or the corresponding amino acid in SEQ ID NO: 28, 30, 35, or 36).

In some embodiments, one or more non-naturally encoded amino acid are incorporated or substituted in one or more of the following regions corresponding to secondary structures in EPO as follows: 1-7 (N-terminus), 8-26 (A helix), 27-54 (AB loop, containing beta sheet 1 (39-41) and mini B' helix (47-52)), 55-83 (B helix), 84-89 (BC loop), 90-112 (C helix), 113-137 (CD loop, containing mini C' helix (114-121) and beta sheet 2 (133-135)), 138-161 (D helix), 162-166 (C-terminus) (SEQ ID NO: 38, or the corresponding amino acids in SEQ ID NO: 37 or 39). In some embodiments, one or more non-naturally encoded amino acids are incorporated in one or more of the following positions in EPO: before position 1 (i.e. at the N terminus), 1, 2, 3, 4, 5, 6, 8, 9, 10, 11, 14, 15, 16, 17, 18, 20, 21, 23, 24, 25, 26, 27, 28, 30, 31, 32, 34, 35, 36, 37, 38, 39, 40, 43, 44, 45, 46, 47, 48, 49, 50, 51, 52, 53, 54, 55, 56, 57, 58, 65, 68, 72, 75, 76, 77, 78, 79, 80, 82, 83, 84, 85, 86, 87, 88, 89, 90, 91, 92, 93, 96, 97, 99, 100, 103, 104, 107, 108, 110, 111, 113, 114, 115, 116, 117, 118, 119, 120, 121, 122, 123, 124, 125, 126, 127, 128, 129, 130, 131, 132, 133, 134, 136, 140, 143, 144, 146, 147, 150, 154, 155, 157, 158, 159, 160, 162, 163, 164, 165, 166, 167 (i.e. at the carboxyl terminus) (SEQ ID NO: 38, or the corresponding amino acids in SEQ ID NO: 37 or 39). In some embodiments, the non-naturally occurring amino acid at one or more of these positions is linked to a water soluble polymer, including but not limited to, positions: before position 1 (i.e. at the N terminus), 1, 2, 3, 4, 5, 6, 8, 9, 10, 11, 14, 15, 16, 17, 18, 20, 21, 23, 24, 25, 26, 27, 28, 30, 31, 32, 34, 35, 36, 37, 38, 39, 40, 43, 44, 45, 46, 47, 48, 49, 50, 51, 52, 53, 54, 55, 56, 57, 58, 65, 68, 72, 75, 76, 77, 78, 79, 80, 82, 83, 84, 85, 86, 87, 88, 89, 90, 91, 92, 93, 96, 97, 99, 100, 103, 104, 107, 108, 110, 111, 113, 114, 115, 116, 117, 118, 119, 120, 121, 122, 123, 124, 125, 126, 127, 128, 129, 130, 131, 132, 133, 134, 136, 140, 143, 144, 146, 147, 150, 154, 155, 157, 158, 159, 160, 162, 163, 164, 165, 166, 167 (i.e. at the carboxyl terminus) (SEQ ID NO: 38 or the corresponding amino acids in SEQ ID NO: 37 or 39). In some embodiments, one or more non-naturally occurring amino acids at these or other positions linked to a water soluble polymer, including, but not limited to, positions 21, 24, 38, 83, 85, 86, 89, 116, 119, 121, 124, 125, 126, 127, and 128, or combination thereof (SEQ ID NO: 38, or the corresponding amino acids in SEQ ID NO: 37 or 39).

A subset of exemplary sites for incorporation of one or more non-naturally encoded amino acid include, but are not limited to, 1, 2, 4, 9, 17, 20, 21, 24, 25, 27, 28, 30, 31, 32, 34, 36, 37, 38, 40, 50, 53, 55, 58, 65, 68, 72, 76, 79, 80, 82, 83, 85, 86, 87, 89, 113, 115, 116, 119, 120, 121, 122, 123, 124, 125, 126, 127, 128, 129, 130, 131, 132, 134, 136, 159, 162, 163, 164, 165, and 166 (SEQ ID NO: 38, or the corresponding amino acids in SEQ ID NO: 37 or 39). An examination of the crystal structure of hEPO and its interactions with the hEPO receptor indicates that the side chains of these amino acid residues are fully or partially accessible to solvent and the side chain of a non-naturally encoded amino acid may point away from the protein surface and out into the solvent.

Exemplary positions for incorporation of one or more non-naturally encoded amino acid include 21, 24, 28, 30, 31, 36, 37, 38, 55, 72, 83, 85, 86, 87, 89, 113, 116, 119, 120, 121, 123, 124, 125, 126, 127, 128, 129, 130, 162, 163, 164, 165, and 166 (SEQ ID NO: 38, or the corresponding amino acids in SEQ ID NO: 37 or 39). An examination of the crystal structure of hEPO and its interactions with the hEPO receptor indicates that the side chains of these amino acid residues are fully exposed to the solvent and the side chain of the native residue points out into the solvent.

Human EPO antagonists include, but are not limited to, those with substitutions at: 2, 3, 5, 8, 9, 10, 11, 14, 15, 16, 17, 18, 20, 23, 43, 44, 45, 46, 47, 48, 49, 50, 52, 75, 78, 93, 96, 97, 99, 100, 103, 104, 107, 108, 110, 131, 132, 133, 140, 143, 144, 146, 147, 150, 154, 155, 159 (hEPO; SEQ ID NO: 38, or corresponding amino acids in SEQ ID NO: 37 or 39).

A wide variety of non-naturally encoded amino acids can be substituted for, or incorporated into, a given position in a 4HB polypeptide. In general, a particular non-naturally encoded amino acid is selected for incorporation based on an examination of the three dimensional crystal structure of a 4HB polypeptide with its receptor, a preference for conservative substitutions (i.e., aryl-based non-naturally encoded amino acids, such as p-acetylphenylalanine or O-propargyl-tyrosine substituting for Phe, Tyr or Trp), and the specific conjugation chemistry that one desires to introduce into the 4HB polypeptide (e.g., the introduction of 4-azidophenylalanine if one wants to effect a Huisgen [3+2] cycloaddition with a water soluble polymer bearing an alkyne moiety or a amide bond formation with a water soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, bio tin, a derivative of biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the 4HB polypeptide to affect other biological traits of the 4HB polypeptide. In some cases, the other additions, substitutions or deletions may increase the stability (including but not limited to, resistance to proteolytic degradation) of the 4HB polypeptide or increase affinity of the 4HB polypeptide for its receptor. In some embodiments, the hGH polypeptide comprises an amino acid substitution selected from the group consisting of F10A, F10H, F10I; M14W, M14Q, M14G; H18D; $H_{21}N$; G120A; R167N; D171S; E174S; F176Y, I179T or any combination thereof in SEQ ID NO: 2. In some cases, the other additions, substitutions or deletions may increase the solubility (including but not limited to, when expressed in *E. coli* or other host cells) of the 4HB polypeptide. In some embodiments additions, substitutions or deletions may increase the polypeptide solubility following expression in *E. coli* recombinant host cells. In some embodiments sites are selected for substitution with a naturally encoded or non-natural amino acid in addition to another site for incorporation of a non-natural amino acid that results in increasing the polypeptide solubility following expression in *E. coli* recombinant host cells. Examples of such sites in hEPO for amino acid substitution to increase solubility are N36, Q86, G113 and/or Q115, which may be substituted with Lys, Arg, Glu, or any other charged naturally encoded or non-naturally encoded amino acid (SEQ ID NO: 38). In some embodiments, the 4HB polypeptides comprise another addition, substitution or deletion that modulates affinity for the 4111B polypeptide receptor, modulates (including but not limited to, increases or decreases) receptor dimerization, stabilizes receptor dimers, modulates circulating half-life, modulates release or bio-availability, facilitates purification, or improves or alters a particular route of administration. For instance, in addition to introducing one or more non-naturally encoded amino acids as set forth herein, one or more of the following substitutions are introduced: F10A, F10H or F100; M14W, M14Q, or M14G; H18D; $H_{21}N$; R167N; D171S; E174S; F176Y and I179T to increase the affinity of the hGH variant for its receptor. For instance, in addition to introducing one or more non-naturally encoded amino acids as set forth herein, one or more of the following substitutions are introduced: S9A, F48S, Y49S, A50S, Q59A, A73G, G101A, T106A, L108A, T132A, R139A, K140A, R143A, S146A, N147A, R150A, and K154A to increase the affinity of the hEPO variant for its receptor (Wen et al., (1994) JBC 269:22839-22846). Similarly, 4HB polypeptides can comprise protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification or other traits of the polypeptide.

In some embodiments, the substitution of a non-naturally encoded amino acid generates an hGH antagonist. A subset of exemplary sites for incorporation of one or more non-naturally encoded amino acid include: 1, 2, 3, 4, 5, 8, 9, 11, 12, 15, 16, 19, 22, 103, 109, 112, 113, 115, 116, 119, 120, 123, 127, or an addition before position 1 (SEQ ID NO: 2, or the corresponding amino acid in SEQ ID NO: 1, 3, or any other GH sequence). In some embodiments, hGH antagonists comprise at least one substitution in the regions 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus) that cause GH to act as an antagonist. In other embodiments, the exemplary sites of incorporation of a non-naturally encoded amino acid include residues within the amino terminal region of helix A and a portion of helix C. In another embodiment, substitution of G120 with a non-naturally encoded amino acid such as p-azido-L-phenylalanine or O-propargyl-L-tyrosine. In other embodiments, the above-listed substitutions are combined with additional substitutions that cause the hGH polypeptide to be an hGH antagonist. For instance, a non-naturally encoded amino acid is substituted at one of the positions identified herein and a simultaneous substitution is introduced at G120 (e.g., G120R, G120K, G120W, G120Y, G120F, or G120E). In some embodiments, the hGH antagonist comprises a non-naturally encoded amino acid linked to a water soluble polymer that is present in a receptor binding region of the hGH molecule.

In some embodiments, the substitution of a non-naturally encoded amino acid generates a hIFN antagonist. A subset of exemplary sites for incorporation of one or more non-naturally encoded amino acid include: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165 (as in SEQ ID NO: 24, or the corresponding amino acids in other IFNs). Another subset of exemplary sites for incorporation of a non-naturally encoded amino acid include: 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, (hIFN; SEQ ID NO: 24 or the corresponding amino acids in SEQ ID NO: 23 or 25). In some embodiments, hIFN antagonists comprise at least one substitution in the regions 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus) that cause IFN to act as an antagonist. In other embodiments, the exemplary sites of incorporation of a non-naturally encoded amino acid include residues within the amino terminal region of helix A and a portion of helix C. In other embodiments, the above-listed substitutions are combined with additional substitutions that cause the hIFN polypeptide to be a hIFN antagonist. In some embodiments, the hIFN antagonist comprises a non-naturally encoded amino acid linked to a water soluble polymer that is present in a receptor binding region of the hIFN molecule.

In some embodiments, the substitution of a non-naturally encoded amino acid generates a hG-CSF antagonist. A subset of exemplary sites for incorporation of one or more non-naturally encoded amino acid include: 6, 7, 8, 9, 10, 11, 12, 13, 16, 17, 19, 20, 21, 23, 24, 28, 30, 41, 47, 49, 50, 70, 71, 105, 106, 109, 110, 112, 113, 116, 117, 120, 121, 123, 124, 125, 127, and 145 (as in SEQ ID NO: 29, or the corresponding amino acids in SEQ ID NO: 28, 30, 35, or 36). In some embodiments, hG-CSF antagonists comprise at least one substitution in the regions 6-30, 40-70, or 105-130 that cause G-CSF to act as an antagonist. In other embodiments, the exemplary sites of incorporation of a non-naturally encoded amino acid include residues within the amino terminal region of helix A and a portion of helix C. In another embodiment, substitution of L70 with a non-naturally encoded amino acid such as p-azido-L-phenylalanine or O-propargyl-L-tyrosine. In other embodiments, the above-listed substitutions are combined with additional substitutions that cause the hG-CSF polypeptide to be a hG-CSF antagonist. For instance, a non-naturally encoded amino acid is substituted at one of the positions identified herein and a simultaneous substitution is introduced at L70. In some embodiments, the hG-CSF antagonist comprises a non-naturally encoded amino acid linked to a water soluble polymer that is present in a receptor binding region of the hG-CSF molecule.

In some embodiments, the substitution of a non-naturally encoded amino acid generates a hEPO antagonist. Human EPO antagonists include, but are not limited to, those with substitutions at: 2, 3, 5, 8, 9, 10, 11, 14, 15, 16, 17, 18, 20, 23, 43, 44, 45, 46, 47, 48, 49, 50, 52, 75, 78, 93, 96, 97, 99, 100, 103, 104, 107, 108, 110, 131, 132, 133, 140, 143, 144, 146, 147, 150, 154, 155, 159, or any combination thereof (hEPO; SEQ ID NO: 38, or corresponding amino acids in SEQ ID NO: 37 or 39). In some embodiments, hEPO antagonists comprise at least one substitution in the regions 10-15 or 100-108 that cause EPO to act as an antagonist. See Elliott et al. (1997) Blood 89: 493-502 and Cheetham et al. (1998) Nature Structural Biology 5: 861-866. In some embodiments, the hEPO polypeptides is modified by containing one or more of the following substitutions, V11S, R14Q, Y15I, S100E, R103A, S104I, and L108K found in the low affinity receptor binding site (site 2). In other embodiments, the exemplary sites of incorporation of a non-naturally encoded amino acid include residues within the amino terminal region of helix A and a portion of helix C. In another embodiment, substitution of L108 with a non-naturally encoded amino acid such as p-azido-L-phenylalanine or O-propargyl-L-tyrosine. In other embodiments, the above-listed substitutions are combined with additional substitutions that cause the hEPO polypeptide to be a hEPO antagonist. For instance, a non-naturally encoded amino acid is substituted at one of the positions identified herein and a simultaneous substitution is introduced at L108 (including but not limited to, L108K, L108R, L108H, L108D, or L108E). In some embodiments, the hEPO antagonist comprises a non-naturally encoded amino acid linked to a water soluble polymer that is present in the Site 2 binding region of the hEPO molecule.

In some cases, 1, 2, 3, 4, 5, 6, 7, 8, 9, 10, or more amino acids are substituted with one or more non-naturally-encoded amino acids. In some cases, the 4HB polypeptide further includes 1, 2, 3, 4, 5, 6, 7, 8, 9, 10, or more substitutions of one or more non-naturally encoded amino acids for naturally-occurring amino acids. For example, in some embodiments, at least two residues in the following regions of hGH are substituted with one or more non-naturally encoded amino acids: 1-5 (N-terminus); 32-46 (N-terminal end of the A-B loop); 97-105 (B-C loop); and 132-149 (C-D loop); and 184-191 (C-terminus). In some embodiments, at least two residues in the following regions of hGH are substituted with one or more non-naturally encoded amino acids: 1-5 (N-terminus), 6-33 (A helix), 34-74 (region between A helix and B helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus). In some embodiments, at least two residues in the following regions of hIFN are substituted with one or more non-naturally encoded amino acids: 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus). In some embodiments, at least two residues in the following regions of hG-CSF are substituted with one or more non-naturally encoded amino acids: 1-10 (N-terminus), 11-39 (A helix), 40-70 (region between A helix and B helix), 71-91 (B helix), 92-99 (region between B helix and C helix), 100-123 (C helix), 124-142 (region between C helix and D helix), 143-172 (D helix), 173-175 (C-terminus), including the short helical segment, the mini-E Helix, at 44-53 between the A Helix and B Helix composed of a $3_{10}$ helix (44-47) and an α helix (48-53). For example, in some embodiments, at least two residues in the following regions of hEPO are substituted with one or more non-naturally encoded amino acids: 1-7 (N-terminus), 8-26 (A helix), 27-54 (AB loop, containing beta sheet 1 (39-41) and mini B' helix (47-52)), 55-83 (B helix), 84-89 (BC loop), 90-112 (C helix), 113-137 (CD loop, containing mini C' helix (114-121) and beta sheet 2 (133-135)), 138-161 (D helix), 162-166 (C-terminus). In some cases, the two or more non-naturally encoded residues are linked to one or more lower molecular weight linear or branched PEGs (approximately 5-20 kDa or less in mass), thereby enhancing binding affinity and comparable serum half-life relative to the species attached to a single, higher molecular weight PEG.

In some embodiments, up to two of the following residues of hGH are substituted with one or more non-naturally-encoded amino acids at position: 29, 30, 33, 34, 35, 37, 39, 40, 49, 57, 59, 66, 69, 70, 71, 74, 88, 91, 92, 94, 95, 98, 99, 101, 103, 107, 108, 111, 122, 126, 129, 130, 131, 133, 134, 135, 136, 137, 139, 140, 141, 142, 143, 145, 147, 154, 155, 156, 159, 183, 186, and 187. In some cases, any of the following pairs of substitutions are made: K38X* and K140X*; K41X* and K145X*; Y35X* and E88X*; Y35X* and F92X*; Y35X* and Y143X*; F92X* and Y143X* wherein X* represents a non-naturally encoded amino acid. Preferred sites for incorporation of two or more non-naturally encoded amino acids include combinations of the following residues: 29, 33, 35, 37, 39, 49, 57, 69, 70, 71, 74, 88, 91, 92, 94, 95, 98, 99, 101, 103, 107, 108, 111, 129, 130, 131, 133, 134, 135, 136, 137, 139, 140, 141, 142, 143, 145, 147, 154, 155, 156, and 187. Particularly preferred sites for incorporation of two or more non-naturally encoded amino acids include combinations of the following residues: 35, 88, 91, 92, 94, 95, 99, 101, 103, 111, 131, 133, 134, 135, 136, 139, 140, 143, 145, and 155.

Preferred sites for incorporation in hGH of two or more non-naturally encoded amino acids include combinations of the following residues: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e. at the carboxyl terminus of the protein) or any combination thereof from SEQ ID NO: 2.

Preferred sites for incorporation in hIFN of two or more non-naturally encoded amino acids include combinations of the following residues: before position 1 (i.e. at the N-terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus of the protein) or any combination thereof.

In some embodiments, up to two of the following residues of hG-CSF are substituted with one or more non-naturally-encoded amino acids at position: 30, 31, 33, 58, 59, 61, 63, 64, 66, 67, 68, 77, 78, 81, 87, 88, 91, 95, 101, 102, 103, 130, 131, 132, 134, 135, 136, 137, 156, 157, 159, 160, 163, 164, 167, 170, and 171. Thus, in some cases, any of the following pairs of substitutions are made: W59X* and T134X*; L131X* and S67X*; S67X* and Q91X*; T134X* and Ser77X* wherein X* represents a non-naturally encoded amino acid. Preferred sites for incorporation of two or more non-naturally encoded amino acids include combinations of the following residues: 30, 31, 33, 58, 59, 61, 63, 64, 66, 67, 68, 77, 78, 81, 87, 88, 91, 95, 101, 102, 103, 130, 131, 132, 134, 135, 136, 137, 156, 157, 159, 160, 163, 164, 167, 170, and 171. Particularly preferred sites for incorporation of two or more non-naturally encoded amino acids include combinations of the following residues: 59, 63, 67, 130, 131, 132, 134, 137, 160, 163, 167, and 171.

Preferred sites for incorporation in hG-CSF of two or more non-naturally encoded amino acids include combinations of the following residues: before position 1 (i.e. at the N terminus), 1, 2, 3, 4, 5, 6, 7, 8, 9, 10, 11, 12, 13, 16, 17, 19, 20, 21, 23, 24, 28, 30, 31, 33, 34, 35, 38, 39, 40, 41, 44, 45, 46, 47, 48, 49, 50, 51, 53, 54, 55, 56, 58, 59, 61, 63, 64, 66, 67, 68, 69, 70, 71, 72, 73, 77, 78, 81, 84, 87, 88, 91, 92, 94, 95, 97, 98, 99, 101, 102, 103, 105, 106, 108, 109, 110, 112, 113, 116, 117, 120, 121, 123, 124, 125, 126, 127, 130, 131, 132, 133, 134, 135, 136, 137, 138, 139, 140, 142, 143, 144, 145, 146, 147, 148, 156, 157, 159, 160, 163, 164, 166, 167, 170, 171, 173, 174, 175, 176 (i.e. at the carboxyl terminus)

In some embodiments, up to two of the following residues are substituted in hEPO with one or more non-naturally-encoded amino acids at position: 1, 2, 4, 9, 17, 20, 21, 24, 25, 27, 28, 30, 31, 32, 34, 36, 37, 38, 40, 50, 53, 55, 58, 65, 68, 72, 76, 79, 80, 82, 83, 85, 86, 87, 89, 113, 115, 116, 119, 120, 121, 122, 123, 124, 125, 126, 127, 128, 129, 130, 131, 132, 134, 136, 159, 162, 163, 164, 165, and 166. Thus, in some cases, any of the following pairs of substitutions are made: N24X* and G113X*; N38X* and Q115X*; N36X* and S85X*; N36X* and A125X*; N36X* and A128X*; Q86X* and S126X* wherein X* represents a non-naturally encoded amino acid. Preferred sites for incorporation of two or more non-naturally encoded amino acids include combinations of the following residues: 21, 24, 28, 30, 31, 36, 37, 38, 55, 72, 83, 85, 86, 87, 89, 113, 116, 119, 120, 121, 123, 124, 125, 126, 127, 128, 129, 130, 162, 163, 164, 165, and 166. Particularly preferred sites for incorporation of two or more non-naturally encoded amino acids include combinations of the following residues: 21, 24, 38, 83, 86, 89, 116, 119, 121, 124, 125, 126, 127, 128, 129, 130 and 162.

Preferred sites for incorporation in hEPO of two or more non-naturally encoded amino acids include combinations of the following residues: before position 1 (i.e. at the N terminus), 1, 2, 3, 4, 5, 6, 8, 9, 10, 11, 14, 15, 16, 17, 18, 20, 21, 23, 24, 25, 26, 27, 28, 30, 31, 32, 34, 35, 36, 37, 38, 39, 40, 43, 44, 45, 46, 47, 48, 49, 50, 51, 52, 53, 54, 55, 56, 57, 58, 65, 68, 72, 75, 76, 77, 78, 79, 80, 82, 83, 84, 85, 86, 87, 88, 89, 90, 91, 92, 93, 96, 97, 99, 100, 103, 104, 107, 108, 110, 111, 113, 114, 115, 116, 117, 118, 119, 120, 121, 122, 123, 124, 125, 126, 127, 128, 129, 130, 131, 132, 133, 134, 136, 140, 143, 144, 146, 147, 150, 154, 155, 157, 158, 159, 160, 162, 163, 164, 165, 166, 167 (i.e. at the carboxyl terminus).

VII. Expression in Non-Eukaryotes and Eukaryotes

To obtain high level expression of a cloned 4HB polynucleotide, one typically subclones polynucleotides encoding a 4HB polypeptide of the invention into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al.

Bacterial expression systems for expressing 4HB polypeptides of the invention are available in, including but not limited to, *E. coli, Bacillus* sp., and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are well known in the art and are also commercially available. In cases where orthogonal tRNAs and aminoacyl tRNA synthetases (described above) are used to express the 4HB polypeptides of the invention, host cells for expression are selected based on their ability to use the orthogonal components. Exemplary host cells include Gram-positive bacteria (including but not limited to *B. brevis, B. subtilis,* or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O—RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 µg/liter, at least 50 µg/liter, at least 75 µg/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

I. Expression Systems, Culture, and Isolation

4HB polypeptides may be expressed in any number of suitable expression systems including, for example, yeast, insect cells, mammalian cells, and bacteria. A description of exemplary expression systems is provided below.

Yeast

As used herein, the term "yeast" includes any of the various yeasts capable of expressing a gene encoding a 4HB polypeptide. Such yeasts include, but are not limited to, ascosporogenous yeasts (*Enidomycetales*), basidiosporogenous yeasts and yeasts belonging to the Fungi imperfecti (*Blastonzycetes*) group. The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomnycoideae (e.g., genera *Pichia, Kluyveromnyces* and *Saccharomyces*). The basidiosporogenous yeasts include the genera *Leucosporidium, Rhodosporidiumn, Sporidiobolus, Filobasidium,* and *Filobasidiella*. Yeasts belonging to the Fungi Imperfecti (*Blastomycetes*) group are divided into two families, Sporobolomycetaceae (e.g., genera *Sporobolomyces* and *Bullera*) and Cryptococcaceae (e.g., genus *Candida*).

Of particular interest for use with the present invention are species within the genera *Pichia, Kluyveromyces, Saccharomyces, Schizosaccharomyces, Hansenula, Torulopsis,* and *Canidida*, including, but not limited to, *P. pastoris, P. guillerimondii, S. cerevisiae, S. carlsbergensis, S. diastaticus, S. douglasii, S. kluyveri, S, norbensis, S. oviformis, K. lactis, K. fragilis, C. albicans, C. maltosa,* and *H. polymorpha*.

The selection of suitable yeast for expression of 4HB polypeptides is within the skill of one of ordinary skill in the art. In selecting yeast hosts for expression, suitable hosts may include those shown to have, for example, good secretion capacity, low proteolytic activity, good secretion capacity, good soluble protein production, and overall robustness. Yeast are generally available from a variety of sources including, but not limited to, the Yeast Genetic Stock Center, Department of Biophysics and Medical Physics, University of California (Berkeley, Calif.), and the American Type Culture Collection ("ATCC") (Manassas, Va.).

The term "yeast host" or "yeast host cell" includes yeast that can be, or has been, used as a recipient for recombinant vectors or other transfer DNA. The term includes the progeny of the original yeast host cell that has received the recombinant vectors or other transfer DNA. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a 4HB polypeptide, are included in the progeny intended by this definition.

Expression and transformation vectors, including extrachromosomal replicons or integrating vectors, have been developed for transformation into many yeast hosts. For example, expression vectors have been developed for *S. cerevisiae* (Sikorski et al., GENETICS (1998) 112:19; Ito et al., J. BACTERIOL. (1983) 153:163; Hinnen et al., PROC. NATL. ACAD. SCI. USA (1978) 75:1929); *C. albicans* (Kurtz et al., MOL. CELL. BIOL. (1986) 6:142); *C. maltosa* (Kunze et al., J. BASIC MICROBIOL. (1985) 25:141); *H. polymorpha* (Gleeson et al., J. GEN. MICROBIOL. (1986) 132:3459; Roggenkamp et al., MOL. GEN.

GENET. (1986) 202:302); *K. fragilis* (Das et al., J. BACTERIOL. (1984) 158:1165); *K. lactis* (De Louvencourt et al., J. BACTERIOL. (1983) 154:737; Van den Berg et al., BIO/TECHNOLOGY (1990) 8:135); *P. guillerimondii* (Kunze et al., J. BASIC MICROBIOL. (1985) 25:141); *P. pastoris* (U.S. Pat. Nos. 5,324,639; 4,929,555; and 4,837,148; Cregg et al., MOL. CELL. BIOL. (1985) 5:3376); *Schizosaccharomyces pombe* (Beach and Nurse, NATURE (1981) 300:706); and *Y. lipolytica* (Davidow et al., CURR. GENET. (1985) 10:380 (1985); Gaillardin et al., CURR. GENET. (1985) 10:49); *A. nidulans* (Ballance et al., BIOCHEM. BIOPHYS. RES. COMMUN. (1983) 112:284-89; Tilburn et al., GENE (1983) 26:205-221; and Yelton et al., PROC. NATL. ACAD. SCI. USA (1984) 81:1470-74); *A. niger* (Kelly and Hynes, EMBO J. (1985) 4:475-479); *T. reesia* (BP 0 244 234); and filamentous fungi such as, e.g., *Neurospora, Penicillium, Tolypocladium* (WO 91/00357), each incorporated by reference herein.

Control sequences for yeast vectors are well known to those of ordinary skill in the art and include, but are not limited to, promoter regions from genes such as alcohol dehydrogenase (ADH) (EP 0 284 044); enolase; glucokinase; glucose-6-phosphate isomerase; glyceraldehydes-3-phosphate-dehydrogenase (GAP or GAPDH); hexokinase; phosphofructokinase; 3-phosphoglycerate mutase; and pyruvate kinase (PyK) (EP 0 329 203). The yeast PHO5 gene, encoding acid phosphatase, also may provide useful promoter sequences (Myanohara et al., PROC. NATL. ACAD. SCI. USA (1983) 80:1). Other suitable promoter sequences for use with yeast hosts may include the promoters for 3-phosphoglycerate kinase (Hitzeman et al., J. BIOL. CHEM. (1980) 255:2073); and other glycolytic enzymes, such as pyruvate decarboxylase, triosephosphate isomerase, and phosphoglucose isomerase (Holland et al., BIOCHEMISTRY (1978) 17:4900; Hess et al., J. ADV. ENZYME REG. (1968) 7:149). Inducible yeast promoters having the additional advantage of transcription controlled by growth conditions may include the promoter regions for alcohol dehydrogenase 2; isocytochrome C; acid phosphatase; metallothionein; glyceraldehyde-3-phosphate dehydrogenase; degradative enzymes associated with nitrogen metabolism; and enzymes responsible for maltose and galactose utilization. Suitable vectors and promoters for use in yeast expression are further described in EP 0 073 657.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2μ plasmid origin is suitable for yeast. A suitable selection gene for use in yeast is the trp1 gene present in the yeast plasmid. See Tschemper et al., GENE (1980) 10:157; Kingsman et al., GENE (1979) 7:141. The trp1 gene provides a selection marker for a mutant strain of yeast lacking the ability to grow in tryptophan. Similarly, Leu2-deficient yeast strains (ATCC 20,622 or 38,626) are complemented by known plasmids bearing the Leu2 gene.

Methods of introducing exogenous DNA into yeast hosts are well known to those of ordinary skill in the art, and typically include, but are not limited to, either the transformation of spheroplasts or of intact yeast host cell treated with alkali cations. For example, transformation of yeast can be carried out according to the method described in Hsiao et al., PROC. NATL. ACAD. SCI. USA (1979) 76:3829 and Van Solingen et al., J. BACT. (1977) 130:946. However, other methods for introducing DNA into cells such as by nuclear injection, electroporation, or protoplast fusion may also be used as described generally in SAMBROOK ET AL., MOLECULAR CLONING: A LAB. MANUAL (2001). Yeast host cells may then be cultured using standard techniques known to those of ordinary skill in the art.

Other methods for expressing heterologous proteins in yeast host cells are well known to those of ordinary skill in the art. See generally U.S. Patent Publication No. 20020055169, U.S. Pat. Nos. 6,361,969; 6,312,923; 6,183,985; 6,083,723; 6,017,731; 5,674,706; 5,629,203; 5,602,034; and 5,089,398; U.S. Reexamined Pat. Nos. RE37,343 and RE35,749; PCT Published Patent Applications WO 99/078621; WO 98/37208; and WO 98/26080; European Patent Applications EP 0 946 736; EP 0 732 403; EP 0 480 480; EP 0 460 071; EP 0 340 986; EP 0 329 203; EP 0 324 274; and EP 0 164 556. See also Gellissen et al., ANTONIE VAN LEEUWENHOEK (1992) 62(1-2):79-93; Romanos et al., YEAST (1992) 8(6):423-488; Goeddel, METHODS IN ENZYMOLOGY (1990) 185:3-7, each incorporated by reference herein.

The yeast host strains may be grown in fermentors during the amplification stage using standard feed batch fermentation methods well known to those of ordinary skill in the art. The fermentation methods may be adapted to account for differences in a particular yeast host's carbon utilization pathway or mode of expression control. For example, fermentation of a *Saccharomyces* yeast host may require a single glucose feed, complex nitrogen source (e.g., casein hydrolysates), and multiple vitamin supplementation. In contrast, the methylotrophic yeast *P. pastoris* may require glycerol, methanol, and trace mineral feeds, but only simple ammonium (nitrogen) salts for optimal growth and expression. See, e.g., U.S. Pat. No. 5,324,639; Elliott et al., J. PROTEIN CHEM. (1990) 9:95; and Fieschko et al., BIOTECH. BIOENG. (1987) 29:1113, incorporated by reference herein.

Such fermentation methods, however, may have certain common features independent of the yeast host strain employed. For example, a growth limiting nutrient, typically carbon, may be added to the fermentor during the amplification phase to allow maximal growth. In addition, fermentation methods generally employ a fermentation medium designed to contain adequate amounts of carbon, nitrogen, basal salts, phosphorus, and other minor nutrients (vitamins, trace minerals and salts, etc.). Examples of fermentation media suitable for use with *Pichia* are described in U.S. Pat. Nos. 5,324,639 and 5,231,178, which are incorporated by reference herein.

Baculovirus-Infected Insect Cells

The term "insect host" or "insect host cell" refers to a insect that can be, or has been, used as a recipient for recombinant vectors or other transfer DNA. The term includes the progeny of the original insect host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a 4HB polypeptide, are included in the progeny intended by this definition.

The selection of suitable insect cells for expression of 4HB polypeptides is well known to those of ordinary skill in the art. Several insect species are well described in the art and are commercially available including *Aedes aegypti, Bombyx mori, Drosophila melanogaster, Spodoptera frugiperda*, and *Trichoplusia ni*. In selecting insect hosts for expression, suitable hosts may include those shown to have, inter alia, good secretion capacity, low proteolytic activity, and overall robustness. Insect are generally available from a variety of sources including, but not limited to, the Insect Genetic Stock Center, Department of Biophysics and Medical Physics, University of California (Berkeley, Calif.); and the American Type Culture Collection ("ATCC") (Manassas, Va.).

Generally, the components of a baculovirus-infected insect expression system include a transfer vector, usually a bacterial plasmid, which contains both a fragment of the baculovirus genome, and a convenient restriction site for insertion of the heterologous gene to be expressed; a wild type baculovirus with sequences homologous to the baculovirus-specific fragment in the transfer vector (this allows for the homologous recombination of the heterologous gene in to the baculovirus genome); and appropriate insect host cells and growth media. The materials, methods and techniques used in constructing vectors, transfecting cells, picking plaques, growing cells in culture, and the like are known in the art and manuals are available describing these techniques.

After inserting the heterologous gene into the transfer vector, the vector and the wild type viral genome are transfected into an insect host cell where the vector and viral genome recombine. The packaged recombinant virus is expressed and recombinant plaques are identified and purified. Materials and methods for baculovirus/insect cell expression systems are commercially available in kit form from, for example, Invitrogen Corp. (Carlsbad, Calif.). These techniques are generally known to those skilled in the art and fully described in SUMMERS AND SMITH, TEXAS AGRICULTURAL EXPERIMENT STATION BULLETIN NO. 1555 (1987), herein incorporated by reference. See also, RICHARDSON, 39 METHODS IN MOLECULAR BIOLOGY: BACULOVIRUS EXPRESSION PROTOCOLS (1995); AUSUBEL ET AL., CURRENT PROTOCOLS IN MOLECULAR BIOLOGY 16.9-16.11 (1994); KING AND POSSEE, THE BACULOVIRUS SYSTEM: A LABORATORY GUIDE (1992); and O'REILLY ET AL., BACULOVIRUS EXPRESSION VECTORS: A LABORATORY MANUAL (1992).

Indeed, the production of various heterologous proteins using baculovirus/insect cell expression systems is well known in the art. See, e.g., U.S. Pat. Nos. 6,368,825; 6,342, 216; 6,338,846; 6,261,805; 6,245,528, 6,225,060; 6,183,987; 6,168,932; 6,126,944; 6,096,304; 6,013,433; 5,965,393; 5,939,285; 5,891,676; 5,871,986; 5,861,279; 5,858,368; 5,843,733; 5,762,939; 5,753,220; 5,605,827; 5,583,023; 5,571,709; 5,516,657; 5,290,686; WO 02/06305; WO 01/90390; WO 01/27301; WO 01/05956; WO 00/55345; WO 00/20032 WO 99/51721; WO 99/45130; WO 99/31257; WO 99/10515; WO 99/09193; WO 97/26332; WO 96/29400; WO 96/25496; WO 96/06161; WO 95/20672; WO 93/03173; WO 92/16619; WO92/03628; WO92/01801; WO90/14428; WO90/10078; WO90/02566; WO90/02186; WO 90/01556; WO 89/01038; WO 89/01037; WO 88/07082, which are incorporated by reference herein.

Vectors that are useful in baculovirus/insect cell expression systems are known in the art and include, for example, insect expression and transfer vectors derived from the baculovirus *Autographa californica* nuclear polyhedrosis virus (AcNPV), which is a helper-independent, viral expression vector. Viral expression vectors derived from this system usually use the strong viral polyhedrin gene promoter to drive expression of heterologous genes. See generally, Reilly ET AL., BACULOVIRUS EXPRESSION VECTORS: A LABORATORY MANUAL (1992).

Prior to inserting the foreign gene into the baculovirus genome, the above-described components, comprising a promoter, leader (if desired), coding sequence of interest, and transcription termination sequence, are typically assembled into an intermediate transplacement construct (transfer vector). Intermediate transplacement constructs are often maintained in a replicon, such as an extra chromosomal element (e.g., plasmids) capable of stable maintenance in a host, such as bacteria. The replicon will have a replication system, thus allowing it to be maintained in a suitable host for cloning and amplification. More specifically, the plasmid may contain the polyhedrin polyadenylation signal (Miller et al., ANN. REV. MICROBIOL. (1988) 42:177) and a prokaryotic ampicillin-resistance (amp) gene and origin of replication for selection and propagation in *E. coli*.

One commonly used transfer vector for introducing foreign genes into AcNPV is pAc373. Many other vectors, known to those of skill in the art, have also been designed including, for example, pVL985, which alters the polyhedrin start codon from ATG to ATT, and which introduces a BamHI cloning site 32 base pairs downstream from the ATT. See Luckow and Summers, 17 VIROLOGY 31 (1989). Other commercially available vectors include, for example, PBlueBac4.5/V5-His; pBlueBacHis2; pMelBac; pBlueBac4.5 (Invitrogen Corp., Carlsbad, Calif.).

After insertion of the heterologous gene, the transfer vector and wild type baculoviral genome are co-transfected into an insect cell host. Methods for introducing heterologous DNA into the desired site in the baculovirus virus are known in the art. See SUMMERS AND SMITH, TEXAS AGRICULTURAL EXPERIMENT STATION BULLETIN NO. 1555 (1987); Smith et al., MOL. CELL. BIOL. (1983) 3:2156; Luckow and Summers, VIROLOGY (1989) 17:31. For example, the insertion can be into a gene such as the polyhedrin gene, by homologous double crossover recombination; insertion can also be into a restriction enzyme site engineered into the desired baculovirus gene. See Miller et al., BIOESSAYS (1989) 4:91.

Transfection may be accomplished by electroporation. See TROTTER AND WOOD, 39 METHODS IN MOLECULAR BIOLOGY (1995); Mann and King, J. GEN. VIROL. (1989) 70:3501. Alternatively, liposomes may be used to transfect the insect cells with the recombinant expression vector and the baculovirus. See, e.g., Liebman et al., BIOTECHIQUES (1999) 26(1):36; Graves et al., BIOCHEMISTRY (1998) 37:6050; Nomura et al., J. BIOL. CHEM. (1998) 273(22):13570; Schmidt et al., PROTEIN EXPRESSION AND PURIFICATION (1998) 12:323; Siffert et al., NATURE GENETICS (1998) 18:45; TILKINS ET AL., CELL BIOLOGY: A LABORATORY HANDBOOK 145-154 (1998); Cai et al., PROTEIN EXPRESSION AND PURIFICATION (1997) 10:263; Dolphin et al., NATURE GENETICS (1997) 17:491; Kost et al., GENE (1997) 190:139; Jakobsson et al., J. BIOL. CHEM. (1996) 271:22203; Rowles et al., J. BIOL. CHEM. (1996) 271(37):22376; Reversey et al., J. BIOL. CHEM. (1996) 271(39):23607-10; Stanley et al., J. BIOL. CHEM. (1995) 270:4121; Sisk et al., J. VIROL. (1994) 68(2):766; and Peng et al., BIOTECHIQUES (1993) 14.2:274. Commercially available liposomes include, for example, Cellfectin® and Lipofectin® (Invitrogen, Corp., Carlsbad, Calif.). In addition, calcium phosphate transfection may be used. See TROTTER AND WOOD, 39 METHODS IN MOLECULAR BIOLOGY (1995); Kitts, NAR (1990) 18(19):5667; and Mann and King, J. GEN. VIROL. (1989) 70:3501.

Baculovirus expression vectors usually contain a baculovirus promoter. A baculovirus promoter is any DNA sequence capable of binding a baculovirus RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Moreover, expression may be either regulated or constitutive.

Structural genes, abundantly transcribed at late times in the infection cycle, provide particularly useful promoter sequences. Examples include sequences derived from the gene encoding the viral polyhedron protein (FRIESEN ET AL., *The Regulation of Baculovirus Gene Expression* in THE MOLECULAR BIOLOGY OF BACULOVIRUSES (1986); EP 0 127 839 and 0 155 476) and the gene encoding the p10 protein (Vlak et al., J. GEN. VIROL. (1988) 69:765).

The newly formed baculovirus expression vector is packaged into an infectious recombinant baculovirus and subsequently grown plaques may be purified by techniques known to those skilled in the art. See Miller et al., BIOESSAYS (1989) 4:91; SUMMERS AND SMITH, TEXAS AGRICULTURAL EXPERIMENT STATION BULLETIN NO. 1555 (1987).

Recombinant baculovirus expression vectors have been developed for infection into several insect cells. For example, recombinant baculoviruses have been developed for, inter alia, *Aedes aegypti* (ATCC No. CCL-125), *Bombyx mori* (ATCC No. CRL-8910), *Drosophila melanogaster* (ATCC No. 1963), *Spodoptera frugiperda*, and *Trichoplusia ni*. See WO 89/046,699; Wright, NATURE (1986) 321:718; Carbonell et al., J. VIROL. (1985) 56:153; Smith et al., MOL. CELL. BIOL. (1983) 3:2156. See generally, Fraser et al., IN VITRO CELL. DEV. BIOL. (1989) 25:225. More specifically, the cell lines used for baculovirus expression vector systems commonly include, but are not limited to, Sf9 (*Spodoptera frugiperda*) (ATCC No. CRL-1711), Sf21 (*Spodoptera frugiperda*) (Invitrogen Corp., Cat. No. 11497-013 (Carlsbad, Calif.)), Tri-368 (*Trichopulsia ni*), and High-Five™ B-TN-5B1-4 (*Trichopulsia ni*).

Cells and culture media are commercially available for both direct and fusion expression of heterologous polypeptides in a baculovirus/expression, and cell culture technology is generally known to those skilled in the art.

E. Coli and other Prokaryotes

Bacterial expression techniques are well known in the art. A wide variety of vectors are available for use in bacterial hosts. The vectors may be single copy or low or high multi-copy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al., ANNU. REV. GENET. (1984) 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., NATURE (1977) 198:1056], and maltose. Additional examples include promoter sequences derived from biosynthetic enzymes such as tryptophan (trp) [Goeddel et al., NUC. ACIDS RES. (1980) 8:4057; Yelverton et al., NUCL. ACIDS RES. (1981) 9:731; U.S. Pat. No. 4,738,921; EP Pub. Nos. 036 776 and 121 775, which are incorporated by reference herein]. The β-galactosidase (bla) promoter system [Weissmann (1981) "The cloning of interferon and other mistakes." In Interferon 3 (Ed. I. Gresser)], bacteriophage lambda PL [Shimatake et al., NATURE (1981) 292:128] and T5 [U.S. Pat. No. 4,689,406, which are incorporated by reference herein] promoter systems also provide useful promoter sequences. Preferred methods of the present invention utilize strong promoters, such as the T7 promoter to induce 4HB polypeptides at high levels. Examples of such vectors are well known in the art and include the pET29 series from Novagen, and the pPOP vectors described in WO99/05297, which is incorporated by reference herein. Such expression systems produce high levels of 4HB polypeptides in the host without compromising host cell viability or growth parameters.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433, which is incorporated by reference herein]. For example, the tac promoter is a hybrid trp-lac promoter comprised of both trp promoter and lac operon sequences that is regulated by the lac repressor [Amanni et al., GENE (1983) 25:167; de Boer et al., PROC. NATL. ACAD. SCI. (1983) 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al., J. MOL. BIOL. (1986) 189:113; Tabor et al., Proc Natl. Acad. Sci. (1985) 82:1074]. In addition, a hybrid promoter can also be comprised of a bacteriophage promoter and an *E. coli* operator region (EP Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al., NATURE (1975) 254:34]. The SD sequence is thought to promote binding of mRNA to the ribosome by the pairing of bases between the SD sequence and the 3' and of *E. coli* 16S rRNA [Steitz et al. "Genetic signals and nucleotide sequences in messenger RNA", In Biological Regulation and Development: Gene Expression (Ed. R. F. Goldberger, 1979)]. To express eukaryotic genes and prokaryotic genes with weak ribosome-binding site [Sambrook et al. "Expression of cloned genes in *Escherichia coli*", Molecular Cloning: A Laboratory Manual, 1989].

The term "bacterial host" or "bacterial host cell" refers to a bacterial that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a 4HB polypeptide, are included in the progeny intended by this definition.

The selection of suitable host bacteria for expression of 4HB polypeptides is well known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. In one embodiment of the methods of the present invention, the *E. coli* host is a strain of BL21. In another embodiment of the methods of the present invention, the *E. coli* host is a protease minus strain including, but not limited to, OMP— and LON—. In another embodiment of the methods of the present invention, the host cell strain is a species of *Pseudomonas*, including but not limited to, *Pseudomonas fluorescens, Pseudomonas aeruginosa*, and *Pseudomonas putida. Pseudomonas fluorescens* biovar 1, designated strain MB101, is available for therapeutic protein production processes by The Dow Chemical Company as a host strain (Midland, Mich. available on the World Wide Web at dow.com). U.S. Pat. Nos. 4,755,465 and 4,859,600, which are incorporated herein, describes the use of *Pseudomonas* strains as a host cell for hGH production.

Once a recombinant host cell strain has been established (i.e., the expression construct has been introduced into the host cell and host cells with the proper expression construct are isolated), the recombinant host cell strain is cultured under conditions appropriate for production of 4HB polypeptides. As will be apparent to one of skill in the art, the method of culture of the recombinant host cell strain will be dependent on the nature of the expression construct utilized and the identity of the host cell. Recombinant host strains are normally cultured using methods that are well known to the art. Recombinant host cells are typically cultured in liquid medium containing assimilatable sources of carbon, nitrogen, and inorganic salts and, optionally, containing vitamins, amino acids, growth factors, and other proteinaceous culture supplements well known to the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the 4HB polypeptide accumulates intracellularly) or harvesting of culture supernatant in either batch or continuous formats. For production in prokaryotic host cells, batch culture and cell harvest are preferred.

The 4HB polypeptides of the present invention are normally purified after expression in recombinant systems. The 4HB polypeptide may be purified from host cells by a variety of methods known to the art. Normally, 4HB polypeptides produced in bacterial host cells is poorly soluble or insoluble (in the form of inclusion bodies). In one embodiment of the present invention, amino acid substitutions may readily be made in the 4HB polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods well known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the *E. coli* host cells to release the inclusion bodies of the 4HB polypeptides. It has been found that yields of insoluble 4HB polypeptide in the form of inclusion bodies may be increased by utilizing only one passage of the *E. Coli* host cells through the homogenizer. When handling inclusion bodies of 4HB polypeptide, it is advantageous to minimize the homogenization time on repetitions in order to maximize the yield of inclusion bodies without loss due to factors such as solubilization, mechanical shearing or proteolysis.

Insoluble or precipitated 4HB polypeptide may then be solubilized using any of a number of suitable solubilization agents known to the art. Preferably, the 4HB polypeptide is solubilized with urea or guanidine hydrochloride. The volume of the solubilized 4HB polypeptide-BP should be minimized so that large batches may be produced using conveniently manageable batch sizes. This factor may be significant in a large-scale commercial setting where the recombinant host may be grown in batches that are thousands of liters in volume. In addition, when manufacturing 4HB polypeptide in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the 4HB polypeptide inclusion bodies in place of the harsher denaturing agent guanidine hydrochloride. The use of urea significantly reduces the risk of damage to stainless steel equipment utilized in the manufacturing and purification process of 4HB polypeptide while efficiently solubilizing the 4BB polypeptide inclusion bodies.

When 4HB polypeptide is produced as a fusion protein, the fusion sequence is preferably removed. Removal of a fusion sequence may be accomplished by enzymatic or chemical cleavage, preferably by enzymatic cleavage. Enzymatic removal of fusion sequences may be accomplished using methods well known to those in the art. The choice of enzyme for removal of the fusion sequence will be determined by the identity of the fusion, and the reaction conditions will be specified by the choice of enzyme as will be apparent to one skilled in the art. The cleaved 4HB polypeptide is preferably purified from the cleaved fusion sequence by well known methods. Such methods will be determined by the identity and properties of the fusion sequence and the 4HB polypeptide, as will be apparent to one skilled in the art. Methods for purification may include, but are not limited to, size-exclusion chromatography, hydrophobic interaction chromatography, ion-exchange chromatography or dialysis or any combination thereof.

The 4HB polypeptide is also preferably purified to remove DNA from the protein solution. DNA may be removed by any suitable method known to the art, such as precipitation or ion exchange chromatography, but is preferably removed by precipitation with a nucleic acid precipitating agent, such as, but not limited to, protamine sulfate. The 4HB polypeptide may be separated from the precipitated DNA using standard well known methods including, but not limited to, centrifugation or filtration. Removal of host nucleic acid molecules is an important factor in a setting where the 4HB polypeptide is to be used to treat humans and the methods of the present invention reduce host cell DNA to pharmaceutically acceptable levels.

Methods for small-scale or large-scale fermentation can also be used in protein expression, including but not limited to, fermentors, shake flasks, fluidized bed bioreactors, hollow fiber bioreactors, roller bottle culture systems, and stirred tank bioreactor systems. Each of these methods can be performed in a batch, fed-batch, or continuous mode process.

Human 4HB polypeptides of the invention can generally be recovered using methods standard in the art. For example, culture medium or cell lysate can be centrifuged or filtered to remove cellular debris. The supernatant may be concentrated or diluted to a desired volume or diafiltered into a suitable buffer to condition the preparation for further purification. Further purification of the 4HB polypeptide of the present invention include separating deamidated and clipped forms of the 4HB polypeptide variant from the intact form.

Any of the following exemplary procedures can be employed for purification of 4HB polypeptides of the invention: affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

Proteins of the present invention, including but not limited to, proteins comprising unnatural amino acids, antibodies to proteins comprising unnatural amino acids, binding partners for proteins comprising unnatural amino acids, etc., can be purified, either partially or substantially to homogeneity, according to standard procedures known to and used by those of skill in the art. Accordingly, polypeptides of the invention can be recovered and purified by any of a number of methods well known in the art, including but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against unnatural amino acids (or proteins comprising unnatural amino acids) are used as purification reagents, including but not limited to, for affinity-based purification of proteins comprising one or more unnatural amino acid(s). Once purified, partially or to homogeneity, as desired, the polypeptides are optionally used for a wide variety of utilities, including but not limited to, as assay components, therapeutics, prophylaxis, diagnostics, research reagents, and/or as immunogens for antibody production.

In addition to other references noted herein, a variety of purification/protein folding methods are well known in the art, including, but not limited to, those set forth in R. Scopes, *Protein Purification*, Springer-Verlag, N.Y. (1982); Deutscher, *Methods in Enzymology Vol.* 182: *Guide to Protein Purification*, Academic Press, Inc. N.Y. (1990); Sandana, (1997) *Bioseparation of Proteins*, Academic Press, Inc.; Bollag et al. (1996) *Protein Methods* 2nd Edition Wiley-Liss, NY; Walker, (1996) *The Protein Protocols Handbook* Humana Press, NJ, Harris and Angal, (1990) *Protein Purification Applications: A Practical Approach* IRL Press at Oxford, Oxford, England; Harris and Angal, *Protein Purification Methods: A Practical Approach* IRL Press at Oxford, Oxford, England; Scopes, (1993) *Protein Purification: Principles and Practice* 3rd Edition Springer Verlag, NY; Janson and Ryden, (1998) *Protein Purification: Principles, High Resolution Methods and Applications, Second Edition* Wiley-VCH, NY; and Walker (1998), *Protein Protocols on CD-ROM* Humana Press, NJ; and the references cited therein.

One advantage of producing a protein or polypeptide of interest with an unnatural amino acid in a eukaryotic host cell or non-eukaryotic host cell is that typically the proteins or polypeptides will be folded in their native conformations. However, in certain embodiments of the invention, those of skill in the art will recognize that, after synthesis, expression and/or purification, proteins can possess a conformation different from the desired conformations of the relevant polypeptides. In one aspect of the invention, the expressed protein is optionally denatured and then renatured. This is accomplished utilizing methods known in the art, including but not limited to, by adding a chaperonin to the protein or polypeptide of interest, by solubilizing the proteins in a chaotropic agent such as guanidine HCl, utilizing protein disulfide isomerase, etc.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) *J. Biol. Chem.*, 268: 14065-14070; Kreitman and Pastan (1993) *Bioconjug. Chem.,* 4: 581-585; and Buchner, et al., (1992) *Anal. Biochem.,* 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of 4HB polypeptide, the 4HB polypeptide thus produced may be misfolded and thus lacks or has reduced biological activity. The bioactivity of the protein may be restored by "refolding". In general, misfolded 4HB polypeptide is refolded by solubilizing (where the 4B polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. 4HB polypeptide may be refolded using standard methods known in the art, such as those described in U.S. Pat. Nos. 4,511,502, 4,511,503, and 4,512,922, which are incorporated by reference herein. The 4HB polypeptide may also be cofolded with other proteins to form heterodimers or heteromultimers. After refolding or cofolding, the 4HB polypeptide is preferably further purified.

General Purification Methods

Any one of a variety of isolation steps may be performed on the cell lysate comprising 4HB polypeptide or on any 4HB polypeptide mixtures resulting from any isolation steps including, but not limited to, affinity chromatography, ion exchange chromatography, hydrophobic interaction chromatography, gel filtration chromatography, high performance liquid chromatography ("HPLC"), reversed phase-HPLC ("RP-HPLC"), expanded bed adsorption, or any combination and/or repetition thereof and in any appropriate order.

Equipment and other necessary materials used in performing the techniques described herein are commercially available. Pumps, fraction collectors, monitors, recorders, and entire systems are available from, for example, Applied Biosystems (Foster City, Calif.), Bio-Rad Laboratories, Inc. (Hercules, Calif.), and Amersham Biosciences, Inc. (Piscataway, N.J.). Chromatographic materials including, but not limited to, exchange matrix materials, media, and buffers are also available from such companies.

Equilibration, and other steps in the column chromatography processes described herein such as washing and elution, may be more rapidly accomplished using specialized equipment such as a pump. Commercially available pumps include, but are not limited to, HILOAD® Pump P-50, Peristaltic Pump P-1, Pump P-901, and Pump P-903 (Amersham Biosciences, Piscataway, N.J.).

Examples of fraction collectors include RediFrac Fraction Collector, FRAC-100 and FRAC-200 Fraction Collectors, and SUPERPRAC® Fraction Collector (Amersham Biosciences, Piscataway, N.J.). Mixers are also available to form pH and linear concentration gradients. Commercially available mixers include Gradient Mixer GM-1 and In-Line Mixers (Amersham Biosciences, Piscataway, N.J.).

The chromatographic process may be monitored using any commercially available monitor. Such monitors may be used to gather information like UV, pH, and conductivity. Examples of detectors include Monitor UV-1, UVICORD® S II, Monitor UV-M II, Monitor UV-900, Monitor UPC-900, Monitor pH/C-900, and Conductivity Monitor (Amersham Biosciences, Piscataway, N.J.). Indeed, entire systems are commercially available including the various AKTA® systems from Amersham Biosciences (Piscataway, N.J.).

In one embodiment of the present invention, for example, the 4HB polypeptide may be reduced and denatured by first denaturing the resultant purified 4HB polypeptide in urea, followed by dilution into TRIS buffer containing a reducing agent (such as DTT) at a suitable pH. In another embodiment, the 4HB polypeptide is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured 4HB polypeptide mixture may then be further isolated or purified.

As stated herein, the pH of the first 4HB polypeptide mixture may be adjusted prior to performing any subsequent isolation steps. In addition, the first 4HB polypeptide mixture or any subsequent mixture thereof may be concentrated using techniques known in the art. Moreover, the elution buffer comprising the first 4HB polypeptide mixture or any subsequent mixture thereof may be exchanged for a buffer suitable for the next isolation step using techniques well known to those of ordinary skill in the art.

Ion Exchange Chromatography

In one embodiment, and as an optional, additional step, ion exchange chromatography may be performed on the first 4HB polypeptide mixture. See generally ION EXCHANGE CHROMATOGRAPHY: PRINCIPLES AND METHODS (Cat. No. 18-1114-21, Amersham Biosciences (Piscataway, N.J.)). Commercially available ion exchange columns include HITRAP®, HIPREP®, and HILOAD® Columns (Amersham Biosciences, Piscataway, N.J.). Such columns utilize strong anion exchangers such as Q SEPHAROSE® Fast Flow, Q SEPHAROSE® High Performance, and Q SEPHAROSE® XL; strong cation exchangers such as SP SEPHAROSE® High Performance, SP SEPHAROSE® Fast Flow, and SP SEPHAROSE® XL; weak anion exchangers such as DEAE SEPHAROSE® Fast Flow; and weak cation exchangers such as CM SEPHAROSE® Fast Flow (Amersham Biosciences, Piscataway, N.J.). Cation exchange column chromatography may be performed on the 4HB polypeptide at any stage of the purification process to isolate substantially purified 4HB polypeptide. The cation exchange chromatography step may be performed using any suitable cation exchange matrix. Useful cation exchange matrices include, but are not limited to, fibrous, porous, non-porous, microgranular, beaded, or cross-linked cation exchange matrix materials. Such cation exchange matrix materials include, but are not limited to, cellulose, agarose, dextran, polyacrylate, polyvinyl, polystyrene, silica, polyether, or composites of any of the foregoing. Following adsorption of the 4HB polypeptide to the cation exchanger matrix, substantially purified 4HB polypeptide may be eluted by contacting the matrix with a buffer having a sufficiently high pH or ionic strength to displace the 4HB polypeptide from the matrix. Suitable buffers for use in high pH elution of substantially purified 4HB polypeptide include, but are not limited to, citrate, phosphate, formate, acetate, HEPES, and MES buffers ranging in concentration from at least about 5 mM to at least about 100 mM.

Reverse-Phase Chromatoraphy

RP-HPLC may be performed to purify proteins following suitable protocols that are known to those of ordinary skill in the art. See, e.g., Pearson et al., ANAL BIOCHEM. (1982) 124: 217-230 (1982); Rivier et al., J. CHROM. (1983) 268:112-119; Kunitani et al., J. CHROM. (1986) 359:391-402. RP-HPLC may be performed on the 4HB polypeptide to isolate substantially purified 4HB polypeptide. In this regard, silica derivatized resins with alkyl functionalities with a wide variety of lengths, including, but not limited to, at least about $C_3$ to at least about $C_{30}$, at least about $C_3$ to at least about $C_{20}$, or at least about $C_3$ to at least about Cog, resins may be used. Alternatively, a polymeric resin may be used. For example, TosoHaas Amberchrome CG1000sd resin may be used, which is a styrene polymer resin. Cyano or polymeric resins with a wide variety of alkyl chain lengths may also be used. Furthermore, the RP-HPLC column may be washed with a solvent such as ethanol. A suitable elution buffer containing an ion pairing agent and an organic modifier such as methanol, isopropanol, tetrahydrofuran, acetonitrile or ethanol, may be used to elute the 4HB polypeptide from the RP-HPLC column. The most commonly used ion pairing agents include, but are not limited to, acetic acid, formic acid, perchloric acid, phosphoric acid, trifluoroacetic acid, heptafluorobutyric acid, triethylamine, tetramethylammonium, tetrabutylammonium, triethylammonium acetate. Elution may be performed using one or more gradients or isocratic conditions, with gradient conditions preferred to reduce the separation time and to decrease peak width. Another method involves the use of two gradients with different solvent concentration ranges. Examples of suitable elution buffers for use herein may include, but are not limited to, ammonium acetate and acetonitrile solutions.

Hydrophobic Interaction Chromatography Purification Techniques

Hydrophobic interaction chromatography (HIC) may be performed on the 4HB polypeptide. See generally HYDROPHOBIC INTERACTION CHROMATOGRAPHY HANDBOOK: PRINCIPLES AND METHODS (Cat. No. 18-1020-90, Amersham Biosciences (Piscataway, N.J.) which is incorporated by reference herein. Suitable HIC matrices may include, but are not limited to, alkyl- or aryl-substituted matrices, such as butyl-, hexyl-, octyl- or phenyl-substituted matrices including agarose, cross-linked agarose, sepharose, cellulose, silica, dextran, polystyrene, poly(methacrylate) matrices, and mixed mode resins, including but not limited to, a polyethyleneamine resin or a butyl- or phenyl-substituted poly(methacrylate) matrix. Commercially available sources for hydrophobic interaction column chromatography include, but are not limited to, HITRAP®, HIPREP®, and HILOAD® columns (Amersham Biosciences, Piscataway, N.J.). Briefly, prior to loading, the HIC column may be equilibrated using standard buffers known to those of ordinary skill in the art, such as an acetic acid/sodium chloride solution or HEPES containing ammonium sulfate. After loading the 4HB polypeptide, the column may then washed using standard buffers and conditions to remove unwanted materials but retaining the 4HB polypeptide on the HIC column. The 4HB polypeptide may be eluted with about 3 to about 10 column volumes of a standard buffer, such as a HEPES buffer containing EDTA and lower ammonium sulfate concentration than the equilibrating buffer, or an acetic acid/sodium chloride buffer, among others. A decreasing linear salt gradient using, for example, a gradient of potassium phosphate, may also be used to elute the 4HB molecules. The eluant may then be concentrated, for example, by filtration such as diafiltration or ultrafiltration. Diafiltration may be utilized to remove the salt used to elute the 4HB polypeptide.

Other Purification Techniques

Yet another isolation step using, for example, gel filtration (GEL FILTRATION: PRINCIPLES AND METHODS (Cat. No. 18-1022-18, Amersham Biosciences, Piscataway, N.J.) which is incorporated by reference herein, HPLC, expanded bed adsorption, ultrafiltration, diafiltration, lyophilization, and the like, may be performed on the first 4HB polypeptide mixture or any subsequent mixture thereof, to remove any excess salts and to replace the buffer with a suitable buffer for the next isolation step or even formulation of the final drug product. The yield of 4HB polypeptide, including substantially purified 4HB polypeptide, may be monitored at each step described herein using techniques known to those of ordinary skill in the art. Such techniques may also used to assess the yield of substantially purified 4HB polypeptide following the last isolation step. For example, the yield of 4HB polypeptide may be monitored using any of several reverse phase high pressure liquid chromatography columns, having a variety of alkyl chain lengths such as cyano RP-HPLC, $C_{18}$RP-HPLC; as well as cation exchange HPLC and gel filtration HPLC.

Purity may be determined using standard techniques, such as SDS-PAGE, or by measuring 4HB polypeptide using Western blot and ELISA assays. For example, polyclonal antibodies may be generated against proteins isolated from negative control yeast fermentation and the cation exchange recovery. The antibodies may also be used to probe for the presence of contaminating host cell proteins.

Additional purification procedures include those described in U.S. Pat. No. 4,612,367 and includes, but is not limited to, (1) applying a mixture comprising a hEPO polypeptide to a reverse phase macroporous acrylate ester copolymer resin support at a pH of from about 7 to about 9; and (2) eluting the hEPO polypeptide from said support with an aqueous eluant having a pH of from about 7 to about 9 and containing from about 20% to about 80% by volume of an organic diluent selected from the group consisting of acetone, acetonitrile, and a combination of acetone and acetonitrile.

A typical process for the purification of EPO protein is disclosed in WO 96/35718 (Burg, published Nov. 14, 1996), and is described below. Blue Sepharose (Pharmacia) consists of Sepharose beads to the surface of which the Cibacron blue dye is covalently bound. Since EPO binds more strongly to Blue Sepharose than most non-proteinaceous contaminants, some proteinaceous impurities and PVA, EPO can be enriched in this step. The elution of the Blue Sepharose column is performed by increasing the salt concentration as well as the pH. The column is filled with 80-100 1 of Blue Sepharose, regenerated with NaOH and equilibrated with equilibration buffer (sodium/calcium chloride and sodium acetate). The acidified and filtered fermentor supernatant is loaded. After completion of the loading, the column is washed first with a buffer similar to the equilibration buffer containing a higher sodium chloride concentration and consecutively with a TRIS-base buffer. The product is eluted with a TRIS-base buffer and collected in a single fraction in accordance with the master elution profile.

Butyl Toyopearl 650 C (Toso Haas) is a polystyrene based matrix to which aliphatic butyl-residues are covalently coupled. Since EPO binds more strongly to this gel than most of the impurities and PVA, it has to be eluted with a buffer containing isopropanol. The column is packed with 30-40 l of Butyl Toyopearl 650 C, regenerated with NaOH, washed with a TRIS-base buffer and equilibrated with a TRIS-base buffer containing isopropanol. The Blue Sepharose eluate is adjusted to the concentration of isopropanol in the column equilibration buffer and loaded onto the column. Then the column is washed with equilibration buffer with increased isopropanol concentration. The product is eluted with elution buffer (TRIS-base buffer with high isopropanol content) and collected in a single fraction in accordance with the master elution profile.

Hydroxyapatite Ultrogel (Biosepra) consists of hydroxyapatite which is incorporated in an agarose matrix to improve the mechanical properties. EPO has a low affinity to hydroxyapatite and can therefore be eluted at lower phosphate concentrations than protein impurities. The column is filled with 30-40 l of Hydroxyapatite Ultrogel and regenerated with a potassium phosphate/calcium chloride buffer and NaOH followed by a TRIS-base buffer. Then it is equilibrated with a TRIS-base buffer containing a low amount of isopropanol and sodium chloride. The EPO containing eluate of the Butyl Toyopearl chromatography is loaded onto the column. Subsequently the column is washed with equilibration buffer and a TRIS-base buffer without isopropanol and sodium chloride. The product is eluted with a TRIS-base buffer containing a low concentration of potassium phosphate and collected in a single fraction in accordance with the master elution profile.

RP-HPLC material Vydac C4 (Vydac) consists of silica gel particles, the surfaces of which carry C4-alkyl chains. The separation of 4HB polypeptide from the proteinaceous impurities is based on differences in the strength of hydrophobic interactions. Elution is performed with an acetonitrile gradient in diluted trifluoroacetic acid. Preparative HPLC is performed using a stainless steel column (filled with 2.8 to 3.2 liter of Vydac C4 silicagel). The Hydroxyapatite Ultrogel eluate is acidified by adding trifluoroacetic acid and loaded onto the Vydac C4 column. For washing and elution an acetonitrile gradient in diluted trifluoroacetic acid is used. Fractions are collected and immediately neutralized with phosphate buffer. The 4HB polypeptide fractions which are within the IPC limits are pooled.

DEAE Sepharose (Pharmacia) material consists of diethylaminoethyl (DEAE)-groups which are covalently bound to the surface of Sepharose beads. The binding of 4HB polypeptide to the DEAE groups is mediated by ionic interactions. Acetonitrile and trifluoroacetic acid pass through the column without being retained. After these substances have been washed off, trace impurities are removed by washing the column with acetate buffer at a low pH. Then the column is washed with neutral phosphate buffer and 4HB polypeptide is eluted with a buffer with increased ionic strength. The column is packed with DEAE Sepharose fast flow. The column volume is adjusted to assure a 4HB polypeptide load in the range of 3-10 mg 4B1 polypeptide/ml gel. The column is washed with water and equilibration buffer (sodium/potassium phosphate). The pooled fractions of the HPLC eluate are loaded and the column is washed with equilibration buffer. Then the column is washed with washing buffer (sodium acetate buffer) followed by washing with equilibration buffer. Subsequently, 4HB polypeptide is eluted from the column with elution buffer (sodium chloride, sodium/potassium phosphate) and collected in a single fraction in accordance with the master elution profile. The eluate of the DEAB Sepharose column is adjusted to the specified conductivity. The resulting drug substance is sterile filtered into Teflon bottles and stored at −70° C.

A wide variety of methods and procedures can be used to assess the yield and purity of a 4HB protein one or more non-naturally encoded amino acids, including but not limited to, the Bradford assay, SDS-PAGE, silver stained SDS-PAGE, coomassie stained SDS-PAGE, mass spectrometry (including but not limited to, MALDI-TOF) and other methods for characterizing proteins known to one skilled in the art.

VIII. Expression in Alternate Systems

Several strategies have been employed to introduce unnatural amino acids into proteins in non-recombinant host cells, mutagenized host cells, or in cell-free systems. These systems are also suitable for use in making the 4HB polypeptides of the present invention. Derivatization of amino acids with reactive side-chains such as Lys, Cys and Tyr resulted in the conversion of lysine to $N^2$-acetyl-lysine. Chemical synthesis also provides a straightforward method to incorporate unnatural amino acids. With the recent development of enzymatic ligation and native chemical ligation of peptide fragments, it is possible to make larger proteins. See, e.g., P. E. Dawson and S. B. H. Kent, *Annu. Rev. Biochem.*, 69:923 (2000). A general in vitro biosynthetic method in which a suppressor tRNA chemically acylated with the desired unnatural amino acid is added to an in vitro extract capable of supporting protein biosynthesis, has been used to site-specifically incorporate over 100 unnatural amino acids into a variety of proteins of virtually any size. See, e.g., V. W. Cornish, D. Mendel and P. G. Schultz, *Angew. Chem. Int. Ed. Engl.*, 1995, 34:621 (1995); C. J. Noren, S. J. Anthony-Cahill, M. C. Griffith, P. G. Schultz, *A general method for site-specific incorporation of unnatural amino acids into proteins, Science* 244:182-188 (1989); and, J. D. Bain, C. G. Glabe, T. A. Dix, A. R. Chamberlin, E. S. Diala, *Biosynthetic site-specific incorporation of a non-natural amino acid into a polypeptide, J. Am. Chem. Soc.* 111:8013-8014 (1989). A broad range of functional groups has been introduced into proteins for studies of protein stability, protein folding, enzyme mechanism, and signal transduction.

An in vivo method, termed selective pressure incorporation, was developed to exploit the promiscuity of wild-type synthetases. See, e.g., N. Budisa, C. Minks, S. Alefelder, W. Wenger, F. M. Dong, L. Moroder and R. Huber, *FASEB J.*, 13:41 (1999). An auxotrophic strain, in which the relevant metabolic pathway supplying the cell with a particular natural amino acid is switched off, is grown in minimal media containing limited concentrations of the natural amino acid, while transcription of the target gene is repressed. At the onset of a stationary growth phase, the natural amino acid is depleted and replaced with the unnatural amino acid analog. Induction of expression of the recombinant protein results in the accumulation of a protein containing the unnatural analog. For example, using this strategy, o, m and p-fluorophenylalanines have been incorporated into proteins, and exhibit two characteristic shoulders in the UV spectrum which can be easily identified, see, e.g., C. Minks, R. Huber, L. Moroder and N. Budisa, *Anal. Biochem.*, 284:29 (2000); trifluoromethionine has been used to replace methionine in bacteriophage T4 lysozyme to study its interaction with chitooligosaccharide ligands by $^{19}$F NMR, see, e.g., H. Duewel, E. Daub, V. Robinson and J. F. Honek, *Biochemistry*, 36:3404 (1997); and trifluoroleucine has been incorporated in place of leucine, resulting in increased thermal and chemical stability of a leucine-zipper protein. See, e.g., Y. Tang, G. Ghirlanda, W. A. Petka, T. Nakajima, W. F. DeGrado and D. A. Tirrell, Angew. *Chem. Int. Ed. Engl.*, 40:1494 (2001). Moreover, selenomethionine and telluromethionine are incorporated into various recombinant proteins to facilitate the solution of phases in X-ray crystallography. See, e.g., W. A. Hendrickson, J. R. Horton and D. M. Lemaster, *EMBO J.*, 9:1665 (1990); J. O. Boles, K. Lewinski, M. Kunkle, J. D. Odom, B. Dunlap, L. Lebioda and M. Hatada, *Nat. Struct. Biol.*, 1:283 (1994); N. Budisa, B. Steipe, P. Demange, C. Eckerskorn, J. Kellermann and R. Huber, *Eur. J. Biochem.*, 230:788 (1995); and, N. Budisa, W. Karnbrock, S. Steinbacher, A. Humm, L. Prade, T. Neuefeind, L. Moroder and R. Huber, *J. Mol. Biol.* 270:616 (1997). Methionine analogs with alkene or alkyne functionalities have also been incorporated efficiently, allowing for additional modification of proteins by chemical means. See, e.g., J. C. M. vanHest and D. A. Tirrell, *FEBS Lett.*, 428:68 (1998); J. C. M. van Hest, K. L. Kiick and D. A. Tirrell, *J. Am. Chem. Soc.*, 122:1282 (2000); and, K. L. Kiick and D. A. Tirrell, *Tetrahedron*, 56:9487 (2000); U.S. Pat. No. 6,586,207; U.S. Patent Publication 2002/0042097, which are incorporated by reference herein.

The success of this method depends on the recognition of the unnatural amino acid analogs by aminoacyl-tRNA synthetases, which, in general, require high selectivity to insure the fidelity of protein translation. One way to expand the scope of this method is to relax the substrate specificity of aminoacyl-tRNA synthetases, which has been achieved in a limited number of cases. For example, replacement of Ala$^{294}$ by Gly in *Escherichia coli* phenylalanyl-tRNA synthetase (PheRS) increases the size of substrate binding pocket, and results in the acylation of tRNAPhe by p-Cl-phenylalanine (p-Cl-Phe). See, M. Ibba, P. Kast and H. Hennecke, *Biochemistry*, 33:7107 (1994). An *Escherichia coli* strain harboring this mutant PheRS allows the incorporation of p-Cl-phenylalanine or p-Br-phenylalanine in place of phenylalanine. See, e.g., M. Ibba and H. Hennecke, *FEBS Lett.*, 364:272 (1995); and, N. Sharma, R. Furter, P. Kast and D. A. Tirrell, *FEBS Lett.*, 467:37 (2000). Similarly, a point mutation Phe130Ser near the amino acid binding site of *Escherichia coli* tyrosyl-tRNA synthetase was shown to allow azatyrosine to be incorporated more efficiently than tyrosine. See, F. Hamano-Takaku, T. Iwama, S. Saito-Yano, K. Takaku, Y. Monden, M. Kitabatake, D. Soll and S, Nishimura, *J. Biol. Chem.*, 275: 40324 (2000).

Another strategy to incorporate unnatural amino acids into proteins in vivo is to modify synthetases that have proofreading mechanisms. These synthetases cannot discriminate and therefore activate amino acids that are structurally similar to the cognate natural amino acids. This error is corrected at a separate site, which deacylates the mischarged amino acid from the tRNA to maintain the fidelity of protein translation. If the proofreading activity of the synthetase is disabled, structural analogs that are misactivated may escape the editing function and be incorporated. This approach has been demonstrated recently with the valyl-tRNA synthetase (ValRS). See, V. Doring, H. D. Mootz, L. A. Nangle, T. L. Hendrickson, V. de Crecy-Lagard, P. Schimmel and P. Marliere, *Science*, 292:501 (2001). ValRS can misaminoacylate tRNAVal with Cys, Thr, or aminobutyrate (Abu); these noncognate amino acids are subsequently hydrolyzed by the editing domain. After random mutagenesis of the *Escherichia coli* chromosome, a mutant *Escherichia coli* strain was selected that has a mutation in the editing site of ValRS. This edit-defective ValRS incorrectly charges tRNAVal with Cys. Because Abu sterically resembles Cys (—SH group of Cys is replaced with —CH$_3$ in Abu), the mutant ValRS also incorporates Abu into proteins when this mutant *Escherichia coli* strain is grown in the presence of Abu. Mass spectrometric analysis shows that about 24% of valines are replaced by Abu at each valine position in the native protein.

Solid-phase synthesis and semisynthetic methods have also allowed for the synthesis of a number of proteins containing novel amino acids. For example, see the following publications and references cited within, which are as follows: Crick, F. J. C., Barrett, L. Brenner, S. Watts-Tobin, R. *General nature of the genetic code for proteins. Nature*, 192: 1227-1232 (1961); Hofmann, K., Bohn, H. *Studies on polypeptides. XXXVI. The effect of pyrazole-imidazole replacements on the S-protein activating potency of an S-peptide fragment, J. Am. Chem*, 88(24):5914-5919 (1966); Kaiser, E. T. *Synthetic approaches to biologically active peptides and proteins including enyzmes, Acc Chem Res*, 47-54 (1989); Nakatsuka, T., Sasaki, T., Kaiser, E. T. *Peptide segment coupling catalyzed by the semisynthetic enzyme thiosubtilisin, J Am Chem Soc*, 3808-3810 (1987); Schnolzer, M., Kent, S B H. *Constructing proteins by dovetailing unprotected synthetic peptides: backbone-engineered HIV protease, Science*, 256(5054):221-225 (1992); Chaiken, I. M. *Semisynthetic peptides and proteins, CRC Crit Rev Biochem*, 11(3):255-301 (1981); Offord, R. E. *Protein engineering by chemical means? Protein Eng.*, 1(3):151-157 (1987); and, Jackson, D. Y., Burnier, J., Quan, C., Stanley, M., Tom, J., Wells, J. A. *A Designed Peptide Ligase for Total Synthesis of Ribonuclease A with Unnatural Catalytic Residues, Science*, 266(5183):243 (1994).

Chemical modification has been used to introduce a variety of unnatural side chains, including cofactors, spin labels and oligonucleotides into proteins in vitro. See, e.g., Corey, D. R., Schultz, P. G. *Generation of a hybrid sequence-specific single-stranded deoxyribonuclease, Science*, 238(4832): 1401-1403 (1987); Kaiser, E. T., Lawrence D. S., Rokita, S. E. *The chemical modification of enzymatic specificity, Annu Rev Biochem*, 54:565-595 (1985); Kaiser, E. T., Lawrence, D. S. *Chemical mutation of enzyme active sites, Science*, 226 (4674):505-511 (1984); Neet, K. E., Nanci A, Koshland, D. E. *Properties of thiol-subtilisin, J. Biol. Chem.*, 243(24):6392-6401 (1968); Polgar, L. B., M. L. *A new enzyme containing a synthetically formed active site. Thiol-subtilisin. J. Am. Chem Soc*, 3153-3154 (1966); and, Pollack, S. J., Nakayama, G. Schultz, P. G. *Introduction of nucleophiles and spectroscopic probes into antibody combining sites, Science.* 242(4881): 1038-1040 (1988).

Alternatively, biosynthetic methods that employ chemically modified aminoacyl-tRNAs have been used to incorporate several biophysical probes into proteins synthesized in vitro. See the following publications and references cited within: Brunner, J. *New Photolabeling and crosslinking methods, Annu. Rev Biochem*, 62:483-514 (1993); and, Krieg, U. C., Walter, P., Hohnson, A. E. *Photocrosslinking of the signal sequence of nascent preprolactin of the 54-kilodalton polypeptide of the signal recognition particle, Proc. Natl. Acad. Sci*, 83(22):8604-8608 (1986).

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotrophic for a particular amino acid. See, e.g., Noren, C. J., Anthony-Cahill, Griffith, M. C., Schultz, P. G. *A general method for site-specific incorporation of unnatural amino acids into proteins, Science*, 244: 182-188 (1989); M. W. Nowak, et al., *Science* 268:439-42 (1995); Bain, J. D., Glabe, C. G., Dix, T. A., Chamberlin, A. R., Diala, E. S. *Biosynthetic site-specific Incorporation of a non-natural amino acid into a polypeptide, J. Am. Chem Soc*, 111:8013-8014 (1989); N. Budisa et al., *FASEB J.* 13:41-51 (1999); Ellman, J. A., Mendel, D., Anthony-Cahill, S., Noren, C. J., Schultz, P. G. *Biosynthetic method for introducing unnatural amino acids site-specifically into proteins, Methods in Enz.*, 301-336 (1992); and, Mendel, D., Cornish, V. W. & Schultz, P. G. *Site-Directed Mutagenesis with an Expanded Genetic Code, Annu Rev Biophys. Biomol Struct.* 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. 5',3' *Exonuclease in phosphorothioate-based olignoucleotide-directed mutagensis*, Nucleic Acids Res, 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins*, Science, 255(5041):197-200 (1992).

Microinjection techniques have also been use incorporate unnatural amino acids into proteins. See, e.g., M. W. Nowak, P. C. Kearney, J. R. Sampson, M. E. Saks, C. G. Labarca, S. K. Silverman, W. G. Zhong, J. Thorson, J. N. Abelson, N. Davidson, P. G. Schultz, D. A. Dougherty and H. A. Lester, *Science*, 268:439 (1995); and, D. A. Dougherty, *Curr. Opin. Chem. Biol.*, 4:645 (2000). A *Xenopus oocyte* was connected with two RNA species made in vitro: an mRNA encoding the target protein with a UAG stop codon at the amino acid position of interest and an amber suppressor tRNA aminoacylated with the desired unnatural amino acid. The translational machinery of the oocyte then inserts the unnatural amino acid at the position specified by UAG. This method has allowed in vivo structure-function studies of integral membrane proteins, which are generally not amenable to in vitro expression systems. Examples include the incorporation of a fluorescent amino acid into tachykinin neurokinin-2 receptor to measure distances by fluorescence resonance energy transfer, see, e.g., G. Turcatti, K. Nemeth, M. D. Edgerton, U. Meseth, F. Talabot, M. Peitsch, J. Knowles, H. Vogel and A. Chollet, *J. Biol. Chem.*, 271:19991 (1996); the incorporation of biotinylated amino acids to identify surface-exposed residues in ion channels, see, e.g., J. P. Gallivan, H. A. Lester and D. A. Dougherty, *Chem. Biol.*, 4:739 (1997); the use of caged tyrosine analogs to monitor conformational changes in an ion channel in real time, see, e.g., J. C. Miller, S. K. Silverman, P. M. England, D. A. Dougherty and H. A. Lester, Neuron, 20:619 (1998); and, the use of alpha hydroxy amino acids to change ion channel backbones for probing their gating mechanisms. See, e.g., P. M. England, Y. Zhang, D. A. Dougherty and H. A. Lester, *Cell*, 96:89 (1999); and, T. Lu, A. Y. Ting, J. Mainland, L. Y. Jan, P. G. Schultz and J. Yang, *Nat. Neurosci.*, 4:239 (2001).

The ability to incorporate unnatural amino acids directly into proteins in vivo offers the advantages of high yields of mutant proteins, technical ease, the potential to study the mutant proteins in cells or possibly in living organisms and the use of these mutant proteins in therapeutic treatments. The ability to include unnatural amino acids with various sizes, acidities, nucleophilicities, hydrophobicities, and other properties into proteins can greatly expand our ability to rationally and systematically manipulate the structures of proteins, both to probe protein function and create new proteins or organisms with novel properties. However, the process is difficult, because the complex nature of tRNA-synthetase interactions that are required to achieve a high degree of fidelity in protein translation.

In one attempt to site-specifically incorporate para-F-Phe, a yeast amber suppressor tRNAPheCUA/phenylalanyl-tRNA synthetase pair was used in a p-F-Phe resistant, Phe auxotrophic *Escherichia coli* strain. See, e.g., R. Furter, *Protein Sci.* 7:419 (1998).

It may also be possible to obtain expression of a 4HB polynucleotide of the present invention using a cell-free (in-vitro) translational system. In these systems, which can include either mRNA as a template (in-vitro translation) or DNA as a template (combined in-vitro transcription and translation), the in vitro synthesis is directed by the ribosomes. Considerable effort has been applied to the development of cell-free protein expression systems. See, e.g., Kim, D.-M. and J. R. Swartz, *Biotechnology and Bioengineering*, 74:309-316 (2001); Kim, D.-M. and J. R. Swartz, *Biotechnology Letters*, 22, 1537-1542, (2000); Kim, D.-M., and J. R. Swartz, *Biotechnology Progress*, 16, 385-390, (2000); Kim, D.-M., and J. R. Swartz, *Biotechnology and Bioengineering*, 66, 180-188, (1999); and Patnaik, R. and J. R. Swartz, *Biotechniques* 24, 862-868, (1998); U.S. Pat. No. 6,337,191; U.S. Patent Publication No. 2002/0081660; WO 00/55353; WO 90/05785, which are incorporated by reference herein. Another approach that may be applied to the expression of 4HB polypeptides comprising a non-naturally encoded amino acid includes the mRNA-peptide fusion technique. See, e.g., R. Roberts and J. Szostak, *Proc. Natl. Acad. Sci. (USA)* 94:12297-12302 (1997); A. Frankel, et al., *Chemistry & Biology* 10:1043-1050 (2003). In this approach, an mRNA template linked to puromycin is translated into peptide on the ribosome. If one or more tRNA molecules has been modified, non-natural amino acids can be incorporated into the peptide as well. After the last mRNA codon has been read, puromycin captures the C-terminus of the peptide. If the resulting mRNA-peptide conjugate is found to have interesting properties in an in vitro assay, its identity can be easily revealed from the MrRNA sequence. In this way, one may screen libraries of 4BB polypeptides comprising one or more non-naturally encoded amino acids to identify polypeptides having desired properties. More recently, in vitro ribosome translations with purified components have been reported that permit the synthesis of peptides substituted with non-naturally encoded amino acids. See, e.g., A. Forster et al., *Proc. Natl Acad. Sci. (USA)* 100:6353 (2003).

IX. Macromolecular Polymers Coupled to 4HB Polypeptides

Various modifications to the non-natural amino acid polypeptides described herein can be effected using the compositions methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to 4HB polypeptides of the present invention to modulate biological properties of the 4HB polypeptide, and/or provide new biological properties to the 4HB molecule. These macromolecular polymers can be linked to the 4HB polypeptide via a naturally encoded amino acid, via a non-naturally encoded amino acid, or any functional substituent of a natural or non-natural amino acid, or any substituent or functional group added to a natural or non-natural amino acid.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated 4HB polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. Preferably, for therapeutic use of the end-product preparation, the polymer will be pharmaceutically acceptable.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG:4HB polypeptide conjugates, the term "therapeutically effective amount" refers to an amount which gives an increase in hematocrit that provides benefit to a patient. The amount will vary from one individual to another and will depend upon a number of factors, including the overall physical condition of the patient and the underlying cause of anemia. For example, a therapeutically effective amount of 4HB polypeptide for a patient suffering from chronic renal failure is 50 to 150 units/kg three times per week. The amount of 4HB polypeptide used for therapy gives an acceptable rate of hematocrit increase and maintains the hematocrit at a beneficial level (usually at least about 30% and typically in a range of 30% to 36%). A therapeutically effective amount of the present compositions may be readily ascertained by one skilled in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the 4HB polypeptide by the formula:

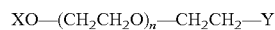

XO—(CH$_2$CH$_2$O)$_n$—CH$_2$CH$_2$—Y where n is 2 to 10,000 and X is H or a terminal modification, including but not limited to, a C$_{1-4}$ alkyl.

In some cases, a PEG used in the invention terminates on one end with hydroxy or methoxy, i.e., X is H or CH$_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a 4HB polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the 4HB polypeptide to form a Huisgen [3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the 4HB polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the 4HB polypeptide variant with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly (ethylene)glycol and other related polymers, including poly (dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly(ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula—$CH_2CH_2O$—$(CH_2CH_2O)_n$—$CH_2CH_2$—, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as R(—PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932, 462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(—YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

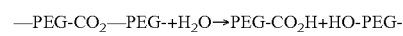

—PEG-CO$_2$—PEG-+H$_2$O→PEG-CO$_2$H+HO-PEG-

It is understood by those skilled in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("TPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

X—A—POLY—B—N=N=N wherein:
N=N=N is an azide moiety;
B is a linking moiety, which may be present or absent;
POLY is a water-soluble non-antigenic polymer;
A is a linking moiety, which may be present or absent and which may be the same as B or different; and
X is a second functional group.
Examples of a linking moiety for A and B include, but are not limited to, a multiply-functionalized allyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those skilled in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182:1379 (1981), Zaplipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zaplipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Macrolol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. No. 5,824,784, U.S. Pat. No. 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In certain embodiments of the present invention, the polymer derivatives of the invention comprise a polymer backbone having the structure:

X—CH$_2$CH$_2$O—(CH$_2$CH$_2$O)$_n$—CH$_2$CH$_2$—N=N=N wherein:
X is a functional group as described above; and
n is about 20 to about 4000.
In another embodiment, the polymer derivatives of the invention comprise a polymer backbone having the structure:

X—CH$_2$CH$_2$O—(CH$_2$CH$_2$O)$_n$—CH$_2$CH$_2$—O—(CH$_2$)$_m$—W—N=N=N wherein:
W is an aliphatic or aromatic linker moiety comprising between 1-10 carbon atoms;
n is about 20 to about 4000; and
X is a functional group as described above. m is between 1 and 10.

The azide-containing PEG derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

$$X\text{-PEG-L} + N_3^- \rightarrow X\text{-PEG-}N_3$$

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below:

$$X\text{-PEG-M} + N\text{-linker-}N=N=N \rightarrow PG\text{-}X\text{-PEG-linker-}N=N=N$$

wherein:
PEG is poly(ethylene glycol) and X is a capping group such as alkoxy or a functional group as described above; and
M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

$$BocHN\text{-PEG-}NH_2 + HO_2C\text{-}(CH_2)_3\text{-}N=N=N$$

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

$$X\text{-A-POLY-B-}C\equiv C\text{-R}$$

wherein:
R can be either H or an alkyl, alkene, alkyoxy, or aryl or substituted aryl group;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and more preferably between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and more preferably 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure:

$$X\text{-}CH_2CH_2O\text{-}(CH_2CH_2O)_n\text{-}CH_2CH_2\text{-}O\text{-}(CH_2)_m\text{-}C\equiv CH$$

wherein:

X is a functional group as described above;

n is about 20 to about 4000; and m is between 1 and 10.

Specific examples of each of the heterobifunctional PEG polymers are shown below.

The acetylene-containing PEG derivatives of the invention can be prepared using methods known to those skilled in the art and/or disclosed herein. In one method, a water soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

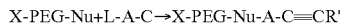

As shown, a preferred polymer backbone for use in the reaction has the formula X-PEG-Nu, wherein PEG is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

wherein:

PEG is poly(ethylene glycol) and X is a capping group such as alkoxy or a functional group as described above; and R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are well known in the art.

Purification of the crude product can usually be accomplished by methods known in the art including, but are not limited to, precipitation of the product followed by chromatography, if necessary.

Water soluble polymers can be linked to the 4HB polypeptides of the invention. The water soluble polymers may be linked via a non-naturally encoded amino acid incorporated in the 4HB polypeptide or any functional group or substituent of a non-naturally encoded or naturally encoded amino acid, or any functional group or substituent added to a non-naturally encoded or naturally encoded amino acid. Alternatively, the water soluble polymers are linked to a 4HB polypeptide incorporating a non-naturally encoded amino acid via a naturally-occurring amino acid (including but not limited to, cysteine, lysine or the amine group of the N-terminal residue). In some cases, the 4HB polypeptides of the invention comprise 1, 2, 3, 4, 5, 6, 7, 8, 9, 10 non-natural amino acids, wherein one or more non-naturally-encoded amino acid(s) are linked to water soluble polymer(s) (including but not limited to, PEG and/or oligosaccharides). In some cases, the 4HB polypeptides of the invention further comprise 1, 2, 3, 4, 5, 6, 7, 8, 9, 10, or more naturally-encoded amino acid(s) linked to water soluble polymers. In some cases, the 4HB polypeptides of the invention comprise one or more non-naturally encoded amino acid(s) linked to water soluble polymers and one or more naturally-occurring amino acids linked to water soluble polymers. In some embodiments, the water soluble polymers used in the present invention enhance the serum half-life of the 4HB polypeptide relative to the unconjugated form.

The number of water soluble polymers linked to a 4HB polypeptide (i.e., the extent of PEGylation or glycosylation) of the present invention can be adjusted to provide an altered (including but not limited to, increased or decreased) pharmacologic, pharmacokinetic or pharmacodynamic characteristic such as in vivo half-life. In some embodiments, the half-life of 4HB is increased at least about 10, 20, 30, 40, 50, 60, 70, 80, 90 percent, 2-fold, 5-fold, 10-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, a 4HB polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

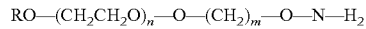

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

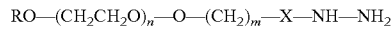

where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure:

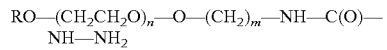

where R is a simple alkyl (methyl, ethyl, propyl, etc.), m is 2-10 and n is 100-1,000.

In another embodiment of the invention, a 4HB polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

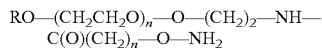
RO—(CH$_2$CH$_2$O)$_n$—O—(CH$_2$)$_2$—NH—C(O)(CH$_2$)$_n$—O—NH$_2$ where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

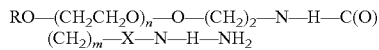
RO—(CH$_2$CH$_2$O)$_n$—O—(CH$_2$)$_2$—N—H—C(O)(CH$_2$)$_m$—X—N—H—NH$_2$ where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure:

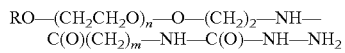
RO—(CH$_2$CH$_2$O)$_n$—O—(CH$_2$)$_2$—NH—C(O)(CH$_2$)$_m$—NH—C(O)—NH—NH$_2$ where R is a simple alkyl (methyl, ethyl, propyl, etc.), m is 2-10 and n is 100-1,000.

In another embodiment of the invention, a 4HB polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, more preferably, from 5-20 kDa.

In another embodiment of the invention, a 4HB polypeptide comprising a non-naturally encoded amino acid is modified with a PEG derivative having a branched structure. For instance, in some embodiments, the hydrazine- or hydrazide-terminal PEG derivative will have the following structure:

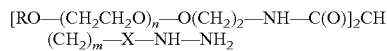
[RO—(CH$_2$CH$_2$O)$_n$—O(CH$_2$)$_2$—NH—C(O)]$_2$CH(CH$_2$)$_m$—X—NH—NH$_2$ where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure:

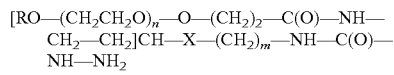
[RO—(CH$_2$CH$_2$O)$_n$—O—(CH$_2$)$_2$—C(O)—NH—CH$_2$—CH$_2$]CH—X—(CH$_2$)$_m$—NH—C(O)—NH—NH$_2$ where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

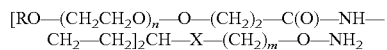
[RO—(CH$_2$CH$_2$O)$_n$—O—(CH$_2$)$_2$—C(O)—NH—CH$_2$—CH$_2$]$_2$CH—X—(CH$_2$)$_m$—O—NH$_2$ where R is a simple alkyl (methyl, ethyl, propyl, etc.), X is optionally NH, O, S, C(O) or not present, m is 2-10 and n is 100-1,000.

The degree and sites at which the water soluble polymer(s) are linked to the 4HB polypeptide can modulate the binding of the 4HB polypeptide to the 4HB polypeptide receptor at Site 1. In some embodiments, the linkages are arranged such that the 4HB polypeptide binds the 4HB polypeptide receptor at Site 1 with a K$_d$ of about 400 nM or lower, with a K$_d$ of 150 nM or lower, and in some cases with a K$_d$ of 100 nM or lower, as measured by an equilibrium binding assay, such as that described in Spencer et al., *J. Biol. Chem.*, 263:7862-7867 (1988) for hGH.

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)). All references and patents cited are incorporated by reference herein.

PEGylation (i.e., addition of any water soluble polymer) of 43 polypeptides containing a non-naturally encoded amino acid, such as p-azido-L-phenylalanine, is carried out by any convenient method. For example, 4HB polypeptide is PEGylated with an alkyne-terminated mPEG derivative. Briefly, an excess of solid mPEG (5000)-O—CH$_2$—C≡CH is added, with stirring, to an aqueous solution of p-azido-L-Phe-containing 4HB polypeptide at room temperature. Typically, the aqueous solution is buffered with a buffer having a pK$_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated 4HB polypeptide variants from free mPEG (5000)-O—CH$_2$—C≡CH and any high-molecular weight complexes of the pegylated 4HB polypeptide which may form when unblocked PEG is activated at both ends of the molecule, thereby crosslinking 4HB polypeptide variant molecules. The conditions during hydrophobic interaction chromatography are such that free mPEG (5000)-O—CH$_2$—C≡CH flows through the column, while any crosslinked PEGylated 4HB polypeptide variant complexes elute after the desired forms, which contain one 4HB polypeptide variant molecule conjugated to one or more PEG groups. Suitable conditions vary depending on the relative sizes of the cross-linked complexes versus the desired conjugates and are readily determined by those skilled in the art. The eluent containing the desired conjugates is concentrated by ultrafiltration and desalted by diafiltration.

If necessary, the PEGylated 4HB polypeptide obtained from the hydrophobic chromatography can be purified further by one or more procedures known to those skilled in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (PROTEIN PURIFICATION METHODS, A PRACTICAL APPROACH (Harris & Angal, Eds.) IRL Press 1989, 293-306). The purity of the 4HB-PEG conjugate can be assessed by proteolytic degradation (including but not limited to, trypsin cleavage) followed by mass spectrometry analysis. Pepinsky B., et al., *J. Pharmcol. & Exp. Ther.* 297 (3):1059-66 (2001).

A water soluble polymer linked to an amino acid of a 4HB polypeptide of the invention can be further derivatized or substituted without limitation.

Azide-Containing PEG Derivatives

In another embodiment of the invention, a 4HB polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure:

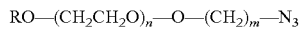

where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

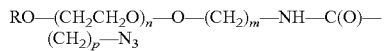

where R is a simple alkyl (methyl, ethyl, propyl, etc.), m is 2-10, p is 2-10 and n is 100-1,000 (i.e., average molecular weight is between 5-40 kDa).

In another embodiment of the invention, a 4HB polypeptide comprising a alkyne-containing amino acid is modified with a branched PEG derivative that contains a terminal azide moiety, with each chain of the branched PEG having a MW ranging from 10-40 kDa and, more preferably, from 5-20 kDa. For instance, in some embodiments, the azide-terminal PEG derivative will have the following structure:

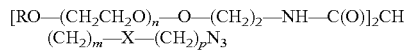

where R is a simple alkyl (methyl, ethyl, propyl, etc.), m is 2-10, p is 2-10, and n is 100-1,000, and X is optionally an O, N, S or carbonyl group (C=O), in each case that can be present or absent.

Alkyne-Containing PEG Derivatives

In another embodiment of the invention, a 4HB, polypeptide is modified with a PEG derivative that contains an alkyne moiety that will react with an azide moiety present on the side chain of the non-naturally encoded amino acid.

In some embodiments, the alkyne-terminal PEG derivative will have the following structure:

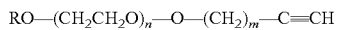

where R is a simple alkyl (methyl, ethyl, propyl, etc.), m is 2-10 and n is 100-1,000 (i.e., average molecular weight is between 5-40 kDa).

In another embodiment of the invention, a 4HB polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

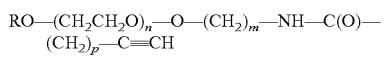

where R is a simple alkyl (methyl, ethyl, propyl, etc.), m is 2-10, p is 2-10 and n is 100-1,000.

In another embodiment of the invention, a 4HB polypeptide comprising an azide-containing amino acid is modified with a branched PEG derivative that contains a terminal alkyne moiety, with each chain of the branched PEG having a MW ranging from 10-40 kDa and, more preferably, from 5-20 kDa. For instance, in some embodiments, the alkyne-terminal PEG derivative will have the following structure:

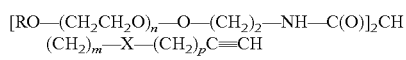

where R is a simple alkyl (methyl, ethyl, propyl, etc.), m is 2-10, p is 2-10, and n is 100-1,000, and X is optionally an O, N, S or carbonyl group (C=O), or not present.

Phosphine-Containing PEG Derivatives

In another embodiment of the invention, a 4HB polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

In some embodiments, the PEG derivative will have the structure:

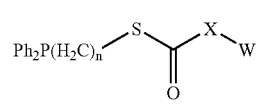

wherein n is 1-10; X can be O, N, S or not present, Ph is phenyl, and W is a water soluble polymer.

In some embodiments, the PEG derivative will have the structure:

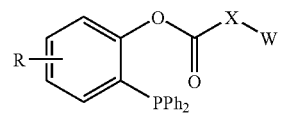

wherein X can be O, N, S or not present, Ph is phenyl, W is a water soluble polymer and R can be H, alkyl, aryl, substituted alkyl and substituted aryl groups. Exemplary R groups include but are not limited to —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Other PEG Derivatives and General PEGylation Techniques

Other exemplary PEG molecules that may be linked to 4HB polypeptides, as well as PEGylation methods include those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0027217; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,612,460; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Enhancing Affinity for Serum Albumin

Various molecules can also be fused to the 4HB polypeptides of the invention to modulate the half-life of 4HB polypeptides in serum. In some embodiments, molecules are linked or fused to 4HB polypeptides of the invention to enhance affinity for endogenous serum albumin in an animal.

For example, in some cases, a recombinant fusion of a 4HB polypeptide and an albumin binding sequence is made. Exemplary albumin binding sequences include, but are not limited to, the albumin binding domain from streptococcal protein G (see. e.g., Makrides et al., *J. Pharmacol. Exp. Ther.* 277:534-542 (1996) and Sjolander et al., *J. Immunol. Methods* 201:115-123 (1997)), or albumin-binding peptides such as those described in, e.g., Dennis, et al., *J. Biol. Chem.* 277:35035-35043 (2002).

In other embodiments, the 4HB polypeptides of the present invention are acylated with fatty acids. In some cases, the fatty acids promote binding to serum albumin. See, e.g., Kurtzhals, et al., *Biochem. J.* 312:725-731 (1995).

In other embodiments, the 4HB polypeptides of the invention are fused directly with serum albumin (including but not limited to, human serum albumin). See, e.g., U.S. Pat. No. 6,548,653, which is incorporated by reference herein, for serum albumin fusions of EPO analogs. Those of skill in the art will recognize that a wide variety of other molecules can also be linked to 4HB in the present invention to modulate binding to serum albumin or other serum components.

X. Glycosylation of 4HB Polypeptides

The invention includes 4HB polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to 4HB polypeptides either in vivo or in vitro. In some embodiments of the invention, a 4HB polypeptide comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the 4HB polypeptide. See, e.g., H. Liu, et al. *J. Am. Chem. Soc.* 125: 1702-1703 (2003).

In some embodiments of the invention, a 4HB polypeptide comprising a carbonyl-containing non-naturally encoded amino acid is modified directly with a glycan with defined structure prepared as an aminooxy derivative. One skilled in the art will recognize that other functionalities, including azide, alkyne, hydrazide, hydrazine, and semicarbazide, can be used to link the saccharide to the non-naturally encoded amino acid.

In some embodiments of the invention, a 4HB polypeptide comprising an azide or alkynyl-containing non-naturally encoded amino acid can then be modified by, including but not limited to, a Huisgen [3+2] cycloaddition reaction with, including but not limited to, alkynyl or azide derivatives, respectively. This method allows for proteins to be modified with extremely high selectivity.

XI. GH Supergene Family Member Dimers and Multimers

The present invention also provides for GH supergene family member combinations (including but not limited to hGH, hIFN, hG-CSF, or hEPO) homodimers, heterodimers, homomultimers, or heteromultimers (i.e., trimers, tetramers, etc.) where a GH supergene family member polypeptide such as hGH, hIFN, hG-CSF, or hEPO containing one or more non-naturally encoded amino acids is bound to another GH supergene family member or variant thereof or any other polypeptide that is a non-GH supergene family member or variant thereof, either directly to the polypeptide backbone or via a linker. Due to its increased molecular weight compared to monomers, the GH supergene family member, such as hGH, hIFN, hG-CSF, or hEPO, dimer or multimer conjugates may exhibit new or desirable properties, including but not limited to different pharmacological, pharmacokinetic, pharmacodynamic, modulated therapeutic half-life, or modulated plasma half-life relative to the monomeric GH supergene family member. In some embodiments, the GH supergene family member, such as hGH, hIFN, hG-CSF, hEPO, dimers of the invention will modulate the dimerization of the GH supergene family member receptor. In other embodiments, the GH supergene family member dimers or multimers of the present invention will act as a GH supergene family member receptor antagonist, agonist, or modulator.

In some embodiments, one or more of the 4HB molecules present in a 4HB containing dimer or multimer comprises a non-naturally encoded amino acid linked to a water soluble polymer that is present within the Site II binding region. As such, each of the 4HB molecules of the dimer or multimer are accessible for binding to the 4HB polypeptide receptor via the Site I interface but are unavailable for binding to a second 4HB polypeptide receptor via the Site II interface. Thus, the 4HB polypeptide dimer or multimer can engage the Site I binding sites of each of two distinct 4HB polypeptide receptors but, as the 4HB molecules have a water soluble polymer attached to a non-genetically encoded amino acid present in the Site II region, the 4HB polypeptide receptors cannot engage the Site II region of the 4HB polypeptide ligand and the dimer or multimer acts as a 4HB polypeptide antagonist. In some embodiments, one or more of the 4HB molecules present in a 4HB polypeptide containing dimer or multimer comprises a non-naturally encoded amino acid linked to a water soluble polymer that is present within the Site I binding region, allowing binding to the Site II region. Alternatively, in some embodiments one or more of the 4HB molecules present in a 4HB polypeptide containing dimer or multimer comprises a non-naturally encoded amino acid linked to a water soluble polymer that is present at a site that is not within the Site I or Site II binding region, such that both are available for binding. In some embodiments a combination of 4HB molecules is used having Site I, Site II, or both available for binding. A combination of 4HB molecules wherein at least one has Site I available for binding, and at least one has Site II available for binding may provide molecules having a desired activity or property. In addition, a combination of 4HB molecules having both Site I and Site II available for binding may produce a super-agonist 4HB molecule.

In some embodiments, the GH supergene family member polypeptides are linked directly, including but not limited to, via an Asn-Lys amide linkage or Cys-Cys disulfide linkage. In some embodiments, the linked GH supergene family member polypeptides, and/or the linked non-GE supergene family member, will comprise different non-naturally encoded amino acids to facilitate dimerization, including but not limited to, an alkyne in one non-naturally encoded amino acid of a first 4HB polypeptide and an azide in a second non-naturally encoded amino acid of a second GH supergene family member polypeptide will be conjugated via a Huisgen [3+2] cycloaddition. Alternatively, a first GH supergene family member, and/or the linked non-GH supergene family member, polypeptide comprising a ketone-containing non-naturally encoded amino acid can be conjugated to a second GH supergene family member polypeptide comprising a hydroxylamine-containing non-naturally encoded amino acid and the polypeptides are reacted via formation of the corresponding oxime.

Alternatively, the two GH supergene family member polypeptides, and/or the linked non-GH supergene family member, are linked via a linker. Any hetero- or homobifunctional linker can be used to link the two GH supergene family member, and/or the linked non-GH supergene family member, polypeptides, which can have the same or different primary sequence. In some cases, the linker used to tether the GH supergene family member, and/or the linked non-GH supergene family member, polypeptides together can be a bifunctional PEG reagent.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more GH supergene family member, such as hGH, hIFN, hG-CSF, or hEPO formed by reactions with water soluble activated polymers that have the structure:

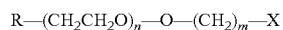

wherein n is from about 5 to 3,000, m is 2-10, X can be an azide, an alkyne, a hydrazine, a hydrazide, an amino oxy group, a hydroxylamine, a acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

XII. Measurement of 4HB Polypeptide Activity and Affinity of 4HB Polypeptide for the 4HB Polypeptide Receptor The hGH receptor can be prepared as described in McFarland et al., *Science*, 245: 494-499 (1989) and Leung, D., et al., *Nature*, 330:537-543 (1987). hGH polypeptide activity can be determined using standard in vitro or in vivo assays. For example, cell lines that proliferate in the presence of hGH (e.g., a cell line expressing the hGH receptor or a lactogenic receptor) can be used to monitor hGH receptor binding. See, e.g., Clark, R., et al., *J. Biol. Chem.* 271(36):21969 (1996); Wada, et al., *Mol. Endocrinol.* 12:146-156 (1998); Gout, P. W., et al. *Cancer Res.* 40, 2433-2436 (1980); WO 99/03887. For a non-PEGylated hGH polypeptide comprising a non-natural amino acid, the affinity of the hormone for its receptor can be measured by using a BIAcore™ biosensor (Pharmacia). See, e.g., U.S. Pat. No. 5,849,535; Spencer, S. A., et al., J. Biol. Chem., 263:7862-7867 (1988). In vivo animal models for testing hGH activity include those described in, e.g., Clark et al., J. Biol. Chem. 271(36):21969-21977 (1996). Assays for dimerization capability of hGH polypeptides comprising one or more non-naturally encoded amino acids can be conducted as described in Cunningham, B., et al., Science, 254:821-825 (1991) and Fuh, G., et al., Science, 256:1677-1680 (1992). All references and patents cited are incorporated by reference herein.

The hIFN receptor can be prepared as described in U.S. Pat. Nos. 6,566,132; 5,889,151; 5,861,258; 5,731,169; 5,578,707, which is incorporated by reference herein. hIFN polypeptide activity can be determined using standard or known in vitro or in vivo assays. For example, cells or cell lines that modulate growth or MHC Class I or II antigen production in response to hIFN or bind hIFN (including but not limited to, cells containing active IFN receptors such as human lymphoblastoid Daudi cells, or recombinant IFN receptor producing cells) can be used to monitor hIFN receptor binding. For a non-PEGylated or PEGylated hIFN polypeptide comprising a non-natural amino acid, the affinity of the hormone for its receptor can be measured by using techniques known in the art such as a BIAcore™ biosensor (Pharmacia). In vivo animal models as well as human clinical trials for testing hIFN activity include those described in, e.g., Kontsek et al., Acta Virol. 43:63 (1999); Youngster et al., Current Pharma Design 8:2139 (2002); Kozlowski et al., BioDrugs 15:419 (2001); U.S. Pat. Nos. 6,180,096; 6,177,074; 6,042,822; 5,981,709; 5,951,974; 5,908,621; 5,711,944; 5,738,846, which are incorporated by reference herein.

Regardless of which methods are used to create the present hIFN analogs, the analogs are subject to assays for biological activity. Tritiated thymidine assays may be conducted to ascertain the degree of cell division. Other biological assays, however, may be used to ascertain the desired activity. Biological assays such as assaying for the ability to inhibit viral replication, also provides indication of IFN activity. See Bailon et al., Bioconj. Chem. 12:195 (2001); Forti et al., Meth. Enzymol. 119:533 (1986); Walter et al., Cancer Biother. & Radiopharm. 13:143 (1998); DiMarco et al., Bio-Chem. Biophys. Res. Corn. 202:1445 (1994); and U.S. Pat. Nos. 4,675,282; 4,241,174; 4,514,507; 4,622,292; 5,766,864, which are incorporated by reference herein. Other in vitro assays may be used to ascertain biological activity. In general, the test for biological activity should provide analysis for the desired result, such as increase or decrease in biological activity (as compared to non-altered IFN), different biological activity (as compared to non-altered IFN), receptor affinity analysis, or serum half-life analysis.

It was previously reported that Daudi cells will bind $^{125}$I-labeled murine IFN and that this binding can be competed for by addition of unlabeled IFN (See e.g. U.S. Pat. Nos. 5,516,514; 5,632,988). The ability of natural IFN and hIFN to compete for binding of $^{125}$I-IFN to human and murine leukemic cells is tested. Highly purified natural IFN (>95% pure; 1 µg) is iodinated [Tejedor, et al., Anal. Biochem., 127, 143 (1982)], and is separated from reactants by gel filtration and ion exchange chromatography. The specific activity of the natural $^{125}$I-IFN may be approximately 100 µCi/µg protein.

The hG-CSF receptor can be prepared as described in U.S. Pat. No. 5,574,136, which is incorporated by reference herein. hG-CSF polypeptide activity can be determined using standard or known in vitro or in vivo assays. For example, cells or cell lines that proliferate in the presence of hG-CSF or bind hG-CSF (including but not limited to, cells containing active G-CSF receptors such as mouse bone marrow cells, WEHI-3B (D+), AML-193 (ATCC), or recombinant G-CSF receptor producing cells) can be used to monitor hG-CSF receptor binding. See, e.g., King et al., Exp. Hematol. 20:223 (1992); U.S. Pat. No. 6,385,505, which are incorporated by reference herein. For a non-PEGylated or PEGylated hG-CSF polypeptide comprising a non-natural amino acid, the affinity of the hormone for its receptor can be measured by using a BIAcore™ biosensor (Pharmacia). In vivo animal models as well as human clinical trials for testing hG-CSF activity include those described in, e.g., U.S. Pat. Nos. 6,166,183; 6,565,841; 6,162,426; 5,718,893, which are incorporated by reference herein.

Regardless of which methods are used to create the present hG-CSF analogs, the analogs are subject to assays for biological activity. Tritiated thymidine assays may be conducted to ascertain the degree of cell division. Other biological assays, however, may be used to ascertain the desired activity. Biological assays such as assaying for the ability to induce terminal differentiation in mouse WEHI-3B (D+) leukemic cell line, also provides indication of G-CSF activity. See Nicola, et al. Blood 54: 614-27 (1979). Other in vitro assays may be used to ascertain biological activity. See Nicola, Ann. Rev. Biochem. 58: 45-77 (1989). In general, the test for biological activity should provide analysis for the desired result, such as increase or decrease in biological activity (as compared to non-altered G-CSF), different biological activity (as compared to non-altered G-CSF), receptor affinity analysis, or serum half-life analysis.

It was previously reported that WEHI-3BD$^+$ cells and human leukemic cells from newly diagnosed leukemias will bind $^{125}$I-labeled murine G-CSF and that this binding can be competed for by addition of unlabeled G-CSF or human CSF-β. The ability of natural G-CSF and hG-CSF to compete for binding of $^{125}$I-G-CSF to human and murine leukemic cells is tested. Highly purified natural G-CSF (>95% pure; 1 µg) is iodinated [Tejedor, et al., Anal. Biochem., 127, 143 (1982)], and is separated from reactants by gel filtration and ion exchange chromatography. The specific activity of the natural $^{125}$I-G-CSF is approximately 100 µCi/µg protein.

The hEPO receptor can be prepared as described in U.S. Pat. Nos. 5,387,808; 5,292,654; 5,278,065, which are incorporated by reference herein. hEPO polypeptide activity can be determined using standard in vitro or in vivo assays. For example, cell lines that proliferate in the presence of hEPO (including but not limited to, UT-7 cells, TF-1 cells, FDCP-1/mEPOR, or spleen cells) can be used to monitor hEPO receptor binding. See, e.g., Wrighton et al., (1997) Nature Biotechnology 15:1261-1265; U.S. Pat. No. 5,773,569; and U.S. Pat. No. 5,830,851, which are incorporated by reference herein. For a non-PEGylated or PEGylated hEPO polypeptide comprising a non-natural amino acid, the affinity of the hormone for its receptor can be measured by using a BIAcore™ biosensor (Pharmacia). In vivo animal models as well as human clinical trials for testing hEPO activity include those described in, e.g., U.S. Pat. No. 6,696,056; Cotes et al., (1961) Nature 191:1065-1067; U.S. Patent Application Pub. No. 2003/0198691; and Pharm Europa Spec. Issue Erythropoietin BRP Bio 1997(2), which are incorporated by reference herein. Assays for dimerization capability of hEPO polypeptides comprising one or more non-naturally encoded amino acids can be conducted as described in U.S. Pat. No. 6,221,608 which is incorporated by reference herein.

The above compilation of references for assay methodologies is not exhaustive, and those skilled in the art will recognize other assays useful for testing for the desired end result.

XIII. Measurement of Potency, Functional In Vivo Half-Life, and Pharmacokinetic Parameters An important aspect of the invention is the prolonged biological half-life that is obtained by construction of the 4HB polypeptide with or without conjugation of the polypeptide to a water soluble polymer moiety. The rapid decrease of 4HB polypeptide serum concentrations has made it important to evaluate biological responses to treatment with conjugated and non-conjugated 4HB polypeptide and variants thereof. Preferably, the conjugated and non-conjugated 4HB polypeptide and variants thereof of the present invention have prolonged serum half-lives also after i.v. administration, making it possible to measure by, e.g. ELISA method or by a primary screening assay. ELISA or RIA kits from either BioSource International (Camarillo, Calif.) or Diagnostic Systems Laboratories (Webster, Tex.) may be used. Another example of an assay for the measurement of in vivo half-life of IFN or variants thereof is described in Kozlowski et al., BioDrugs 15:419 (2001); Bailon et al., Bioconj. Chem. 12:195 (2001); Youngster et al., Current Pharm. Design 8:2139 (2002); U.S. Pat. Nos. 6,524,570; 6,250,469; 6,180,096; 6,177,074; 6,042,822; 5,981,709; 5,591,974; 5,908,621; 5,738,846, which are incorporated by reference herein. Another example of an assay for the measurement of in vivo half-life of G-CSF or variants thereof is described in U.S. Pat. No. 5,824,778, which is incorporated by reference herein. Measurement of in vivo biological half-life is carried out as described herein.

The potency and functional in vivo half-life of an hGH polypeptide comprising a non-naturally encoded amino acid can be determined according to the protocol described in Clark, R., et al., *J. Biol. Chem.* 271, 36, 21969-21977 (1996). The potency and functional in vivo half-life of a hIFN polypeptide comprising a non-naturally encoded amino acid can be determined according to the protocol described in U.S. Pat. Nos. 5,711,944; 5,382,657, which are incorporated by reference herein. The potency and functional in vivo half-life of a hG-CSF polypeptide comprising a non-naturally encoded amino acid can be determined according to the protocol described in U.S. Pat. Nos. 6,646,110; 6,555,660; 6,166,183; 5,985,265; 5,824,778; 5,773,581, which are incorporated by reference herein. The potency and functional in vivo half-life of a hEPO polypeptide comprising a non-naturally encoded amino acid can be determined according to the protocol described in U.S. Pat. Nos. 6,586,398; 5,583,272; and U.S. Patent application Publication No. 2003/0198691A1, which are incorporated by reference herein.

Pharmacokinetic parameters for a 4HB polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a 4HB polypeptide comprising a non-naturally encoded amino acid not conjugated to a water soluble polymer and about 4 days for a 4HB polypeptide comprising a non-naturally encoded amino acid and conjugated to a water soluble polymer. Pharmacokinetic data for 4HB polypeptides is well-studied in several species and can be compared directly to the data obtained for 4HB polypeptides comprising a non-naturally encoded amino acid. See Mordenti J., et al., *Pharm. Res.* 8(11): 1351-59 (1991) for studies related to hGH.

The specific activity of 4HB polypeptides in accordance with this invention can be determined by various assays known in the art. The biological activity of the purified hG-CSF proteins of this invention are such that administration of the hG-CSF protein by injection to human patients results in bone marrow cells increasing production of white blood cells compared to non-injected or control groups of subjects. The biological activity of the purified hEPO proteins of this invention are such that administration of the hEPO protein by injection to human patients results in bone marrow cells increasing production of reticulocytes and red blood cells compared to non-injected or control groups of subjects. The biological activity of the hEPO muteins, or fragments thereof, obtained and purified in accordance with this invention can be tested by methods according to Pharm. Europa Spec. Issue Erythropoietin BRP Bio 1997(2). Another biological assay for determining the activity of hEPO is the normocythaemic mouse assay (Pharm. Europa Spec. Issue Erythropoietin BRP Bio 1997(2)). The biological activity of the 4HB polypeptide muteins, or fragments thereof, obtained and purified in accordance with this invention can be tested by methods described or referenced herein or known to those skilled in the art.

Further examples of assays for the measurement of in vivo biological activity of hG-CSF or variants thereof are described in U.S. Pat. Nos. 5,681,720; 5,795,968; 5,824,778; 5,985,265; and Bowen et al., Experimental Hematology 27:425-432 (1999), each of which is incorporated by reference herein.

XIV. Administration and Pharmaceutical Compositions

The polypeptides or proteins of the invention (including but not limited to, hGH, hIFN, hG-CSF, hEPO, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are well known in the art and can be applied to administration of the polypeptides of the invention.

Therapeutic compositions comprising one or more polypeptide of the invention are optionally tested in one or more appropriate in vitro and/or in vivo animal models of disease, to confirm efficacy, tissue metabolism, and to estimate dosages, according to methods well known in the art. In particular, dosages can be initially determined by activity, stability or other suitable measures of unnatural herein to natural amino acid homologues (including but not limited to, comparison of a 4HB polypeptide modified to include one or more unnatural amino acids to a natural amino acid 4HB polypeptide), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art.

The 4HB polypeptide comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, G-CSF, GM-CSF, IFNs, interleukins, antibodies, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or, including but not limited to, to inhibit infection by a pathogen, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, cancers, inherited diseases, diabetes, AIDS, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acids at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human 4HB polypeptides of the invention can be administered directly to a mammalian subject. Administration is by any of the routes normally used for introducing 4HB polypeptide to a subject. The 4HB polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated. Administration can be either local or systemic. The formulations of compounds can be presented in unit-dose or multi-dose sealed containers, such as ampoules and vials. 4HB polypeptides of the invention can be prepared in a mixture in a unit dosage injectable form (including but not limited to, solution, suspension, or emulsion) with a pharmaceutically acceptable carrier. 4HB polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences*, 17$^{th}$ ed. 1985)).

Suitable carriers include buffers containing phosphate, borate, HEPES, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counter ions such as sodium; and/or nonionic surfactants such as Tween™, Pluronics™, or PEG.

4HB polypeptides of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.,* 15: 167-277 (1981); Langer, *Chem. Tech.,* 12: 98-105 (1982), ethylene vinyl acetate (Langer et al., supra) or poly-D-(−)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (U. Sidman et al., *Biopolymers,* 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Epstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. All references and patents cited are incorporated by reference herein.

Liposomally entrapped 4HB polypeptides can be prepared by methods described in, e.g., DE 3,218,121; Epstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Composition and size of liposomes are well known or able to be readily determined empirically by one skilled in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591(1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the 4HB polypeptide of the present invention administered parenterally per dose is in the range of about 0.01 μg/kg/day to about 100 μg/kg, or about 0.05 mg/kg to about 1 mg/kg, of patient body weight, although this is subject to therapeutic discretion. The frequency of dosing is also subject to therapeutic discretion, and may be more frequent or less frequent than the commercially available 4HB polypeptide products approved for use in humans. Generally, a PEGylated 4HB polypeptide of the invention can be administered by any of the routes of administration described above.

XV. Therapeutic Uses of 4HB Polypeptides of the Invention

The 4HB polypeptides of the invention are useful for treating a wide range of disorders.

The hGH agonist polypeptides of the invention may be useful, for example, for treating growth deficiency, immune disorders, and for stimulating heart function. Individuals with growth deficiencies include, e.g., individuals with Turner's Syndrome, GH-deficient individuals (including children), children who experience a slowing or retardation in their normal growth curve about 2-3 years before their growth plate closes (sometimes known as "short normal children"), and individuals where the insulin-like growth factor-I (IGF-I) response to GH has been blocked chemically (i.e., by glucocorticoid treatment) or by a natural condition such as in adult patients where the IGF-I response to GH is naturally reduced.

An agonist hGH variant may act to stimulate the immune system of a mammal by increasing its immune function, whether the increase is due to antibody mediation or cell mediation, and whether the immune system is endogenous to the host treated with the hGH polypeptide or is transplanted from a donor to the host recipient given the hGH polypeptide (as in bone marrow transplants). "Immune disorders" include any condition in which the immune system of an individual has a reduced antibody or cellular response to antigens than normal, including those individuals with small spleens with reduced immunity due to drug (e.g., chemotherapeutic) treatments. Examples individuals with immune disorders include, e.g., elderly patients, individuals undergoing chemotherapy or radiation therapy, individuals recovering from a major illness, or about to undergo surgery, individuals with AIDS, Patients with congenital and acquired B-cell deficiencies such as hypogammaglobulinemia, common varied agammaglobulinemia, and selective immunoglobulin deficiencies (e.g., IgA deficiency, patients infected with a virus such as rabies with an incubation time shorter than the immune response of the patient; and individuals with hereditary disorders such as diGeorge syndrome.

hGH antagonist polypeptides of the invention may be useful for the treatment of gigantism and acromegaly, diabetes and complications (diabetic retinopathy, diabetic neuropathy) arising from diabetes, vascular eye diseases (e.g., involving proliferative neovascularization), nephropathy, and GH-responsive malignancies.

Vascular eye diseases include, e.g., retinopathy (caused by, e.g., pre-maturity or sickle cell anemia) and macular degeneration.

GH-responsive malignancies include, e.g., Wilm's tumor, sarcomas (e.g., osteogenic sarcoma), breast, colon, prostate, and thyroid cancer, and cancers of tissues that express GH receptor mRNA (i.e., placenta, thymus, brain, salivary gland, prostate, bone marrow, skeletal muscle, trachea, spinal cord, retina, lymph node and from Burkitt's lymphoma, colorectal carcinoma, lung carcinoma, lymphoblastic leukemia, and melanoma).

Average quantities of the hGH may vary and in particular should be based upon the recommendations and prescription of a qualified physician. The exact amount of hGH is a matter of preference subject to such factors as the exact type of condition being treated, the condition of the patient being treated, as well as the other ingredients in the composition.

Administration of the hIFN products of the present invention results in any of the activities demonstrated by commercially available IFN preparations in humans. The pharmaceutical compositions containing the hIFN glycoprotein products may be formulated at a strength effective for administration by various means to a human patient experiencing disorders that may be affected by IFN agonists or antagonists, such as but not limited to, anti-proliferatives, anti-inflammatory, or antivirals are used, either alone or as part of a condition or disease. Average quantities of the hIFN glycoprotein product may vary and in particular should be based upon the recommendations and prescription of a qualified physician. The exact amount of hIFN is a matter of preference subject to such factors as the exact type of condition being treated, the condition of the patient being treated, as well as the other ingredients in the composition. The hIFN of the present invention may thus be used to interrupt or modulate a viral replication cycle, modulate inflammation, or as anti-proliferative agents. Among the conditions treatable by the present invention include HCV, HBV, and other viral infections, tumor cell growth or viability, and multiple sclerosis. The invention also provides for administration of a therapeutically effective amount of another active agent such as an anti-cancer chemotherapeutic agent. The amount to be given may be readily determined by one skilled in the art based upon therapy with hIFN.

Administration of the hG-CSF products of the present invention results in white blood cell formation in humans. The pharmaceutical compositions containing the hG-CSF glycoprotein products may be formulated at a strength effective for administration by various means to a human patient experiencing disorders characterized by low or defective white blood cell production, either alone or as part of a condition or disease. Average quantities of the hG-CSF glycoprotein product may vary and in particular should be based upon the recommendations and prescription of a qualified physician. The exact amount of hG-CSF is a matter of preference subject to such factors as the exact type of condition being treated, the condition of the patient being treated, as well as the other ingredients in the composition. The hG-CSF of the present invention may thus be used to stimulate white blood cell production and correct depressed red cell levels. Most commonly, white cell levels are decreased due to cancer, infection or chemotherapy. Among the conditions treatable by the present invention include neutropenia associated with a bacterial infection, neutropenia associated with myelosuppressive therapy, such as chemotherapeutic or anti-viral drugs (such as AZT), neutropenia associated with the progression of non-myeloid cancers, and anemia associated with viral infections (such as HIV). Also treatable are conditions which may lead to neutropenia in an otherwise healthy individual, such as an anticipated treatment with anti-cancer agents. In general, any condition treatable with hG-CSF may also be treated with the PEG:hG-CSF conjugates of the present invention. The invention also provides for administration of a therapeutically effective amount of another active agent such as an anti-cancer chemotherapeutic agent. The amount to be given may be readily determined by one skilled in the art based upon therapy with hG-CSF.

The hEPO polypeptides of the invention are useful for treating a wide range of disorders. Administration of the hEPO products of the present invention results in red blood cell formation in humans. The pharmaceutical compositions containing the hEPO glycoprotein products may be formulated at a strength effective for administration by various means to a human patient experiencing blood disorders, characterized by low or defective red blood cell production, either alone or as part condition or disease. Average quantities of the hEPO glycoprotein product may vary and in particular should be based upon the recommendations and prescription of a qualified physician. The exact amount of hEPO is a matter of preference subject to such factors as the exact type of condition being treated, the condition of the patient being treated, as well as the other ingredients in the composition. The hEPO of the present invention may thus be used to stimulate red blood cell production and correct depressed red cell levels. Most commonly, red cell levels are decreased due to anemia. Among the conditions treatable by the present invention include anemia associated with a decline or loss of kidney function (chronic renal failure), anemia associated with myelosuppressive therapy, such as chemotherapeutic or antiviral drugs (such as AZT), anemia associated with the progression of non-myeloid cancers, and anemia associated with viral infections (such as HIV). Also treatable are conditions which may lead to anemia in an otherwise healthy individual, such as an anticipated loss of blood during surgery. In general, any condition treatable with hEPO may also be treated with the PEG:hEPO conjugates of the present invention. The invention also provides for administration of a therapeutically effective amount of iron in order to maintain increased erythropoiesis during therapy. The amount to be given may be readily determined by one skilled in the art based upon therapy with hEPO.

EXAMPLES

The following examples are offered to illustrate, but not to limit the claimed invention.

Example 1

This example describes one of the many potential sets of criteria for the selection of preferred sites of incorporation of non-naturally encoded amino acids into hGH.

This example demonstrates how preferred sites within the hGH polypeptide were selected for introduction of a non-naturally encoded amino acid. The crystal structure 3HHR, composed of hGH complexed with two molecules of the extracellular domain of receptor (hGHbp), was used to determine preferred positions into which one or more non-naturally encoded amino acids could be introduced. Other hGH structures (e.g. 1AXI) were utilized to examine potential variation of primary and secondary structural elements between crystal structure datasets. The coordinates for these structures are available from the Protein Data Bank (PDB) (Berstein et al. *J. Mol. Biol.* 1997, 112, pp 535) or via The Research Collaboratory for Structural Bioinformatics PD3 available on the World Wide Web at rcsb.org. The structural model 3HHR contains the entire mature 22 kDa sequence of hGH with the exception of residues 148-153 and the C-terminal F191 residue which were omitted due to disorder in the crystal. Two disulfide bridges are present, formed by C53 and C165 and C182 and C185. Sequence numbering used in this example is according to the amino acid sequence of mature hGH (22 kDa variant) shown in SEQ ID NO:2.

The following criteria were used to evaluate each position of hGH for the introduction of a non-naturally encoded amino acid: the residue (a) should not interfere with binding of either hGHbp based on structural analysis of 3HHR, 1AXI, and 1HWG (crystallographic structures of hGH conjugated with hGHbp monomer or dimer), b) should not be affected by alanine or homolog scanning mutagenesis (Cunningham et al. Science (1989) 244:1081-1085 and Cummingham et al. *Science* (1989) 243:1330-1336), (c) should be surface exposed and exhibit minimal van der Waals or hydrogen bonding interactions with surrounding residues, (d) should be either deleted or variable in hGH variants (e.g. Tyr35, Lys38, Phe92, Lys140), (e) would result in conservative changes upon substitution with a non-naturally encoded amino acid and (f) could be found in either highly flexible regions (including but not limited to CD loop) or structurally rigid regions (including but not limited to Helix B). In addition, further calculations were performed on the hGH molecule, utilizing the Cx program (Pintar et al. *Bioinformatics*, 18, pp 980) to evaluate the extent of protrusion for each protein atom. As a result, in some embodiments, one or more non-naturally encoded encoded amino acids are incorporated at, but not limited to, one or more of the following positions of hGH: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids in SEQ ID NO: 1 or 3).

In some embodiments, one or more non-naturally encoded amino acids are substituted at one or more of the following positions: 29, 30, 33, 34, 35, 37, 39, 40, 49, 57, 59, 66, 69, 70, 71, 74, 88, 91, 92, 94, 95, 98, 99, 101, 103, 107, 108, 111, 122, 126, 129, 130, 131, 133, 134, 135, 136, 137, 139, 140, 141, 142, 143, 145, 147, 154, 155, 156, 159, 183, 186, and 187 (SEQ ID NO: 2 or the corresponding amino acids of SEQ ID NO: 1 or 3).

In some embodiments, one or more non-naturally encoded amino acids are substituted at one or more of the following positions: 29, 33, 35, 37, 39, 49, 57, 69, 70, 71, 74, 88, 91, 92, 94, 95, 98, 99, 101, 103, 107, 108, 111, 129, 130, 131, 133, 134, 135, 136, 137, 139, 140, 141, 142, 143, 145, 147, 154, 155, 156, 186, and 187 (SEQ ID NO: 2 or the corresponding amino acids of SEQ ID NO: 1 or 3).

In some embodiments, one or more non-naturally encoded amino acids are substituted at one or more of the following positions: 35, 88, 91, 92, 94, 95, 99, 101, 103, 111, 131, 133, 134, 135, 136, 139, 140, 143, 145, and 155 (SEQ ID NO: 2 or the corresponding amino acids of SEQ ID NO: 1 or 3).

In some embodiments, one or more non-naturally encoded amino acids are substituted at one or more of the following positions: 30, 74, 103 (SEQ ID NO: 2 or the corresponding amino acids of SEQ ID NO: 1 or 3). In some embodiments, one or more non-naturally encoded amino acids are substituted at one or more of the following positions: 35, 92, 143, 145 (SEQ ID NO: 2 or the corresponding amino acids of SEQ ID NO: 1 or 3).

In some embodiments, the non-naturally occurring amino acid at one or more of these positions is linked to a water soluble polymer, including but not limited to, positions: before position 1 (i.e. at the N-terminus), 1, 2, 3, 4, 5, 8, 9, 11, 12, 15, 16, 19, 22, 29, 30, 32, 33, 34, 35, 36, 37, 38, 39, 40, 41, 42, 43, 44, 45, 46, 47, 48, 49, 52, 55, 57, 59, 65, 66, 69, 70, 71, 74, 88, 91, 92, 94, 95, 97, 98, 99, 100, 101, 102, 103, 104, 105, 106, 107, 108, 109, 111, 112, 113, 115, 116, 119, 120, 122, 123, 126, 127, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 161, 168, 172, 183, 184, 185, 186, 187, 188, 189, 190, 191, 192 (i.e., at the carboxyl terminus of the protein) (SEQ ID NO: 2 or the corresponding amino acids of SEQ ID NO: 1 or 3). In some embodiments, the non-naturally occurring amino acid at one or more of these positions is linked to a water soluble polymer: 30, 35, 74, 92, 103, 143, 145 (SEQ ID NO: 2 or the corresponding amino acids of SEQ ID NO: 1 or 3). In some embodiments, the non-naturally occurring amino acid at one or more of these positions is linked to a water soluble polymer: 35, 92, 143, 145 (SEQ ID NO: 2 or the corresponding amino acids of SEQ ID NO: 1 or 3).

Some sites for generation of an hGH antagonist include: 1, 2, 3, 4, 5, 8, 9, 11, 12, 15, 16, 19, 22, 103, 109, 112, 113, 115, 116, 119, 120, 123, 127, or an addition before position 1, or any combination thereof (SEQ ID NO: 2, or the corresponding amino acid in SEQ ID NO: 1, 3, or any other GH sequence). These sites were chosen utilizing criteria (c)-(e) of the agonist design. The antagonist design may also include site-directed modifications of site I residues to increase binding affinity to hGHbp.

Example 2

This example details cloning and expression of a hGH polypeptide including a non-naturally encoded amino acid in *E. coli*. This example also describes one method to assess the biological activity of modified hGH polypeptides.

Methods for cloning hGH and fragments thereof are detailed in U.S. Pat. Nos. 4,601,980; 4,604,359; 4,634,677; 4,658,021; 4,898,830; 5,424,199; and 5,795,745, which are incorporated by reference herein. cDNA encoding the fall length hGH or the mature form of hGH lacking the N-terminal signal sequence are shown in SEQ ID NO: 21 and SEQ ID NO: 22 respectively.

An introduced translation system that comprises an orthogonal tRNA (O-tRNA) and an orthogonal aminoacyl tRNA synthetase (O—RS) is used to express hGH containing a non-naturally encoded amino acid. The O—RS preferentially aminoacylates the O-tRNA with a non-naturally encoded amino acid. In turn the translation system inserts the non-naturally encoded amino acid into hGH, in response to an encoded selector codon.

TABLE 2

| O-RS and O-tRNA sequences. | | |
|---|---|---|
| SEQ ID NO: 4 | M. jannaschii mtRNA$_{CUA}^{Tyr}$ | tRNA |
| SEQ ID NO: 5 | HLAD03; an optimized amber supressor tRNA | tRNA |
| SEQ ID NO: 6 | HL325A; an optimized AGGA frameshift supressor tRNA | tRNA |
| SEQ ID NO: 7 | Aminoacyl tRNA synthetase for the incorporation of p-azido-L-phenylalanine p-Az-PheRS(6) | RS |
| SEQ ID NO: 8 | Aminoacyl tRNA synthetase for the incorporation of p-benzoyl-L-phenylalanine p-BpaRS(1) | RS |
| SEQ ID NO: 9 | Aminoacyl tRNA synthetase for the incorporation of propargyl-phenylalanine Propargyl-PheRS | RS |
| SEQ ID NO: 10 | Aminoacyl tRNA synthetase for the incorporation of propargyl-phenylalanine Propargyl-PheRS | RS |

TABLE 2-continued

O-RS and O-tRNA sequences.

| SEQ ID NO: 11 | Aminoacyl tRNA synthetase for the incorporation of propargyl-phenylalanine Propargyl-PheRS | RS |
| SEQ ID NO: 12 | Aminoacyl tRNA synthetase for the incorporation of p-azido-phenylalanine p-Az-PheRS(1) | RS |
| SEQ ID NO: 13 | Aminoacyl tRNA synthetase for the incorporation of p-azido-phenylalanine p-Az-PheRS(3) | RS |
| SEQ ID NO: 14 | Aminoacyl tRNA synthetase for the incorporation of p-azido-phenylalanine p-Az-PheRS(4) | RS |
| SEQ ID NO: 15 | Aminoacyl tRNA synthetase for the incorporation of p-azido-phenylalanine p-Az-PheRS(2) | RS |
| SEQ ID NO: 16 | Aminoacyl tRNA synthetase for the incorporation of p-acetyl-phenylalanine (LW1) | RS |
| SEQ ID NO: 17 | Aminoacyl tRNA synthetase for the incorporation of p-acetyl-phenylalanine (LW5) | RS |
| SEQ ID NO: 18 | Aminoacyl tRNA synthetase for the incorporation of p-acetyl-phenylalanine (LW6) | RS |
| SEQ ID NO: 19 | Aminoacyl tRNA synthetase for the incorporation of p-azido-phenylalanine (AzPheRS-5) | RS |
| SEQ ID NO: 20 | Aminoacyl tRNA synthetase for the incorporation of p-azido-phenylalanine (AzPheRS-6) | RS |

The transformation of E. coli with plasmids containing the modified hGH gene and the orthogonal aminoacyl tRNA synthetase/tRNA pair (specific for the desired non-naturally encoded amino acid) allows the site-specific incorporation of non-naturally encoded amino acid into the hGH polypeptide. The transformed E. coli, grown at 37° C. in media containing between 0.01-100 mM of the particular non-naturally encoded amino acid, expresses modified hGH with high fidelity and efficiency. The His-tagged hGH containing a non-naturally encoded amino acid is produced by the E. coli host cells as inclusion bodies or aggregates. The aggregates are solubilized and affinity purified under denaturing conditions in 6M guanidine HCl. Refolding is performed by dialysis at 4° C. overnight in 50 mM TRIS-HCl, pH8.0, 40 µM CuSO$_4$, and 2% (w/v) Sarkosyl. The material is then dialyzed against 20mM TRIS-HCl, pH 8.0, 100 mM NaCl, 2 mM CaCl$_2$, followed by removal of the His-tag. See Boissel et al., (1993) 268:15983-93. Methods for purification of hGH are well known in the art and are confirmed by SDS-PAGE, Western Blot analyses, or electrospray-ionization ion trap mass spectrometry and the like.

Figure 6:
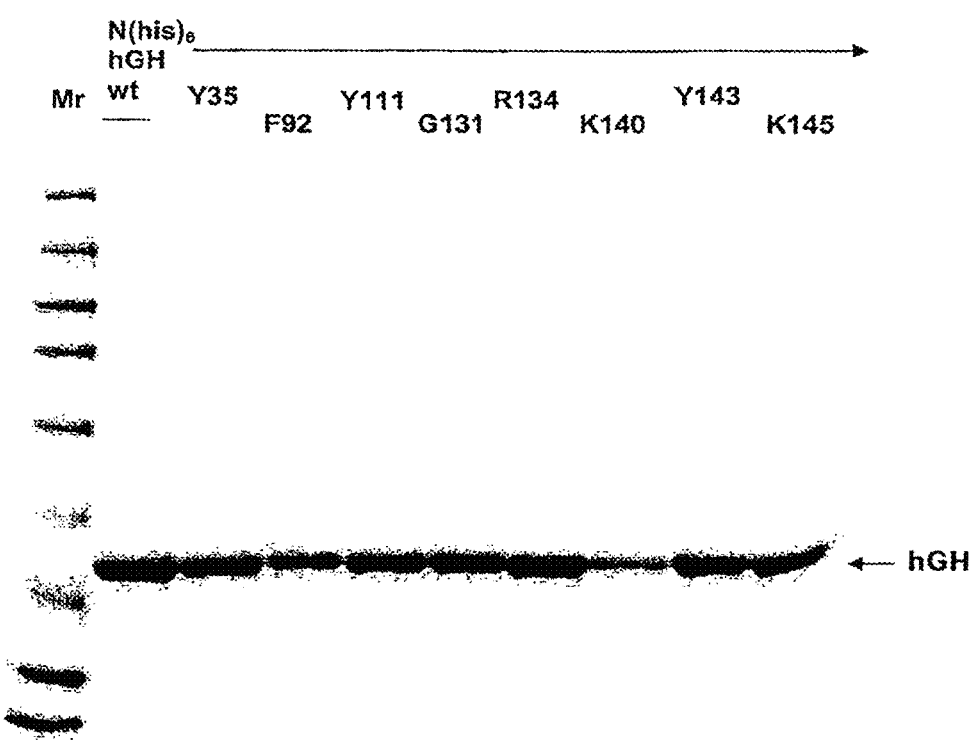
FIG. 6—A Coomassie blue stained SDS-PAGE is shown demonstrating the expression of hGH comprising the non-naturally encoded amino acid p-acetyl phenylalanine at each of the following positions: Y35, F92, Y111, G131, R134, K140, Y143, or K145.

FIG. 6 is an SDS-PAGE of purified hGH polypeptides. The His-tagged mutant hGH proteins were purified using the Pro-Bond Nickel-Chelating Resin (Invitrogen, Carlsbad, Calif.) via the standard His-tagged protein purification procedures provided by the manufacturer, followed by an anion exchange column prior to loading on the gel. Lane 1 shows the molecular weight marker, and lane 2 represents N-His hGH without incorporation of a non-natural amino acid. Lanes 3-10 contain N-His hGH mutants comprising the non-natural amino acid p-acetyl-phenylalanine at each of the positions Y35, F92, Y111, G131, R134, K140, Y143, and K145, respectively.

To further assess the biological activity of modified hGH polypeptides, an assay measuring a downstream marker of hGH's interaction with its receptor was used. The interaction of hGH with its endogenously produced receptor leads to the tyrosine phosphorylation of a signal transducer and activator of transcription family member, STAT5, in the human IM-9 lymphocyte cell line. Two forms of STAT5, STAT5A and STAT5B were identified from an IM-9 cDNA library. See, e.g., Silva et al., Mol. Endocrinol. (1996) 10(5):508-518. The human growth hormone receptor on IM-9 cells is selective for human growth hormone as neither rat growth hormone nor human prolactin resulted in detectable STAT5 phosphorylation. Importantly, rat GHR (L43R) extra cellular domain and the G120R bearing hGH compete effectively against hGH stimulated pSTAT5 phoshorylation.

IM-9 cells were stimulated with hGH polypeptides of the present invention. The human IM-9 lymphocytes were purchased from ATCC (Manassas, Va.) and grown in RPMI 1640 supplemented with sodium pyruvate, penicillin, streptomycin (Invitrogen, Carlsbad, San Diego) and 10% heat inactivated fetal calf serum (Hyclone, Logan, Utah). The IM-9 cells were starved overnight in assay media (phenol-red free RPMI, 10 nM Hepes, 1% heat inactivated charcoal/dextran treated FBS, sodium pyravate, penicillin and streptomycin) before stimulation with a 12-point dose range of hGH polypeptides for 10 min at 37° C. Stimulated cells were fixed with 1% formaldehyde before permeabilization with 90% ice-cold methanol for 1 hour on ice. The level of STAT5 phosphorylation was detected by intra-cellular staining with a primary phospho-STAT5 antibody (Cell Signaling Technology, Beverly, Mass.) at room temperature for 30 min followed by a PE-conjugated secondary antibody. Sample acquisition was performed on the FACS Array with acquired data analyzed on the Flowjo software (Tree Star Inc., Ashland, Oreg.). EC$_{50}$ values were derived from dose response curves plotted with mean fluorescent intensity (MFI) against protein concentration utilizing Sigmaplot.

Table 3 below summarizes the IM-9 data generated with mutant hGH polypeptides. Various hGH polypeptides with a non-natural amino acid substitution at different positions were tested with human IM-9 cells as described. Specifically, FIG. 7, Panel A shows the IM-9 data for a His-tagged hGH polypeptide, and FIG. 7, Panel B shows the IM-9 data for His-tagged hGH comprising the non-natural amino acid p-acetyl-phenylalanine substitution for Y143. The same assay was used to assess biological activity of hGH polypeptides comprising a non-natural amino acid that is PEGylated.

TABLE 3

| GH | EC$_{50}$ (nM) | GH | EC$_{50}$ (nM) |
| --- | --- | --- | --- |
| WHO WT | 0.4 ± 0.1 (n = 8) | N-6His G120R | >200,000 |
| N-6His WT | 0.6 ± 0.3 (n = 3) | N-6His G120pAF | >200,000 |
| rat GH WT | >200,000 | N-6His G131pAF | 0.8 ± 0.5 (n = 3) |
| N-6His Y35pAF | 0.7 ± 0.2 (n = 4) | N-6His P133pAF | 1.0 |
| N-6His E88pAF | 0.9 | N-6HisR134pAF | 0.9 ± 0.3 (n = 4) |
| N-6His Q91pAF | 2.0 ± 0.6 (n = 2) | N-6His T135pAF | 0.9 |
| N-6His F92pAF | 0.8 ± 0.4 (n = 9) | N-6HisG136pAF | 1.4 |
| N-6His R94pAF | 0.7 | N-6His F139pAF | 3.3 |
| N-6His S95pAF | 16.7 ± 1.0 (n = 2) | N-6HisK140pAF | 2.7 ± 0.9 (n = 2) |
| N-6His N99pAF | 8.5 | N-6HisY143pAF | 0.8 ± 0.3 (n = 3) |

TABLE 3-continued

| GH | EC$_{50}$ (nM) | GH | EC$_{50}$ (nM) |
|---|---|---|---|
| N-6His Y103pAF | 130,000 | N-6HisK145pAF | 0.6 ± 0.2 (n = 3) |
| N-6His Y111pAF | 1.0 | N-6HisA155pAF | 1.3 |
| WHO WT | 0.4 ± 0.1 (n = 8) | G120R | >200,000 |
| N-6His WT | 0.6 ± 0.3 (n = 3) | G120pAF | >200,000 |
| rat GH WT | >200,000 | G131pAF | 0.8 ± 0.5 (n = 3) |
| Y35pAF | 0.7 ± 0.2 (n = 4) | P133pAF | 1.0 |
| E88pAF | 0.9 | R134pAF | 0.9 ± 0.3 (n = 4) |
| Q91pAF | 2.0 ± 0.6 (n = 2) | T135pAF | 0.9 |
| F92pAF | 0.8 ± 0.4 (n = 9) | G136pAF | 1.4 |
| R94pAF | 0.7 | F139pAF | 3.3 |
| S95pAF | 16.7 ± 1.0 (n = 2) | K140pAF | 2.7 ± 0.9 (n = 2) |
| N99pAF | 8.5 | Y143pAF | 0.8 ± 0.3 (n = 3) |
| Y103pAF | 130,000 | K145pAF | 0.6 ± 0.2 (n = 3) |
| Y111pAF | 1.0 | A155pAF | 1.3 |

Example 3

This example details introduction of a carbonyl-containing amino acid and subsequent reaction with an aminooxy-containing PEG.

This Example demonstrates a method for the generation of a 4HB polypeptide that incorporates a ketone-containing non-naturally encoded amino acid that is subsequently reacted with an aminooxy-containing PEG of approximately 5,000 MW. Each of the residues 35, 88, 91, 92, 94, 95, 99, 101, 103, 111, 120, 131, 133, 134, 135, 136, 139, 140, 143, 145, and 155 identified according to the criteria of Example 1 (hGH), the residues identified according to the criteria of Example 32 (hIFN), each of the residues 59, 63, 67, 130, 131, 132, 134, 137, 160, 163, 167, and 171 identified according to the criteria of Example 36 (hG-CSF), or each of the residues 21, 24, 38, 83, 85, 86, 89, 116, 119, 121, 124, 125, 126, 127, and 128 identified according to the criteria of Example 40 (hEPO) is separately substituted with a non-naturally encoded amino acid having the following structure:

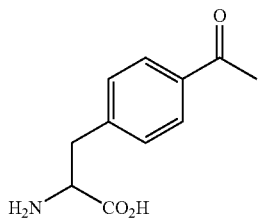

The sequences utilized for site-specific incorporation of p-acetyl-phenylalamine into hGH are SEQ ID NO: 2 (hGH), and SEQ ID NO: 4 (muttRNA, *M. jannaschii* mtRNA$_{CUE}^{Tyr}$), and 16, 17 or 18 (TyrRS LW1, 5, or 6) described in Example 2 above. The sequences utilized for site-specific incorporation of p-acetyl-phenylalanine into hIFN are SEQ ID NO: 24 (hIFN), and SEQ ID NO: 4 (muttRNA), and 16, 17 or 18 (TyrRS LW1, 5, or 6) described in Example 2 above. The sequences utilized for site-specific incorporation of p-acetyl-phenylalanine into hG-CSF are SEQ ID NO: 29 (hG-CSF), and SEQ ID NO: 4 (muttRNA), and 16, 17 or 18 (TyrRS LW1, 5, or 6) described in Example 2 above. The sequences utilized for site-specific incorporation of p-acetyl-phenylalanine into hEPO are SEQ ID NO: 38 (hEPO), and SEQ ID NO: 4 (muttRNA), and 16, 17 or 18 (TyrRS LW1, 5, or 6) described in Example 2 above.

Once modified, the 4HB polypeptide variant comprising the carbonyl-containing amino acid is reacted with an aminooxy-containing PEG derivative of the form:

$$R\text{-PEG(N)}\text{—}O\text{—}(CH_2)_n\text{—}O\text{—}NH_2$$

where R is methyl, n is 3 and N is approximately 5,000 MW. The purified 4HB containing p-acetylphenylalanine dissolved at 10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 10 to 100-fold excess of aminooxy-containing PEG, and then stirred for 10-16 hours at room temperature (Jencks, W. *J. Am. Chem. Soc.* 1959, 81, pp 475). The PEG-4HB is then diluted into appropriate buffer for immediate purification and analysis.

Example 4

Conjugation with a PEG consisting of a hydroxylamine group linked to the PEG via an amide linkage.

A PEG reagent having the following structure is coupled to a ketone-containing non-naturally encoded amino acid using the procedure described in Example 3:

$$R\text{-PEG(N)}\text{—}O\text{—}(CH_2)_2\text{—}NH\text{—}C(O)(CH_2)_n\text{—}O\text{—}NH_2$$

where R=methyl, n=4 and N is approximately 20,000 MW. The reaction, purification, and analysis conditions are as described in Example 3.

Example 5

This example details the introduction of two distinct non-naturally encoded amino acids into 4HB polypeptides.

This example demonstrates a method for the generation of a hGH polypeptide that incorporates non-naturally encoded amino acid comprising a ketone functionality at two positions among the following residues: E30, E74, Y103, K38, K41, K140, and K145. The hGH polypeptide is prepared as described in Examples 1 and 2, except that the suppressor codon is introduced at two distinct sites within the nucleic acid.

This example demonstrates a method for the generation of a hIFN polypeptide that incorporates non-naturally encoded amino acid comprising a ketone functionality at two positions among the residues identified according to Example 32, wherein X* represents a non-naturally encoded amino acid. The hIFN polypeptide is prepared as described in Examples 32 and 33, except that the suppressor codon is introduced at two distinct sites within the nucleic acid.

This example demonstrates a method for the generation of a hG-CSF polypeptide that incorporates non-naturally encoded amino acid comprising a ketone functionality at two positions among the following residues: W59X* and T134X*; L131X* and S67X*; S67X* and Q91X*; T134X* and Ser77X* (as in SEQ ID NO: 29, or the corresponding amino acids in SEQ ID NO: 28, 30, 35, or 36) wherein X* represents a non-naturally encoded amino acid. The hG-CSF polypeptide is prepared as described in Examples 36 and 37, except that the suppressor codon is introduced at two distinct sites within the nucleic acid.

This example demonstrates a method for the generation of a hEPO polypeptide that incorporates non-naturally encoded amino acid comprising a ketone functionality at two positions among the following residues: N24X* and G113X*; N38X* and Q115X*; N36X* and S85X*; N36X* and A125X*;

N36X* and A128X*; Q86X* and S126X* wherein X* represents a non-naturally encoded amino acid. The hEPO polypeptide is prepared as described in Examples 40 and 41, except that the suppressor codon is introduced at two distinct sites within the nucleic acid.

Example 6

This example details conjugation of 4HB polypeptide to a hydrazide-containing PEG and subsequent in situ reduction.

A 4HB polypeptide incorporating a carbonyl-containing amino acid is prepared according to the procedure described in Examples 2 and 3, Examples 33 and 3, Examples 37 and 3, and Examples 41 and 3. Once modified, a hydrazide-containing PEG having the following structure is conjugated to the 4HB polypeptide:

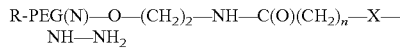

where R=methyl, n=2 and N=10,000 MW and X is a carbonyl (C=O) group. The purified 4HB containing p-acetylphenylalanine is dissolved at between 0.1-10 mg/mL in 25 mM MES (Sigma Chemical, St. Louis, Mo.) pH 6.0, 25 mM Hepes (Sigma Chemical, St. Louis, Mo.) pH 7.0, or in 10 mM Sodium Acetate (Sigma Chemical, St. Louis, Mo.) pH 4.5, is reacted with a 1 to 100-fold excess of hydrazide-containing PEG, and the corresponding hydrazone is reduced in situ by addition of stock 1M NaCNBH$_3$ (Sigma Chemical, St. Louis, Mo.), dissolved in H$_2$O, to a final concentration of 10-50 mM. Reactions are carried out in the dark at 4° C. to RT for 18-24 hours. Reactions are stopped by addition of 1 M Tris (Sigma Chemical, St. Louis, Mo.) at about pH 7.6 to a final Tris concentration of 50 mM or diluted into appropriate buffer for immediate purification.

Example 7

This example details introduction of an alkyne-containing amino acid into a 4HB polypeptide and derivatization with mPEG-azide.

The following residues, 35, 88, 91, 92, 94, 95, 99, 101, 131, 133, 134, 135, 136, 140, 143, 145, and 155, are each substituted with the following non-naturally encoded amino acid (hGH; SEQ ID NO: 2):

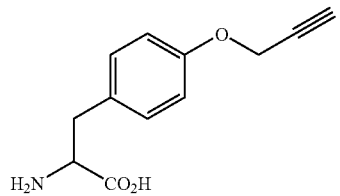 [SMILES: C#CCOc1ccc(CC(N)C(=O)O)cc1]

The sequences utilized for site-specific incorporation of p-propargyl-tyrosine into hGH are SEQ ID NO: 2 (hGH), SEQ ID NO: 4 (muttRNA, *M. jannaschii* mtRNA$_{CUA}^{Try}$), and 9, or 11 described in Example 2 above. Any of the residues of hIFN identified according to Example 32 are substituted with this non-naturally encoded amino acid. The sequences utilized for site-specific incorporation of p-propargyl-tyrosine into hIFN are SEQ ID NO: 24 (hIFN), SEQ ID NO: 4 (muttRNA, *M. jannaschii* mtRNA$_{CUA}^{Try}$), and 9, 10 or 11 described in Example 2 above. The following residues of hG-CSF, 59, 63, 67, 130, 131, 132, 134, 137, 160, 163, 167, and 171 are each substituted with this non-naturally encoded amino acid. The sequences utilized for site-specific incorporation of p-propargyl-tyrosine into hG-CSF are SEQ ID NO: 29 (hG-CSF), SEQ ID NO: 4 (muttRNA, *M. jannaschii* mtRNA$_{CUA}^{Try}$), and 9, 10 or 11 described in Example 2 above. The following residues of hEPO, 21, 24, 38, 83, 85, 86, 89, 116, 119, 121, 124, 125, 126, 127, and 128, are each substituted with this non-naturally encoded amino acid. The sequences utilized for site-specific incorporation of p-propargyl-tyrosine into hEPO are SEQ ID NO: 38 (hEPO), SEQ ID NO: 4 (muttRNA, *M. jannaschii* mtRNA$_{CUA}^{Try}$), and 9, 10 or 11 described in Example 2 above. The 4HB polypeptide containing the propargyl tyrosine is expressed in *E. coli* and purified using the conditions described in Example 3.

The purified 4HB containing propargyl-tyrosine dissolved at between 0.1-10 mg/mL in PB buffer (100 mM sodium phosphate, 0.15 M NaCl, pH=8) and a 10 to 1000-fold excess of an azide-containing PEG is added to the reaction mixture. A catalytic amount of CuSO$_4$ and Cu wire are then added to the reaction mixture. After the mixture is incubated (including but not limited to, about 4 hours at room temperature or 37° C., or overnight at 4° C.), H$_2$O is added and the mixture is filtered through a dialysis membrane. The sample can be analyzed for the addition, including but not limited to, by similar procedures described in Example 3.

In this Example, the PEG will have the following structure:

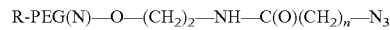

where R is methyl, n is 4 and N is 10,000 MW.

Example 8

This example details substitution of a large, hydrophobic amino acid in a 4HB polypeptide with propargyl tyrosine.

A Phe, Trp or Tyr residue present within one the following regions of hGH: 1-5 (N-terminus), 6-33 (A helix), 34-74 (region between A helix and 13 helix, the A-B loop), 75-96 (B helix), 97-105 (region between B helix and C helix, the B-C loop), 106-129 (C helix), 130-153 (region between C helix and D helix, the C-D loop), 154-183 (D helix), 184-191 (C-terminus) (SEQ ID NO: 2), is substituted with the following non-naturally encoded amino acid as described in Example 7. Similarly, a Phe, Trp or Tyr residue present within one the following regions of hIFN: 1-9 (N-terminus), 10-21 (A helix), 22-39 (region between A helix and B helix), 40-75 (B helix), 76-77 (region between B helix and C helix), 78-100 (C helix), 101-110 (region between C helix and D helix), 111-132 (D helix), 133-136 (region between D and E helix), 137-155 (E helix), 156-165 (C-terminus), (as in SEQ ID NO: 24 or the corresponding amino acids of other IFN polypeptides), is substituted with the following non-naturally encoded amino acid as described in Example 7. Also, a Phe, Trp or Tyr residue present within one the following regions of hG-CSF: 1-10 (N-terminus), 11-39 (A helix), 40-70 (region between A helix and B helix), 71-91 (B helix), 92-99 (region between B helix and C helix), 100-123 (C helix), 124-142 (region between C helix and D helix), 143-172 (D helix), 173-175 (C-terminus), including the short helical segment, the mini-E Helix, at 44-53 between the A Helix and B Helix composed of a 3$_{10}$ helix (44-47) and a α helix (48-53), (as in SEQ ID NO: 29, and the corresponding amino acids of SEQ ID NO: 28 or 30 without the N-terminal 30 amino acids which are the secretion signal sequence, 35, or 36), is substituted with the following non-naturally encoded amino acid as described in Example 7. A Phe, Trp or Tyr residue present within one the following regions of hEPO: 1-7 (N-terminus), 8-26 (A helix), 27-54 (AB loop, containing beta sheet 1 (39-41) and mini B' helix (47-52)), 55-83 (B helix), 84-89 (BC loop), 90-112 (C helix), 113-137 (CD loop, containing mini C' helix (114-121) and beta sheet 2 (133-135)), 138-161 (D helix), 162-166 (C-terminus) is substituted with the following non-naturally encoded amino acid as described in Example 7:

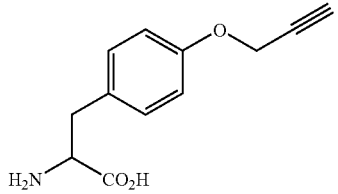 [SMILES: C#CCOc1ccc(CC(N)C(=O)O)cc1]

Once modified, a PEG is attached to the 4HB polypeptide variant comprising the alkyne-containing amino acid. The PEG will have the following structure:

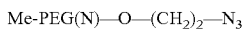

and coupling procedures would follow those in Example 7. This will generate a 4HB polypeptide variant comprising a non-naturally encoded amino acid that is approximately isosteric with one of the naturally-occurring, large hydrophobic amino acids and which is modified with a PEG derivative at a distinct site within the polypeptide.

Example 9

This example details generation of a 4HB polypeptide homodimer, heterodimer, homomultimer, or heteromultimer separated by one or more PEG linkers.

The alkyne-containing 4HB polypeptide variant produced in Example 7 is reacted with a bifunctional PEG derivative of the form:

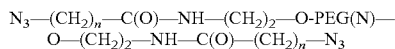

where n is 4 and the PEG has an average MW of approximately 5,000, to generate the corresponding 4HB polypeptide homodimer where the two 4HB molecules are physically separated by PEG. In an analogous manner a 4HB polypeptide may be coupled to one or more other polypeptides to form heterodimers, homomultimers, or heteromultimers. Coupling, purification, and analyses will be performed as in Examples 7 and 3.

Example 10

This example details coupling of a saccharide moiety to a 4HB polypeptide.

One residue of the following is substituted with the non-natural encoded amino acid below: 29, 30, 33, 34, 35, 37, 39, 40, 49, 57, 59, 66, 69, 70, 71, 74, 88, 91, 92, 94, 95, 98, 99, 101, 103, 107, 108, 111, 122, 126, 129, 130, 131, 133, 134, 135, 136, 137, 139, 140, 141, 142, 143, 145, 147, 154, 155, 156, 159, 183, 186, and 187 (hGH, SEQ ID NO: 2) as described in Example 3. Similarly, one residue of the following is substituted with the non-natural encoded amino acid below: 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165 (as in SEQ ED NO: 24, or the corresponding amino acids of other IFN polypeptides). One residue of the following is substituted with the non-natural encoded amino acid below: 30, 31, 33, 58, 59, 61, 63, 64, 66, 67, 68, 77, 78, 81, 87, 88, 91, 95, 101, 102, 103, 130, 131, 132, 134, 135, 136, 137, 156, 157, 159, 160, 163, 164, 167, 170, and 171 (as in SEQ ID NO: 29, or the corresponding amino acids in SEQ ID NO: 28, 30, 35, 36, or other G-CSF polypeptides), as described in Example 3. One residue of the following is substituted with the non-natural encoded amino acid below: 21, 24, 28, 30, 31, 36, 37, 38, 55, 72, 83, 85, 86, 87, 89, 113, 116, 119, 120, 121, 123, 124, 125, 126, 127, 128, 129, 130, 162, 163, 164, 165, 166 (as in SEQ ID NO: 38, or the corresponding amino acids of other EPO polypeptides) as described in Example 3.

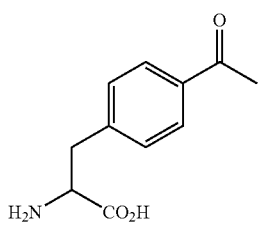

Once modified, the 4HB polypeptide variant comprising the carbonyl-containing amino acid is reacted with a β-linked aminooxy analogue of N-acetylglucosamine (GlcNAc). The 4HB polypeptide variant (10 mg/mL) and the aminooxy saccharide (21 mM) are mixed in aqueous 100 mM sodium acetate buffer (pH 5.5) and incubated at 37° C. for 7 to 26 hours. A second saccharide is coupled to the first enzymatically by incubating the saccharide-conjugated 4HB polypeptide (5 mg/mL) with UDP-galactose (16 nM) and P-1,4-galacytosyltransferase (0.4 units/mL) in 150 mM HEPES buffer (pH 7.4) for 48 hours at ambient temperature (Schanbacher et al. *J. Biol. Chem.* 1970, 245, 5057-5061).

Example 11

This example details generation of a PEGylated 4HB polypeptide antagonist.

One of the following residues, 1, 2, 3, 4, 5, 8, 9, 11, 12, 15, 16, 19, 22, 103, 109, 112, 113, 115, 116, 119, 120, 123, or 127 (hGH, SEQ ID NO: 2 or the corresponding amino acids in SEQ ID NO: 1 or 3), is substituted with the following non-naturally encoded amino acid as described in Example 3. One of the following residues, 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165, (hIFN; SEQ ID NO: 24 or the corresponding amino acids in SEQ ID NO: 23 or 25) is substituted with the following non-naturally encoded amino acid as described in Example 3; a hIFN polypeptide comprising one of these substitutions may potentially act as a weak antagonist or weak agonist depending on the site selected and the desired activity. One of the following residues, 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, (HEFN; SEQ ID NO: 24 or the corresponding amino acids in SEQ ID NO: 23 or 25) is substituted with the following non-naturally encoded amino acid as described in Example 3. One of the following residues, 6, 7, 8, 9, 10, 11, 12, 13, 16, 17, 19, 20, 21, 23, 24, 28, 30, 41, 47, 49, 50, 70, 71, 105, 106, 109, 110, 112, 113, 116, 117, 120, 121, 123, 124, 125, 127, 145, (hG-CSF; SEQ ID NO: 29, or the corresponding amino acids in SEQ ID NO: 28, 30, 35, or 36) is substituted with the following non-naturally encoded amino acid as described in Example 3. One of the following residues, 2, 3, 5, 8, 9, 10, 11, 14, 15, 16, 17, 18, 20, 23, 43, 44, 45, 46, 47, 48, 49, 50, 52, 75, 78, 93, 96, 97, 99, 100, 103, 104, 107, 108, 110, 131, 132, 133, 140, 143, 144, 146, 147, 150, 154, 155, 159 (hEPO; SEQ ID NO: 38, or corresponding amino acids in SEQ ID NO: 37 or 39) is substituted with the following non-naturally encoded amino acid as described in Example 3.

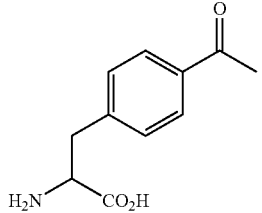

Once modified, the 4HB polypeptide variant comprising the carbonyl-containing amino acid will be reacted with an aminooxy-containing PEG derivative of the form:

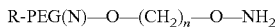

where R is methyl, n is 4 and N is 20,000 MW to generate a 4HB polypeptide antagonist comprising a non-naturally encoded amino acid that is modified with a PEG derivative at a single site within the polypeptide. Coupling, purification, and analyses are performed as in Example 3.

Example 12

Generation of a 4HB Polypeptide Homodimer, Heterodimer, Homomultimer, or Heteromultimer in which the 4HB Molecules are Linked Directly A 4HB polypeptide variant comprising the alkyne-containing amino acid can be directly coupled to another 4HB polypeptide variant comprising the azido-containing amino acid, each of which comprise non-naturally encoded amino acid substitutions at the sites described in, but not limited to, Example 10. This will generate the corresponding 4HB polypeptide homodimer where the two 4HB polypeptide variants are physically joined at the site II binding interface. In an analogous manner a 4HB polypeptide polypeptide may be coupled to one or more other polypeptides to form heterodimers, homomultimers, or heteromultimers. Coupling, purification, and analyses are performed as in Examples 3, 6, and 7.

Example 13

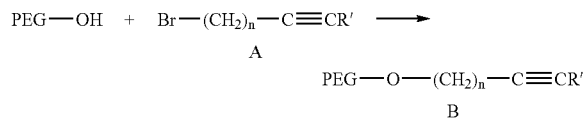

The polyalkylene glycol (P—OH) is reacted with the allyl halide (A) to form the ether (B). In these compounds, n is an integer from one to nine and R' can be a straight- or branched-chain, saturated or unsaturated C1, to C20 alkyl or heteroalkyl group. R' can also be a C3 to C7 saturated or unsaturated cyclic alkyl or cyclic heteroalkyl, a substituted or unsubstituted aryl or heteroaryl group, or a substituted or unsubstituted alkaryl (the alkyl is a C1 to C20 saturated or unsaturated alkyl) or heteroalkaryl group. Typically, PEG-OH is polyethylene glycol (PEG) or monomethoxy polyethylene glycol (mPEG) having a molecular weight of 800 to 40,000 Daltons (Da).

Example 14

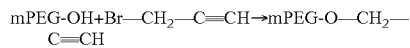

mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). A solution of propargyl bromide, dissolved as an 80% weight solution in xylene (0.56 mL, 5 mmol, 50 equiv., Aldrich), and a catalytic amount of KI were then added to the solution and the resulting mixture was heated to reflux for 2 hours. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford propargyl-O-PEG.

Example 15

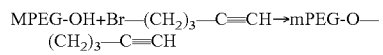

The mPEG-OH with a molecular weight of 20,000 Da (mPEG-OH 20 kDa; 2.0 g, 0.1 mmol, Sunbio) was treated with NaH (12 mg, 0.5 mmol) in THF (35 mL). Fifty equivalents of 5-bromo-1-pentyne (0.53 mL, 5 mmol, Aldrich) and a catalytic amount of KI were then added to the mixture. The resulting mixture was heated to reflux for 16 hours. Water (1 mL) was then added and the solvent was removed under vacuum. To the residue was added $CH_2Cl_2$ (25 mL) and the organic layer was separated, dried over anhydrous $Na_2SO_4$, and the volume was reduced to approximately 2 mL. This $CH_2Cl_2$ solution was added to diethyl ether (150 mL) drop-wise. The resulting precipitate was collected, washed with several portions of cold diethyl ether, and dried to afford the corresponding alkyne. 5-chloro-1-pentyne may be used in a similar reaction.

Example 16

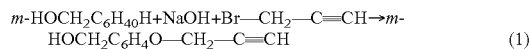 (1)

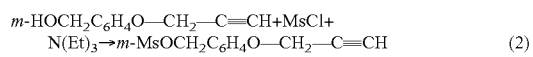 (2)

 (3)

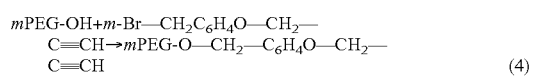 (4)

To a solution of 3-hydroxybenzylalcohol (2.4 g, 20 mmol) in THF (50 mL) and water (2.5 mL) was first added powdered sodium hydroxide (1.5 g, 37.5 mmol) and then a solution of propargyl bromide, dissolved as an 80% weight solution in xylene (3.36 mL, 30 mmol). The reaction mixture was heated at reflux for 6 hours. To the mixture was added 10% citric acid (2.5 mL) and the solvent was removed under vacuum. The residue was extracted with ethyl acetate (3×15 mL) and the combined organic layers were washed with saturated NaCl solution (10 mL), dried over MgSO$_4$ and concentrated to give the 3-propargyloxybenzyl alcohol.

Methanesulfonyl chloride (2.5 g, 15.7 mmol) and triethylamine (2.8 mL, 20 mmol) were added to a solution of compound 3 (2.0 g, 11.0 mmol) in CH$_2$Cl$_2$ at 0° C. and the reaction was placed in the refrigerator for 16 hours. A usual work-up afforded the mesylate as a pale yellow oil. This oil (2.4 g, 9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous Na$_2$SO$_4$, and concentrated to give the desired bromide.

mPEG-OH 20 kDa (1.0 g, 0.05 mmol, Sunbio) was dissolved in THF (20 mL) and the solution was cooled in an ice bath. NaH (6 mg, 0.25 mmol) was added with vigorous stirring over a period of several minutes followed by addition of the bromide obtained from above (2.55 g, 11.4 mmol) and a catalytic amount of KI. The cooling bath was removed and the resulting mixture was heated to reflux for 12 hours. Water (1.0 mL) was added to the mixture and the solvent was removed under vacuum. To the residue was added CH$_2$Cl$_2$ (25 mL) and the organic layer was separated, dried over anhydrous Na$_2$SO$_4$, and the volume was reduced to approximately 2 mL. Dropwise addition to an ether solution (150 mL) resulted in a white precipitate, which was collected to yield the PEG derivative.

Example 17

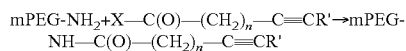

mPEG-NH$_2$+X—C(O)—(CH$_2$)$_n$—C≡CR'→mPEG-NH—C(O)—(CH$_2$)$_n$—C≡CR'

The terminal alkyne-containing poly(ethylene glycol) polymers can also be obtained by coupling a poly(ethylene glycol) polymer containing a terminal functional group to a reactive molecule containing the alkyne functionality as shown above. n is between 1 and 10. R' can be H or a small alkyl group from C1 to C4.

Example 18

HO$_2$C—(CH$_2$)$_2$—C≡CH+NHS+DCC→NHSO—C(O)—(CH$_2$)$_2$—C≡CH (1)

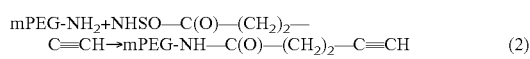

mPEG-NH$_2$+NHSO—C(O)—(CH$_2$)$_2$—C≡CH→mPEG-NH—C(O)—(CH$_2$)$_2$—C≡CH (2)

4-pentynoic acid (2.943 g, 3.0 mmol) was dissolved in CH$_2$Cl$_2$ (25 mL). N-hydroxysuccinimide (3.80 g, 3.3 mmol) and DCC (4.66 g, 3.0 mmol) were added and the solution was stirred overnight at room temperature. The resulting crude NHS ester 7 was used in the following reaction without further purification.

mPEG-NH$_2$ with a molecular weight of 5,000 Da (mPEG-NH$_2$, 1 g, Sunbio) was dissolved in THF (50 mL) and the mixture was cooled to 4° C. NHS ester 7 (400 mg, 0.4 mmol) was added portion-wise with vigorous stirring. The mixture was allowed to stir for 3 hours while warming to room temperature. Water (2 mL) was then added and the solvent was removed under vacuum. To the residue was added CH$_2$Cl$_2$ (50 mL) and the organic layer was separated, dried over anhydrous Na$_2$SO$_4$, and the volume was reduced to approximately 2 mL. This CH$_2$Cl$_2$ solution was added to ether (150 mL) drop-wise. The resulting precipitate was collected and dried in vacuo.

Example 19

This Example represents the preparation of the methane sulfonyl ester of poly(ethylene glycol), which can also be referred to as the methanesulfonate or mesylate of poly(ethylene glycol). The corresponding tosylate and the halides can be prepared by similar procedures.

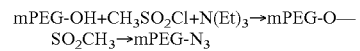

mPEG-OH+CH$_3$SO$_2$Cl+N(Et)$_3$→mPEG-O—SO$_2$CH$_3$→mPEG-N$_3$

The mPEG-OH (MW=3,400, 25 g, 10 mmol) in 150 mL of toluene was azeotropically distilled for 2 hours under nitrogen and the solution was cooled to room temperature. 40 mL of dry CH$_2$Cl$_2$ and 2.1 mL of dry triethylamine (15 mmol) were added to the solution. The solution was cooled in an ice bath and 1.2 mL of distilled methanesulfonyl chloride (15 mmol) was added dropwise. The solution was stirred at room temperature under nitrogen overnight, and the reaction was quenched by adding 2 mL of absolute ethanol. The mixture was evaporated under vacuum to remove solvents, primarily those other than toluene, filtered, concentrated again under vacuum, and then precipitated into 100 mL of diethyl ether. The filtrate was washed with several portions of cold diethyl ether and dried in vacuo to afford the mesylate.

The mesylate (20 g, 8 mmol) was dissolved in 75 ml of THF and the solution was cooled to 4° C. To the cooled solution was added sodium azide (1.56 g, 24 mmol). The reaction was heated to reflux under nitrogen for 2 hours. The solvents were then evaporated and the residue diluted with CH$_2$Cl$_2$ (50 mL). The organic fraction was washed with NaCl solution and dried over anhydrous MgSO$_4$. The volume was reduced to 20 ml and the product was precipitated by addition to 150 ml of cold dry ether.

Example 20

N$_3$—C$_6$H$_4$—CO$_2$H→N$_3$—C$_6$H$_4$CH$_2$OH (1)

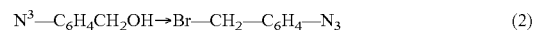

N$^3$—C$_6$H$_4$CH$_2$OH→Br—CH$_2$—C$_6$H$_4$—N$_3$ (2)

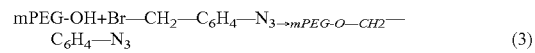

mPEG-OH+Br—CH$_2$—C$_6$H$_4$—N$_3$→mPEG-O—CH2—C$_6$H$_4$—N$_3$ (3)

4-azidobenzyl alcohol can be produced using the method described in U.S. Pat. No. 5,998,595, which is incorporated by reference herein. Methanesulfonyl chloride (2.5 g, 15.7 mmol) and triethylamine (2.8 mL, 20 mmol) were added to a solution of 4-azidobenzyl alcohol (1.75 g, 11.0 mmol) in CH$_2$Cl$_2$ at 0° C. and the reaction was placed in the refrigerator for 16 hours. A usual work-up afforded the mesylate as a pale yellow oil. This oil (9.2 mmol) was dissolved in THF (20 mL) and LiBr (2.0 g, 23.0 mmol) was added. The reaction mixture was heated to reflux for 1 hour and was then cooled to room temperature. To the mixture was added water (2.5 mL) and the solvent was removed under vacuum. The residue was extracted with ethyl acetate (3×15 mL) and the combined organic layers were washed with saturated NaCl solution (10 mL), dried over anhydrous Na$_2$SO$_4$, and concentrated to give the desired bromide.

mPEG-OH 20 kDa (2.0 g, 0.1 mmol, Sunbio) was treated with NaH (12 mg, 0.5 mmol) in THF (35 mL) and the bromide (3.32 g, 15 mmol) was added to the mixture along with a catalytic amount of KI. The resulting mixture was heated to reflux for 12 hours. Water (1.0 mL) was added to the mixture and the solvent was removed under vacuum. To the residue was added $CH_2Cl_2$ (25 mL) and the organic layer was separated, dried over anhydrous $Na_2SO_4$, and the volume was reduced to approximately 2 mL. Dropwise addition to an ether solution (150 mL) resulted in a precipitate, which was collected to yield mPEG-O—$CH_2$—$C_6H_4$—$N_3$.

Example 21

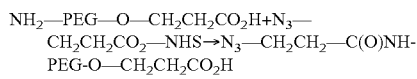

$NH_2$—PEG-O—$CH_2CH_2CO_2H$ (MW 3,400 Da, 2.0 g) was dissolved in a saturated aqueous solution of $NaHCO_3$ (10 mL) and the solution was cooled to 0° C. 3-azido-1-N-hydroxysuccinimido propionate (5 equiv.) was added with vigorous stirring. After 3 hours, 20 mL of $H_2O$ was added and the mixture was stirred for an additional 45 minutes at room temperature. The pH was adjusted to 3 with 0.5 $NH_2SO_4$ and NaCl was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the omega-carboxy-azide PEG derivative.

Example 22

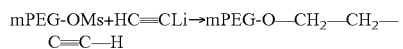

To a solution of lithium acetylide (4 equiv.), prepared as known in the art and cooled to −78° C. in THF, is added dropwise a solution of mPEG-OMs dissolved in THF with vigorous stirring. After 3 hours, the reaction is permitted to warm to room temperature and quenched with the addition of 1 mL of butanol. 20 mL of $H_2O$ is then added and the mixture was stirred for an additional 45 minutes at room temperature. The pH was adjusted to 3 with 0.5 N $H_2SO_4$ and NaCl, was added to a concentration of approximately 15 wt %. The reaction mixture was extracted with $CH_2Cl_2$ (100 mL×3), dried over $Na_2SO_4$ and concentrated. After precipitation with cold diethyl ether, the product was collected by filtration and dried under vacuum to yield the 1-(but-3-ynyloxy)-methoxypolyethylene glycol (in PEG).

Example 23

The azide- and acetylene-containing amino acids were incorporated site-selectively into proteins using the methods described in L. Wang, et al., (2001), *Science* 292:498-500, J. W. Chin et al., *Science* 301:964-7 (2003)), J. W. Chin et al., (2002), *Journal of the American Chemical Society* 124:9026-9027; J. W. Chin, & P. G. Schultz, (2002), *Chem Bio Chem* 11:1135-1137; J. W. Chin, et al., (2002), *PNAS United States of America* 99:11020-11024: and, L. Wang, & P. G. Schultz, (2002), *Chem. Comm.*, 1-10. Once the amino acids were incorporated, the cycloaddition reaction was carried out with 0.01 mM protein in phosphate buffer (PB), pH 8, in the presence of 2 mM PEG derivative, 1 mM $CuSO_4$, and ~1 mg Cu-wire for 4 hours at 37° C.

Example 24

This example describes the synthesis of p-Acetyl-D,L-phenylalanine (pAF) and m-PEG-hydroxylamine derivatives.

The racemic pAF was synthesized using the previously described procedure in Zhang, Z., Smith, B. A. C., Wang, L., Brock, A., Cho, C. & Schultz, P. G., Biochemistry, (2003) 42, 6735-6746.

To synthesize the m-PEG-hydroxylamine derivative, the following procedures were completed. To a solution of (N-t-Boc-aminooxy)acetic acid (0.382 g, 2.0 mmol) and 1,3-Diisopropylcarbodiimide (0.16 mL, 1.0 mmol) in dichloromethane (DCM, 70 mL), which was stirred at room temperature (RT) for 1 hour, methoxy-polyethylene glycol amine (m-PEG-$NH_2$, 7.5 g, 0.25 mmol, Mt. 30 K, from Bio-Vectra) and Diisopropylethylamine (0.1 mL, 0.5 mmol) were added. The reaction was stirred at RT for 48 hours, and then was concentrated to about 100 mL. The mixture was added dropwise to cold ether (800 mL). The t-Boc-protected product precipitated out and was collected by filtering, washed by ether 3×100 mL. It was further purified by re-dissolving in DCM (100 mL) and precipitating in ether (800 mL) twice. The product was dried in vacuum yielding 7.2 g (96%), confirmed by NMR and Nihydrin test.

The deBoc of the protected product (7.0 g) obtained above was carried out in 50% TFA/DCM (40 mL) at 0° C. for 1 hour and then at RT for 1.5 hour. After removing most of TFA in vacuum, the TFA salt of the hydroxylamine derivative was converted to the HCl salt by adding 4N HCl in dioxane (1 mL) to the residue. The precipitate was dissolved in DCM (50 mL) and re-precipitated in ether (800 mL). The final product (6.8 g, 97%) was collected by filtering, washed with ether 3×100 mL, dried in vacuum, stored under nitrogen. Other PEG (5K, 20K) hydroxylamine derivatives were synthesized using the same procedure.

Example 25

This example describes expression and purification methods used for hGH polypeptides comprising a non-natural amino acid. Host cells have been transformed with orthogonal tRNA, orthogonal aminoacyl tRNA synthetase, and hGH constructs.

A small stab from a frozen glycerol stock of the transformed DH10B(fis3) cells were first grown in 2 ml defined medium (glucose minimal medium supplemented with leucine, isoleucine, trace metals, and vitamins) with 100 µg/ml ampicillin at 37° C. When the $OD_{600}$ reached 2-5, 60 µl was transferred to 60 ml fresh defined medium with 100 µg/ml ampicillin and again grown at 37° C. to an $OD_{600}$ of 2-5. 50 ml of the culture was transferred to 2 liters of defined medium with 100 µg/ml ampicillin in a 5 liter fermenter (Sartorius BBI). The fermenter pH was controlled at pH 6.9 with potassium carbonate, the temperature at 37° C., the air flow rate at 5 lpm, and foam with the polyalkylene defoamer KFO F119 (Lubrizol). Stirrer speeds were automatically adjusted to maintain dissolved oxygen levels ≥30% and pure oxygen was used to supplement the air sparging if stirrer speeds reached their maximum value. After 8 hours at 37° C., the culture was fed a 50× concentrate of the defined medium at an exponentially increasing rate to maintain a specific growth rate of 0.15 hour$^{-1}$. When the $OD_{600}$ reached approximately 100, a racemic mixture of para-acetyl-phenylalanine was added to a final concentration of 3.3 mM, and the temperature was lowered to 28° C. After 0.75 hour, isopropyl-b-D-thiogalactopyranoside was added to a final concentration of 0.25 mM. Cells were grown an additional 8 hour at 28° C., pelleted, and frozen at −80° C. until further processing.

The His-tagged mutant hGH proteins were purified using the ProBond Nickel-Chelating Resin (Invitrogen, Carlsbad, Calif.) via the standard His-tagged protein purification procedures provided by Invitrogen's instruction manual, followed by an anion exchange column.

The purified hGH was concentrated to 8 mg/ml and buffer exchanged to the reaction buffer (20 mM sodium acetate, 150 mM NaCl, 1 mM EDTA, pH 4.0). MPEG-Oxyamine powder was added to the hGH solution at a 20:1 molar ratio of PEG: hGH. The reaction was carried out at 28° C. for 2 days with gentle shaking. The PEG-hGH was purified from un-reacted PEG and hGH via an anion exchange column.

The quality of each PEGylated mutant hGH was evaluated by three assays before entering animal experiments. The purity of the PEG-hGH was examined by running a 4-12% acrylamide NuPAGE Bis-Tris gel with MES SDS running buffer under non-reducing conditions (invitrogen). The gels were stained with Coomassie blue. The PEG-hGH band was greater than 95% pure based on densitometry scan. The endotoxin level in each PEG-hGH was tested by a kinetic LAL assay using the KTA$^2$ kit from Charles River Laboratories (Wilmington, Mass.), and it was less than 5 EU per dose. The biological activity of the PEG-hGH was assessed with the IM-9 pSTAT5 bioassay (mentioned in Example 2), and the $EC_{50}$ value was less than 15 nM.

Example 26

This example describes methods for evaluating purification and homogeneity of hGH polypeptides comprising a non-natural amino acid.

Figure 8:
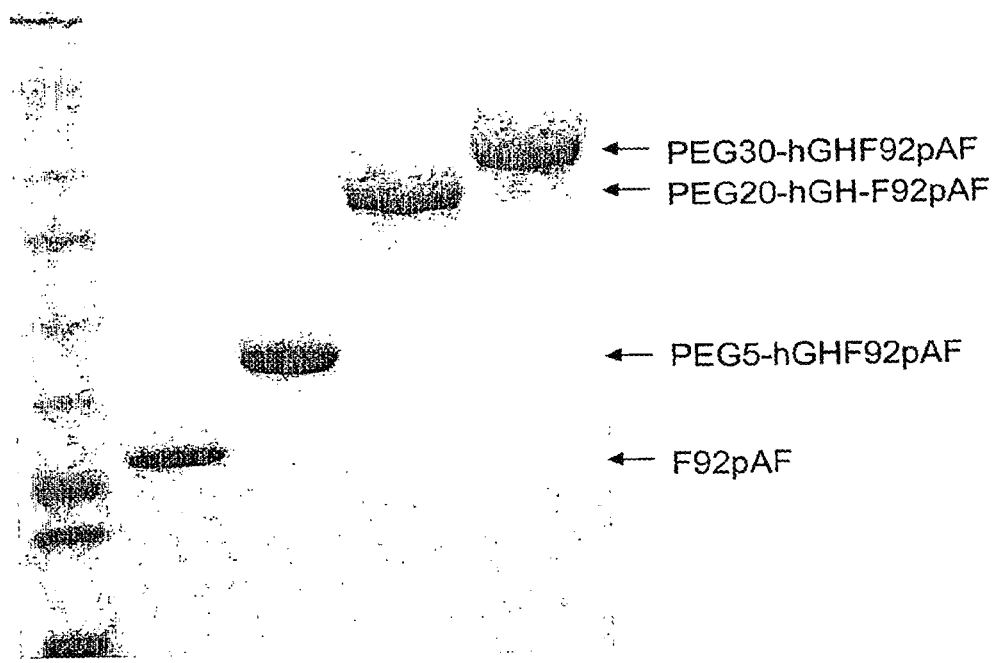
FIG. 8—A Coomassie blue stained SDS-PAGE is shown demonstrating the production of hGH comprising a non-naturally encoded amino acid that is PEGylated by covalent linkage of PEG (5, 20 and 30 kDa) to the non-naturally encoded amino acid.
Figure 9:
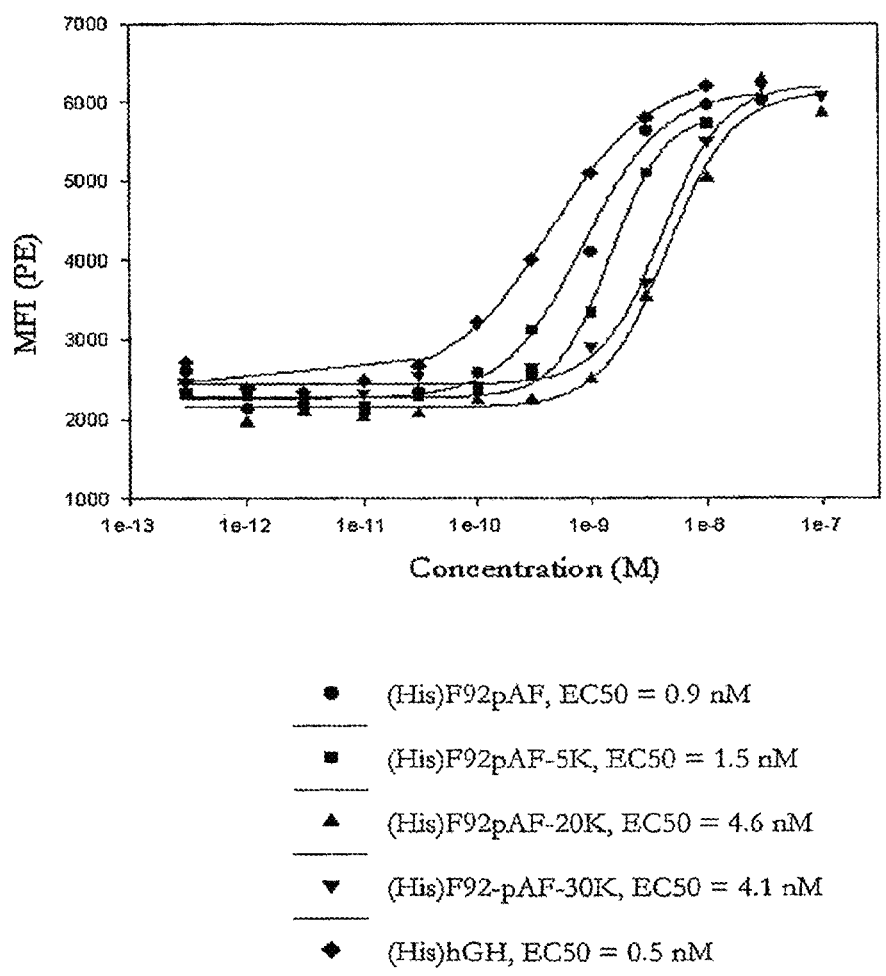
FIG. 9—A diagram is shown demonstrating the biological activity of the various PEGylated forms of hGH comprising a non-naturally encoded amino acid on IM9 cells.

FIG. 8 is a SDS-PAGE of hGH polypeptides comprising a non-natural amino acid at position 92. Lanes 3, 4, and 5 of the gel show hGH comprising a p-acetyl-phenylalanine at position 92 covalently linked to either a 5 kDa, 20 kDa, or 30 kDa PEG molecule. Additional hGH polypeptides comprising a non-natural amino acid that is PEGylated are shown FIG. 11. Five µg of each PEG-hGH protein was loaded onto each SDS-PAGE. FIG. 11, Panel A: Lane 1, molecular weight marker; lane 2, WHO rhGH reference standard (2 µg); lanes 3 and 7, 30KPEG-F92pAF; lane 4, 30KPEG-Y35pAF; lane 5, 30 KPEG-R134pAF; lane 6, 20KPEG-R134pAF; lane 8, WHO rhGH reference standard (20 µg). FIG. 11, Panel B: Lane 9, molecular weight marker, lane 10, WHO rhGH reference standard (2 µg); lane 11, 30KPEG-F92pAF; lane 12, 30KPEG-K145pAF; lane 13, 30 KPEG-Y143pAF; lane 14, 30KPEG-G31pAF; lane 15, 30 KPEG-F92pAF/G120R, lane 16 WHO rhGH reference standard (20 µg). FIG. 9 shows the biological activity of PEGylated hGH polypeptides (5 kDa, 20 kDa, or 30 kDa PEG) in IM-9 cells; methods were performed as described in Example 2.

The purity of the hGH-PEG conjugate can be assessed by proteolytic degradation (including but not limited to, trypsin cleavage) followed by mass spectrometry analysis. Pepinsky B., et al., *J. Pharmcol & Exp. Ther.* 297(3):1059-66 (2001). Methods for performing tryptic digests are also described in the European Pharmacopoeia (2002) 4$^{th}$ Edition, pp. 1938). Modifications to the methods described were performed. Samples are dialyzed overnight in 50 mM TRIS-HCl, pH 7.5. rhGH polypeptides were incubated with trypsin (TPCK-treated trypsin, Worthington) at a mass ratio of 66:1 for 4 hours in a 37° C. water bath. The samples were incubated on ice for several minutes to stop the digestion reaction and subsequently maintained at 4° C. during HPLC analysis. Digested samples (~200 µg) were loaded onto a 25×0.46 cm Vydac C-8 column (5-µm bead size, 100 Å pore size) in 0.1% trifluoroacetic acid and eluted with a gradient from 0 to 80% acetonitrile over 70 min at a flow rate of 1 ml/min at 30° C. The elution of tryptic peptides was monitored by absorbance at 214 nm.

FIG. 10, Panel A depicts the primary structure of hGH with the trypsin cleavage sites indicated and the non-natural amino acid substitution, F92pAF, specified with an arrow (Figure modified from Becker et al. Biotechnol Appl Biochem. (1988) 10(4):326-337). Panel B shows superimposed tryptic maps of peptides generated from a hGH polypeptide comprising a non-naturally encoded amino acid that is PEGylated (30K PEG His$_6$-F92pAF rhGH, labeled A), peptides generated from a hGH polypeptide comprising a non-naturally encoded amino acid (His$_6$-F92pAF rhGH, labeled B), and peptides generated from wild type hGH (WHO rhGH, labeled C). Comparison of the tryptic maps of WHO rhGH and His$_6$-F92pAF rhGH reveals only two peak shifts, peptide peak 1 and peptide peak 9, and the remaining peaks are identical. These differences are caused by the addition of the His$_6$ on the N-terminus of the expressed His$_6$-F92pAF rhGH, resulting in peak 1 shifting; whereas the shift in peak 9 is caused by the substitution of phenylalanine at residue 92 with p-acetyl-phenylalanine. Panel C—A magnification of peak 9 from Panel B is shown. Comparison of the HiS$_6$—F92pAF and the 30K PEG His$_6$-F92pAF rhGH tryptic maps reveals the disappearance of peak 9 upon pegylation of His$_6$-F92pAF rhGH, thus confirming that modification is specific to peptide 9.

Example 27

This example describes a homodimer formed from two hGH polypeptides each comprising a non-natural amino acid.

FIG. 12 compares IM-9 assay results from a His-tagged hGH polypeptide comprising a p-acetyl-phenylalanine substitution at position 92 with a homodimer of this modified polypeptide joined with a linker that is bifunctional having functional groups and reactivity as described in Example 25 for PEGylation of hGH.

Example 28

This example describes a monomer and dimer hGH polypeptide that act as a hGH antagonist.

Figure 14:
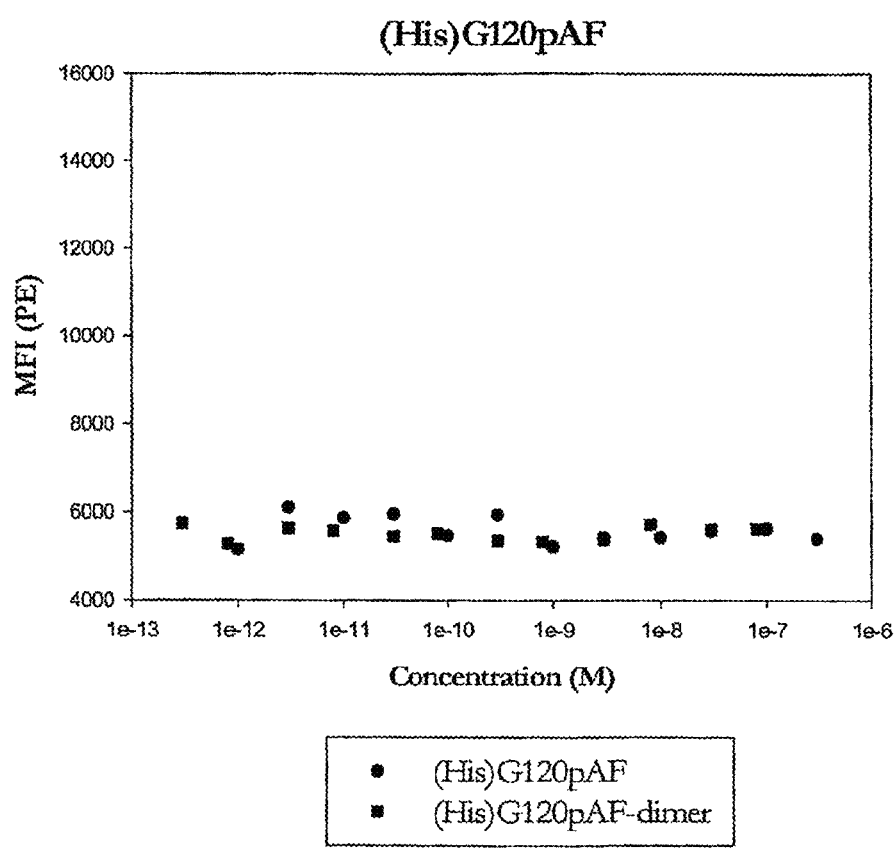
FIG. 14—A diagram is shown indicating that a dimer of the hGH antagonist shown in FIG. 13, Panel B also lacks biological activity in the IM-9 assay.

An hGH mutein in which a G120R substitution has been introduced into site II is able to bind a single hGH receptor, but is unable to dimerize two receptors. The mutein acts as an hGH antagonist in vitro, presumably by occupying receptor sites without activating intracellular signaling pathways (Fuh, G., et al., *Science* 256:1677-1680 (1992)). FIG. 13, Panel A shows IM-9 assay data measuring phosphorylation of pSTAT5 by hGH with the G120R substitution. A hGH polypeptide with a non-natural amino acid incorporated at the same position (G120) resulted in a molecule that also acts as an hGH antagonist, as shown in FIG. 13, Panel B. A dimer of the hGH antagonist shown in FIG. 13, Panel B was constructed joined with a linker that is bifunctional having functional groups and reactivity as described in Example 25 for PEGylation of hGH. FIG. 14 shows that this dimer also lacks biological activity in the IM-9 assay.

Additional assays were performed comparing hGH polypeptide comprising a G120pAF substitution with a dimer of G120pAF modified hGH polypeptides joined by a PEG linker. WHO hGH induced phosphorylation of STAT5 was competed with a dose-response range of the monomer and the dimer joined by a PEG linker. Surface receptor competition studies were also performed showing that the monomer and the dimer compete with GH for cell surface receptor binding on IM-9 and rat GHR (L43R)/BAF3 cells. The dimer acted as a more potent antagonist than the monomer. Table 4 shows the data from these studies.

TABLE 4

| Cell line | IM-9 | IM-9 | Rat GHR (L43R)/BAF3 |
|---|---|---|---|
| Assay | Inhibition of pSTAT5 $IC_{50}$ (nM) | Surface receptor competition $IC_{50}$ (nM) | Surface receptor competition $IC_{50}$ (nM) |
| G120pAF monomer | 3.3 | 8.4 | 3.1 |
| (G120pAF) dimer, PEG linker | 0.7 | 2.7 | 1.4 |

Example 29

This example details the measurement of hGH activity and affinity of hGH polypeptides for the hGH receptor.

Cloning and Purification of Rat GH Receptor

The extracellular domain of rat GH receptor (GHR ECD, amino acids S29-T238) was cloned into pET20b vector (Novagen) between Nde I and Hind III sites in frame with C-terminal 6H is tag. A mutation of L43 to R was introduced to further approximate the human GH receptor binding site (Souza et al., *Proc Natl Acad Sci USA*. (1995) 92(4): 959-63). Recombinant protein was produced in BL21 (DE3) *E. coli* cells (Novagen) by induction with 0.4 mM IPTG at 30° C. for 4-5 hours. After lysing the cells, the pellet was washed four times by resuspending in a dounce with 30 mL of 50 mM Tris, pH 7.6, 100 mM NaCl, 1 in M EDTA, 1% Triton X-100, and twice with the same buffer without Triton X-100. At this point inclusion bodies consisted of more than 95% GHR ECD and were solubilized in 0.1M Tris, pH 11.5, 2M urea. Refolding was accomplished by means of passing an aliquot of the inclusion body solution through a S100 (Sigma) gel filtration column, equilibrated with 50 mM Tris, pH 7.8, 1 M L-arginine, 3.7 mM cystamine, 6.5 mM cysteamine. Fractions containing soluble protein were combined and dialyzed against 50 mM Tris, pH 7.6, 200 mM NaCl, 10% glycerol. The sample was briefly centrifuged to remove any precipitate and incubated with an aliquot of Talon resin (Clontech), according to manufacturer's instructions. After washing the resin with 20 volumes of dialysis buffer supplemented with 5 mM imidazole, protein was eluted with 120 mM imidazole in dialysis buffer. Finally, the sample was dialyzed overnight against 50 mM Tris, pH 7.6, 30 mM NaCl, 1 mM EDTA, 10% glycerol, centrifuged briefly to remove any precipitate, adjusted to 20% glycerol final concentration, aliquoted and stored at −80 C. Concentration of the protein was measured by OD(280) using calculated extinction coefficient of $\epsilon=65,700\ M^{-1}*cm^{-1}$.

Biocore™ Analysis of Binding of GH to GHR

Approximately 600-800 RUs of soluble GHR ECD was immobilized on a Biacore™ CM5 chip, using a standard amine-coupling procedure, as recommended by the manufacturer. Even though a significant portion of the receptor was inactivated by this technique, it was found experimentally that this level of immobilization was sufficient to produce maximal specific GH binding response of about 100-150 RUs, with no noticeable change in binding kinetics. See, e.g., Cunningham et al. *J Mol. Biol.* (1993) 234(3): 554-63 and Wells J A. *Proc Natl Acad Sci USA* (1996) 93(1): 1-6).

Various concentrations of wild type or mutant GH (0.1-300 nM) in HBS-EP buffer (Biacore™, Pharmacia) were injected over the GHR surface at a flow rate of 40 µl/min for 4-5 minutes, and dissociation was monitored for 15 minutes post-injection. The surface was regenerated by a 15 second pulse of 4.5M $MgCl_2$. Only a minimal loss of binding affinity (1-5%) was observed after at least 100 regeneration cycles. Reference cell with no receptor immobilized was used to subtract any buffer bulk effects and non-specific binding.

Kinetic binding data obtained from GH titration experiments was processed with BiaEvaluation 4.1 software (BIA-CORE™). "Bivalent analyte" association model provided satisfactory fit ($chi^2$ values generally below 3), in agreement with proposed sequential 1:2 (GH:GHR) dimerization (Wells J A. *Proc Natl Acad Sci USA* (1996) 93(1): 1-6). Equilibrium dissociation constants (Kd) were calculated as ratios of individual rate constants ($k_{off}/k_{on}$).

Table 5 indicates the binding parameters from Biacore™ using rat GHR ECD (L43R) immobilized on a CM5 chip.

TABLE 5

| GH | $k_{on}, \times 10^{-5}\ 1/M*s$ | $k_{off}, \times 10^{4}, 1/s$ | $K_d$, nM |
|---|---|---|---|
| WHO WT | 6.4 | 3.8 | 0.6 |
| N-6His WT | 9 | 5.6 | 0.6 |
| rat GH WT | 0.33 | 83 | 250 |
| N12pAF | 12.5 | 4.6 | 0.4 |
| R16pAF | 6.8 | 4.8 | 0.7 |
| Y35pAF | 7.8 | 5.3 | 0.7 |
| E88pAF | 6.8 | 5.4 | 0.8 |
| Q91pAF | 6.6 | 4.9 | 0.7 |
| F92pAF | 8.6 | 5.0 | 0.6 |
| R94pAF | 5.6 | 6.0 | 1.1 |
| S95pAF | 0.7 | 3.1 | 4.3 |
| N99pAF | 2.2 | 3.8 | 1.7 |
| Y103pAF | ~0.06 | ~6 | >100 |
| Y111pAF | 8.4 | 4.8 | 0.6 |
| G120R | 2.2 | 22 | 10 |
| G120pAF | 1.1 | 23 | 20 |
| G131pAF | 6.0 | 5.3 | 0.9 |
| P133pAF | 6.4 | 4.9 | 0.8 |
| R134pAF | 8.4 | 5.8 | 0.7 |
| T135pAF | 7.2 | 4.5 | 0.6 |
| G136pAF | 6.2 | 4.3 | 0.7 |
| F139pAF | 6.8 | 4.4 | 0.7 |
| K140pAF | 7.2 | 3.7 | 0.5 |
| Y143pAF | 7.8 | 6.7 | 0.9 |
| K145pAF | 6.4 | 5.0 | 0.8 |
| A155pAF | 5.8 | 4.4 | 0.8 |
| F92pAF-5KD PEG | 6.2 | 2.3 | 0.4 |
| F92pAF-20KD PEG | 1.7 | 1.8 | 1.1 |
| F92pAF-30KD PEG | 1.3 | 0.9 | 0.7 |
| R134pAF-5KD PEG | 6.8 | 2.7 | 0.4 |
| R134pAF-30KD PEG | 0.7 | 1.7 | 2.4 |
| Y35pAF-30KD PEG | 0.9 | 0.7 | 0.7 |
| (G120pAF) dimer | 0.4 | 1.5 | 3.4 |
| (F92pAF) dimer | 3.6 | 1.8 | 0.5 |

GHR Stable Cell Lines

The IL-3 dependent mouse cell line, BAF3, was routinely passaged in RPMI 1640, sodium pyruvate, penicillin, streptomycin, 10% heat-inactivated fetal calf serum, 50 uM 2-mercaptoethanol and 10% WEHI-3 cell line conditioned medium as source of IL-3. All cell cultures were maintained at 37° C. in a humidified atmosphere of 5% $CO_2$.

The BAF3 cell line was used to establish the rat GHR (L43R) stable cell clone, 2E2-2B12-F4. Briefly, $1 \times 10^7$ mid-confluent BAF3 cells were electroporated with 15 ug of linearized pcDNA3.1 plasmid containing the full length rat GHR (L43R) cDNA. Transfected cells were allowed to recover for 48 hours before cloning by limiting dilution in media containing 800 ug/ml G418 and 5 nM WHO hGH. GHR expressing transfectants were identified by surface staining with antibody against human GHR (R&D Systems, Minneapolis, Minn.) and analyzed on a FACS Array (BD Biosciences, San Diego, Calif.). Transfectants expressing a good level of GHR were then screened for proliferative activity against WHO hGH in a BrdU proliferation assay (as described below). Stably transfected rat GHR (L43R) cell clones were established upon two further rounds of repeated subcloning of desired transfectants in the presence of 1.2 mg/ml G418 and 5 nM hGH with constant profiling for surface receptor expression and proliferative capability. Cell clone, 2E2-2'112-F4, thus established is routinely maintained in BAF3 media plus 1.2 mg/ml G418 in the absence of hGH.

Proliferation by BrdU Labeling

Serum starved rat GHR (L43R) expressing BAF3 cell line, 2E2-2B12-F4, were plated at a density of $5 \times 10^4$ cells/well in a 96-well plate. Cells were activated with a 12-point dose range of hGH proteins and labeled at the same time with 50 uM BrdU (Sigma, St. Louis, Mo.). After 48 hours in culture, cells were fixed/permeabilized with 100 ul of BD cytofix/cytoperm solution (BD Biosciences) for 30 min at room temperature. To expose BrdU epitopes, fixed/permeablilized cells were treated with 30 ug/well of DNase (Sigma) for 1 hour at 37° C. Immunofluorescent staining with APC-conjugated anti-BrdU antibody (BD Biosciences) enabled sample analysis on the FACS Array.

Table 6 shows the bioactivity of PEG hGH mutants as profiled on the pSTAT5 (IM-9) and BrdU proliferation assays. WHO hGH is expressed as unity for comparison between assays.

TABLE 6

| hGH | pSTAT5 EC$_{50}$ (nM) | Proliferation EC$_{50}$ (nM) |
|---|---|---|
| WHO WT | 1.0 | 1.0 |
| Y35pAF | 1.3 | 1.6 ± 0.8 (n = 3) |
| Y35pAF-30KPEG | 10 | 5.4 ± 2.8 (n = 4) |
| Y35pAF-40KPEG | 53.3 | 24.0 + 11.0 (n = 3) |
| F92pAF | 2.2 ± 0.4 (n = 9) | 1.4 ± 0.7 (n = 4) |
| F92pAF-5KPEG | 5.1 + 0.4 (n = 3) | ND |
| F92pAF-20KPEG | 10.5 + 0.8 (n = 3) | ND |
| F92pAF-30KPEG | 8.8 ± 1.2 (n = 8) | 4.1 ± 0.9 (n = 3) |
| F92pAF/G120R | >200,000 | >200,000 |
| F92pAF/G120R-30KPEG | >200,000 | >200,000 |
| G131pAF | 2.3 ± 1.8 (n = 2) | 2.1 ± 1.1 (n = 3) |
| G131pAF-30KPEG | 23.8 ± 1.7 (n = 2) | 4.6 ± 2.4 (n = 3) |
| R134pAF | 1.1 ± 0.2 (n = 2) | 1.7 ± 0.3 (n = 3) |
| R134pAF-20KPEG | 5.3 | ND |
| R134pAF-30KPEG | 11.3 ± 1.1 (n = 2) | 2.5 ± 0.7 (n = 4) |
| Y143pAF | 1.6 ± 0.1 (n = 2) | 1.8 ± 0.6 (n = 2) |
| Y143pAF-30KPEG | 12.3 ± 0.9 (n = 2) | 6.6 ± 2.7 (n = 3) |
| K145pAF | 2.3 ± 0.5 (n = 2) | 3.0 ± 1.4 (n = 2) |
| K145pAF-30KPEG | 20.6 ± 9.8 (n = 2) | 5.3 ± 3.5 (n = 3) |

Example 30

This example describes methods to measure in vitro and in vivo activity of PEGylated hGH.

Cell Binding Assays

Cells ($3 \times 10^6$) are incubated in duplicate in PBS/1% BSA (100 µl) in the absence or presence of various concentrations (volume: 10 µl) of unlabeled GH, hGH or GM-CSF and in the presence of $^{125}$I-GH (approx. 100,000 cpm or 1 ng) at 0° C. for 90 minutes (total volume: 120 µl). Cells are then resuspended and layered over 200 µl ice cold FCS in a 350 µl plastic centrifuge tube and centrifuged (1000 g; 1 minute). The pellet is collected by cutting off the end of the tube and pellet and supernatant counted separately in a gamma counter (Packard).

Specific binding (cpm) is determined as total binding in the absence of a competitor (mean of duplicates) minus binding (cpm) in the presence of 100-fold excess of unlabeled GH (non-specific binding). The non-specific binding is measured for each of the cell types used. Experiments are run on separate days using the same preparation of $^{125}$I-GH and should display internal consistency. $^{125}$I-GH demonstrates binding to the GH receptor-producing cells. The binding is inhibited in a dose dependent manner by unlabeled natural GH or hGH, but not by GM-CSF or other negative control. The ability of hGH to compete for the binding of natural $^{125}$I-GH, similar to natural GH, suggests that the receptors recognize both forms equally well.

In Vivo Studies of PEGylated hGH

PEG-hGH, unmodified hGH and buffer solution are administered to mice or rats. The results will show superior activity and prolonged half life of the PEGylated hGH of the present invention compared to unmodified hGH which is indicated by significantly increased bodyweight.

Measurement of the In Vivo Half-Life of Conjugated and Non-Conjugated hGH and Variants Thereof.

All animal experimentation was conducted in an AAALAC accredited facility and under protocols approved by the Institutional Animal Care and Use Committee of St. Louis University. Rats were housed individually in cages in rooms with a 12-hour light/dark cycle. Animals were provided access to certified Purina rodent chow 5001 and water ad libitum. For hypophysectomized rats, the drinking water additionally contained 5% glucose.

Pharmacokinetic Studies

The quality of each PEGylated mutant hGH was evaluated by three assays before entering animal experiments. The purity of the PEG-HGH was examined by running a 4-12% acrylamide NuPAGE Bis-Tris gel with MES SDS running buffer under non-reducing conditions (Invitrogen, Carlsbad, Calif.). The gels were stained with Coomassie blue. The PEG-hGH band was greater than 95% pure based on densitometry scan. The endotoxin level in each PEG-hGH was tested by a kinetic LAL assay using the KTA$^2$ kit from Charles River Laboratories (Wilmington, Mass.), and was less than 5 EU per dose. The biological activity of the PEG-hGH was assessed with the IM-9 pSTAT5 bioassay (described in Example 2), and the EC$_{50}$ value confirmed to be less than 15 nM.

Pharmacokinetic properties of PEG-modified growth hormone compounds were compared to each other and to nonPEGylated growth hormone in male Sprague-Dawley rats (261-425 g) obtained from Charles River Laboratories. Catheters were surgically installed into the carotid artery for blood collection. Following successful catheter installation, animals were assigned to treatment groups (three to six per group) prior to dosing. Animals were dosed subcutaneously with 1 mg/kg of compound in a dose volume of 0.41-0.55 ml/kg. Blood samples were collected at various time points via the indwelling catheter and into EDTA-coated microfuge tubes. Plasma was collected after centrifugation, and stored at −80° C. until analysis. Compound concentrations were measured using antibody sandwich growth hormone ELISA kits from either BioSource International (Camarillo, Calif.) or Diagnostic Systems Laboratories (Webster, Tex.). Concentrations were calculated using standards corresponding to the analog that was dosed. Pharmacokinetic parameters were estimated using the modeling program WinNonlin (Pharsight, version 4.1). Noncompartmental analysis with linear-up/log-down trapezoidal integration was used, and concentration data was uniformly weighted.

Figure 15:
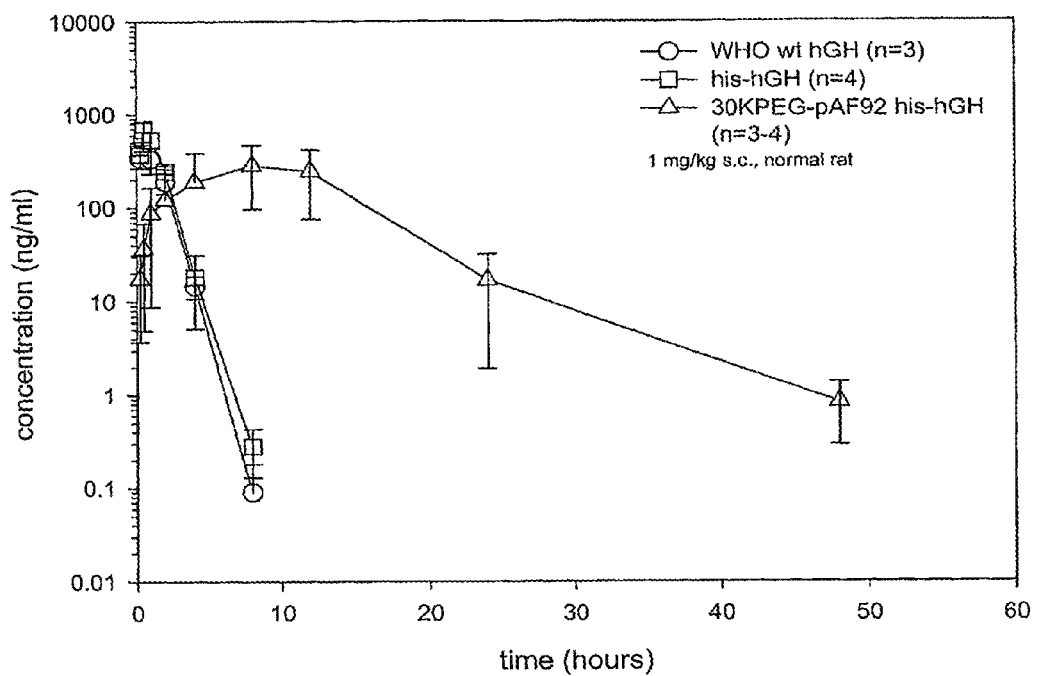
FIG. 15—A diagram is shown comparing the serum half-life in rats of hGH polypeptide comprising a non-naturally encoded amino acid that is PEGylated with hGH polypeptide that is not PEGylated.

FIG. 15 shows the mean (+/−S.D.) plasma concentrations following a single subcutaneous dose in rats. Rats (n=3-4 per group) were given a single bolus dose of 1 mg/kg hGH wild-type protein (WHO hGH), His-tagged hGH polypeptide (his-hGH), or His-tagged hGH polypeptide comprising non-natural amino acid p-acetyl-phenylalanine at position 92 covalently linked to 30KDa PEG (30 KPEG-pAF92(his) hGH). Plasma samples were taken over the indicated time intervals and assayed for injected compound as described. 30 KPEG-pAF92 (his)hGH has dramatically extended circulation compared to control hGH.

Figure 16:
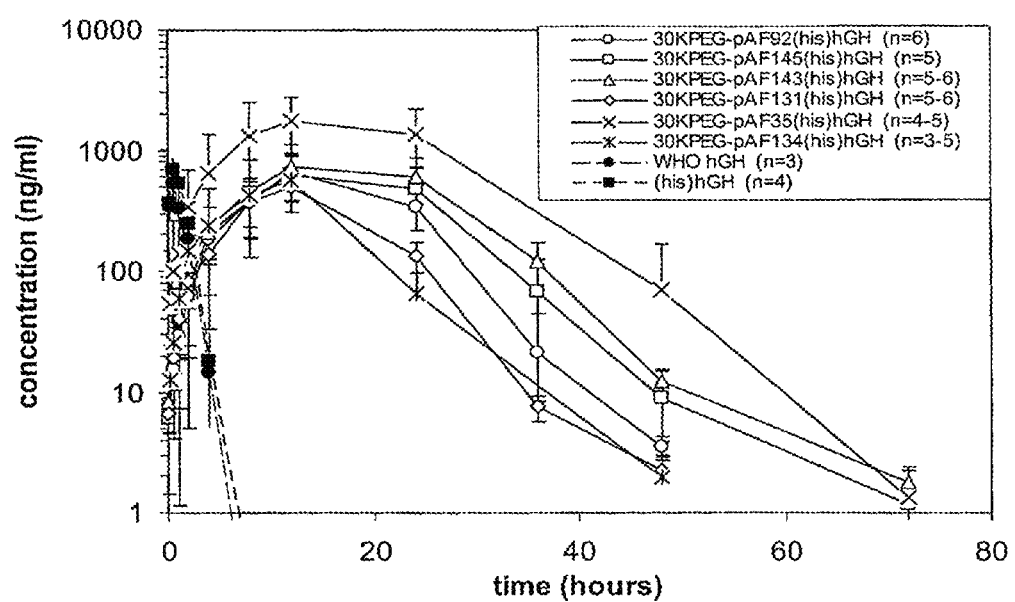
FIG. 16—A diagram is shown comparing the serum half-life in rats of hGH polypeptides comprising a non-naturally encoded amino acid that is PEGylated.

FIG. 16 shows the mean (+/−S.D.) plasma concentrations following a single subcutaneous dose in rats. Rats (n=3-6 per group) were given a single bolus dose of 1 mg/kg protein. hGH polypeptides comprising non-natural amino acid p-acetyl-phenylalanine covalently linked to 30 kDa PEG at each of six different positions were compared to WHO hGH and (his)-hGH. Plasma samples were taken over the indicated time intervals and assayed for injected compound as described. Table 7 shows the pharmacokinetic parameter values for single-dose administration of hGH polypeptides shown in FIG. 16. Concentration vs time curves were evaluated by noncompartmental analysis (Pharsight, version 4.1). Values shown are averages (+/−standard deviation). $C_{max}$: maximum concentration; terminal $t_{1/2}$: terminal half-life; $AUC_{0 \to inf}$: area under the concentration-time curve extrapolated to infinity; MRT: mean residence time; Cl/f: apparent total, plasma clearance; Vz/f: apparent volume of distribution during terminal phase.

rats. Rats (n=5-7 per group) were given a single bolus dose of 2.1 mg/kg protein. Results from hGH polypeptides comprising non-natural amino acid p-acetyl-phenylalanine covalently linked to 30 kDa PEG at each of two different positions (position 35, 92) are shown. Plasma samples were taken over the indicated time intervals and assayed for injected compound as described.

The peptide IGF-1 is a member of the family of somatomedins or insulin-like growth factors. IGF-1 mediates many of the growth-promoting effects of growth hormone. IGF-1 concentrations were measured using a competitive binding enzyme immunoassay kit against the provided rat/mouse IGF-1 standards (Diagnostic Systems Laboratories). Significant difference was determined by t-test using two-tailed distribution, unpaired, equal variance. FIG. 18, Panel A shows the evaluation of compounds in hypophysectomized rats. Rats (n=5-7 per group) were given either a single dose or daily dose subcutaneously. Animals were sequentially weighed, anesthetized, bled, and dosed (when applicable) daily. Bodyweight results are shown for placebo treatments, wild type hGH (hGH), His-tagged hGH ((his)hGH), and hGH polypeptides comprising p-acetyl-phenylalanine covalently-linked to 30 kDa PEG at positions 35 and 92. FIG. 18, Panel B-A diagram is shown of the effect on circulating plasma IGF-1 levels after administration of a single dose of hGH polypeptides comprising a non-naturally encoded amino acid

TABLE 7

Pharmacokinetic parameter values for single-dose 1 mg/kg bolus s.c. administration in normal male Sprague-Dawley rats.

| Compound (n) | Parameter | | | | | |
|---|---|---|---|---|---|---|
| | Cmax (ng/ml) | Terminal $t_{1/2}$ (h) | $AUC_{0 \to inf}$ (ng × hr/ml) | MRT (h) | Cl/f (ml/hr/kg) | Vz/f (ml/kg) |
| WHO hGH (3) | 529 (±127) | 0.53 (±0.07) | 759 (±178) | 1.29 (±0.05) | 1,368 (±327) | 1051 (±279) |
| (his)hGH (4) | 680 (±167) | 0.61 (±0.05) | 1,033 (±92) | 1.30 (±0.17) | 974 (±84) | 853 (±91) |
| 30KPEG-pAF35(his)hGH (4) | 1,885 (±1,011) | 4.85 (±0.80) | 39,918 (±22,683) | 19.16 (±4.00) | 35 (±27) | 268 (±236) |
| 30KPEG-pAF92(his)hGH (6) | 663 (±277) | 4.51 (±0.90) | 10,539 (±6,639) | 15.05 (±2.07) | 135 (±90) | 959 (±833) |
| 30KPEG-pAF131(his)hGH (5) | 497 (±187) | 4.41 (±0.27) | 6,978 (±2,573) | 14.28 (±0.92) | 161 (±61) | 1,039 (±449) |
| 30KPEG-pAF134(his)hGH (3) | 566 (±204) | 4.36 (±0.33) | 7,304 (±2,494) | 12.15 (±1.03) | 151 (±63) | 931 (±310) |
| 30KPEG-pAF143(his)hGH (5) | 803 (±149) | 6.02 (±1.43) | 17,494 (±3,654) | 18.83 (±1.59) | 59 (±11) | 526 (±213) |
| 30KPEG-pAF145(his)hGH (5) | 634 (±256) | 5.87 (±0.09) | 13,162 (±6,726) | 17.82 (±0.56) | 88 (±29) | 743 (±252) |

Pharmacodynamic Studies

Hypophysectomized male Sprague-Dawley rats were obtained from Charles River Laboratories. Pituitaries were surgically removed at 3-4 weeks of age. Animals were allowed to acclimate for a period of three weeks, during which time bodyweight was monitored. Animals with a bodyweight gain of 0-8 g over a period of seven days before the start of the study were included and randomized to treatment groups. Rats were administered either a bolus dose or daily dose subcutaneously. Throughout the study rats were daily and sequentially weighed, anesthetized, bled, and dosed (when applicable). Blood was collected from the orbital sinus using a heparinized capillary tube and placed into an EDTA coated microfuge tube. Plasma was isolated by centrifugation and stored at −80° C. until analysis.

Figure 17:
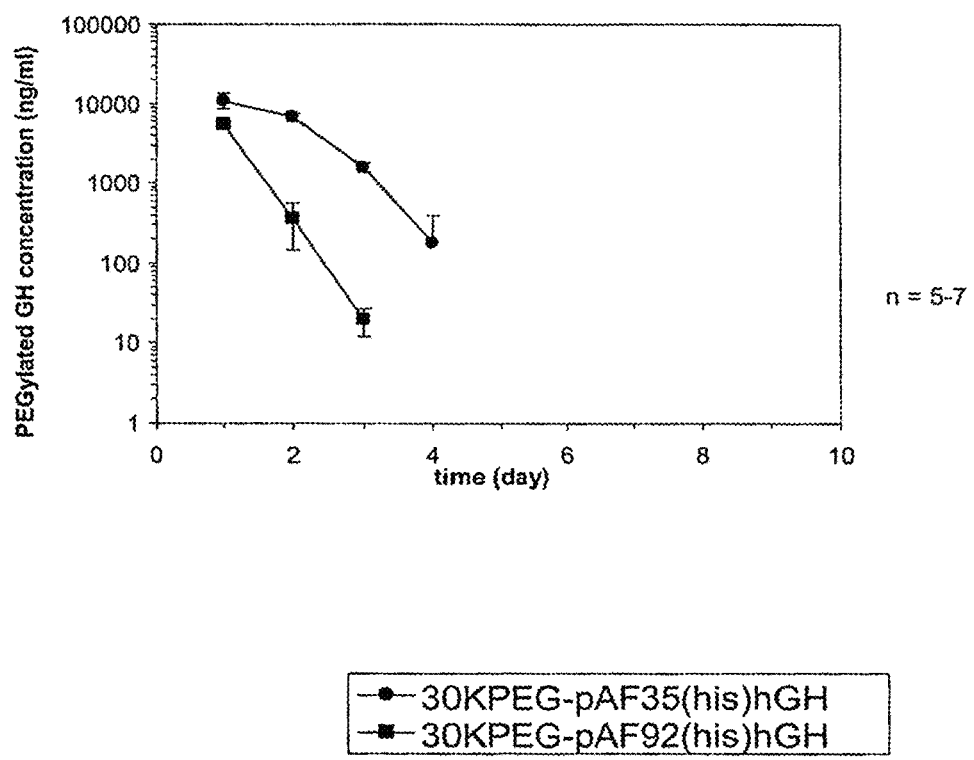
FIG. 17—A diagram is shown comparing the serum half-life in rats of hGH polypeptides comprising a non-naturally encoded amino acid that is PEGylated. Rats were dosed once with 2.1 mg/kg.

FIG. 17 shows the mean (+/−S.D.) plasma concentrations following a single subcutaneous dose in hypophysectomized that is PEGylated. Bars represent standard deviation. In FIG. 18, Panel A, the bodyweight gain at day 9 for 30 KPEG-pAF35(his)hGH compound is statistically different (p<0.0005) from the 30 KPEG-pAF92(his)hGH compound, in that greater weight gain was observed.

FIG. 18, Panel C shows the evaluation of compounds in hypophysectomized rats. Rats (n=11 per group) were given either a single dose or daily dose subcutaneously. Animals were sequentially weighed, anesthetized, bled, and dosed (when applicable) daily. Bodyweight results are shown for placebo treatments, wild type hGH (hGH), and hGH polypeptides comprising p-acetyl-phenylalanine covalently-linked to 30 kDa PEG at positions 92, 134, 145, 131, and 143. FIG. 18, Panel D-A diagram is shown of the effect on circulating plasma IGF-1 levels after administration of a single dose of hGH polypeptides comprising a non-naturally encoded amino acid that is PEGylated (position 92, 134, 145, 131, 143) compared to placebo treatments and wild type hGH. FIG. 18, Panel E shows the mean (+/−S.D.) plasma concentrations corresponding to hGH polypeptides comprising a non-naturally encoded amino acid that is PEGylated (position 92, 134, 145, 131, 143). Plasma samples were taken over the indicated time intervals and assayed for injected compound as described. Bars represent standard deviation.

Example 31

Human Clinical Trial of the Safety and/or Efficacy of PEGylated hGH Comprising a Non-Naturally Encoded Amino Acid.

Objective

To compare the safety and pharmacokinetics of subcutaneously administered PEGylated recombinant human hGH comprising a non-naturally encoded amino acid with one or more of the commercially available hGH products (including, but not limited to Humatrope™ (Eli Lilly & Co.), Nutropin™ (Genentech), Norditropin™ (Novo-Nordisk), Genotropin™ (Pfizer) and Saizen/Serostim™ (Serono)).

Patients

Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to hGH within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design

This will be a Phase I, single-center, open-label, randomized, two-period crossover study in healthy male volunteers. Eighteen subjects are randomly assigned to one of two treatment sequence groups (nine subjects/group). GH is administered over two separate dosing periods as a bolus s.c. injection in the upper thigh using equivalent doses of the PEGylated hGH comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated hGH as well. Multiple formulations of GH that are approved for human use may be used in this study. Humatrope™ (Eli Lilly & Co.), Nutropin™ (Genentech), Norditropin™ (Novo-Nordisk), Genotropin™ (Pfizer) and Saizen/Serostim™ (Serono)) are commercially available GH products approved for human use. The experimental formulation of hGH is the PEGylated hGH comprising a non-naturally encoded amino acid.

Blood Sampling

Serial blood is drawn by direct vein puncture before and after administration of hGH. Venous blood samples (5 mL) for determination of serum GH concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods An ELISA kit procedure (Diagnostic Systems Laboratory [DSL], Webster Tex.), is used for the determination of serum GH concentrations.

Safety Determinations

Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis

Post-dose serum concentration values are corrected for pre-dose baseline GH concentrations by subtracting from each of the post-dose values the mean baseline GH concentration determined from averaging the GH levels from the three samples collected at 30, 20, and 10 minutes before dosing. Pre-dose serum GH concentrations are not included in the calculation of the mean value if they are below the quantification level of the assay. Pharmacokinetic parameters are determined from serum concentration data corrected for baseline GH concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results

The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results

Mean serum GH concentration-time profiles (uncorrected for baseline GH levels) in all 18 subjects after receiving a single dose of one or more of commercially available hGH products (including, but not limited to Humatrope™ (Eli Lilly & Co.), Nutropin™ (Genentech), Norditropin™ (Novo-Nordisk), Genotropin™ (Pfizer) and Saizen/Serostim™ (Serono)) are compared to the PEGylated hGH comprising a non-naturally encoded amino acid at each time point measured. All subjects should have pre-dose baseline GH concentrations within the normal physiologic range. Pharmacokinetic parameters are determined from serum data corrected for pre-dose mean baseline GH concentrations and the $C_{max}$ and $t_{max}$ are determined. The mean $t_{max}$ for the clinical comparator(s) chosen (Humatrope™ (Eli Lilly & Co.), Nutropin™ (Genentech), Norditropin™ (Novo-Nordisk), Genotropin™ (Pfizer), Saizen/Serostim™ (Serono)) is significantly shorter than the $t_{max}$ for the PEGylated hGH comprising the non-naturally encoded amino acid. Terminal half-life values are significantly shorter for the commercially available hGH products tested compared with the terminal half-life for the PEGylated hGH comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of PEGylated hGH comprising non-naturally encoded amino acid will be safe and well tolerated by healthy male subjects. Based on a comparative incidence of adverse events, clinical laboratory values, vital signs, and physical examination results, the safety profiles of the commercially available forms of hGH and PEGylated hGH comprising non-naturally encoded amino acid will be equivalent. The PEGylated hGH comprising non-naturally encoded amino acid potentially provides large clinical utility to patients and health care providers.

Example 32

This example describes one of the many potential sets of criteria for the selection of preferred sites of incorporation of non-naturally encoded amino acids into hIFN.

This example demonstrates how preferred sites within the hIFN polypeptide were selected for introduction of a non-naturally encoded amino acid. The crystal structure with PDB ID 1RH2 and the NMR structure 1ITF (twenty-four different NMR structures) were used to determine preferred positions into which one or more non-naturally encoded amino acids could be introduced. The coordinates for these structures are available from the Protein Data Bank (PDB) or via The Research Collaboratory for Structural Bioinformatics PDB available on the World Wide Web at rcsb.org.

Sequence numbering used in this example is according to the amino acid sequence of mature hIFN shown in SEQ ID NO: 24.

The following criteria were used to evaluate each position of hIFN for the introduction of a non-naturally encoded amino acid: the residue (a) should not interfere with binding of either hIFNbp based on structural analysis of crystallographic structures of hIFN conjugated with hIFNbp, b) should not be affected by alanine scanning mutagenesis, (c) should be surface exposed and exhibit minimal van der Waals or hydrogen bonding interactions with surrounding residues, (d) should be either deleted or variable in hIFN variants, (e) would result in conservative changes upon substitution with a non-naturally encoded amino acid and (f) could be found in either highly flexible regions (including but not limited to CD loop) or structurally rigid regions (including but not limited to Helix B). Publications used in site evaluation include: Bioconj. Chemistry 2001 (12) 195-202; Current Pharmaceutical Design 2002 (8) 2139-2157; Neuroimmunology 2001 (12), 857-859; BBRC 1994 (202) 1445-1451; Cancer Biotherapy+Radiopharmaceuticals 1998 (vol13) 143-153; Structure 1996 (14) 1453-1463; JMB 1997 (274) 661-675. In addition, further calculations were performed on the hIFN molecule, utilizing the Cx program (Pintar et al. *Bioinformatics,* 18, pp 980) to evaluate the extent of protrusion for each protein atom. As a result, in some embodiments, one or more non-naturally encoded encoded amino acid are substituted at, but not limited to, one or more of the following positions of hIFN (as in SEQ ID NO: 24, or the corresponding amino acids in other IFN's): before position 1 (i.e., at the N-terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, or 166 (i.e. at the carboxyl terminus). In some embodiments, the IFN polypeptides of the invention comprise one or more non-naturally occurring amino acids at one or more of the following positions: 100, 106, 107, 108, 111, 113, 114. In some embodiments, the IFN polypeptides of the invention comprise one or more non-naturally occurring amino acids at one or more of the following positions: 41, 45, 46, 48, 49. In some embodiments, the IFN polypeptides of the invention comprise one or more non-naturally occurring amino acids at one or more of the following positions: 61, 64, 65, 101, 103, 110, 117, 120, 121, 149. In some embodiments, the IFN polypeptides of the invention comprise one or more non-naturally occurring amino acids at one or more of the following positions: 6, 9, 12, 13, 16, 96, 156, 159, 160, 161, 162. In some embodiments, the IFN polypeptides of the invention comprise one or more non-naturally occurring amino acids at one or more of the following positions: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165. In some embodiments, the non-naturally occurring amino acid at these or other positions is linked to a water soluble polymer, including but not limited to positions: before position 1 (i.e. the N terminus), 1, 2, 3, 4, 5, 6, 7, 8, 9, 12, 13, 16, 19, 20, 22, 23, 24, 25, 26, 27, 28, 30, 31, 32, 33, 34, 35, 40, 41, 42, 45, 46, 48, 49, 50, 51, 58, 61, 64, 65, 68, 69, 70, 71, 73, 74, 77, 78, 79, 80, 81, 82, 83, 85, 86, 89, 90, 93, 94, 96, 97, 100, 101, 103, 105, 106, 107, 108, 109, 110, 111, 112, 113, 114, 117, 118, 120, 121, 124, 125, 127, 128, 129, 131, 132, 133, 134, 135, 136, 137, 148, 149, 152, 153, 156, 158, 159, 160, 161, 162, 163, 164, 165, 166 (i.e. at the carboxyl terminus). In some embodiments the water soluble polymer is coupled to the IFN polypeptide at one or more amino acid positions: 6, 9, 12, 13, 16, 41, 45, 46, 48, 49, 61, 64, 65, 96, 100, 101, 103, 106, 107, 108, 110, 111, 113, 114, 117, 120, 121, 149, 156, 159, 160, 161 and 162 (SEQ ID NO: 24, or the corresponding amino acid in SEQ ID NO: 23, 25, or any other IFN polypeptide). In some embodiments, the IFN polypeptides of the invention comprise one or more non-naturally occurring amino acids at one or more of the following positions providing an antagonist: 2, 3, 4, 5, 7, 8, 16, 19, 20, 40, 42, 50, 51, 58, 68, 69, 70, 71, 73, 97, 105, 109, 112, 118, 148, 149, 152, 153, 158, 163, 164, 165; a hIFN polypeptide comprising one of these substitutions may potentially act as a weak antagonist or weak agonist depending on the intended site selected and desired activity. Human IFN antagonists include, but are not limited to, those with substitutions at 22, 23, 24, 25, 26, 27, 28, 30, 31, 32, 33, 34, 35, 74, 77, 78, 79, 80, 82, 83, 85, 86, 89, 90, 93, 94, 124, 125, 127, 128, 129, 131, 132, 133, 134, 135, 136, 137, or any combinations thereof (hIFN; SEQ ID NO: 24 or the corresponding amino acids in SEQ ID NO: 23 or 25).

Example 33

This example details cloning and expression of a modified hIFN polypeptide in *E. coli*.

This example demonstrates how an hIFN polypeptide including a non-naturally encoded amino acid can be expressed in *E. coli*. See Nagata et. al., Nature, vol. 284, 316-320 (1980) and U.S. Pat. No. 4,364,863. cDNA encoding the full length hIFN and the mature form of hIFN lacking the N-terminal signal sequence are shown in SEQ ID NO: 26 and SEQ ID NO: 27, respectively. The fall length and mature hIFN encoding cDNA is inserted into the pBAD HISc, pET20b, and pET19b expression vectors following optimization of the sequence for cloning and expression without altering amino acid sequence.

An introduced translation system that comprises an orthogonal tRNA (O-tRNA) and an orthogonal aminoacyl tRNA synthetase (O—RS) is used to express hIFN containing a non-naturally encoded amino acid, as described in Example 2 for hGH expression.

Example 34

This example describes methods to measure in vitro and in vivo activity of PEGylated IFN.

Cell Binding Assays.

Cells ($3 \times 10^6$) are incubated in duplicate in PBS/1% BSA (100 µl) in the absence or presence of various concentrations (volume: 10 µl) of unlabeled IFN, hIFN or GM-CSF and in the presence of $^{125}$I-IFN (approx. 100,000 cpm or 1 ng) at 0° C. for 90 minutes (total volume: 120 µl). Cells are then resuspended and layered over 200 µl ice cold FCS in a 350 µl plastic centrifuge tube and centrifuged (1000 g; 1 minute). The pellet is collected by cutting off the end of the tube and pellet and supernatant counted separately in a gamma counter (Packard).

Specific binding (cpm) is determined as total binding in the absence of a competitor (mean of duplicates) minus binding (cpm) in the presence of 100-fold excess of unlabeled IFN (non-specific binding). The non-specific binding is measured for each of the cell types used. Experiments are run on separate days using the same preparation of $^{125}$I-IFN and should display internal consistency. $^{125}$I-IFN demonstrates binding to the Daudi cells. The binding is inhibited in a dose dependent manner by unlabeled natural IFN or hIFN, but not by GM-CSF or other negative control. The ability of hFN to compete for the binding of natural $^{125}$I-IFN, similar to natural IFN, suggests that the receptors recognize both forms equally well.

In Vivo Studies from PEGylated IFN

PEG-hIFN, unmodified hIFN and buffer solution are administered to mice or rats. The results will show superior activity and prolonged half life of the PEGylated hIFN of the present invention compared to unmodified hIFN which is indicated by significantly increased inhibition of viral replication using the same dose per mouse.

Measurement of the In Vivo Half-Life of Conjugated and Non-Conjugated hIFN and Variants Thereof.

Male Sprague Dawley rats (about 7 weeks old) are used. On the day of administration, the weight of each animal is measured. 100 µg per kg body weight of the non-conjugated and conjugated hIFN samples are each injected intravenously into the tail vein of three rats. At 1 minute, 30 minutes, 1, 2, 4, 6, and 24 hours after the injection, 500 µl of blood is withdrawn from each rat while under $CO_2$-anesthesia. The blood samples are stored at room temperature for 1.5 hours followed by isolation of serum by centrifugation (4° C., 18000×g for 5 minutes). The serum samples are stored at −80° C. until the day of analysis. The amount of active IFN in the serum samples is quantified by the IFN in vitro activity assay after thawing the samples on ice.

Antiviral Activity

There are many assays known to those skilled in the art that measure the degree of resistance of cells to viruses (McNeill T A, J Immunol Methods. (1981) 46(2):121-7). These assays generally can be categorized into three types: inhibition of cytopathic effect; virus plaque formation; and reduction of virus yield. Viral cytopathic effect assays measure the degree of protection induced in cell cultures pretreated with IFN and subsequently infected with viruses. Vesicular stomatitis virus, for instance, is an appropriate virus for use in such an assay. This type of assay is convenient for screening numerous different IFNs, as it can be performed in 96-well plates. Plaque-reduction assays measure the resistance of IFN-treated cell cultures to a plaque-forming virus (for instance, measles virus). One benefit to this assay is that it allows precise measurement of a 50% reduction in plaque formation. Finally, virus yield assays measure the amount of virus released from cells during, for instance, a single growth cycle. Such assays are useful for testing the antiviral activity of IFNs against viruses that do not cause cytopathic effects, or that do not build plaques in target-cell cultures. The multiplicity of infection (moi) is an important factor to consider when using either plaque-reduction or virus-yield assays.

Other clinically important interferon characteristics are also easily assayed in the laboratory setting. One such characteristic is the ability of an interferon polypeptide to bind to specific cell-surface receptors. For instance, some IFNα-2bs exhibit different cell-surface properties compared to IFNα-2b, the IFN most widely used in clinical trials. While IFNα-2b is an effective antiviral agent, it causes significant adverse side effects. Interferons that exhibit distinct binding properties from IFNα-2b may not cause the same adverse effects. Therefore, interferons that compete poorly with IFNα-2b for binding sites on cells are of clinical interest. Competitive interferon binding assays are well known in the art (Hu et al., J Biol. Chem. (1993) June 15; 268(17):12591-5; Di Marco et al., (1994) Biochem. Biophys. Res. Comm. 202:1445-1451). In general, such assays involve incubation of cell culture cells with a mixture of $^{125}$I-labeled IFNα-2b and an unlabeled interferon of interest. Unbound interferon is then removed, and the amount of bound label (and by extension, bound $^{125}$I-labeled IFNα-2b) is measured. By comparing the amount of label that binds to cells in the presence or absence of competing interferons, relative binding affinities can be calculated.

Another prominent effect of IFNα's is their ability to inhibit cell growth, which is of major importance in determining anti-tumor action. Growth inhibition assays are well established, and usually depend on cell counts or uptake of tritiated thymidine ([$^3$H] thymidine) or another radiolabel. The human lymphoblastoid Daudi cell line has proven to be extremely sensitive to IFNα's, and if has been used to measure antiproliferative activity in many IFNα's and derived hybrid polypeptides (Meister et al., J Gen Virol. (1986) August; 67 (Pt 8):1633-43). Use of this cell line has been facilitated by its ability to be grown in suspension cultures (Evinger and Pestka, (1981) Methods Enzymol. 79:362-368). IFNα's also exhibit many immunomodulatory activities (Zoon et al., (1986) In, The Biology of the Interferon System. Cantell and Schellenkens, Eds., Martinus Nyhoff Publishers, Amsterdam).

Although IFNs were first discovered by virologists, their first clinical use (in 1979) was as therapeutic agents for myeloma (Joshua et al., (1997) Blood Rev. 11(4):191-200). IFNα's have since been shown to be efficacious against a myriad of diseases of viral, malignant, angiogenic, allergic, inflammatory, and fibrotic origin (Tilg, (1997) Gastroenterology. 112(3):1017-1021). It has also proven efficacious in the treatment of metastatic renal carcinoma and chronic myeloid leukemia (Williams and Linch, (1997) Br. J. Hosp. Med. 57(9):436-439). Clinical uses of IFNs are reviewed in Gresser (1997) J. Leukoc. Biol. 61(5):567-574 and Pfeffer (1997) Semin. Oncol. 24(3 Suppl. 9):S9-S63S969.

Example 35

Human Clinical Trial of the Safety and/or Efficacy of PEGylated hIFN Comprising a Non-Naturally Encoded Amino Acid Objective To compare the safety and pharmacokinetics of subcutaneously administered PEGylated recombinant human hIFN comprising a non-naturally encoded amino acid with the commercially available hIFN products Roferon A® or Intron A®.

Patients

Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to hIFN within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design

This will be a Phase I, single-center, open-label, randomized, two-period crossover study in healthy male volunteers. Eighteen subjects are randomly assigned to one of two treatment sequence groups (nine subjects/group). IFN is administered over two separate dosing periods as a bolus s.c. injection in the upper thigh using equivalent doses of the PEGylated hIFN comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated hIFN as well. Multiple formulations of IFN that are approved for human use may be used in this study. Roferon A® and/or Intron A® are commercially available IFN products approved for human use. The experimental formulation of hIFN is the PEGylated hIFN comprising a non-naturally encoded amino acid.

Blood Sampling

Serial blood is drawn by direct vein puncture before and after administration of hIFN. Venous blood samples (5 mL) for determination of serum IFN concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Bach serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods

An ELISA kit procedure (BioSource International (Camarillo, Calif.)), is used for the determination of serum IFN concentrations.

Safety Determinations

Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis

Post-dose serum concentration values are corrected for pre-dose baseline IFN concentrations by subtracting from each of the post-dose values the mean baseline IFN concentration determined from averaging the IFN levels from the three samples collected at 30, 20, and 10 minutes before dosing. Pre-dose serum IFN concentrations are not included in the calculation of the mean value if they are below the quantification level of the assay. Pharmacokinetic parameters are determined from serum concentration data corrected for baseline IFN concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results

The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results

Mean serum IFN concentration-time profiles (uncorrected for baseline IFN levels) in all 18 subjects after receiving a single dose of commercially available hIFN (e.g. Roferon A® or Intron A®) are compared to the PEGylated hIFN comprising a non-naturally encoded amino acid at each time point measured. All subjects should have pre-dose baseline IFN concentrations within the normal physiologic range. Pharmacokinetic parameters are determined from serum data corrected for pre-dose mean baseline IFN concentrations and the $C_{max}$ and $t_{max}$ are determined. The mean $t_{max}$ for hIFN (e.g. Roferon®) is significantly shorter than the $t_{max}$ for the PEGylated hIFN comprising the non-naturally encoded amino acid. Terminal half-life values are significantly shorter for hIFN (e.g. Intron A®) compared with the terminal half-life for the PEGylated hIFN comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of PEGylated hIFN comprising non-naturally encoded amino acid will be safe and well tolerated by healthy male subjects. Based on a comparative incidence of adverse events, clinical laboratory values, vital signs, and physical examination results, the safety profiles of hIFN (e.g. Roferon A®) and PEGylated hIFN comprising non-naturally encoded amino acid will be equivalent. The PEGylated hIFN comprising non-naturally encoded amino acid potentially provides large clinical utility to patients and health care providers.

Example 36

This example describes one of the many potential sets of criteria for the selection of preferred sites of incorporation of non-naturally encoded amino acids into hG-CSF.

This example demonstrates how preferred sites within the hG-CSF polypeptide were selected for introduction of a non-naturally encoded amino acid. The crystal structure 1CD9 composed of two molecules of hG-CSF complexed with two molecules of the extracellular domain of receptor (hG-CSFbp), was used to determine preferred positions into which one or more non-naturally encoded amino acids could be introduced. Other hG-CSF structures (including but not limited to 1PGR, 1RHG, and 1GNC) were utilized to examine potential variation of primary, secondary, or tertiary structural elements between crystal structure datasets. The coordinates for these structures are available from the Protein Data Bank (PDB) (Bernstein et al. *J. Mol. Biol.* 1997, 112, pp 535) or via The Research Collaboratory for Structural Bioinformatics PDB available on the World Wide Web at rcsb.org. The structural model 1CD9 contains the entire mature 19 kDa sequence of hG-CSF with the exception of the N-terminal residues 1-4 and residues 129-136. Two disulfide bridges are present, formed by C37 and C43 and C65 and C75.

Sequence numbering used in this example is according to the amino acid sequence of mature hG-CSF shown in SEQ ID NO: 29.

The following criteria were used to evaluate each position of hG-CSF for the introduction of a non-naturally encoded amino acid: the residue (a) should not interfere with binding of either hG-CSFbp based on structural analysis of ICD9 and 1RHG (crystallographic structures of hG-CSF conjugated with hG-CSFbp), b) should not be affected by alanine scanning mutagenesis (Reidhaar-Olson J F et al., Biochemistry (1996) July 16; 35(28):9034-41; Young D C et al. Protein Sci. (1997) June; 6(6):1228-36; Layton et al. (1997) JBC 272(47): 29735-29741), (c) should be surface exposed and exhibit minimal van der Waals or hydrogen bonding interactions with surrounding residues, (d) should be either deleted or variable in hG-CSF variants, (e) would result in conservative changes upon substitution with a non-naturally encoded amino acid and (f) could be found in either highly flexible regions (including but not limited to CD loop) or structurally rigid regions (including but not limited to Helix B). In addition, further calculations were performed on the hG-CSF molecule, utilizing the Cx program (Pintar et al. *Bioinformatics,* 18, pp 980) to evaluate the extent of protrusion for each protein atom. As a result, in some embodiments, one or more non-naturally encoded amino acid are substituted at, but not limited to, one or more of the following positions of hG-CSF (as in SEQ ID NO: 29, or the corresponding amino acids in SEQ ID NO: 28, 30, 35, or 36): before position 1 (i.e. at the N terminus), 1, 2, 3, 4, 5, 6, 7, 8, 9, 10, 11, 12, 13, 16, 17, 19, 20, 21, 23, 24, 28, 30, 31, 33, 34, 35, 38, 39, 40, 41, 44, 45, 46, 47, 48, 49, 50, 51, 53, 54, 55, 56, 58, 59, 61, 63, 64, 66, 67, 68, 69, 70, 71, 72, 73, 77, 78, 81, 84, 87, 88, 91, 92, 94, 95, 97, 98, 99, 101, 102, 103, 105, 106, 108, 109, 110, 112, 113, 116, 117, 120, 121, 123, 124, 125, 126, 127, 130, 131, 132, 133, 134, 135, 136, 137, 138, 139, 140, 142, 143, 144, 145, 146, 147, 148, 156, 157, 159, 160, 163, 164, 166, 167, 170, 171, 173, 174, 175, 176 (i.e. at the carboxyl terminus).

In some embodiments, the G-CSF polypeptides of the invention comprise one or more non-naturally occurring amino acids at one or more of the following positions: 30, 31, 33, 58, 59, 61, 63, 64, 66, 67, 68, 77, 78, 81, 87, 88, 91, 95, 101, 102, 103, 130, 131, 132, 134, 135, 136, 137, 156, 157, 159, 160, 163, 164, 167, 170, 171 (SEQ ID NO: 29, or the corresponding amino acids in SEQ ID NO: 28, 30, 35, or 36). In some embodiments, the G-CSF polypeptides of the invention comprise one r more non-naturally occurring amino acids at one or more of the following positions: 59, 63, 67, 130, 131, 132, 134, 137, 160, 163, 167, and 171 (as in SEQ ID NO: 29, or the corresponding amino acids in SEQ ID NO: 28, 30, 35, or 36). In some embodiments, the non-naturally occurring amino acid at one or more of these positions is linked to a water soluble polymer, including but not limited to positions: before position 1 (i.e. at the N terminus), 1, 2, 3, 4, 5, 6, 7, 8, 9, 10, 11, 12, 13, 16, 17, 19, 20, 21, 23, 24, 28, 30, 31, 33, 34, 35, 38, 39, 40, 41, 44, 45, 46, 47, 48, 49, 50, 51, 53, 54, 55, 56, 58, 59, 61, 63, 64, 66, 67, 68, 69, 70, 71, 72, 73, 77, 78, 81, 84, 87, 88, 91, 92, 94, 95, 97, 98, 99, 101, 102, 103, 105, 106, 108, 109, 110, 112, 113, 116, 117, 120, 121, 123, 124, 125, 126, 127, 130, 131, 132, 133, 134, 135, 136, 137, 138, 139, 140, 142, 143, 144, 145, 146, 147, 148, 156, 157, 159, 160, 163, 164, 166, 167, 170, 171, 173, 174, 175, 176 (i.e. at the carboxyl terminus) (SEQ ID NO: 29, or the corresponding amino acids in SEQ ID NO: 28, 30, 35, or 36).

Some sites for generation of a hG-CSF antagonist include: 6, 7, 8, 9, 10, 11, 12, 13, 16, 17, 19, 20, 21, 23, 24, 28, 30, 41, 47, 49, 50, 70, 71, 105, 106, 109, 110, 112, 113, 116, 117, 120, 121, 123, 124, 125, 127, 145, or any combination thereof (as in SEQ ID NO: 29, and the corresponding amino acids in SEQ ID NO: 28, 30, 35, or 36). These sites were chosen utilizing criteria (c)-(e) of the agonist design. The antagonist design may also include site-directed modifications of at the receptor binding regions to increase binding affinity to hG-CSFbp.

Example 37

This example details cloning and expression of a modified hG-CSF polypeptide in E. coli.

This example demonstrates how an hG-CSF polypeptide including a non-naturally encoded amino acid can be expressed in *E. coli*. Isolation of hG-CSF and production of G-CSF in host cells such as *E. coli* are described in, e.g., U.S. Pat. Nos. 4,810,643; 4,999,291; 5,580,755; and 6,716,606, which are incorporated by reference herein. cDNA encoding the full length hG-CSF, the mature form of hG-CSF (methionyl hG-CSF), and a variant of the mature form of hG-CSF are shown in SEQ ID NO: 31, 32 and 33, respectively. The full length and mature hG-CSF encoding cDNA is inserted into the pBAD HISc, pET20b, and pET19b expression vectors following optimization of the sequence for cloning and expression without altering amino acid sequence (SEQ ID NO: 34).

An introduced translation system that comprises an orthogonal tRNA (O-tRNA) and an orthogonal aminoacyl tRNA synthetase (O—RS) is used to express hG-CSF containing a non-naturally encoded amino acid, as described in Example 2 for hGH expression.

Example 38

In Vitro and In Vivo Activity of PEGylated hG-CSF

PEG-hG-CSF, unmodified hG-CSF and buffer solution are administered to mice or rats. The results will show superior activity and prolonged half life of the PEGylated hG-CSF of the present invention compared to unmodified hG-CSF which is indicated by significantly increased amounts of neutrophils and a shift of white blood cell count maximum using the same dose per mouse.

$^{3}$H-thymidine Assay.

The $^{3}$H-thymidine assay is performed using standard methods. Bone marrow is obtained from sacrificed female Balb C mice. Bone marrow cells are briefly suspended, centrifuged, and resuspended in a growth medium. A 160 μl aliquot containing approximately 10,000 cells is placed into each well of a 96 well micro-titer plate. Samples of the purified G-CSF analog (as prepared above) are added to each well, and incubated for 68 hours. Tritiated thymidine is added to the wells and allowed to incubate for five additional hours. After the five hour incubation time, the cells are harvested, filtered, and thoroughly rinsed. The filters are added-to a vial containing scintillation fluid. The beta emissions are counted (LKB Betaplate scintillation counter). Standards and analogs are analyzed in triplicate, and samples which fell substantially above or below the standard curve are re-assayed with the proper dilution. The results are reported as the average of the triplicate analog data relative to the unaltered recombinant human G-CSF standard results.

Proliferation induction of human bone marrow cells is assayed on the basis of increased incorporation of $^{3}$H-thymidine. Human bone marrow from healthy donors is subjected to a density cut with Ficoll-Hypaque (1.077 g/ml, Pharmacia) and low density cells are suspended in Iscove's medium (GIBCO) containing 10% fetal bovine serum and glutamine pen-strep. Subsequently, $2\times10^{4}$ human bone marrow cells are incubated with either control medium or the recombinant *E. coli*-derived hG-CSF material of Example 37 in 96 flat bottom well plates at 37° C. in 5% $CO_2$ in air for 2 days. The samples are assayed in duplicate and the concentration varied over a 10,000 fold range. Cultures are then pulsed for 4 hours with 0.5 μCi/well of 3H-Thymidine (New England Nuclear, Boston, Mass.). $^{3}$H-Thymidine uptake is measured as described in Venuta, et al., Blood, 61, 781 (1983). In this assay human G-CSF isolates can induce $^{3}$H-Thymidine incorporation into human bone marrow cells at levels approximately 4-10 times higher than control supernatants. The *E. coli*-derived hG-CSF material of the present invention has similar properties.

WEHI-3B $D^{+}$ Differentiation Induction.

The ability of hG-CSF polypeptides of the present invention to induce differentiation of the murine myelomonocytic leukemic cell line WEHI-3B $D^{+}$ is assayed in semi-solid agar medium as described in Metcalf, Int. J. Cancer, 25, 225 (1980). The recombinant hG-CSF product and media controls are incubated with about 60 WEHI-3B $D^{+}$ cells/well at 37° C. in 5% $CO_2$ in air for 7 days. The samples are incubated in 24 flat bottom well plates and the concentration varied over a 2000-fold range. Colonies are classified as undifferentiated, partially differentiated or wholly differentiated and colony cell counts are counted microscopically. The *E. coli*-derived hG-CSF material is found to induce differentiation.

CFU-GM, BFU-E and CFU-GEMM Assays.

Natural isolates of human G-CSF and hG-CSF are found to cause human bone marrow cells to proliferate and differentiate. These activities are measured in CFU-GM [Broxmeyer, et al., Exp. Hematol., 5, 87, (1971)], BFU-E and CFU-GEMM assays [Lu, et al., Blood, 61, 250 (1983)] using low density, non-adherent bone marrow cells from healthy human volunteers. A comparison of CFU-GM, BFU-E and CFU-GEMM biological activities using either 500 units of G-CSF or hG-CSF are performed.

Colony assays are performed with low density non-adherent bone marrow cells. Human bone marrow cells are subject to a density cut with Ficoll-Hypaque (density, 1.077 g/cm$^{3}$; Pharmacia). The low density cells are then resuspended in Iscove's modified Dulbecco's medium containing fetal calf serum and placed for adherence on Falcon tissue culture dishes (No. 3003, Becton Dickinson, Cockeysville, Md.) for 1½ hours at 37° C.

Medium control consists of Iscove's modified Dulbecco medium plus 10% FCS, 0.2 mM hemin and 1 unit of a recombinant erythropoietin. For the CFU-GM assay target cells are plated at $1\times10^{5}$ in 1 ml of 0.3% agar culture medium that includes supplemented McCoy's 5A medium and 10% heat inactivated fetal calf serum. Cultures are scored for colonies (greater than 40 cells per aggregate) and morphology is assessed on day 7 of culture. The number of colonies is shown as the mean±SEM as determined from quadruplicate plates.

For the BFU-E and CFU-GEMM assays, cells ($1\times10^{5}$) are added to a 1 ml mixture of Iscove's modified Dulbecco medium (Gibco), 0.8% methylcellulose, 30% fetal calf serum 0.05 nM 2-mercaptoethanol, 0.2 mM hemin and 1 unit of recombinant erythropoietin. Dishes are incubated in a humidified atmosphere of 5% $CO_2$ and 5% $O_2$. Low oxygen tension is obtained using an oxyreducer from Reming Bioinstruments (Syracuse, N.Y.). Colonies are scored after 14 days of incubation. The number of colonies is determined as the mean±SEM, as determined from duplicate plates.

Colonies formed in the CFU-GM assay are all expected to be chloracetate esterase positive and non-specific esterase (alpha-naphthyl acetate esterase) negative, consistent with the colonies being granulocyte in type. Both natural G-CSF and hG-CSF are expected to have a specific activity of an approximately $1 \times 10^8$ U/mg pure protein, when assayed by serial dilution in a CFU-GM assay. It is important to note that the hG-CSF is extremely pure and free of other potential mammalian growth factors by virtue of its production in *E. coli*. Thus hG-CSF is capable of supporting mixed colony formation (CFU-GEMM) and BFU-E when added in the presence of recombinant erythropoietin.

Cell Binding Assays.

Murine WEHI-3BD$^+$ and human peripheral blood myeloid leukemic cell preparations (ANLL) are tested for their ability to bind $^{125}$I-G-CSF. Murine and freshly obtained human peripheral blood myeloid leukemic cells are washed three times with PBS/1% BSA. WEHI-3BD$^+$ cells ($5 \times 10^6$) or fresh leukemic cells ($3 \times 10^6$) are incubated in duplicate in PBS/1% BSA (100 µl) in the absence or presence of various concentrations (volume: 10 µl) of unlabeled G-CSF, hG-CSF or GM-CSF and in the presence of $^{125}$I-G-CSF (approx. 100,000 cpm or 1 ng) at 0° C. for 90 minutes (total volume: 120 µl). Cells are then resuspended and layered over 200 µice cold FCS in a 350 µl plastic centrifuge tube and centrifuged (1000 g; 1 minute). The pellet is collected by cutting off the end of the tube and pellet and supernatant counted separately in a gamma counter (Packard).

Specific binding (cpm) is determined as total binding in the absence of a competitor (mean of duplicates) minus binding (cpm) in the presence of 100-fold excess of unlabeled G-CSF (non-specific binding). The non-specific binding is measured for each of the cell types used. Experiments are run on separate days using the same preparation of $^{125}$I-G-CSF and should display internal consistency. $^{125}$I-G-CSF demonstrates binding to the WEHI-3B D$^+$ leukemic cells. The binding is inhibited in a dose dependent manner by unlabeled natural G-CSF or hG-CSF, but not by GM-CSF. The ability of hG-CSF to compete for the binding of natural $^{125}$I-G-CSF, similar to natural G-CSF, suggests that the receptors recognize both forms equally well.

G-CSF Induces Granulocytic and Monocytic Differentiation of Light Density Bone Marrow Cells Obtained from Leukemia Patients.

Cells from patients are cultured for four days in medium alone or in the presence of $1 \times 10^5$ units of hG-CSF. Cells from the control cultures incubated in medium alone are promyelocyte in type, while cells cultured in the presence of hG-CSF will show mature cells of the myeloid type including a metamyelocyte, giant band form and segmented neutrophilis and monocyte. The actual differentiation of at least 100 cells is evaluated morphologically. The hG-CSF treated cells consist of blasts, myelocytes, metamyelocytes, band forms plus segmented neutrophils, promonocytes and monocytes. Control cells are expected to be blasts.

Measurement of the In Vivo Half-Life of Conjugated and Non-Conjugated hG-CSF and Variants Thereof.

Male Sprague Dawley rats (about 7 weeks old) are used. On the day of administration, the weight of each animal is measured. 100 µg per kg body weight of the non-conjugated and conjugated hG-CSF samples are each injected intravenously into the tail vein of three rats. At 1 minute, 30 minutes, 1, 2, 4, 6, and 24 hours after the injection, 500 µl of blood is withdrawn from each rat while under $CO_2$-anesthesia. The blood samples are stored at room temperature for 1.5 hours followed by isolation of serum by centrifugation (4° C., 18000×g for 5 minutes). The serum samples are stored at −80° C. until the day of analysis. The amount of active G-CSF in the serum samples is quantified by the G-CSF in vitro activity assay after thawing the samples on ice.

Measurement of the In Vivo Biological Activity in Healthy Rats of Conjugated and Non-Conjugated hG-CSF and Variants Thereof.

Measurement of the in vivo biological effects of hG-CSF in SPF Sprague Dawley rats is used to evaluate the biological efficacy of conjugated and non-conjugated G-CSF and variants thereof. On the day of arrival the rats are randomly allocated into groups of 6. The animals are rested for a period of 7 days wherein individuals in poor condition or at extreme weights are rejected. The weight range of the rats at the start of the resting period is 250-270 g.

On the day of administration the rats are fasted for 16 hours followed by subcutaneous injection of 100 µg per kg body weight of hG-CSF or a variant thereof. Each hG-CSF sample is injected into a group of 6 randomized rats. Blood samples of 300 µg EDTA stabilized blood are drawn from a tail vein of the rats prior to dosing and at 6, 12, 24, 36, 48, 72, 96, 120 and 144 hours after dosing. The blood samples are analyzed for the following hematological parameters: hemoglobin, red blood cell count, hematocrit, mean cell volume, mean cell hemoglobin concentration, mean cell hemoglobin, white blood cell count, differential leukocyte count (neutrophils, lymphocytes, eosinophils, basophils, monocytes). On the basis of these measurements the biological efficacy of conjugated and non-conjugated hG-CSF and variants thereof is evaluated.

Measurement of the In Vivo Biological Activity in Rats with Chemotherapy-Induced Neutropenia of Conjugated and Non-Conjugated hG-CSF and Variants Thereof.

SPF Sprague Dawley rats are utilized for this analysis. On the day of arrival the rats are randomly allocated into groups of 6. The animals are rested for a period of 7 days wherein individuals in poor condition or at extreme weights are rejected. The weight range of the rats at the start of the resting period is 250-270 g.

24 hours before administration of the hG-CSF samples the rats are injected i.p. with 50 mg per kg body weight of cyclophosphamide (CPA) to induce neutropenia that mimics neutropenia resulting from anti-cancer chemotherapy. At day 0, 100 µg per kg body weight of hG-CSF or a variant thereof is injected s.c. Each hG-CSF sample is injected into a group of 6 randomized rats. Blood samples of 300 µl EDTA stabilized blood are drawn from a tail vein of the rats prior to dosing and at 6, 12, 24, 36, 48, 72, 96, 120, 144 and 168 hours after dosing. The blood samples are analyzed for the following hematological parameters: hemoglobin, red blood cell count, hematocrit, mean cell volume, mean cell hemoglobin concentration, mean cell hemoglobin, white blood cell count, differential leukocyte count (neutrophils, lymphocytes, cosinophils, basophils, monocytes). On the basis of these measurements the biological efficacy of conjugated and non-conjugated hG-CSF and variants thereof is evaluated.

Example 39

Human Clinical Trial of the Safety and/or Efficacy of PEGylated hG-CSF Comprising a Non-Naturally Encoded Amino Acid Objective To compare the safety and pharmacokinetics of subcutaneously administered PEGylated recombinant human hG-CSF comprising a non-naturally encoded amino acid with the commercially available hG-CSF products NEULASTA® or NEUPOGEN®.

Patients

Eighteen healthy volunteers ranging between 20-40 years of age and weighing between 60-90 kg are enrolled in the study. The subjects will have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to hG-CSF within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design

This will be a Phase I, single-center, open-label, randomized, two-period crossover study in healthy male volunteers. Eighteen subjects are randomly assigned to one of two treatment sequence groups (nine subjects/group). G-CSF is administered over two separate dosing periods as a bolus s.c. injection in the upper thigh using equivalent doses of the PEGylated hG-CSF comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated hG-CSF as well. Multiple formulations of G-CSF that are approved for human use may be used in this study. Filgrastim marketed as NEUPOGEN® and/or pegfilgrastim marketed as NEULASTA® are commercially available G-CSF products approved for human use. The experimental formulation of hG-CSF is the PEGylated hG-CSF comprising a non-naturally encoded amino acid.

Blood Sampling

Serial blood is drawn by direct vein puncture before and after administration of hG-CSF. Venous blood samples (5 mL) for determination of serum G-CSF concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods

An ELISA kit procedure (BioSource International (Camarillo, Calif.)), is used for the determination of serum G-CSF concentrations.

Safety Determinations

Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis

Post-dose serum concentration values are corrected for pre-dose baseline G-CSF concentrations by subtracting from each of the post-dose values the mean baseline G-CSF concentration determined from averaging the G-CSF levels from the three samples collected at 30, 20, and 10 minutes before dosing. Pre-dose serum G-CSF concentrations are not included in the calculation of the mean value if they are below the quantification level of the assay. Pharmacokinetic parameters are determined from serum concentration data corrected for baseline G-CSF concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results

The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appear similar.

Pharmacokinetic Results

Mean serum G-CSF concentration-time profiles (uncorrected for baseline G-CSF levels) in all 18 subjects after receiving a single dose of commercially available hG-CSF (NEUPOGEN® or NEULASTA®) are compared to the PEGylated hG-CSF comprising a non-naturally encoded amino acid at each time point measured. All subjects should have pre-dose baseline G-CSF concentrations within the normal physiologic range. Pharmacokinetic parameters are determined from serum data corrected for pre-dose mean baseline G-CSF concentrations and the $C_{max}$ and $t_{max}$ are determined. The mean $t_{max}$ for hG-CSF (NEUPOGEN®) is significantly shorter than the $t_{max}$ for the PEGylated hG-CSF comprising the non-naturally encoded amino acid. Terminal half-life values are significantly shorter for hG-CSF (NEUPOGEN®) compared with the terminal half-life for the PEGylated hG-CSF comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of PEGylated hG-CSF comprising non-naturally encoded amino acid will be safe and well tolerated by healthy male subjects. Based on a comparative incidence of adverse events, clinical laboratory values, vital signs, and physical examination results, the safety profiles of hG-CSF (NEUPOGEN®) and PEGylated hG-CSF comprising non-naturally encoded amino acid will be equivalent. The PEGylated hG-CSF comprising non-naturally encoded amino acid potentially provides large clinical utility to patients and health care providers.

Example 40

This example describes one of the many potential sets of criteria for the selection of preferred sites of incorporation of non-naturally encoded amino acids into hEPO.

This example demonstrates how preferred sites within the hEPO polypeptide were selected for introduction of a non-naturally encoded amino acid. The crystal structure 1CN4 composed of hEPO (with site mutations including 24, 38, 83) complexed with two molecules of the extracellular domain of receptor (hEPObp), was used to determine preferred positions into which one or more non-naturally encoded amino acids could be introduced. Other hEPO structures (including but not limited to 1EER (mutations at 24, 28, 83, 121, 122) and 1BUY) were utilized to examine potential variation of primary, secondary, or tertiary structural elements between crystal structure datasets. The coordinates for these structures are available from the Protein Data Bank (PDB) (Bernstein et al. *J. Mol. Biol.* 1997, 112, pp 535) or via The Research Collaboratory for Structural Bioinformatics PDB available on the World Wide Web at rcsb.org. The structural model 1CN4 contains the entire mature 18 kDa sequence of hEPO with the exception of residues 124-130, the N-terminal A1, and the C-terminal T163, G164, D165, and R166 residues which were omitted due to disorder in the crystal. Two disulfide bridges are present, formed by C7 and C161 and C29 and C33.

Sequence numbering used in this example is according to the amino acid sequence of mature hEPO (18 kDa variant) shown in SEQ ID NO: 38.

The following criteria were used to evaluate each position of hEPO for the introduction of a non-naturally encoded amino acid: the residue (a) should not interfere with binding of either hEPObp based on structural analysis of 1CN4, 1EER, and 1BUY (crystallographic structures of hEPO conjugated with hEPObp), b) should not be affected by alanine scanning mutagenesis (Bittorf, T. et al. *FEBS,* 336:133-136 (1993), Wen, D., et al. *JBC,* 269:22839-22846 (1994), and Elliott, S. et al. *Blood,* 89:493-502 (1997), (c) should be surface exposed and exhibit minimal van der Waals or hydrogen bonding interactions with surrounding residues, (d) should be either deleted or variable in hEPO variants (Bittorf, T. et al. *FEBS,* 336:133-136 (1993), Wen, D., et al. *JBC,* 269:22839-22846 (1994), (e) would result in conservative changes upon substitution with a non-naturally encoded amino acid and (f) could be found in either highly flexible regions (including but not limited to CD loop) or structurally rigid regions (including but not limited to Helix B). In addition, further calculations were performed on the hEPO molecule, utilizing the Cx program (Pintar et al. *Bioinformatics,* 18, pp 980) to evaluate the extent of protrusion for each protein atom. As a result, in some embodiments, one or more non-naturally encoded encoded amino acid is incorporated at, but not limited to, one or more of the following positions of hEPO: before position 1 (i.e. at the N terminus), 1, 2, 3, 4, 5, 6, 8, 9, 10, 11, 14, 15, 16, 17, 18, 20, 21, 23, 24, 25, 26, 27, 28, 30, 31, 32, 34, 35, 36, 37, 38, 39, 40, 43, 44, 45, 46, 47, 48, 49, 50, 51, 52, 53, 54, 55, 56, 57, 58, 65, 68, 72, 75, 76, 77, 78, 79, 80, 82, 83, 84, 85, 86, 87, 88, 89, 90, 91, 92, 93, 96, 97, 99, 100, 103, 104, 107, 108, 110, 111, 113, 114, 115, 116, 117, 118, 119, 120, 121, 122, 123, 124, 125, 126, 127, 128, 129, 130, 131, 132, 133, 134, 136, 140, 143, 144, 146, 147, 150, 154, 155, 157, 158, 159, 160, 162, 163, 164, 165, 166, 167 (i.e. at the carboxyl terminus), or combinations thereof (SEQ ID NO: 38 or the corresponding amino acids in SEQ ID NO: 37 or 39).

A subset of exemplary sites for incorporation of one or more non-naturally encoded amino acid include, but are not limited to, 1, 2, 4, 9, 17, 20, 21, 24, 25, 27, 28, 30, 31, 32, 34, 36, 37, 38, 40, 50, 53, 55, 58, 65, 68, 72, 76, 79, 80, 82, 83, 85, 86, 87, 89, 113, 115, 116, 119, 120, 121, 122, 123, 124, 125, 126, 127, 128, 129, 130, 131, 132, 134, 136, 159, 162, 163, 164, 165, and 166 in EPO (SEQ ID NO: 38 or the corresponding amino acids in SEQ ID NO: 37 or 39). Exemplary positions for incorporation of one or more non-naturally encoded amino acid include 21, 24, 28, 30, 31, 36, 37, 38, 55, 72, 83, 85, 86, 87, 89, 113, 116, 119, 120, 121, 123, 124, 125, 126, 127, 128, 129, 130, 162, 163, 164, 165, and 166 in EPO (SEQ ID NO: 38 or the corresponding amino acids in SEQ ID NO: 37 or 39).

In some embodiments, the non-naturally occurring amino acid at one or more of these positions is linked to a water soluble polymer, including but not limited to, positions: before position 1 (i.e. at the N terminus), 1, 2, 3, 4, 5, 6, 8, 9, 10, 11, 14, 15, 16, 17, 18, 20, 21, 23, 24, 25, 26, 27, 28, 30, 31, 32, 34, 35, 36, 37, 38, 39, 40, 43, 44, 45, 46, 47, 48, 49, 50, 51, 52, 53, 54, 55, 56, 57, 58, 65, 68, 72, 75, 76, 77, 78, 79, 80, 82, 83, 84, 85, 86, 87, 88, 89, 90, 91, 92, 93, 96, 97, 99, 100, 103, 104, 107, 108, 110, 111, 113, 114, 115, 116, 117, 118, 119, 120, 121, 122, 123, 124, 125, 126, 127, 128, 129, 130, 131, 132, 133, 134, 136, 140, 143, 144, 146, 147, 150, 154, 155, 157, 158, 159, 160, 162, 163, 164, 165, 166, 167 (i.e. at the carboxyl terminus) (SEQ ID NO: 38 or the corresponding amino acids in SEQ ID NO: 37 or 39). In some embodiments, one or more non-naturally occurring amino acids at these or other positions linked to a water soluble polymer, including but not limited to, positions 21, 24, 38, 83, 85, 86, 89, 116, 119, 121, 124, 125, 126, 127, and 128, or combination thereof (SEQ ID NO: 38 or the corresponding amino acids in SEQ ID NO: 37 or 39).

Some sites for generation of a hEPO antagonist include: 2, 3, 5, 8, 9, 10, 11, 14, 15, 16, 17, 18, 20, 23, 43, 44, 45, 46, 47, 48, 49, 50, 52, 75, 78, 93, 96, 97, 99, 100, 103, 104, 107, 108, 110, 131, 132, 133, 140, 143, 144, 146, 147, 150, 154, 155, 159, or any combination thereof (hEPO; SEQ ID NO: 38, or corresponding amino acids in SEQ ID NO: 37 or 39). These sites were chosen utilizing criteria (c)-(e) of the agonist design. The antagonist design may also include site-directed modifications of site 1 residues to increase binding affinity to hEPObp.

Example 41

This example details cloning and expression of a modified hEPO polypeptide in *E. coli.*

This example demonstrates how a hEPO polypeptide including a non-naturally encoded amino acid can be expressed in *E. coli.* Nucleotide sequences encoding hEPO were produced generally as described in Matthews et al., (1996) PNAS 93:9471-76. Fetal liver, adult liver, fetal kidney and adult kidney cDNA libraries were used as templates for cloning cDNA encoding fall length and mature hEPO, with fetal liver giving the best result. Primers used for cloning full length and mature hEPO were 5'cagttacatatgggagttcacgaatgtcctgcctgg3' SEQ ID NO: 44; and 5'cagttacatatgctccaccaagattaatctgtg3' SEQ ID NO: 45, respectively. The 3' primer sequence was 5'ctgcaactcgagtcatctgtcccctgtcctgcag3' SEQ ID NO: 46. The reaction conditions for the cloning were 94° C. for two minutes, with 30 cycles of 94° C. for 30 seconds, 50° C. for one minute, 72° C. for 2 minutes, and 72° C. for 7 minutes, followed by 4° C. reaction termination. Three molecules were identified as encoding the full length hEPO, the mature form of hEPO lacking the N-terminal signal sequence, and a variant of the mature form of hEPO, each shown in SEQ ID NO: 40; SEQ ID NO: 41; and SEQ ID NO: 42, respectively. The full length and mature hEPO encoding cDNA was inserted into both the pBAD HISc, and pET20b expression vectors following optimization of the sequence for cloning and expression without altering amino acid sequence (SEQ ID NO: 43).

An introduced translation system that comprises an orthogonal tRNA (O-tRNA) and an orthogonal aminoacyl tRNA synthetase (O—RS) is used to express hG-CSF containing a non-naturally encoded amino acid, as described in Example 2 for hGH expression.

Example 42

In Vitro and In Vivo Activity of PEGylated hEPO Determined by the Normocythaemic Mouse Assay PEG-hEPO, unmodified hEPO and buffer solution are administered to mice. The results will show superior activity and prolonged half life of the PEGylated hEPO of the present invention compared to unmodified hEPO which is indicated by significantly increased amounts of reticulocytes and a shift of reticulocyte count maximum using the same dose per mouse.

The normocythaemic mouse bioassay is known in the art (Pharm. Europa Spec. Issue Erythropoietin BRP Bio 1997 (2)). The samples are diluted with BSA-PBS. Normal healthy mice, 7-15 weeks old, are administered s.c. 0.2 ml of PEGylated hEPO of the present invention. Over a period of 4 days starting 72 hours after the administration, blood is drawn by puncture of the tail vein and diluted such that 1 μl of blood was present in 1 ml of an 0.15 μmol acridine orange staining solution. The staining time is 3 to 10 minutes. The reticulocyte counts are carried out microfluorometrically in a flow cytometer by analysis of the red fluorescence histogram (per 30,000 blood cells analyzed). Each investigated group consists of 5 mice per day, and the mice are bled only once.

Bioassay

In addition, hEPO polypeptides of the present invention are evaluated with respect to in vitro biological activity using an hEPO receptor binding assay and a cell proliferation assay in which bioactivity is determined by Ba/F3-huhEPOR cell proliferation. The protocol for each assay is described in Wrighton et al. (1997) Nature Biotechnology 15:1261-1265, and in U.S. Pat. Nos. 5,773,569 and 5,830,851. $EC_{50}$ values for the hEPO polypeptides prepared according to this invention are the concentration of compound required to produce 50% of the maximal activity obtained with recombinant erythropoietin.

Example 43

Human Clinical Trial of the Safety and/or Efficacy of PEGylated hEPO Comprising a Non-Naturally Encoded Amino Acid Objective To compare the safety and pharmacokinetics of subcutaneously administered PEGylated recombinant human hEPO comprising a non-naturally encoded amino acid with the commercially available hEPO product PROCRIT® or ARANESP®.

Patients

Eighteen healthy volunteers ranging in age between 20-40 years of age and weighed between 60-90 kg are enrolled in this study. The subjects have no clinically significant abnormal laboratory values for hematology or serum chemistry, and a negative urine toxicology screen, HIV screen, and hepatitis B surface antigen. They should not have any evidence of the following: hypertension; a history of any primary hematologic disease; history of significant hepatic, renal, cardiovascular, gastrointestinal, genitourinary, metabolic, neurologic disease; a history of anemia or seizure disorder; a known sensitivity to bacterial or mammalian-derived products, PEG, or human serum albumin; habitual and heavy consumer to beverages containing caffeine; participation in any other clinical trial or had blood transfused or donated within 30 days of study entry; had exposure to hEPO within three months of study entry; had an illness within seven days of study entry; and have significant abnormalities on the pre-study physical examination or the clinical laboratory evaluations within 14 days of study entry. All subjects are evaluable for safety and all blood collections for pharmacokinetic analysis are collected as scheduled. All studies are performed with institutional ethics committee approval and patient consent.

Study Design

This is a Phase I, single-center, open-label, randomized, two-period crossover study in healthy male volunteers. Eighteen subjects are randomly assigned to one of two treatment sequence groups (nine subjects/group). EPO is administered over two separate dosing periods as a bolus s.c. injection in the upper thigh using equivalent doses of the PEGylated hEPO comprising a non-naturally encoded amino acid and the commercially available product chosen. The dose and frequency of administration of the commercially available product is as instructed in the package label. Additional dosing, dosing frequency, or other parameter as desired, using the commercially available products may be added to the study by including additional groups of subjects. Each dosing period is separated by a 14-day washout period. Subjects are confined to the study center at least 12 hours prior to and 72 hours following dosing for each of the two dosing periods, but not between dosing periods. Additional groups of subjects may be added if there are to be additional dosing, frequency, or other parameter, to be tested for the PEGylated hEPO as well. Multiple formulations of EPO that are approved for human use may be used in this study. Epoetin alfa marketed as PROCRIT® and/or darbepoitein marketed as ARANESP® are commercially available EPO products approved for human use. The experimental formulation of hEPO is the PEGylated hEPO comprising a non-naturally encoded amino acid.

Blood Sampling

Serial blood is drawn by direct vein puncture before and after administration of EPO. Venous blood samples (5 mL) for determination of serum erythropoietin concentrations are obtained at about 30, 20, and 10 minutes prior to dosing (3 baseline samples) and at approximately the following times after dosing: 30 minutes and at 1, 2, 5, 8, 12, 15, 18, 24, 30, 36, 48, 60 and 72 hours. Each serum sample is divided into two aliquots. All serum samples are stored at −20° C. Serum samples are shipped on dry ice. Fasting clinical laboratory tests (hematology, serum chemistry, and urinalysis) are performed immediately prior to the initial dose on day 1, the morning of day 4, immediately prior to dosing on day 16, and the morning of day 19.

Bioanalytical Methods

A radioimmunoassay (RIA) kit procedure (Diagnostic Systems Laboratory [DSL], Webster Tex.), is used for the determination of serum erythropoietin concentrations. The commercially available RIA is a double-antibody, competitive method that uses a rabbit polyclonal antiserum to human urinary erythropoietin as the primary antibody and an $^{125}$I-labeled human urinary erythropoietin as the tracer. Epoetin alfa or darbepoietin is substituted for urinary erythropoietin provided in the DSL kit, in standards and quality control samples. Standard concentrations used in the assay are 7.8, 15.6, 31.3, 50, 62.5, 100, and 125 mIU/mL. Sensitivity, defined as the mean back-fit value for the lowest standard giving acceptable precision, is 8.6 mIU/mL, and the assay range is extended to 2,000 mIU/mL through quality control dilutions.

Safety Determinations

Vital signs are recorded immediately prior to each dosing (Days 1 and 16), and at 6, 24, 48, and 72 hours after each dosing. Safety determinations are based on the incidence and type of adverse events and the changes in clinical laboratory tests from baseline. In addition, changes from pre-study in vital sign measurements, including blood pressure, and physical examination results are evaluated.

Data Analysis

Post-dose serum concentration values are corrected for pre-dose baseline erythropoietin concentrations by subtracting from each of the post-dose values the mean baseline erythropoietin concentration determined from averaging the erythropoietin levels from the three samples collected at 30, 20, and 10 minutes before dosing. Pre-dose serum erythropoietin concentrations are not included in the calculation of the mean value if they are below the quantification level of the assay. Pharmacokinetic parameters are determined from serum concentration data corrected for baseline erythropoietin concentrations. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Safety Results

The incidence of adverse events is equally distributed across the treatment groups. There are no clinically significant changes from baseline or pre-study clinical laboratory tests or blood pressures, and no notable changes from pre-study in physical examination results and vital sign measurements. The safety profiles for the two treatment groups should appeared similar.

Pharmacokinetic Results

Mean serum erythropoietin concentration-time profiles (uncorrected for baseline erythropoietin levels) in all 18 subjects after receiving a single dose of commercially available hEPO (PROCRIT® or ARANESP®) are compared to the PEGylated hEPO comprising a non-naturally encoded amino acid at each time point measured. All subjects should have pre-dose baseline erythropoietin concentrations within the normal physiologic range. Pharmacokinetic parameters are determined from serum data corrected for pre-dose mean baseline erythropoietin concentrations and the $C_{max}$ and $t_{max}$ are determined. The mean $t_{max}$ for hEPO (PROCRIT®) is significantly shorter than the $t_{max}$ for the PEGylated hEPO comprising the non-naturally encoded amino acid. Terminal half-life values are significantly shorter for hEPO (PROCRIT®) compared with the terminal half-life for the PEGylated hEPO comprising a non-naturally encoded amino acid.

Although the present study is conducted in healthy male subjects, similar absorption characteristics and safety profiles would be anticipated in other patient populations; such as male or female patients with cancer or chronic renal failure, pediatric renal failure patients, patients in autologous predeposit programs, or patients scheduled for elective surgery.

In conclusion, subcutaneously administered single doses of PEGylated hEPO comprising non-naturally encoded amino acid are safe and well tolerated by healthy male subjects. Based on a comparative incidence of adverse events, clinical laboratory values, vital signs, and physical examination results, the safety profiles of hEPO (PROCRIT®) and PEGylated hEPO comprising non-naturally encoded amino acid are equivalent. The PEGylated hEPO comprising non-naturally encoded amino acid potentially provides large clinical utility to patients and health care providers.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference herein in their entirety for all purposes.

TABLE 8

4 Helical Bundle Sequences Cited.

| SEQ ID # | Sequence Name |
|---|---|
| 1 | Full-length amino acid sequence of hGH |
| 2 | The mature amino acid sequence of hGH (isoform 1) |
| 3 | The 20-kDa hGH variant in which residues 32-46 of hGH are deleted |
| 21 | Nucleotide Sequence for full length hGH |
| 22 | Nucleotide Sequence for mature hGH |
| 23 | Full-length amino acid sequence of hIFN |
| 24 | The mature amino acid sequence of hIFN |
| 25 | The mature amino acid sequence of consensus hIFN |
| 26 | Nucleotide Sequence of full length hIFN |
| 27 | Nucleotide sequence of mature hIFN cDNA |
| 28 | Full-length amino acid sequence of hG-CSF |
| 29 | The mature amino acid sequence of hG-CSF Splice variant missing V66, S67, and E68, having N-terminal M |
| 30 | Full Length Splice variant missing V66, S67, and E68 of the full length protein |
| 31 | Nucleotide Sequence of full length hG-CSF |
| 32 | Nucleotide sequence of mature hG-CSF cDNA |
| 33 | Nucleotide sequence of mature hG-CSF cDNA splice variant missing V66, S67, and E68 |

TABLE 8-continued

4 Helical Bundle Sequences Cited.

| SEQ ID # | Sequence Name |
|---|---|
| 34 | Nucleotide Sequence for Mature form splice variant missing V66, S67, and E68, Optimized for expression of mature hG-CSF cDNA in E. coli |
| 35 | VARIANT 157 L -> M (in dbSNP: 2227329) |
| 36 | VARIANT 174 A -> T (in dbSNP: 2227330) |
| 37 | Full-length amino acid sequence of hEPO |
| 38 | The mature amino acid sequence of hEPO |
| 39 | SNP variant (G113R) of the mature amino acid sequence of hEPO |
| 40 | Nucleotide sequence of full length hEPO cDNA |
| 41 | Nucleotide sequence of mature hEPO cDNA |
| 42 | Nucleotide sequence of G113R hEPO cDNA |
| 43 | Optimized for expression of mature hEPO cDNA in E. coli |
| 44 | 5' Primer for cloning full length hEPO cDNA |
| 45 | 5' Primer for cloning mature hEPO cDNA |
| 46 | 3' Primer for cloning full length and mature hEPO cDNA |

What is claimed is:

1. An isolated four helical bundle (4HB) polypeptide chosen from the group consisting of human growth hormone, interferon, erythropoietin, and granulocyte cell stimulating factor, comprising a ribosomally incorporated para-acetyl-phenylalanine within the C-D loop of the 4HB polypeptide, wherein the 4HB polypeptide with para-acetyl-phenylalanine has at least a 2-fold increased serum half-life over the wild type 4HB polypeptide.

2. The 4HB polypeptide of claim 1, wherein the 4HB polypeptide further comprises an amino acid substitution made within the N-terminus, C-terminus, A-B loop, B-C loop, C-D loop or, when present, the E helix or D-E loop.

3. The 4HB polypeptide of claim 1, wherein the 4HB polypeptide further comprises an amino acid substitution, addition or deletion that modulates affinity of the 4HB polypeptide for a 4HB receptor.

4. The 4HB polypeptide of claim 1, wherein the 4HB polypeptide further comprises an amino acid substitution, addition or deletion that increases the stability or solubility of the 4HB polypeptide.

5. The 4HB polypeptide of claim 1, wherein the 4HB polypeptide further comprises an amino acid substitution, addition or deletion that increases the expression of the 4HB polypeptide in a recombinant host cell or increases synthesis of the 4HB polypeptide in vitro.

6. The 41-1B polypeptide of claim 1, wherein the 4HB polypeptide further comprises an amino acid substitution, addition or deletion that increases protease resistance of the 4HB polypeptide.

7. The 4HB polypeptide of claim 1, wherein the non-naturally encoded amino acid includes a side chain functional group that reacts selectively with a linker, polymer, or biologically active molecule.

8. The 4HB polypeptide of claim 1, wherein the non-naturally encoded amino acid comprises a carbonyl group.

9. The 4HB polypeptide of claim 1, wherein the 4HB polypeptide comprises one or more post-translational modifications.

10. The 4HB polypeptide of claim 1, wherein the 4HB polypeptide is linked to a linker, polymer, or biologically active molecule.

11. The 4HB polypeptide of claim 10, wherein the 4HB polypeptide is linked to a water soluble polymer.

12. The 4HB polypeptide of claim 1, wherein the 4HB polypeptide is linked to a multifunctional polymer, bifunctional linker, or at least one additional 4HB polypeptide.

13. The 4HB polypeptide of claim 12, wherein the bifunctional linker or bifunctional polymer is linked to a second polypeptide.

14. The 4HB polypeptide of claim 13, wherein the second polypeptide is a 4HB polypeptide.

15. The 4HB polypeptide of claim 11, wherein the water soluble polymer comprises a poly (ethylene glycol) moiety.

16. The 4HB polypeptide of claim 11, wherein said water soluble polymer is linked to a non-naturally encoded amino acid present in said 4HB polypeptide.

17. The 4HB polypeptide of claim 1, wherein the 4HB polypeptide further comprises one or more free amide or free sulfhydryl groups.

18. The 4HB polypeptide of claim 17, wherein the free amide or free sulfhydryl groups are present in naturally occurring amino acids.

* * * * *

SEQUENCE LISTING

```
<160> NUMBER OF SEQ ID NOS: 46

<210> SEQ ID NO 1
<211> LENGTH: 217
<212> TYPE: PRT
<213> ORGANISM: Homo sapiens

<400> SEQUENCE: 1

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 2
<211> LENGTH: 191
<212> TYPE: PRT
<213> ORGANISM: Homo sapiens

<400> SEQUENCE: 2
```

```
Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
 50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
            130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 3
<211> LENGTH: 176
<212> TYPE: PRT
<213> ORGANISM: Homo sapiens

<400> SEQUENCE: 3

Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Asn
            20                  25                  30

Pro Gln Thr Ser Leu Cys Phe Ser Glu Ser Ile Pro Thr Pro Ser Asn
            35                  40                  45

Arg Glu Glu Thr Gln Gln Lys Ser Asn Leu Glu Leu Leu Arg Ile Ser
 50                  55                  60

Leu Leu Leu Ile Gln Ser Trp Leu Glu Pro Val Gln Phe Leu Arg Ser
 65                  70                  75                  80

Val Phe Ala Asn Ser Leu Val Tyr Gly Ala Ser Asp Ser Asn Val Tyr
                85                  90                  95

Asp Leu Leu Lys Asp Leu Glu Glu Gly Ile Gln Thr Leu Met Gly Arg
            100                 105                 110

Leu Glu Asp Gly Ser Pro Arg Thr Gly Gln Ile Phe Lys Gln Thr Tyr
            115                 120                 125

Ser Lys Phe Asp Thr Asn Ser His Asn Asp Asp Ala Leu Leu Lys Asn
            130                 135                 140

Tyr Gly Leu Leu Tyr Cys Phe Arg Lys Asp Met Asp Lys Val Glu Thr
145                 150                 155                 160

Phe Leu Arg Ile Val Gln Cys Arg Ser Val Glu Gly Ser Cys Gly Phe
                165                 170                 175

<210> SEQ ID NO 4
```

```
<211> LENGTH: 77
<212> TYPE: DNA
<213> ORGANISM: Methanococcus jannaschii

<400> SEQUENCE: 4
ccggcggtag ttcagcaggg cagaacggcg gactctaaat ccgcatggcg ctggttcaaa      60
tccggcccgc cggacca                                                    77

<210> SEQ ID NO 5
<211> LENGTH: 88
<212> TYPE: DNA
<213> ORGANISM: Halobacterium sp. NRC-1

<400> SEQUENCE: 5
cccagggtag ccaagctcgg ccaacggcga cggactctaa atccgttctc gtaggagttc      60
gagggttcga tcccttccc tgggacca                                         88

<210> SEQ ID NO 6
<211> LENGTH: 89
<212> TYPE: DNA
<213> ORGANISM: Halobacterium sp. NRC-1

<400> SEQUENCE: 6
gcgagggtag ccaagctcgg ccaacggcga cggacttcct aatccgttct cgtaggagtt     60
cgagggttcg aatccctccc ctcgcacca                                       89

<210> SEQ ID NO 7
<211> LENGTH: 306
<212> TYPE: PRT
<213> ORGANISM: Methanococcus jannaschii

<400> SEQUENCE: 7
```

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser

```
            195                 200                 205
Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                    245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
290                 295                 300

Arg Leu
305

<210> SEQ ID NO 8
<211> LENGTH: 306
<212> TYPE: PRT
<213> ORGANISM: Methanococcus jannaschii

<400> SEQUENCE: 8

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Thr Ser His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                    245                 250                 255
```

```
Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 9
<211> LENGTH: 305
<212> TYPE: PRT
<213> ORGANISM: Methanococcus jannaschii

<400> SEQUENCE: 9

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305
```

<210> SEQ ID NO 10
<211> LENGTH: 305
<212> TYPE: PRT
<213> ORGANISM: Methanococcus jannaschii

<400> SEQUENCE: 10

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ile Pro Tyr
145                 150                 155                 160

Leu Pro Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
        195                 200                 205

Gly Asn Phe Ile Ala Val Asp Asp Ser Pro Glu Glu Ile Arg Ala Lys
    210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
        275                 280                 285

Ala Val Ala Glu Glu Leu Ile Lys Ile Leu Glu Pro Ile Arg Lys Arg
    290                 295                 300

Leu
305

<210> SEQ ID NO 11
<211> LENGTH: 305
<212> TYPE: PRT
<213> ORGANISM: Methanococcus jannaschii

<400> SEQUENCE: 11

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Lys Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Ala Ile Tyr
145                 150                 155                 160

Leu Ala Val Asp Val Ala Val Gly Gly Met Glu Gln Arg Lys Ile His
                165                 170                 175

Met Leu Ala Arg Glu Leu Leu Pro Lys Lys Val Val Cys Ile His Asn
            180                 185                 190

Pro Val Leu Thr Gly Leu Asp Gly Glu Gly Lys Met Ser Ser Ser Lys
            195                 200                 205

Gly Asn Phe Ile Ala Val Asp Asp Ser Pro Glu Glu Ile Arg Ala Lys
210                 215                 220

Ile Lys Lys Ala Tyr Cys Pro Ala Gly Val Val Glu Gly Asn Pro Ile
225                 230                 235                 240

Met Glu Ile Ala Lys Tyr Phe Leu Glu Tyr Pro Leu Thr Ile Lys Arg
                245                 250                 255

Pro Glu Lys Phe Gly Gly Asp Leu Thr Val Asn Ser Tyr Glu Glu Leu
            260                 265                 270

Glu Ser Leu Phe Lys Asn Lys Glu Leu His Pro Met Asp Leu Lys Asn
            275                 280                 285

Ala Val Ala Glu Glu Leu Ile Lys Ile Leu Glu Pro Ile Arg Lys Arg
290                 295                 300

Leu
305

<210> SEQ ID NO 12
<211> LENGTH: 306
<212> TYPE: PRT
<213> ORGANISM: Methanococcus jannaschii

<400> SEQUENCE: 12

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp

```
                65                  70                  75                  80
Glu Ile Arg Lys Ile Gly Asp Tyr Asn Lys Lys Val Phe Glu Ala Met
                    85                  90                  95
Gly Leu Lys Ala Lys Tyr Val Tyr Gly Ser Asn Phe Gln Leu Asp Lys
                100                 105                 110
Asp Tyr Thr Leu Asn Val Tyr Arg Leu Ala Leu Lys Thr Leu Lys
                115                 120                 125
Arg Ala Arg Arg Ser Met Glu Leu Ile Ala Arg Glu Asp Asn Pro
130                 135                 140
Lys Val Ala Glu Val Ile Tyr Pro Ile Met Gln Val Asn Pro Leu His
145                 150                 155                 160
Tyr Gln Gly Val Asp Val Ala Val Gly Gly Met Glu Gln Arg Lys Ile
                165                 170                 175
His Met Leu Ala Arg Glu Leu Leu Pro Lys Val Val Cys Ile His
                180                 185                 190
Asn Pro Val Leu Thr Gly Leu Asp Gly Glu Gly Lys Met Ser Ser Ser
                195                 200                 205
Lys Gly Asn Phe Ile Ala Val Asp Asp Ser Pro Glu Glu Ile Arg Ala
                210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
                260                 265                 270
Leu Glu Ser Leu Phe Lys Asn Lys Glu Leu His Pro Met Asp Leu Lys
                275                 280                 285
Asn Ala Val Ala Glu Glu Leu Ile Lys Ile Leu Glu Pro Ile Arg Lys
                290                 295                 300
Arg Leu
305

<210> SEQ ID NO 13
<211> LENGTH: 306
<212> TYPE: PRT
<213> ORGANISM: Methanococcus jannaschii

<400> SEQUENCE: 13

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Thr
                20                  25                  30
Ile Gly Phe Glu Pro Ser Gly Lys Ile His Leu Gly His Tyr Leu Gln
                35                  40                  45
Ile Lys Lys Met Ile Asp Leu Gln Asn Ala Gly Phe Asp Ile Ile Ile
            50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                    85                  90                  95
Gly Leu Lys Ala Lys Tyr Val Tyr Gly Ser Ser Phe Gln Leu Asp Lys
                100                 105                 110
Asp Tyr Thr Leu Asn Val Tyr Arg Leu Ala Leu Lys Thr Thr Leu Lys
                115                 120                 125
```

```
Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
    290                 295                 300

Arg Leu
305

<210> SEQ ID NO 14
<211> LENGTH: 306
<212> TYPE: PRT
<213> ORGANISM: Methanococcus jannaschii

<400> SEQUENCE: 14

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Val His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190
```

```
Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu
        260                 265                 270

Leu Glu Ser Leu Phe Lys Asn Lys Glu Leu His Pro Met Asp Leu Lys
                275                 280                 285

Asn Ala Val Ala Glu Glu Leu Ile Lys Ile Leu Glu Pro Ile Arg Lys
    290                 295                 300

Arg Leu
305
```

<210> SEQ ID NO 15
<211> LENGTH: 306
<212> TYPE: PRT
<213> ORGANISM: Methanococcus jannaschii

<400> SEQUENCE: 15

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ser His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
```

```
                    245                 250                 255
Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 16
<211> LENGTH: 306
<212> TYPE: PRT
<213> ORGANISM: Methanococcus jannaschii

<400> SEQUENCE: 16

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300
```

Arg Leu
305

<210> SEQ ID NO 17
<211> LENGTH: 306
<212> TYPE: PRT
<213> ORGANISM: Methanococcus jannaschii

<400> SEQUENCE: 17

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Thr His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 18
<211> LENGTH: 306
<212> TYPE: PRT
<213> ORGANISM: Methanococcus jannaschii

<400> SEQUENCE: 18

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Gly His
145                 150                 155                 160

Tyr Leu Gly Val Asp Val Ile Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
            275                 280                 285

Asn Ala Val Ala Glu Glu Leu Ile Lys Ile Leu Glu Pro Ile Arg Lys
290                 295                 300

Arg Leu
305

<210> SEQ ID NO 19
<211> LENGTH: 306
<212> TYPE: PRT
<213> ORGANISM: Methanococcus jannaschii

<400> SEQUENCE: 19

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
50                  55                  60
```

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
            85                  90                  95

Gly Leu Lys Ala Lys Tyr Val Tyr Gly Ser Arg Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Val Ile His
145                 150                 155                 160

Tyr Asp Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 20
<211> LENGTH: 306
<212> TYPE: PRT
<213> ORGANISM: Methanococcus jannaschii

<400> SEQUENCE: 20

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gly
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
            85                  90                  95

Gly Leu Lys Ala Lys Tyr Val Tyr Gly Ser Thr Phe Gln Leu Asp Lys
            100                 105                 110

Asp Tyr Thr Leu Asn Val Tyr Arg Leu Ala Leu Lys Thr Thr Leu Lys

```
            115                 120                 125
Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Tyr Tyr
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 21
<211> LENGTH: 654
<212> TYPE: DNA
<213> ORGANISM: Homo sapiens

<400> SEQUENCE: 21
atggctacag gctcccggac gtccctgctc ctggcttttg gcctgctctg cctgccctgg    60
cttcaagagg gcagtgcctt cccaaccatt cccttatcca ggcttttga caacgctatg   120 ctccgcgccc atcgtctgca ccagctggcc tttgacacct accaggagtt tgaagaagcc   180
tatatcccaa aggaacagaa gtattcattc ctgcagaacc cccagacctc cctctgtttc   240
tcagagtcta ttccgacacc ctccaacagg gaggaaacac aacagaaatc caacctagag   300
ctgctccgca tctccctgct gctcatccag tcgtggctgg agcccgtgca gttcctcagg   360
agtgtcttcg ccaacagcct ggtgtacggc gcctctgaca gcaacgtcta tgacctccta   420
aaggacctag aggaaggcat ccaaacgctg atggggaggc tggaagatgg cagccccgg   480 actgggcaga tcttcaagca gacctacagc aagttcgaca caaactcaca caacgatgac   540
gcactactca gaactacgg gctgctctac tgcttcagga aggacatgga caaggtcgag   600
acattcctgc gcatcgtgca gtgccgctct gtggagggca gctgtggctt ctag         654

<210> SEQ ID NO 22
<211> LENGTH: 576
<212> TYPE: DNA
<213> ORGANISM: Homo sapiens

<400> SEQUENCE: 22
ttcccaacca tttcccttatc caggcttttt gacaacgcta tgctccgcgc ccatcgtctg    60
caccagctgg cctttgacac ctaccaggag tttgaagaag cctatatccc aaaggaacag   120
```

-continued

```
aagtattcat tcctgcagaa cccccagacc tccctctgtt tctcagagtc tattccgaca      180
ccctccaaca gggaggaaac acaacagaaa tccaacctag agctgctccg catctccctg      240
ctgctcatcc agtcgtggct ggagcccgtg cagttcctca ggagtgtctt cgccaacagc      300
ctggtgtacg gcgcctctga cagcaacgtc tatgacctcc taaaggacct agaggaaggc      360
atccaaacgc tgatggggag gctggaagat ggcagccccc ggactgggca gatcttcaag      420
cagacctaca gcaagttcga cacaaactca cacaacgatg acgcactact caagaactac      480
gggctgctct actgcttcag gaaggacatg gacaaggtcg agacattcct gcgcatcgtg      540
cagtgccgct ctgtggaggg cagctgtggc ttctag                               576
```

<210> SEQ ID NO 23
<211> LENGTH: 188
<212> TYPE: PRT
<213> ORGANISM: Homo sapiens

<400> SEQUENCE: 23

```
Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185
```

<210> SEQ ID NO 24
<211> LENGTH: 165
<212> TYPE: PRT
<213> ORGANISM: Homo sapiens

<400> SEQUENCE: 24

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
```

```
                     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                     85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
        130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 25
<211> LENGTH: 166
<212> TYPE: PRT
<213> ORGANISM: Homo sapiens

<400> SEQUENCE: 25

Cys Asp Leu Pro Gln Thr His Ser Leu Gly Asn Arg Arg Ala Leu Ile
  1               5                  10                  15

Leu Leu Ala Gln Met Arg Arg Ile Ser Pro Phe Ser Cys Leu Lys Asp
                 20                  25                  30

Arg His Asp Phe Gly Phe Pro Gln Glu Glu Phe Asp Gly Asn Gln Phe
             35                  40                  45

Gln Lys Ala Gln Ala Ile Ser Val Leu His Glu Met Ile Gln Gln Thr
         50                  55                  60

Phe Asn Leu Phe Ser Thr Lys Asp Ser Ser Ala Ala Trp Asp Glu Ser
 65                  70                  75                  80

Leu Leu Glu Lys Phe Tyr Thr Glu Leu Tyr Gln Gln Leu Asn Asp Leu
                 85                  90                  95

Glu Ala Cys Val Ile Gln Glu Val Gly Val Glu Thr Pro Leu Met
                100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Arg Leu Arg Arg Lys Glu
                165

<210> SEQ ID NO 26
<211> LENGTH: 567
<212> TYPE: DNA
<213> ORGANISM: Homo sapiens

<400> SEQUENCE: 26
atggccttga cctttgcttt actggtggcc tcctggtgc tcagctgcaa gtcaagctgc     60
tctgtgggct gtgatctgcc tcaaacccac agcctgggta gcaggaggac cttgatgctc    120
ctggcacaga tgaggagaat ctctcttttc tcctgcttga aggacagaca tgactttgga    180
tttccccagg aggagtttgg caaccagttc caaaaggctg aaaccatccc tgtcctccat    240
```

```
gagatgatcc agcagatctt caatctcttc agcacaaagg actcatctgc tgcttgggat      300
gagaccctcc tagacaaatt ctacactgaa ctctaccagc agctgaatga cctggaagcc      360
tgtgtgatac aggggtggg ggtgacagag actcccctga tgaaggagga ctccattctg      420
gctgtgagga aatacttcca aagaatcact ctctatctga aagagaagaa atacagccct      480
tgtgcctggg aggttgtcag agcagaaatc atgagatctt tttctttgtc aacaaacttg      540
caagaaagtt taagaagtaa ggaatga                                          567
```

<210> SEQ ID NO 27
<211> LENGTH: 498
<212> TYPE: DNA
<213> ORGANISM: Homo sapiens

<400> SEQUENCE: 27

```
tgtgatctgc ctcaaaccca cagcctgggt agcaggagga ccttgatgct cctggcacag       60
atgaggagaa tctctctttt ctcctgcttg aaggacagac atgactttgg atttccccag      120
gaggagtttg gcaaccagtt ccaaaaggct gaaaccatcc ctgtcctcca tgagatgatc      180
cagcagatct tcaatctctt cagcacaaag gactcatctg ctgcttggga tgagaccctc      240
ctagacaaat tctacactga actctaccag cagctgaatg acctggaagc ctgtgtgata      300 caggggtgg gggtgacaga gactcccctg atgaaggagg actccattct ggctgtgagg      360
aaatacttcc aaagaatcac tctctatctg aaagagaaga atacagccc ttgtgcctgg      420 gaggttgtca gcagaaat catgagatct ttttctttgt caacaaactt gcaagaaagt      480
ttaagaagta aggaatga                                                    498
```

<210> SEQ ID NO 28
<211> LENGTH: 207
<212> TYPE: PRT
<213> ORGANISM: Homo sapiens

<400> SEQUENCE: 28

```
Met Ala Gly Pro Ala Thr Gln Ser Pro Met Lys Leu Met Ala Leu Gln
1               5                  10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175
```

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 29
<211> LENGTH: 175
<212> TYPE: PRT
<213> ORGANISM: Homo sapiens

<400> SEQUENCE: 29

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 30
<211> LENGTH: 204
<212> TYPE: PRT
<213> ORGANISM: Homo sapiens

<400> SEQUENCE: 30

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

```
Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
            195                 200
```

```
<210> SEQ ID NO 31
<211> LENGTH: 624
<212> TYPE: DNA
<213> ORGANISM: Homo sapiens

<400> SEQUENCE: 31
atggctggac ctgccaccca gagccccatg aagctgatgg ccctgcagct gctgctgtgg      60
cacagtgcac tctggacagt gcaggaagcc acccccctgg ccctgccag ctccctgccc     120 cagagcttcc tgctcaagtg cttagagcaa gtgaggaaga tccagggcga tggcgcagcg     180
ctccaggaga agctggtgag tgagtgtgcc acctacaagc tgtgccaccc cgaggagctg     240
gtgctgctcg acactctct gggcatcccc tgggctcccc tgagcagctg ccccagccag     300
gccctgcagc tggcaggctg cttgagccaa ctccatagcg ccttttcct ctaccagggg     360 ctcctgcagg ccctggaagg gatctccccc gagttgggtc ccaccttgga cacactgcag     420
ctggacgtcg ccgactttgc caccaccatc tggcagcaga tggaagaact gggaatggcc     480
cctgccctgc agcccaccca gggtgccatg ccggccttcg cctctgcttt ccagcgccgg     540
gcaggagggg tcctggttgc ctcccatctg cagagcttcc tggaggtgtc gtaccgcgtt     600
ctacgccacc ttgcccagcc ctga                                             624

<210> SEQ ID NO 32
<211> LENGTH: 522
<212> TYPE: DNA
<213> ORGANISM: Homo sapiens

<400> SEQUENCE: 32
actccactgg gtccagcaag ctctctgccg cagtctttcc tgctgaagtc tctcgaacag      60
gtacgtaaaa ttcaaggcag cggtgcggct ctgcaggaaa agctgtgcgc aacctacaaa     120
ctgtgccacc ctgaggaact ggtgctgctc ggtcactctc tggggatccc gtgggctcca     180
ctgagctctt gcccgtccca agctttacaa ctggcaggct gcttgagcca gctgcactcc     240
ggtctgttcc tgtaccaggg tctgctgcag gctctagaag gcatctctcc tgaattgggg     300 cccacccctgg acacactgca gctggacgtt gccgacttcg ctactaccat atggcaacag     360
atggaggaac tgggtatggc tccggcactg cagccgactc agggtgcgat gccagcattc     420
gcctctgctt tccagcggcg cgcaggcggt gttctggttg cctcccatct tcagagcttc     480
ctcgaggtgt cttaccgcgt tctgcgtcac ctggcccagc cg                         522

<210> SEQ ID NO 33
<211> LENGTH: 615
<212> TYPE: DNA
<213> ORGANISM: Homo sapiens

<400> SEQUENCE: 33
```

```
atggctggac ctgccaccca gagccccatg aagctgatgg ccctgcagct gctgctgtgg      60
cacagtgcac tctggacagt gcaggaagcc accccctgg gccctgccag ctccctgccc     120
cagagcttcc tgctcaagtg cttagagcaa gtgaggaaga tccagggcga tggcgcagcg     180
ctccaggaga agctgtgtgc cacctacaag ctgtgccacc cgaggagct ggtgctgctc      240 ggacactctc tgggcatccc ctgggctccc tgagcagct gccccagcca ggccctgcag      300
ctggcaggct gcttgagcca actccatagc ggcttttcc tctaccaggg gctcctgcag      360
gccctggaag ggatctcccc cgagttgggt cccaccttgg acacactgca gctggacgtc      420
gccgactttg ccaccaccat ctggcagcag atggaagaac tgggaatggc ccctgccctg      480
cagcccaccc agggtgccat gccggccttc gcctctgctt tccagcgccg ggcaggaggg      540
gtcctggttg cctcccatct gcagagcttc ctggaggtgt cgtaccgcgt tctacgccac      600
cttgcccagc cctga                                                     615
```

<210> SEQ ID NO 34
<211> LENGTH: 522
<212> TYPE: DNA
<213> ORGANISM: Homo sapiens

<400> SEQUENCE: 34

```
acgcctctgg gtccggcgtc ttcgctgcca aatcgttct tgctcaaatc actggaacag       60
gtccgcaaaa tccaggggag cggcgcggcc cttcaggaaa aactgtgtgc cacatataaa     120
ctttgtcacc cggaagagct cgttttactg ggacatagtc tgggtattcc ttgggcaccg     180
ttaagctcat gtccttctca agcgctgcag ctggccggtt gtctgagcca actgcacagt     240
ggcctgtttc tatatcaagg cctcctacag gcgttggaag ggatttcgcc ggagcttggt     300
ccgactctgg ataccttaca attagatgtc gcggattttg cgaccactat ttggcaacaa     360
atggaggaac tgggcatggc accggctctg caacccacac aaggtgccat gccagccttc     420
gcgagcgcct tccagcgccg tgcaggcggc gttttggttg cgtctcatct gcagtccttt     480
cttgaggtca gctatcgcgt tctgcggcat ctggcccagc ca                        522
```

<210> SEQ ID NO 35
<211> LENGTH: 207
<212> TYPE: PRT
<213> ORGANISM: Homo sapiens

<400> SEQUENCE: 35

Met Ala Gly Pro Ala Thr Gln Ser Pro Met Lys Leu Met Ala Leu Gln
1               5                  10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile

```
                115                 120                 125
Ser Pro Glu Leu Gly Pro Thr Leu Asp Thr Leu Gln Leu Asp Val Ala
        130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
        180                 185                 190

Phe Leu Glu Val Ser Tyr Arg Val Leu Arg His Leu Ala Gln Pro
            195                 200                 205

<210> SEQ ID NO 36
<211> LENGTH: 207
<212> TYPE: PRT
<213> ORGANISM: Homo sapiens

<400> SEQUENCE: 36

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
                20                  25                  30

Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
        50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
        130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
        180                 185                 190

Phe Leu Glu Val Ser Tyr Arg Val Leu Arg His Leu Ala Gln Pro
            195                 200                 205

<210> SEQ ID NO 37
<211> LENGTH: 193
<212> TYPE: PRT
<213> ORGANISM: Homo sapiens

<400> SEQUENCE: 37

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
```

```
                35                  40                  45
Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
            130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 38
<211> LENGTH: 166
<212> TYPE: PRT
<213> ORGANISM: Homo sapiens

<400> SEQUENCE: 38

Ala Pro Pro Arg Leu Ile Cys Asp Ser Arg Val Leu Glu Arg Tyr Leu
1                5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
 50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 39
<211> LENGTH: 166
<212> TYPE: PRT
<213> ORGANISM: Homo sapiens

<400> SEQUENCE: 39
```

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
50                  55                      60

Gln Gly Leu Ala Leu Leu Ser Glu Ala Val Leu Arg Gly Gln Ala Leu
65              70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Arg Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

```
<210> SEQ ID NO 40
<211> LENGTH: 582
<212> TYPE: DNA
<213> ORGANISM: Homo sapiens

<400> SEQUENCE: 40
atgggggtgc acgaatgtcc tgcctggctg tggcttctcc tgtccctgct gtcgctccct     60
ctgggcctcc cagtcctggg cgccccacca cgcctcatct gtgacagccg agtcctggag    120
aggtacctct tggaggccaa ggaggccgag aatatcacga cgggctgtgc tgaacactgc    180
agcttgaatg agaatatcac tgtcccagac accaaagtta atttctatgc ctggaagagg    240
atggaggtcg ggcagcaggc cgtagaagtc tggcagggcc tggccctgct gtcggaagct    300
gtcctgcggg gccaggccct gttggtcaac tcttcccagc cgtgggagcc ctgcagctg     360
catgtggata agccgtcag tggccttcgc agcctcacca ctctgcttcg gctctgcga     420
gcccagaagg aagccatctc ccctccagat gcggcctcag ctgctccact ccgaacaatc    480
actgctgaca ctttccgcaa actcttccga gtctactcca atttcctccg gggaaagctg    540
aagctgtaca gggggaggc ctgcaggaca ggggacagat ga                        582
```

```
<210> SEQ ID NO 41
<211> LENGTH: 501
<212> TYPE: DNA
<213> ORGANISM: Homo sapiens

<400> SEQUENCE: 41
gccccaccac gcctcatctg tgacagccga gtcctggaga ggtacctctt ggaggccaag     60
gaggccgaga atatcacgac gggctgtgct gaacactgca gcttgaatga gaatatcact    120
gtcccagaca ccaaagttaa tttctatgcc tggaagagga tggaggtcgg gcagcaggcc    180
gtagaagtct ggcagggcct ggccctgctg tcggaagctg tcctgcgggg ccaggccctg    240
ttggtcaact cttcccagcc gtgggagccc ctgcagctgc atgtggataa agccgtcagt    300
```

```
ggccttcgca gcctcaccac tctgcttcgg gctctgcgag cccagaagga agccatctcc    360
cctccagatg cggcctcagc tgctccactc cgaacaatca ctgctgacac tttccgcaaa    420
ctcttccgag tctactccaa tttcctccgg ggaaagctga agctgtacac aggggaggcc    480
tgcaggacag gggacagatg a                                              501

<210> SEQ ID NO 42
<211> LENGTH: 501
<212> TYPE: DNA
<213> ORGANISM: Homo sapiens

<400> SEQUENCE: 42
gccccaccac gcctcatctg tgacagccga gtcctggaga ggtacctctt ggaggccaag     60
gaggccgaga atatcacgac gggctgtgct gaacactgca gcttgaatga gaatatcact    120
gtcccagaca ccaaagttaa tttctatgcc tggaagagga tggaggtcgg gcagcaggcc    180
gtagaagtct ggcagggcct ggccctgctg tcggaagctg tcctgcgggg ccaggccctg    240
ttggtcaact cttcccagcc gtgggagccc ctgcagctgc atgtggataa agccgtcagt    300
ggccttcgca gcctcaccac tctgcttcgg gctctgggag cccagaagga agccatctcc    360
cctccagatg cggcctcagc tgctccactc cgaacaatca ctgctgacac tttccgcaaa    420
ctcttccgag tctactccaa tttcctccgg ggaaagctga agctgtacac aggggaggcc    480
tgcaggacag gggacagatg a                                              501

<210> SEQ ID NO 43
<211> LENGTH: 503
<212> TYPE: DNA
<213> ORGANISM: Homo sapiens

<400> SEQUENCE: 43
atgctccacc aagattaatc tgtgacagcc gagtcctgga gaggtacctc ttggaggcca     60
aggaggccga gaatatcacg acgggctgtg ctgaacactg cagcttgaat gagaatatca    120
ctgtcccaga caccaaagtt aatttctatg cctggaagag gatggaggtc gggcagcagg    180
ccgtagaagt ctggcagggc ctggccctgc tgtcggaagc tgtcctgcgg ggccaggccc    240
tgttggtcaa ctcttcccag ccgtgggagc cctgcagct gcatgtggat aaagccgtca    300
gtggccttcg cagcctcacc actctgcttc gggctctgcg agcccagaag gaagccatct    360
cccctccaga tgcggcctca gctgctccac tccgaacaat cactgctgac actttccgca    420
aactcttccg agtctactcc aatttcctcc ggggaaagct gaagctgtac acaggggagg    480
cctgcaggac aggggacaga tga                                            503

<210> SEQ ID NO 44
<211> LENGTH: 36
<212> TYPE: DNA
<213> ORGANISM: Homo sapiens

<400> SEQUENCE: 44
cagttacata tgggagttca cgaatgtcct gcctgg                               36

<210> SEQ ID NO 45
<211> LENGTH: 33
<212> TYPE: DNA
<213> ORGANISM: Homo sapiens

<400> SEQUENCE: 45
```

```
cagttacata tgctccacca agattaatct gtg                              33

<210> SEQ ID NO 46
<211> LENGTH: 34
<212> TYPE: DNA
<213> ORGANISM: Homo sapiens

<400> SEQUENCE: 46
ctgcaactcg agtcatctgt cccctgtcct gcag                             34
```